(12) United States Patent
Seiwert et al.

(10) Patent No.: US 7,932,277 B2
(45) Date of Patent: Apr. 26, 2011

(54) PEPTIDE INHIBITORS OF HEPATITIS C VIRUS REPLICATION

(75) Inventors: Scott Seiwert, Pacifica, CA (US); Steven W. Andrews, Longmont, CO (US); Leonid Beigelman, San Mateo, CA (US); Lawrence M. Blatt, San Francisco, CA (US); Brad Buckman, Oakland, CA (US); Kevin R. Condroski, Lafayette, CO (US); Yutong Jiang, Longmont, CO (US); Robert J. Kaus, Longmont, CO (US); April L. Kennedy, Denver, CO (US); Timothy S. Kercher, Boulder, CO (US); Michael A. Lyon, Superior, CO (US); Bin Wang, Longmont, CO (US)

(73) Assignees: InterMune, Inc., Brisbane, CA (US); Array Biopharma Inc., Boulder, CO (US)

(*) Notice: Subject to any disclaimer, the term of this patent is extended or adjusted under 35 U.S.C. 154(b) by 162 days.

(21) Appl. No.: 12/118,624

(22) Filed: May 9, 2008

(65) Prior Publication Data

US 2009/0297476 A1    Dec. 3, 2009

Related U.S. Application Data

(63) Continuation of application No. 60/917,300, filed on May 10, 2007.

(60) Provisional application No. 61/023,041, filed on Jan. 23, 2008.

(51) Int. Cl.
| | |
|---|---|
| *A61K 31/4035* | (2006.01) |
| *A61K 31/428* | (2006.01) |
| *A61K 31/4025* | (2006.01) |
| *A61K 31/401* | (2006.01) |
| *C07D 207/09* | (2006.01) |
| *C07D 403/12* | (2006.01) |
| *C07D 417/12* | (2006.01) |

(52) U.S. Cl. ........ 514/367; 514/414; 514/422; 514/423; 548/465; 548/170; 548/517; 548/537

(58) Field of Classification Search ........................ None
See application file for complete search history.

(56) References Cited

U.S. PATENT DOCUMENTS

| | | |
|---|---|---|
| 3,547,119 A | 12/1970 | Hall et al. |
| 4,211,771 A | 7/1980 | Witkowski et al. |
| 4,311,137 A | 1/1982 | Gerard |
| 4,531,937 A | 7/1985 | Yates |
| 4,755,173 A | 7/1988 | Konopka et al. |
| 5,034,394 A | 7/1991 | Daluge |
| 5,232,928 A | 8/1993 | Skiles |
| 5,310,562 A | 5/1994 | Margolin |
| 5,518,729 A | 5/1996 | Margolin |
| 5,541,206 A | 7/1996 | Kempf et al. |
| 5,624,949 A | 4/1997 | Heath et al. |
| 5,635,523 A | 6/1997 | Kempf et al. |
| 5,648,497 A | 7/1997 | Kempf et al. |
| 5,656,627 A | 8/1997 | Bemis et al. |
| 5,716,632 A | 2/1998 | Margolin |
| 5,756,466 A | 5/1998 | Bemis et al. |
| 5,846,987 A | 12/1998 | Kempf et al. |
| 5,847,135 A | 12/1998 | Bemis et al. |
| 5,968,895 A | 10/1999 | Gefter et al. |
| 6,017,328 A | 1/2000 | Fischell et al. |
| 6,090,822 A | 7/2000 | Margolin |
| 6,232,333 B1 | 5/2001 | Lipari et al. |
| 6,268,207 B1 | 7/2001 | Bailey |
| 6,277,830 B1 | 8/2001 | Ganguly et al. |
| 6,323,180 B1 | 11/2001 | Llinas-Brunet et al. |
| 6,329,417 B1 | 12/2001 | Llinas-Brunet et al. |
| 6,410,531 B1 | 6/2002 | Llinas-Brunet et al. |
| 6,420,380 B2 | 7/2002 | Llinas-Brunet et al. |
| 6,534,523 B1 | 3/2003 | Llinas-Brunet et al. |
| 6,608,027 B1 | 8/2003 | Tsantrizo et al. |
| 6,642,204 B2 | 11/2003 | Llinas-Brunet et al. |
| 6,693,072 B2 | 2/2004 | Gallion et al. |
| 6,767,991 B1 | 7/2004 | Llinas-Brunet et al. |
| 6,828,301 B2 | 12/2004 | Chen et al. |
| 6,846,802 B2 | 1/2005 | Chen et al. |
| 6,858,600 B2 | 2/2005 | Hamilton et al. |
| 6,867,185 B2 | 3/2005 | Campbell et al. |

(Continued)

FOREIGN PATENT DOCUMENTS

CA        2370400 A1      8/2003

(Continued)

OTHER PUBLICATIONS

Simmen et al., "Preclinical characterization of TMC435350, a novel macrocyclic inhibitor of the HCV NS3/4A serine protease", Tibotec Poster, Mechelen, Belgium, 14th International Symposium on Hepatitis C Virus & Related Viruses, Glasgow, UK, Sep. 2007, 1 page.
The Merck Index, An Encyclopedia of Chemicals, Drugs, and Biologicals, "ABACAVIR", 14th Edition, 2006, p. 1.
The Merck Index, An Encyclopedia of Chemicals, Drugs, and Biologicals, "DIDANOSINE", 14th Edition, 2006, p. 525.
www.medknowledge.de/neu/2002/IV-2002-32-biln-2061-pipeline.htm_4_pages, (2002).

(Continued)

*Primary Examiner* — Yong Chu
*Assistant Examiner* — Michael Barker
(74) *Attorney, Agent, or Firm* — Knobbe, Martens, Olson & Bear, LLP

(57) ABSTRACT

The embodiments provide compounds of the general Formula I, as well as compositions, including pharmaceutical compositions, comprising a subject compound. The embodiments provide compounds of the general Formula II, as well as compositions, including pharmaceutical compositions, comprising a subject compound. The embodiments further provide treatment methods, including methods of treating a hepatitis C virus infection and methods of treating liver fibrosis, the methods generally involving administering to an individual in need thereof an effective amount of a subject compound or composition.

79 Claims, No Drawings

U.S. PATENT DOCUMENTS

| | | |
|---|---|---|
| 6,867,303 B2 | 3/2005 | Grela |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,909,000 B2 | 6/2005 | Farmer et al. |
| 6,914,122 B2 | 7/2005 | Venkatraman et al. |
| 6,919,423 B2 | 7/2005 | Llinas-Brunet |
| 6,995,174 B2 | 2/2006 | Wang et al. |
| 7,012,066 B2 | 3/2006 | Saksena et al. |
| 7,041,698 B2 | 5/2006 | Ripka et al. |
| 7,091,184 B2 | 8/2006 | Llinas-Brunet et al. |
| 7,119,072 B2 | 10/2006 | Llinas-Brunet et al. |
| 7,125,845 B2 | 10/2006 | Wu et al. |
| 7,132,504 B2 | 11/2006 | Scola et al. |
| 7,135,462 B2 | 11/2006 | Scola et al. |
| 7,148,347 B2 | 12/2006 | Brandenburg et al. |
| 7,157,424 B2 | 1/2007 | Chen et al. |
| 7,173,004 B2 | 2/2007 | McPhee et al. |
| 7,173,057 B2 | 2/2007 | Chen et al. |
| 7,176,208 B2 | 2/2007 | Nakajima et al. |
| 7,183,374 B2 | 2/2007 | Brenner et al. |
| 7,186,747 B2 | 3/2007 | Arasappan et al. |
| 7,189,844 B2 | 3/2007 | Gallou et al. |
| 7,205,330 B2 | 4/2007 | Bogen et al. |
| 7,208,600 B2 | 4/2007 | Cottrell et al. |
| 7,273,851 B2 | 9/2007 | Miao et al. |
| 7,273,885 B2 | 9/2007 | Pitlik et al. |
| 7,309,708 B2 | 12/2007 | Tu et al. |
| 7,323,447 B2 | 1/2008 | Sin et al. |
| 7,342,041 B2 | 3/2008 | Njoroge et al. |
| 7,399,749 B2 | 7/2008 | Arasappan et al. |
| 7,470,664 B2 | 12/2008 | Holloway et al. |
| 7,485,625 B2 | 2/2009 | Velazquez et al. |
| 7,491,794 B2 | 2/2009 | Blatt et al. |
| 7,494,660 B2 | 2/2009 | Lin et al. |
| 2002/0016294 A1 | 2/2002 | Venkatraman et al. |
| 2002/0016442 A1 | 2/2002 | Llinas-Brunet et al. |
| 2002/0037998 A1 | 3/2002 | Llinas-Brunet et al. |
| 2002/0107181 A1 | 8/2002 | Chen et al. |
| 2002/0111313 A1 | 8/2002 | Campbell et al. |
| 2003/0181363 A1 | 9/2003 | Llinas-Brunet et al. |
| 2003/0186895 A1 | 10/2003 | Llinas-Brunet et al. |
| 2003/0191067 A1 | 10/2003 | Llinas-Brunet et al. |
| 2003/0195228 A1 | 10/2003 | Chen et al. |
| 2003/0224977 A1 | 12/2003 | Llinas-Brunet et al. |
| 2003/0236242 A1 | 12/2003 | Perni et al. |
| 2004/0002448 A1 | 1/2004 | Tsantrizos et al. |
| 2004/0018986 A1 | 1/2004 | Pitlik et al. |
| 2004/0033959 A1 | 2/2004 | Chen et al. |
| 2004/0038872 A1 | 2/2004 | Campbell et al. |
| 2004/0048802 A1 | 3/2004 | Ripka et al. |
| 2004/0072761 A1 | 4/2004 | Campbell et al. |
| 2004/0077551 A1 | 4/2004 | Campbell et al. |
| 2004/0106559 A1 | 6/2004 | Wang et al. |
| 2004/0138109 A1 | 7/2004 | Chen et al. |
| 2004/0180815 A1 | 9/2004 | Nakajima et al. |
| 2004/0229776 A1 | 11/2004 | Chen et al. |
| 2004/0229777 A1 | 11/2004 | Cerreta et al. |
| 2004/0229848 A1 | 11/2004 | Demuth et al. |
| 2004/0248779 A1 | 12/2004 | Dersch et al. |
| 2004/0259804 A1 | 12/2004 | Karanewsky et al. |
| 2004/0266668 A1 | 12/2004 | Nakajima et al. |
| 2005/0049187 A1 | 3/2005 | Brandenburg et al. |
| 2005/0065073 A1 | 3/2005 | Wu et al. |
| 2005/0075279 A1 | 4/2005 | Llinas-Brunet et al. |
| 2005/0080005 A1 | 4/2005 | Llinas-Brunet et al. |
| 2005/0080017 A1 | 4/2005 | Cottrell et al. |
| 2005/0090432 A1 | 4/2005 | McPhee et al. |
| 2005/0119189 A1 | 6/2005 | Cottrell et al. |
| 2005/0119453 A1 | 6/2005 | Brenner et al. |
| 2005/0136400 A1 | 6/2005 | Lin et al. |
| 2005/0137139 A1 | 6/2005 | Perni et al. |
| 2005/0143316 A1 | 6/2005 | Tu et al. |
| 2005/0153877 A1 | 7/2005 | Miao et al. |
| 2005/0153900 A1 | 7/2005 | Velazquez et al. |
| 2005/0154186 A1 | 7/2005 | Gallou et al. |
| 2005/0192212 A1 | 9/2005 | Llinas-Brunet et al. |
| 2005/0197301 A1 | 9/2005 | Njoroge et al. |
| 2005/0209135 A1 | 9/2005 | Busacca et al. |
| 2005/0215423 A1 | 9/2005 | Brenner et al. |
| 2005/0215486 A1 | 9/2005 | Cottrell et al. |
| 2005/0215513 A1 | 9/2005 | Boojamra et al. |
| 2005/0222047 A1 | 10/2005 | Chen et al. |
| 2005/0245458 A1 | 11/2005 | Arasappan et al. |
| 2005/0261200 A1 | 11/2005 | Miao et al. |
| 2005/0267018 A1 | 12/2005 | Blatt et al. |
| 2005/0267040 A1 | 12/2005 | Scola et al. |
| 2005/0267043 A1 | 12/2005 | Bogen et al. |
| 2005/0267151 A1 | 12/2005 | Busacca et al. |
| 2005/0272663 A1 | 12/2005 | Arasappan et al. |
| 2006/0019905 A1 | 1/2006 | Bailey et al. |
| 2006/0046956 A1 | 3/2006 | Sannigrahi et al. |
| 2006/0046965 A1 | 3/2006 | Bailey et al. |
| 2006/0063915 A1 | 3/2006 | Gallou et al. |
| 2006/0063916 A1 | 3/2006 | Gallou |
| 2006/0069099 A1 | 3/2006 | Fu et al. |
| 2006/0122123 A1 | 6/2006 | Chaudhary et al. |
| 2006/0183694 A1 | 8/2006 | Sin et al. |
| 2006/0198824 A1 | 9/2006 | Malcolm et al. |
| 2006/0199773 A1 | 9/2006 | Sausker et al. |
| 2006/0205638 A1 | 9/2006 | Busacca et al. |
| 2006/0210969 A1 | 9/2006 | Rice et al. |
| 2006/0252698 A1 | 11/2006 | Malcolm |
| 2006/0252951 A1 | 11/2006 | Leitner et al. |
| 2006/0269516 A1 | 11/2006 | Presta et al. |
| 2006/0275366 A1 | 12/2006 | Malcolm et al. |
| 2006/0276404 A1 | 12/2006 | Ghosal et al. |
| 2006/0276405 A1 | 12/2006 | Albrecht |
| 2006/0276407 A1 | 12/2006 | Albrecht et al. |
| 2006/0281688 A1 | 12/2006 | Zhang et al. |
| 2006/0281689 A1 | 12/2006 | Malcolm |
| 2006/0287248 A1 | 12/2006 | Malcolm |
| 2007/0004635 A1 | 1/2007 | Albrecht et al. |
| 2007/0010431 A1 | 1/2007 | Malcolm et al. |
| 2007/0010455 A1 | 1/2007 | Hewawasam et al. |
| 2007/0021351 A1 | 1/2007 | White et al. |
| 2007/0027071 A1 | 2/2007 | Holloway et al. |
| 2007/0032433 A1 | 2/2007 | Saksena et al. |
| 2007/0054842 A1 | 3/2007 | Blatt et al. |
| 2007/0054864 A1 | 3/2007 | Graupe et al. |
| 2007/0072809 A1 | 3/2007 | Cho et al. |
| 2007/0093414 A1 | 4/2007 | Carini et al. |
| 2007/0099825 A1 | 5/2007 | D'Andrea et al. |
| 2007/0112001 A1 | 5/2007 | Anselm et al. |
| 2007/0161574 A1 | 7/2007 | Rosenquist et al. |
| 2007/0231262 A1 | 10/2007 | Lin et al. |
| 2007/0274951 A1 | 11/2007 | Tong et al. |
| 2007/0281885 A1 | 12/2007 | Sun et al. |
| 2007/0287664 A1 | 12/2007 | Ralston, II et al. |
| 2007/0299078 A1 | 12/2007 | Niu et al. |
| 2008/0014173 A1 | 1/2008 | Scola et al. |
| 2008/0019942 A1 | 1/2008 | Seiwert et al. |
| 2008/0032936 A1 | 2/2008 | Gai et al. |
| 2008/0038225 A1 | 2/2008 | Sun et al. |
| 2008/0039470 A1 | 2/2008 | Niu et al. |
| 2008/0107623 A1 | 5/2008 | Davidson et al. |
| 2008/0107624 A1 | 5/2008 | D'Andrea et al. |
| 2008/0107625 A1 | 5/2008 | D'Andrea et al. |
| 2008/0119461 A1 | 5/2008 | Sin et al. |
| 2008/0125444 A1 | 5/2008 | Sun et al. |
| 2008/0187516 A1 | 8/2008 | Sun et al. |
| 2008/0267916 A1 | 10/2008 | Gai et al. |
| 2008/0267917 A1 | 10/2008 | Niu et al. |
| 2008/0267918 A1 | 10/2008 | Gai et al. |
| 2008/0269228 A1 | 10/2008 | Moore et al. |
| 2008/0269502 A1 | 10/2008 | Gantz et al. |
| 2008/0274080 A1 | 11/2008 | Or et al. |
| 2008/0274082 A1 | 11/2008 | Gai et al. |
| 2008/0279821 A1 | 11/2008 | Niu et al. |
| 2008/0286230 A1 | 11/2008 | Sommadossi et al. |
| 2008/0287449 A1 | 11/2008 | Niu et al. |
| 2008/0317712 A1 | 12/2008 | Niu et al. |
| 2009/0004140 A1 | 1/2009 | Qiu et al. |
| 2009/0005387 A1 | 1/2009 | Niu et al. |
| 2009/0035267 A1 | 2/2009 | Moore et al. |
| 2009/0035268 A1 | 2/2009 | Sun et al. |
| 2009/0035272 A1 | 2/2009 | Moore et al. |

| | | |
|---|---|---|
| 2009/0041721 A1 | 2/2009 | Niu et al. |
| 2009/0047244 A1 | 2/2009 | Parsy et al. |
| 2009/0047248 A1 | 2/2009 | Sun et al. |
| 2009/0047252 A1 | 2/2009 | Cai et al. |
| 2009/0048297 A1 | 2/2009 | Phadke et al. |
| 2009/0053175 A1 | 2/2009 | Or et al. |
| 2009/0060874 A1 | 3/2009 | Qiu et al. |
| 2009/0062311 A1 | 3/2009 | Simmen et al. |
| 2009/0075869 A1 | 3/2009 | Holloway et al. |
| 2009/0082261 A1 | 3/2009 | Chen et al. |
| 2009/0082366 A1 | 3/2009 | Czarnik |
| 2009/0093533 A1 | 4/2009 | Beigelman et al. |
| 2009/0098085 A1 | 4/2009 | Sun et al. |
| 2009/0104151 A1 | 4/2009 | Hanson et al. |
| 2009/0105471 A1 | 4/2009 | Blatt et al. |
| 2009/0111757 A1 | 4/2009 | Lin et al. |
| 2009/0111969 A1 | 4/2009 | Blatt et al. |
| 2009/0111982 A1 | 4/2009 | Blatt et al. |
| 2009/0123423 A1 | 5/2009 | Gai et al. |
| 2009/0123425 A1 | 5/2009 | Moore et al. |
| 2009/0124661 A1 | 5/2009 | Holloway et al. |
| 2009/0124808 A1 | 5/2009 | Busacca et al. |
| 2009/0130059 A1 | 5/2009 | Sun et al. |
| 2009/0148407 A1 | 6/2009 | Blatt et al. |
| 2009/0149491 A1 | 6/2009 | Liu et al. |
| 2009/0155209 A1 | 6/2009 | Blatt et al. |
| 2009/0155210 A1 | 6/2009 | Gai et al. |
| 2009/0169510 A1 | 7/2009 | Blatt et al. |
| 2009/0180985 A1 | 7/2009 | Liu et al. |
| 2009/0202480 A1 | 8/2009 | Parsy et al. |
| 2009/0203008 A1 | 8/2009 | Ludmerer et al. |
| 2009/0203629 A1 | 8/2009 | Holsinger |
| 2009/0269305 A1 | 10/2009 | Seiwert et al. |
| 2009/0274657 A1 | 11/2009 | Gai et al. |
| 2009/0286843 A1 | 11/2009 | Blatt et al. |
| 2009/0297476 A1 | 12/2009 | Seiwert et al. |
| 2010/0022578 A1 | 1/2010 | Raboisson et al. |
| 2010/0074867 A1 | 3/2010 | Venkatraman et al. |
| 2010/0087382 A1 | 4/2010 | Bailey et al. |
| 2010/0119479 A1 | 5/2010 | Buckman et al. |

FOREIGN PATENT DOCUMENTS

| | | |
|---|---|---|
| CL | 01958-96 | 7/1997 |
| CL | 2703-97 | 12/1997 |
| CL | 39715 | 6/1998 |
| CL | 01184-98 | 3/1999 |
| CL | 1797-99 | 8/1999 |
| CL | 1804-99 | 8/1999 |
| CL | 795-00 | 4/2000 |
| CL | 766-01 | 10/2001 |
| CL | 144-03 | 1/2003 |
| CL | 167-03 | 1/2003 |
| CL | 168-03 | 1/2003 |
| CL | 1161-04 | 12/2004 |
| CL | 120-05 | 1/2005 |
| EA | 2006 07738 | 12/2006 |
| EP | 0206497 A2 | 12/1986 |
| EP | 0349242 A2 | 1/1990 |
| JP | 2002/542160 | 10/2000 |
| RU | 2247126 C2 | 2/2005 |
| WO | WO 97/18207 | 5/1997 |
| WO | WO 97/43310 | 11/1997 |
| WO | WO 98/17679 | 4/1998 |
| WO | WO 98/46630 | 10/1998 |
| WO | WO 98/51665 | 11/1998 |
| WO | WO 99/07733 | 2/1999 |
| WO | WO 99/07734 | 2/1999 |
| WO | WO 99/47545 | 9/1999 |
| WO | WO 00/09543 | 2/2000 |
| WO | WO 00/09558 | 2/2000 |
| WO | WO 00/23421 | 4/2000 |
| WO | WO 00/59929 A1 | 10/2000 |
| WO | WO 01/74768 | 10/2001 |
| WO | WO 01/81325 | 11/2001 |
| WO | WO 02/18369 | 3/2002 |
| WO | WO 02/060926 | 8/2002 |
| WO | WO 03/002518 | 1/2003 |
| WO | WO 03/053349 | 7/2003 |
| WO | WO 03/053349 A2 | 7/2003 |
| WO | WO 03/062228 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 2004/009121 | 1/2004 |
| WO | WO 2004/026896 | 4/2004 |
| WO | WO 2004/037855 | 5/2004 |
| WO | WO 2004/039833 | 5/2004 |
| WO | WO 2004/072243 | 8/2004 |
| WO | WO 2004/089974 | 10/2004 |
| WO | WO 2004/092162 | 10/2004 |
| WO | WO 2004/092203 | 10/2004 |
| WO | WO 2004/093798 | 11/2004 |
| WO | WO 2004/093915 | 11/2004 |
| WO | WO 2004/094452 | 11/2004 |
| WO | WO 2004/096286 | 11/2004 |
| WO | WO 2004/103996 | 12/2004 |
| WO | WO 2004/113365 | 12/2004 |
| WO | WO 2005/003147 | 1/2005 |
| WO | WO 2005/007601 A2 | 1/2005 |
| WO | WO 2005/010029 | 2/2005 |
| WO | WO 2005/021584 | 3/2005 |
| WO | WO 2005/028501 | 3/2005 |
| WO | WO 2005/035525 | 4/2005 |
| WO | WO 2005/037214 A2 | 4/2005 |
| WO | WO 2005/039552 | 5/2005 |
| WO | WO 2005/046712 | 5/2005 |
| WO | WO 2005/051410 | 6/2005 |
| WO | WO 2005/051980 | 6/2005 |
| WO | WO 2005/056182 | 6/2005 |
| WO | WO 2005/070955 | 8/2005 |
| WO | WO 2005/073195 | 8/2005 |
| WO | WO 2005/073216 | 8/2005 |
| WO | WO 2005/075502 | 8/2005 |
| WO | WO 2005/095403 | 10/2005 |
| WO | WO 2005/097820 | 10/2005 |
| WO | WO 2005/107745 | 11/2005 |
| WO | WO 2005/113581 | 12/2005 |
| WO | WO 2006/000085 | 1/2006 |
| WO | WO 2006/020276 | 2/2006 |
| WO | WO 2006/043145 | 4/2006 |
| WO | WO 2006/045096 | 4/2006 |
| WO | WO 2006/075021 | 7/2006 |
| WO | WO 2006/086381 | 8/2006 |
| WO | WO 2006/113942 | 10/2006 |
| WO | WO 2006/119061 | 11/2006 |
| WO | WO 2006/122188 | 11/2006 |
| WO | WO 2007/011658 | 1/2007 |
| WO | WO 2007/011777 | 1/2007 |
| WO | WO 2007/014919 | 2/2007 |
| WO | WO 2007/014922 | 2/2007 |
| WO | WO 2007/014926 | 2/2007 |
| WO | WO 2007/014927 | 2/2007 |
| WO | WO 2007/015824 | 2/2007 |
| WO | WO 2007/016441 | 2/2007 |
| WO | WO 2007/016476 | 2/2007 |
| WO | WO 2007/017144 | 2/2007 |
| WO | WO 2007/022459 | 2/2007 |
| WO | WO 2007/030656 | 3/2007 |
| WO | WO 2007/044893 | 4/2007 |
| WO | WO 2007/044933 | 4/2007 |
| WO | WO 2007/056120 | 5/2007 |
| WO | WO 2007/089618 | 8/2007 |
| WO | WO 2007/092616 | 8/2007 |
| WO | WO 2007/104162 | 9/2007 |
| WO | WO 2007/106317 | 9/2007 |
| WO | WO 2007/111866 | 10/2007 |
| WO | WO 2007/130499 | 11/2007 |
| WO | WO 2007/133865 | 11/2007 |
| WO | WO 2007/143694 | 12/2007 |
| WO | WO 2007/146695 | 12/2007 |
| WO | WO 2007/148135 | 12/2007 |
| WO | WO 2008/005565 | 1/2008 |
| WO | WO 2008/019266 | 2/2008 |
| WO | WO 2008/019289 | 2/2008 |
| WO | WO 2008/019303 | 2/2008 |

| | | |
|---|---|---|
| WO | WO 2008/021733 | 2/2008 |
| WO | WO 2008/021871 | 2/2008 |
| WO | WO 2008/021960 | 2/2008 |
| WO | WO 2008/022006 | 2/2008 |
| WO | WO 2008/033389 | 3/2008 |
| WO | WO 2008/033466 | 3/2008 |
| WO | WO 2008/046860 | 4/2008 |
| WO | WO 2008/051514 | 5/2008 |
| WO | WO 2008/057208 | 5/2008 |
| WO | WO 2008/057209 | 5/2008 |
| WO | WO 2008/057995 | 5/2008 |
| WO | WO 2008/060927 A2 | 5/2008 |
| WO | WO 2008/064057 | 5/2008 |
| WO | WO 2008/064061 | 5/2008 |
| WO | WO 2008/064066 | 5/2008 |
| WO | WO 2008/064218 | 5/2008 |
| WO | WO 2008/070358 | 6/2008 |
| WO | WO 2008/073282 | 6/2008 |
| WO | WO 2008/086161 | 7/2008 |
| WO | WO 2008/095058 | 8/2008 |
| WO | WO 2008/095999 | 8/2008 |
| WO | WO 2008/096001 | 8/2008 |
| WO | WO 2008/098368 | 8/2008 |
| WO | WO 2008/106130 | 9/2008 |
| WO | WO 2008/106139 | 9/2008 |
| WO | WO 2008/118332 | 10/2008 |
| WO | WO 2008/128121 | 10/2008 |
| WO | WO 2008/128921 | 10/2008 |
| WO | WO 2008/134397 | 11/2008 |
| WO | WO 2008/134398 | 11/2008 |
| WO | WO 2008/137126 | 11/2008 |
| WO | WO 2008/137779 | 11/2008 |
| WO | WO 2008/137779 A1 | 11/2008 |
| WO | WO 2008/141227 | 11/2008 |
| WO | WO 2009/003009 | 12/2008 |
| WO | WO 2009/005676 | 1/2009 |
| WO | WO 2009/005677 | 1/2009 |
| WO | WO 2009/005690 | 1/2009 |
| WO | WO 2009/008913 | 1/2009 |
| WO | WO 2009/051840 | 4/2009 |
| WO | WO 2009/053828 | 4/2009 |
| WO | WO 2009/064955 | 5/2009 |
| WO | WO 2009/064975 | 5/2009 |
| WO | WO 2009/070692 | 6/2009 |
| WO | WO 2009/073713 | 6/2009 |
| WO | WO 2009/073719 | 6/2009 |
| WO | WO 2009/073780 | 6/2009 |
| WO | WO 2009/076173 | 6/2009 |
| WO | WO 2009/079352 | 6/2009 |
| WO | WO 2009/079353 | 6/2009 |
| WO | WO 2009/082697 | 7/2009 |
| WO | WO 2009/082701 | 7/2009 |
| WO | WO 2009/085659 | 7/2009 |
| WO | WO 2009/094438 | 7/2009 |
| WO | WO 2009/094443 | 7/2009 |
| WO | WO 2009/129109 | 10/2009 |
| WO | WO 2009/134624 | 11/2009 |
| WO | WO2009/137432 | 11/2009 |

OTHER PUBLICATIONS

Zucca et al., Regioselective Solid-phase 4-Amino-de-chlorination of 2,3,6-Trichloropyrimidine by Resin-supported N-Potassium Carbamates, Tetra Lttr., 2001, 42: 1033-1035.

International Preliminary Report on Patentability dated Nov. 10, 2009 in PCT/US2008/063304, filed May 9, 2008.

Zhou et al., Phenotypic and Structural Analyses of Hepatitis C Virus NS3 Protease Arg155 Variants, J Bio Chem., Jun. 6, 2007, 282(31): 22619-22628.

Ronn et al., Exploration of Acyl Sulfonamides as Carboxylic Acid Replacements in Protease Inhibitors of the Hepatitis C Virus Full-length NS3, Bioorg & Med Chem., 14(2): 544-559, Jan. 15, 2006.

Beaulieu et al., Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease., J. Org. Chem., 2005, pp. 5869-5879.

Belokon et al., A General Method for the Asymmetric Synthesis of anti-Diastereoisomers of b-Substituted L-2-Aminobutanoic Acids via Chiral Nickel Schiff's Base Complexes of Dehydroaminobutanoic Acid. X-Ray Crystal and Molecular Structure of the Nickel Complex of the Schiff's Base from [(Benzylprolyl)amino]benzophenone and Dehydroaminobutanoic Acid. , (1990) 8: 2301-2310., J. Chem. Soc. Perkin Trans. 1, 1990, Issue 8, pp. 2301-2310.

EFS File History of U.S. Appl. No. 11/093,884, filed Mar. 29, 2005 (US Patent No. 7,491,794, issued Feb. 17, 2009).

EFS File History of U.S. Appl. No. 11/491,126, filed Jul. 21, 2006, as of Aug. 28, 2009.

Farina, Efficient Synthesis of BILN 2061, a Potent HCV Protease inhibitor, by a Convergent Approach Based on Ring-Closing Metathesis: ACS ProSpectives Conference Series., Process Chemistry in the Pharmaceutical Industry, Feb. 6-9, 2005, pp. 1-28.

Faucher et al., Synthesis of BILN 2061, an HCV NS3 Protease Inhibitor with Proven Antiviral Effect in Humans., Org. Lett., 2004, 6(17): 2901-2904.

Foster, FRCP, Ph.D., Past, Present, and Future Hepatitis C., Seminars in Liver Disease, 2004, 24(2): pp. 97-104.

Franciscus, What Did We Learn From AASLD? Part 3, HCV Advocate Newsletter, (2003) 6(2): pp. 1, 3, 6 & 9 ¿ Qué Hemos Aprendido sobre la Hepatitis C en la Conferencia AASLD de 2002? Link:, http://www.hcvadvocate.org/news/NewsUpdates_pdf/2.4.1_HCV_Advocate_2003/advocate0203.pdf, 2002, pp. 4 pages., Online: http://www.hcvadvocate.org/news/NewsUpdate.

Galgoci et al., A convenient synthesis of methyl (Z)-1-carbamoyl-2-ethenylcyclopropanecarboxylate and (Z)-1-carbamoyl-2-ethenylcyclopropanecarboxylic acid., Synth. Commun., 1994, 24(17): 2477-2483.

Gonzalez et al., Synthetic studies on L-Proline and (4R)-hydroxy-L-proline derivatives., Synthesis, 2004, Issue 8, pp. 1171-1182.

Goodman & Gilman, (1996) p. 47, with partial translation, Pharmacological Basis of Therapeutics, 9th Edition, McGraw-Hill, 1996, Issue I, pp. 47 & 1-2, Interamericana, Mexico, partial.

Goudreau et al., "Potent Inhibitors of the Hepatitis C Virus NS3 Protease: Design and Synthesis of Macrocyclic Substrate-Based ⊐-Strand Mimics," J Org Chem. (2004), 69(19):6185-6201.

Goudreau et al., The Therapeutic Potential of NS3 Protease Inhibitors in HCV Infection., Expert Opin. Investig. Drugs, 2005, 14(9): 1129-1144.

Hinrichsen et al., Short-term antiviral efficacy of BILN 2061, a hepatitis C virus serine protease inhibitor, in hepatitis C genotype 1 patients. (2004), 127(5): 1347-1355, Gastroenterology, 2004, vol. 5, Issue 127, pp. 1347-1355.

LaPlante et al., Dynamics and structure-based design of drugs targeting the critical serine protease of the hepatitis C virus from a peptidic substrate to BILN 2061, Abstract Only,, Current Medicinal Chemistry: Anti-Infective Agents, 2005, vol. 2, Issue 4, pp. 111-132. (Abstract Only).

Lin et al., Combination of a hepatitis C virus NS3-NS4A protease inhibitor and alpha interferon synergistically inhibits viral RNA replication and facilitates viral RNA clearance in replicon cells., Antimicrobal Agents & Chemo., 2004, vol. 12, Issue 48, pp. 4784-4792.

Llinas-Brunet et al., Structure-Activity Study on a Novel Series of Macrocyclic Inhibitors of the Hepatitis C Virus NS3 Protease Leading to the Discovery of BILN 2061., J. Med. Chem., 2004, vol. 7, Issue 47, pp. 1605-1608.

Lu et al., Mutations conferring resistance to a potent hepatitis C virus serine protease inhibitor in vitro., Antimicrobial Agents and Chemotherapy, 2004, vol. 6, Issue 48, pp. 2260-2266.

Marchetti et al., Synthesis of Two Novel Cyclic Biphenyl Ether Analogs of an Inhibitor of HCV NS3 Protease. (1999) S1, 1000-1002., Synlett., 1999, Issue 51, pp. 1000-1002.

Ni et al., Progress and development of small molecule HCV antivirals. (Abstract only), Curr. Opin Drug Disc Devel, 2004, 7(4): pp. 446-459.

Perni et al., Inhibitors of hepatitis C Virus NS3•4A protease 1. Non-Charged Tetrapeptide Variants., Bioorg. Med. Chem. Lett., 2003, 13(22): 4059-4063.

Perni et al., Inhibitors of hepatitis C virus NS3•4A protease 2. Warhead SAR and optimization, Bioorg. Med. Chem. Lett., 2004, 14(6): 1441-6.

Perni et al., Inhibitors of hepatitis C virus NS3•4A protease. Part 3. P2 proline variants, Bioorg. Med. Chem. Lett. 2004, 14(8):1939-42.

Sulkowski, Orally available Hepatitis C Virus (HCV) protease inhibitor (BILN 2061) demonstrates potent anti-viral activity in persons infected with HCV genotype 1. www.natap.org/2002/AASLD/day14.htm., AASLD Conference Report, 2002, pp. 1.

Sun et al., P4 cap modified tetrapeptidyl a-ketoamides as potent HCV NS3 protease inhibitors. Bioorg. Med. Chem. Lett., 2004, 14(16): 4333-4338.

Thibeault et al., Sensitivity of NS3 serine proteases from hepatitis C virus genotypes 2 and 3 to the inhibitor BILN 2061. J. Virol., 2004, 78(14): 7352-7359.

Thorstensson et al., Synthesis of Novel Potent Hepatitis C Virus NS3 Protease Inhibitors. Discovery of 4-Hydroxy-cyclopent-2-ene-1,2-dicarboxylic Acid as a N-Acyl-L-Hydroxy-proline Bioisostere., Bioorg. Med. Chem., 2007, 15: 827-838.

Tsantrizos, "The design of a potent inhibitor of the hepatitis C virus NS3 protease: BILN 2061—From the NMR tube to the clinic," *Biopolymers* (2004), 76(4): 309-323. (Abstract Only).

Tsantrizos et al., Macrocyclic Inhibitors of the NS3 Protease as Potential Therapeutic Agents of Hepatitis C Virus Infection. , Angew. Chem. Int. Ed., 2003, 42(12): 1356-1360.

International Search Report for International Application No. PCT/US2008/063304 dated Sep. 26, 2008.

Brunt, *"Grading and Staging the Histopathological Lesions of Chronic Hepatitis: The Knodell Histology Activity Index and Beyond"* Hepatology vol. 31, No. 1, 241-246, 2000.

Ishak et al., *"Histological grading and staging of chronic hepatitis"* Journal of Hepatology, 22:696-699, 1995.

Khan et al., *"Diastereoselective Synthesis of trans-2-(1-Triphenylmethyl-1Himidazol-4-YL)Cyclopropanecarboxylic Acids: Key Intermediates for the Preparation of Potent and Chiral Histamine H3 Receptor Agents"* Bioorganic & Medicinal Chemistry Letters, 1997, vol. 7, No. 23, 3017-3022.

Knodell et al., *"Formulation and Application of a Numerical Scoring System for Assessing Histological Activity in Asymptomatic Chronic Active Hepatitis"* Hepatology vol. 1, No. 5, p. 431, 1981.

Lohmann et al., *"Replication of Subgenomic Hepatitis C Virus RNAs in a Hepatoma Cell Line"* Science 285; 110-113 (1999).

Ma et al., *"Accelerating Effect Induced by the Structure of α-Amino Acid in the Copper-Catalyzed Coupling Reaction of Aryl Halides with α-Amino Acids. Synthesis of Benzolactam-V8"* Journal of American Chemical Society, 1998, 120, 12459-12467.

McKenna, et al., *"The scope and limitations of the Suzuki-Miyaura cross-coupling reactions of 6- and 8-substituted 1,2,3,4-tetrahydroisoquinoline-3-carboxylates"* Tetrahedron Letters, 2001, 42, 5795-5800.

Merck Index, *"Ribavirin"* Compound No. 8199, ICN Pharmaceuticals, Inc., Eleventh Edition, 1989.

Bedossa et al.—The French Metavir Cooperative Study Group, *"Intraobserver and Interobserver Variations in Liver Biopsy Interpretation in Patients with Chronic Hepatitis C"* Hepatology 20:15-20, 1994.

Peter J. Scheuer, *"Classification of chronic viral hepatitis: a need for reassessment"* Journal of Hepatology 13:372, 1991.

Yao et al., *"Molecular views of viral polyprotein processing revealed by the crystal structure of the hepatitis C virus bifunctional protease-helicase"* Structure Nov. 1999, 7, 1353-1363.

Falchi et al., 4-(4,6-Dimethoxy[1,3,5]triazin-2-yl)-4-methyl-morpholinium Chloride (DMTMM): A valuable Alternative to PyBOP for Solid Phase Peptide Synthesis, (Jan. 2000) 2: 275-277.

Kwong et al., Hepatitis C virus NS3/4A protease, Antiviral Res. (Jul. 1998) 40: 1-18.

Lalezari et al., Potent Antiviral Activity of the HCV Nucleoside Polymerase Inhibitor R7128 with Peg-IFN and Ribavirin: Interim Results of R7128 500MG BID for 28 Days, XP026661792, J Hepatol. 48, Jan. 1, 2008, S29, 66, Abstract only.

Pause et al., An NS3 Serine Protease Inhibitor Abrogates Replication of Subgenomic Hepatitits C Virus RNA, J Bio Chem., (Mar. 2003) 278(22): 20374-20380.

Šebestík et al., Acridin-9-yl Exchange: A Proposal for the Action of Some 9-Aminoacridine Drugs, Biopolymers (Peptide Science) (Aug. 2006) 84: 605-614.

Shibnev et al., 2-Methoxy-6,9-Dichloroacridine in Peptide Synthesis as a Fluorescent Label, Bioorganicheskaya Khimiuya (1984) 10(5): 610-617, Abstract Only.

Blatt et al., ITMN-191 Concentrations Achieved in the Liver of Animals Promote HCV Replicon Clearance in Vitro and this Effect is Enhanced by PEG-IFN Alpha-2a, XP022087916, J Hepatol., Apr. 1, 2007, 46: S219, Abstract #576, 1 page.

European Office Action dated Aug. 10, 2010 for European Application No. 08769417.0, filed May 9, 2008.

Georgian Office Action dated Jul. 23, 2010 for Georgia Application No. 11597/01, filed May 9, 2008.

Reddy et al., Antiviral Activity, Pharmacokinetics, Safety and Tolerability of R7128, a Novel Nucleoside HCV RNA Polymerase Inhibitor, Following Multiple, Ascending, Oral Doses in Patients with HCV Genotype 1 Infection who have Failed Prior Interferon Therapy, Hepatology 46(4): Suppl. S, 862A-863A, Oct. 2007, AASLD LB9, Abstract Only.

Syrian Office Action dated Feb. 6, 2010 for Syrian Application No. 8307, filed May 9, 2008.

PEPTIDE INHIBITORS OF HEPATITIS C VIRUS REPLICATION

CROSS-REFERENCE TO RELATED APPLICATIONS

This application claims the benefit of U.S. Provisional Application No. 60/917,300, filed May 10, 2007, and U.S. Provisional Application No. 61/023,041, filed Jan. 23, 2008, which are incorporated herein by reference in their entireties.

BACKGROUND OF THE INVENTION

1. Field of the Invention

The present invention relates to compounds, processes for their synthesis, compositions and methods for the treatment of hepatitis C virus (HCV) infection.

2. Description of the Related Art

Hepatitis C virus (HCV) infection is the most common chronic blood borne infection in the United States. Although the numbers of new infections have declined, the burden of chronic infection is substantial, with Centers for Disease Control estimates of 3.9 million (1.8%) infected persons in the United States. Chronic liver disease is the tenth leading cause of death among adults in the United States, and accounts for approximately 25,000 deaths annually, or approximately 1% of all deaths. Studies indicate that 40% of chronic liver disease is HCV-related, resulting in an estimated 8,000-10,000 deaths each year. HCV-associated end-stage liver disease is the most frequent indication for liver transplantation among adults.

Antiviral therapy of chronic hepatitis C has evolved rapidly over the last decade, with significant improvements seen in the efficacy of treatment. Nevertheless, even with combination therapy using pegylated IFN-α plus ribavirin, 40% to 50% of patients fail therapy, i.e., are nonresponders or relapsers. These patients currently have no effective therapeutic alternative. In particular, patients who have advanced fibrosis or cirrhosis on liver biopsy are at significant risk of developing complications of advanced liver disease, including ascites, jaundice, variceal bleeding, encephalopathy, and progressive liver failure, as well as a markedly increased risk of hepatocellular carcinoma.

The high prevalence of chronic HCV infection has important public health implications for the future burden of chronic liver disease in the United States. Data derived from the National Health and Nutrition Examination Survey (NHANES III) indicate that a large increase in the rate of new HCV infections occurred from the late 1960s to the early 1980s, particularly among persons between 20 to 40 years of age. It is estimated that the number of persons with long-standing HCV infection of 20 years or longer could more than quadruple from 1990 to 2015, from 750,000 to over 3 million. The proportional increase in persons infected for 30 or 40 years would be even greater. Since the risk of HCV-related chronic liver disease is related to the duration of infection, with the risk of cirrhosis progressively increasing for persons infected for longer than 20 years, this will result in a substantial increase in cirrhosis-related morbidity and mortality among patients infected between the years of 1965-1985.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins of the virus. In the case of HCV, the generation of mature non-structural proteins (NS2, NS3, NS4, NS4A, NS4B, NS5A, and NS5B) is effected by two viral proteases. The first viral protease cleaves at the NS2-NS3 junction of the polyprotein. The second viral protease is serine protease contained within the N-terminal region of NS3 (herein referred to as "NS3 protease"). NS3 protease mediates all of the subsequent cleavage events at sites downstream relative to the position of NS3 in the polyprotein (i.e., sites located between the C-terminus of NS3 and the C-terminus of the polyprotein). NS3 protease exhibits activity both in cis, at the NS3-NS4 cleavage site, and in trans, for the remaining NS4A-NS4B, NS4B-NS5A, and NS5A-NS5B sites. The NS4A protein is believed to serve multiple functions, acting as a cofactor for the NS3 protease and possibly assisting in the membrane localization of NS3 and other viral replicase components. Apparently, the formation of the complex between NS3 and NS4A is necessary for NS3-mediated processing events and enhances proteolytic efficiency at all sites recognized by NS3. The NS3 protease also exhibits nucleoside triphosphatase and RNA helicase activities. NS5B is an RNA-dependent RNA polymerase involved in the replication of HCV RNA.

SUMMARY OF THE INVENTION

The present embodiments provide compounds of the general Formula I:

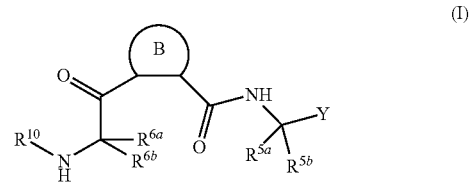

wherein:

B is a ring selected from the group consisting of

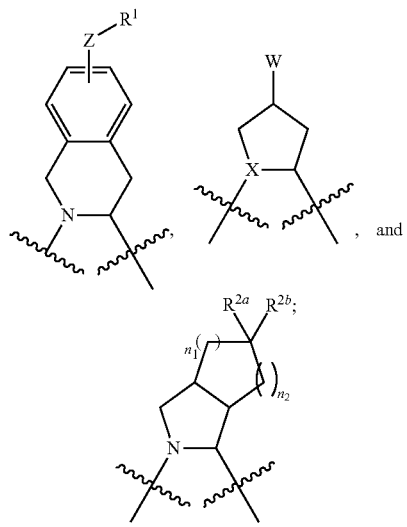

Z is a bond, O, CH$_2$, NH or S;
X is N or CH;
n$_1$ is 0, 1, 2 or 3;
n$_2$ is 0 or 1;

R¹ is H, $C_{1-7}$ alkyl, $C_{3-7}$ cycloalkyl, optionally substituted heterocycle, optionally substituted phenyl, benzyloxy, or substituted benzyl;

$R^{2a}$ and $R^{2b}$ are independently hydrogen or optionally substituted $C_{1-3}$ alkyl;

W is hydrogen, $OR^{3a}$, $O(CO)R^{3a}$, $O(CO)NR^{3a}R^{3b}$, $SR^{3a}$, $NH^{3a}$, $NH(CO)R^{3a}$, $CHR^{3a}R^{3b}$, $NH(CS)R^{3a}$, optionally substituted heterocycle, optionally substituted phenyl,

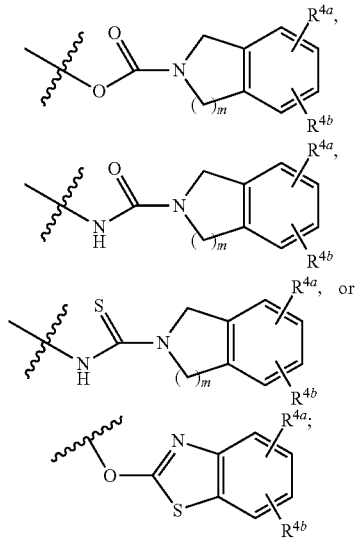

$R^{3a}$ and $R^{3b}$ are independently hydrogen, $C_{1-8}$ alkyl, $C_{3-7}$ cycloalkyl, $C_{4-10}$ cycloalkyl-alkyl, optionally substituted $C_{6-10}$ aryl, optionally substituted $C_{5-10}$ heteroaryl, optionally substituted $C_{7-10}$ aralkyl, optionally substituted $C_{6-12}$ heteroaryl-alkyl, optionally substituted heterocycle, optionally substituted phenyl, optionally substituted bicyclic ring system, or optionally substituted benzyl;

m is 1 or 2;

$R^{4a}$ and $R^{4b}$ are independently hydrogen, halogen, hydroxy, nitro, amino, cyano, $C(O)R^7$, $C(O)OR^7$, $C(O)NR^7R^8$, $C(S)NR^7R^8$, $S(O)R^7$, $S(O)_2R^7$, $C_{1-8}$ alkyl optionally substituted with up to 5 fluoro, $C_{1-8}$ alkoxy optionally substituted with up to 5 fluoro, $C_{1-8}$ alkylthio group optionally substituted with up to 5 fluoro, or $C_{1-8}$ alkylamino optionally substituted with up to 5 fluoro;

$R^7$ and $R^8$ are independently optionally substituted alkyl, optionally substituted aryl, or optionally substituted heteroaryl;

$R^{5a}$ and $R^{5b}$ are independently hydrogen, $C_{1-8}$ alkyl optionally substituted with up to 5 fluoro, $C_{1-8}$ cycloalkyl-alkyl, $C_{2-8}$ alkenyl, $C_{3-7}$ cycloalkyl optionally substituted with up to 5 fluoro, optionally substituted aryl, optionally substituted heteroaryl, optionally substituted $C_{7-10}$ aralkyl, or optionally substituted $C_{6-12}$ heteroaryl-alkyl; alternatively $R^{5a}$ and $R^{5b}$ are taken together to form a three to six-membered carbocyclic or heterocyclic ring system optionally substituted by 1-3 substituents selected from the group consisting of $C_{1-6}$ alkyl, $C_{2-6}$ alkenyl, and optionally substituted $C_{3-7}$ cycloalkyl;

$R^{6a}$ and $R^{6b}$ are independently hydrogen, $C_{1-8}$ alkyl optionally substituted with up to 5 fluoro, $C_{2-8}$ alkenyl, $C_{3-7}$ cycloalkyl optionally substituted with up to 5 fluoro, $C_{4-7}$ cycloalkyl-alkyl, optionally substituted aryl, optionally substituted heteroaryl, optionally substituted $C_{7-10}$ aralkyl, or optionally substituted $C_{6-12}$ heteroaryl-alkyl; alternatively $R^{6a}$ and $R^{6b}$ are taken together to form an optionally substituted three to six-membered carbocyclic or heterocyclic ring system;

$R^{8a}$ and $R^{8b}$ are independently hydrogen, optionally substituted alkyl, optionally substituted aryl, optionally substituted heteroaryl, or optionally substituted $C_{3-8}$ heterocyclic;

Y is selected from the group consisting of —C(O)NHS(O)$_2R^{9a}$, —C(O)NHS(O)$_2NR^{9a}R^{9b}$, C(O)NHS(O)$R^{9a}$, —C(O)NHS(O)NR$^{9a}R^{9b}$, —C(O)C(O)OH, —C(O)NHR$^{9a}$, —C(O)R$^{9a}$, —C(O)OR$^{9a}$, —C(O)NHC(O)R$^{9a}$, —C(O)OH, —C(O)C(O)NR$^{9a}R^{9b}$, and —C(O)NHOR$^{9a}$; and $R^{9a}$ and $R^{9b}$ are independently hydrogen, optionally substituted $C_{1-6}$ alkyl, optionally substituted $C_{3-7}$ cycloalkyl, optionally substituted $C_{4-9}$ cycloalkyl-alkyl, optionally substituted aryl, optionally substituted heteroaryl, $C_{7-9}$ aralkyl, or optionally substituted $C_{6-12}$ heteroaryl-alkyl, or $NR^{9a}R^{9b}$ forms a substituted or unsubstituted three-to six-membered heterocyclic ring;

$R^{10}$ is an aryl or heteroaryl optionally substituted by 1-3 substituents selected from the group consisting of halogen, hydroxy, nitro, amino, cyano, $C(O)R^{8a}$, $C(O)OR^{8a}$, $C(O)NR^{8a}R^{8b}$, $C(S)NR^{8a}R^{8b}$, $OR^{8a}$ and $S(O)_2R^{8a}$, $C_{3-8}$ heterocyclic, $C_{1-8}$ alkyl optionally substituted with up to 5 fluoro or cyano, $C_{1-8}$ alkoxy optionally substituted with up to 5 fluoro, $C_{1-8}$ alkylthio group optionally substituted with up to 5 fluoro, and $C_{1-8}$ alkylamino optionally substituted with up to 5 fluoro;

with the provisos that:
if B is

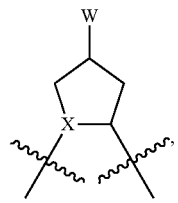

X is N, and W is $OR^{3a}$, then $R^{3a}$ is not optionally substituted quinazolinyl, optionally substituted quinolinyl, optionally substituted napthalenyl, or naphthalenylmethyl; and if B is

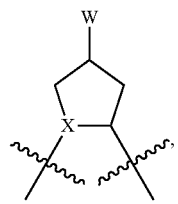

X is N, W is H, and Y is —C(O)OH then $R^7$ is not optionally substituted acridinyl or optionally substituted 1,3,5-triazinyl.

The present embodiments also provide compounds of the general Formula II:

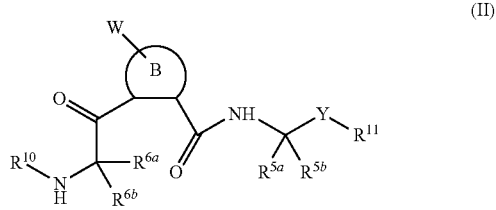

(II)

or a pharmaceutically acceptable salt, prodrug, or ester thereof, wherein:

$R^{5a}$ and $R^{5b}$ are independently hydrogen, $C_{1-8}$ alkyl optionally substituted with up to 5 fluoro, $C_{1-8}$ cycloalkyl-alkyl, $C_{2-8}$ alkenyl, $C_{3-7}$ cycloalkyl optionally substituted with up to 5 fluoro, optionally substituted aryl, optionally substituted heteroaryl, optionally substituted $C_{7-10}$ aralkyl, or optionally substituted $C_{6-12}$ heteroaryl-alkyl; alternatively $R^{5a}$ and $R^{5b}$ are taken together to form a three to six-membered carbocyclic or heterocyclic ring system optionally substituted by 1-3 substituents selected from the group consisting of $C_{1-6}$ alkyl, $C_{2-6}$ alkenyl, and optionally substituted $C_{3-7}$ cycloalkyl;

$R^{6a}$ and $R^{6b}$ are independently hydrogen, $C_{1-8}$ alkyl optionally substituted with up to 5 fluoro, $C_{2-8}$ alkenyl, $C_{3-7}$ cycloalkyl optionally substituted with up to 5 fluoro, $C_{4-7}$ cycloalkyl-alkyl, optionally substituted aryl, optionally substituted heteroaryl, optionally substituted $C_{7-10}$ aralkyl, or optionally substituted $C_{6-12}$ heteroaryl-alkyl; alternatively $R^{6a}$ and $R^{6b}$ are taken together to form an optionally substituted three to six-membered carbocyclic or heterocyclic ring system;

$R^{10}$ is an aryl or heteroaryl optionally substituted by 1-3 substituents selected from the group consisting of halogen, hydroxy, nitro, amino, cyano, $C(O)R^{8a}$, $C(O)OR^{8a}$, $C(O)NR^{8a}R^{8b}$, $C(S)NR^{8a}R^{8b}$, $OR^{8a}$, $S(O)_2R^{8a}$, $C_{3-8}$ heterocyclic $C_{1-8}$ alkoxy optionally substituted with up to 5 fluoro, $C_{1-8}$ alkylthio group optionally substituted with up to 5 fluoro, $C_{1-8}$ alkylamino optionally substituted with up to 5 fluoro, and $C_{1-8}$ alkyl optionally substituted with up to 5 fluoro or cyano;

$R^{8a}$ and $R^{8b}$ are independently hydrogen, optionally substituted alkyl, optionally substituted aryl, optionally substituted heteroaryl, or optionally substituted $C_{3-8}$ heterocyclic;

B is a ring system selected from the group consisting of:

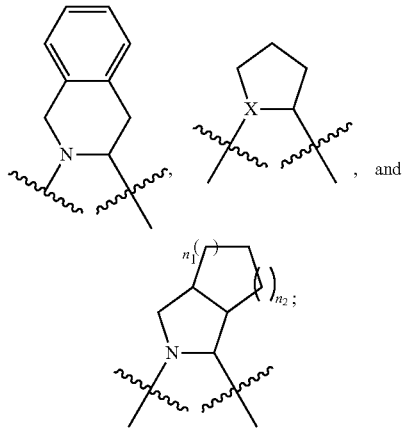

$n_1$ is 0, 1, 2 or 3;
$n_2$ is 0 or 1;
X is N or CH;
Y is a group configured to hydrogen bond to an NS3 protease His57 imidazole moiety and to hydrogen bond to a NS3 protease Gly137 nitrogen atom;
$R^{11}$ is a group configured to form a non-polar interaction with at least one NS3 protease S1' pocket moiety selected from the group consisting of Lys136, Gly137, Ser138, His57, Gly58, Gln41, Gly42, and Phe43; and
W is a group configured to form a non-polar interaction with at least one NS3 protease S2 pocket moiety selected from the group consisting of His57, Arg155, Val78, Asp79, and Gln80.

The present embodiments provide for a method of inhibiting NS3/NS4 protease activity comprising contacting a NS3/NS4 protease with a compound disclosed herein.

The present embodiments provide for a method of treating hepatitis by modulating NS3/NS4 protease comprising contacting a NS3/NS4 protease with a compound disclosed herein.

Preferred embodiments provide a pharmaceutical composition comprising: a) a preferred compound; and b) a pharmaceutically acceptable carrier.

Preferred embodiments provide a method of treating a hepatitis C virus infection in an individual, the method comprising administering to the individual an effective amount of a composition comprising a preferred compound.

Preferred embodiments provide a method of treating liver fibrosis in an individual, the method comprising administering to the individual an effective amount of a composition comprising a preferred compound.

Preferred embodiments provide a method of increasing liver function in an individual having a hepatitis C virus infection, the method comprising administering to the individual an effective amount of a composition comprising a preferred compound.

DETAILED DESCRIPTION OF THE EMBODIMENTS

Definitions

As used herein, the term "hepatic fibrosis," used interchangeably herein with "liver fibrosis," refers to the growth of scar tissue in the liver that can occur in the context of a chronic hepatitis infection.

The terms "individual," "host," "subject," and "patient" are used interchangeably herein, and refer to a mammal, including, but not limited to, primates, including simians and humans.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splancnic and portal hemodynamics; and the like.

The term "sustained viral response" (SVR; also referred to as a "sustained response" or a "durable response"), as used herein, refers to the response of an individual to a treatment regimen for HCV infection, in terms of serum HCV titer. Generally, a "sustained viral response" refers to no detectable HCV RNA (e.g., less than about 500, less than about 200, or less than about 100 genome copies per milliliter serum) found in the patient's serum for a period of at least about one month, at least about two months, at least about three months, at least about four months, at least about five months, or at least about six months following cessation of treatment.

"Treatment failure patients" as used herein generally refers to HCV-infected patients who failed to respond to previous therapy for HCV (referred to as "non-responders") or who initially responded to previous therapy, but in whom therapeutic response was not maintained (referred to as "relapsers"). The previous therapy generally can include treatment with IFN-α monotherapy or IFN-α combination therapy, where the combination therapy may include administration of IFN-α and an antiviral agent such as ribavirin.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, murines, simians, humans, mammalian farm animals, mammalian sport animals, and mammalian pets.

As used herein, the term "a Type I interferon receptor agonist" refers to any naturally occurring or non-naturally occurring ligand of human Type I interferon receptor, which binds to and causes signal transduction via the receptor. Type I interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

As used herein, the term "Type II interferon receptor agonist" refers to any naturally occurring or non-naturally occurring ligand of human Type II interferon receptor that binds to and causes signal transduction via the receptor. Type II interferon receptor agonists include native human interferon-γ, recombinant IFN-γ species, glycosylated IFN-γ species, pegylated IFN-γ species, modified or variant IFN-γ species, IFN-γ fusion proteins, antibody agonists specific for the receptor, non-peptide agonists, and the like.

As used herein, the term "a Type III interferon receptor agonist" refers to any naturally occurring or non-naturally occurring ligand of human IL-28 receptor α ("IL-28R"), the amino acid sequence of which is described by Sheppard, et al., infra., that binds to and causes signal transduction via the receptor.

As used herein, the term "interferon receptor agonist" refers to any Type I interferon receptor agonist, Type II interferon receptor agonist, or Type III interferon receptor agonist.

The term "dosing event" as used herein refers to administration of an antiviral agent to a patient in need thereof, which event may encompass one or more releases of an antiviral agent from a drug dispensing device. Thus, the term "dosing event," as used herein, includes, but is not limited to, installation of a continuous delivery device (e.g., a pump or other controlled release injectable system); and a single subcutaneous injection followed by installation of a continuous delivery system.

"Continuous delivery" as used herein (e.g., in the context of "continuous delivery of a substance to a tissue") is meant to refer to movement of drug to a delivery site, e.g., into a tissue in a fashion that provides for delivery of a desired amount of substance into the tissue over a selected period of time, where about the same quantity of drug is received by the patient each minute during the selected period of time.

"Controlled release" as used herein (e.g., in the context of "controlled drug release") is meant to encompass release of substance (e.g., a Type I or Type III interferon receptor agonist, e.g., IFN-α) at a selected or otherwise controllable rate, interval, and/or amount, which is not substantially influenced by the environment of use. "Controlled release" thus encompasses, but is not necessarily limited to, substantially continuous delivery, and patterned delivery (e.g., intermittent delivery over a period of time that is interrupted by regular or irregular time intervals).

"Patterned" or "temporal" as used in the context of drug delivery is meant delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug delivery device" is meant to encompass any device wherein the release (e.g., rate, timing of release) of a drug or other desired substance contained therein is controlled by or determined by the device itself and not substantially influenced by the environment of use, or releasing at a rate that is reproducible within the environment of use.

By "substantially continuous" as used in, for example, the context of "substantially continuous infusion" or "substantially continuous delivery" is meant to refer to delivery of drug in a manner that is substantially uninterrupted for a pre-selected period of drug delivery, where the quantity of drug received by the patient during any 8 hour interval in the pre-selected period never falls to zero. Furthermore, "substantially continuous" drug delivery can also encompass delivery of drug at a substantially constant, pre-selected rate or range of rates (e.g., amount of drug per unit time, or volume of drug formulation for a unit time) that is substantially uninterrupted for a pre-selected period of drug delivery.

By "substantially steady state" as used in the context of a biological parameter that may vary as a function of time, it is meant that the biological parameter exhibits a substantially constant value over a time course, such that the area under the curve defined by the value of the biological parameter as a function of time for any 8 hour period during the time course (AUC8 hr) is no more than about 20% above or about 20% below, and preferably no more than about 15% above or about 15% below, and more preferably no more than about 10% above or about 10% below, the average area under the curve of the biological parameter over an 8 hour period during the time course (AUC8 hr average). The AUC8 hr average is defined as the quotient (q) of the area under the curve of the biological parameter over the entirety of the time course (AUCtotal) divided by the number of 8 hour intervals in the time course (total/3 days), i.e., q=(AUCtotal)/(total/3 days). For example, in the context of a serum concentration of a drug, the serum concentration of the drug is maintained at a substantially steady state during a time course when the area under the curve of serum concentration of the drug over time for any 8 hour period during the time course (AUC8 hr) is no more than about 20% above or about 20% below the average area under the curve of serum concentration of the drug over an 8 hour period in the time course (AUC8 hr average), i.e., the AUC8 hr is no more than 20% above or 20% below the AUC8 hr average for the serum concentration of the drug over the time course.

The term "alkyl" used herein refers to a monovalent straight or branched chain radical of from one to twenty carbon atoms, including, but not limited to, methyl, ethyl, n-propyl, isopropyl, n-butyl, isobutyl, tert-butyl, n-hexyl, and the like.

The term "halo" used herein refers to fluoro, chloro, bromo, or iodo.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether fused or not fused. Examples of aryl groups include, but are not limited to, phenyl, naphthyl, biphenyl, phenanthrenyl, naphthacenyl, and the like.

The term "cycloalkyl" used herein refers to saturated aliphatic ring system radical having three to twenty carbon atoms including, but not limited to, cyclopropyl, cyclopentyl, cyclohexyl, cycloheptyl, and the like.

The term "cycloalkenyl" used herein refers to aliphatic ring system radical having three to twenty carbon atoms having at least one carbon-carbon double bond in the ring. Examples of cycloalkenyl groups include, but are not limited to, cyclopropenyl, cyclopentenyl, cyclohexenyl, cycloheptenyl, and the like.

The term "polycycloalkyl" used herein refers to saturated aliphatic ring system radical having at least two rings that are fused with or without bridgehead carbons. Examples of polycycloalkyl groups include, but are not limited to, bicyclo[4.4.0]decanyl, bicyclo[2.2.1]heptanyl, adamantyl, norbornyl, and the like.

The term "polycycloalkenyl" used herein refers to aliphatic ring system radical having at least two rings that are fused with or without bridgehead carbons in which at least one of the rings has a carbon-carbon double bond. Examples of polycycloalkenyl groups include, but are not limited to, norbornylenyl, 1,1'-bicyclopentenyl, and the like.

The term "polycyclic hydrocarbon" used herein refers to a ring system radical in which all of the ring members are carbon atoms. Polycyclic hydrocarbons can be aromatic or can contain less than the maximum number of non-cumulative double bonds. Examples of polycyclic hydrocarbon include, but are not limited to, naphthyl, dihydronaphthyl, indenyl, fluorenyl, and the like.

The term "heterocyclic" or "heterocyclyl" used herein refers to cyclic ring system radical having at least one non-aromatic ring in which one or more ring atoms are not carbon, namely heteroatom. Monocyclic "heterocyclic" or "heterocyclyl" moieties are nonaromatic. Bicyclic "heterocyclic" or "heterocyclyl" moieties include one nonaromatic ring wherein at least one heteroatom is present in the nonaromatic ring. Examples of heterocyclic groups include, but are not limited to, morpholinyl, tetrahydrofuranyl, dioxolanyl, pyrrolidinyl, oxazolyl, pyranyl, pyrrolyl, isoindoline and the like.

The term "heteroaryl" used herein refers to an aromatic ring system radical in which one or more ring atoms are not carbon, namely heteroatom, whether one ring or multiple fused rings. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridinyl, pyrrolyl, oxazolyl, indolyl, and the like.

The term "heteroatom" used herein refers to, for example, oxygen, sulfur and nitrogen.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "cycloalkylalkyl" used herein refers to one or more cycloalkyl groups appended to an alkyl radical. Examples of cycloalkylalkyl include, but are not limited to, cyclohexylmethyl, cyclohexylethyl, cyclopentylmethyl, cyclopentylethyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "heterocyclylalkyl" used herein refers to one or more heterocyclyl groups appended to an alkyl radical. Examples of heterocyclylalkyl include, but are not limited to, morpholinylmethyl, morpholinylethyl, morpholinylpropyl, tetrahydrofuranylmethyl, pyrrolidinylpropyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage. Examples of alkoxy groups include, but are not limited to, methoxy, ethoxy, propoxy, isopropoxy, butoxy, n-butoxy, sec-butoxy, t-butoxy and the like.

The term "arylthio" used herein refers to an aryl radical covalently bonded to the parent molecule through an —S— linkage.

The term "alkylamino" used herein refers to nitrogen radical with one or more alkyl groups attached thereto. Thus, monoalkylamino refers to nitrogen radical with one alkyl group attached thereto and dialkylamino refers to nitrogen radical with two alkyl groups attached thereto.

The term "cyanoamino" used herein refers to nitrogen radical with nitrile group attached thereto.

The term "carbamyl" used herein refers to RNHCOO—.

The term "keto" and "carbonyl" used herein refers to C=O.

The term "carboxy" used herein refers to —COOH.

The term "sulfamyl" used herein refers to —$SO_2NH_2$.

The term "sulfonyl" used herein refers to —$SO_2$—.

The term "sulfinyl" used herein refers to —SO—.

The term "thiocarbonyl" used herein refers to C=S.

The term "thiocarboxy" used herein refers to CSOH.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group. When substituted, the substituent group(s) is (are) one or more group(s) individually and independently selected from $C_1$-$C_6$ alkyl, $C_1$-$C_6$ alkenyl, $C_1$-$C_6$ alkynyl, $C_3$-$C_6$ cycloalkyl, $C_3$-$C_6$ heterocycloalkyl (e.g., tetrahydrofuryl), aryl, heteroaryl, halo (e.g., chloro, bromo, iodo and fluoro), cyano, hydroxy, $C_1$-$C_6$ alkoxy, aryloxy, sulfhydryl (mercapto), $C_1$-$C_6$ alkylthio, arylthio, mono-and di-($C_1$-$C_6$)alkyl amino, quaternary ammonium salts, amino($C_1$-$C_6$)alkoxy, hydroxy($C_1$-$C_6$)alkylamino, amino($C_1$-$C_6$)alkylthio, cyanoamino, nitro, carbamyl, keto (oxo), carbonyl, carboxy, glycolyl, glycyl, hydrazino, guanyl, sulfamyl, sulfonyl, sulfinyl, thiocarbonyl, thiocarboxy, and combinations thereof. The protecting groups that can form the protective derivatives of the above substituents are known to those of skill in the art and can be found in references such as Greene and Wuts *Protective Groups in Organic Synthesis*; John Wiley and Sons: New York, 1999. Wherever a substituent is described as "optionally substituted" that substituent can be substituted with the above substituents.

As used herein, "hydrogen bond" refers to an attractive force between an electronegative atom (such as oxygen, nitrogen, sulfur or halogen) and a hydrogen atom which is linked covalently to another electronegative atom (such as oxygen, nitrogen, sulfur or halogen). See, e.g., Stryer et. al. "Biochemistry", Fifth Edition 2002, Freeman & Co. N.Y. Typically, the hydrogen bond is between a hydrogen atom and two unshared electrons of another atom. A hydrogen bond between hydrogen and an electronegative atom not covalently bound to the hydrogen may be present when the hydrogen atom is at a distance of about 2.5 angstroms to about 3.8 angstroms from the not-covalently bound electronegative atom, and the angle formed by the three atoms (electronegative atom covalently bound to hydrogen, hydrogen, and electronegative atom not-covalently bound electronegative atom) deviates from 180 degrees by about 45 degrees or less. The distance between the hydrogen atom and the not-covalently bound electronegative atom may be referred to herein as the "hydrogen bond length," and the angle formed by the three atoms (electronegative atom covalently bound to hydrogen, hydrogen, and electronegative atom not-covalently bound electronegative atom) may be referred to herein as the "hydrogen bond angle." In some instances, stronger hydrogen bonds are formed when the hydrogen bond length is shorter; thus, in some instances, hydrogen bond lengths may range from about 2.7 angstroms to about 3.6 angstroms, or about 2.9 angstroms to about 3.4 angstroms. In some instances, stronger hydrogen bonds are formed when the hydrogen bond angle is closer to being linear; thus, in some instances, hydrogen bond angles may deviate from 180 degrees by about 25 degrees or less, or by about 10 degrees or less.

As used herein, an NS3 protease S1' pocket moiety refers to a moiety of the NS3 protease that interacts with the amino acid positioned one residue C-terminal to the cleavage site of the substrate polypeptide cleaved by NS3 protease (e.g., the NS3 protease moieties that interact with amino acid S in the polypeptide substrate DLEVVT-STWVLV). Exemplary moieties include, but are not limited to, atoms of the peptide backbone or side chains of amino acids Lys136, Gly137, Ser139, His57, Gly58, Gln41, Ser42, and Phe43, see Yao. et. al., Structure 1999, 7, 1353.

As used herein, an NS3 protease S2 pocket moiety refers to a moiety of the NS3 protease that interacts with the amino acid positioned two residues N-terminal to the cleavage site of the substrate polypeptide cleaved by NS3 protease (e.g., the NS3 protease moieties that interact with amino acid V in the polypeptide substrate DLEVVT-STWVLV). Exemplary moieties include, but are not limited to, atoms of the peptide backbone or side chains of amino acids His57, Arg155, Val78, Asp79, Gln80 and Asp81, see Yao. et. al., Structure 1999, 7, 1353.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis-and trans-isomeric forms of the compounds. Both cis-and trans-isomers, as well as the mixtures of cis-and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound. A prodrug is a compound that undergoes biotransformation (chemical conversion) before exhibiting its pharmacological effects. For example, a prodrug can thus be viewed as a drug containing specialized protective groups used in a transient manner to alter or to eliminate undesirable properties in the parent molecule. Thus, reference herein to a compound includes all of the aforementioned forms unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein can also be used in the practice or testing of the embodiments, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The present embodiments provide compounds of Formula I, as well as pharmaceutical compositions and formulations comprising any compound of Formula I. A subject compound is useful for treating HCV infection and other disorders, as discussed below.

The present embodiments provide compounds of Formula II, as well as pharmaceutical compositions and formulations comprising any compound of Formula II. A subject compound is useful for treating HCV infection and other disorders, as discussed below.

Compositions

The present embodiments provide compounds of the general Formula I:

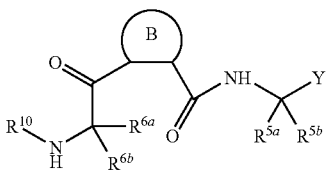

(I)

wherein:
B is a ring selected from the group consisting of

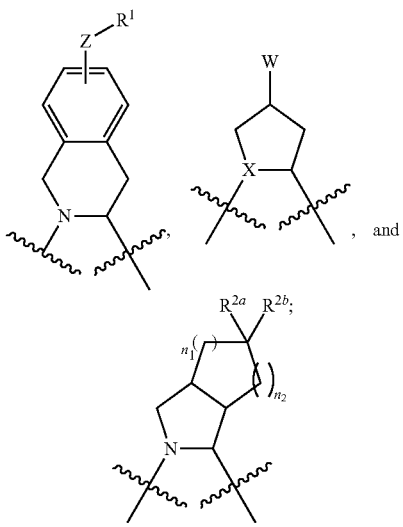

Z is a bond, O, $CH_2$, NH or S;
X is N or CH;
$n_1$ is 0, 1, 2 or 3;
$n_2$ is 0 or 1;
$R^1$ is H, $C_{1-7}$ alkyl, $C_{3-7}$ cycloalkyl, optionally substituted heterocycle, optionally substituted phenyl, benzyloxy, or substituted benzyl;
$R^{2a}$ and $R^{2b}$ are independently hydrogen or optionally substituted $C_{1-3}$ alkyl;
W is hydrogen, $OR^{3a}$, $O(CO)R^{3a}$, $O(CO)NR^{3a}R^{3b}$, $SR^{3a}$, $NHR^{3a}$, $NH(CO)R^{3a}$, $CHR^{3a}R^{3b}$, $NH(CS)R^{3a}$, optionally substituted heterocycle, optionally substituted phenyl,

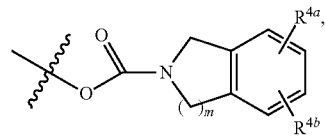

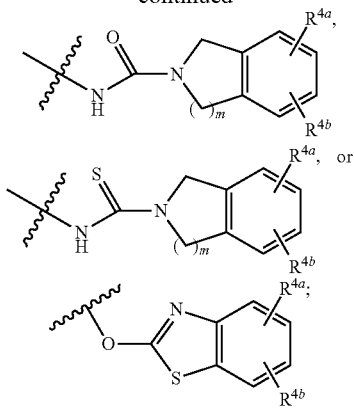

$R^{3a}$ and $R^{3b}$ are independently hydrogen, $C_{1-8}$ alkyl, $C_{3-7}$ cycloalkyl, $C_{4-10}$ cycloalkyl-alkyl, optionally substituted $C_{6-10}$ aryl, optionally substituted $C_{5-10}$ heteroaryl, optionally substituted $C_{7-10}$ aralkyl, optionally substituted $C_{6-12}$ heteroaryl-alkyl, optionally substituted heterocycle, optionally substituted phenyl, optionally substituted bicyclic ring system, or optionally substituted benzyl;
m is 1 or 2;
$R^{4a}$ and $R^{4b}$ are independently hydrogen, halogen, hydroxy, nitro, amino, cyano, $C(O)R^7$, $C(O)OR^7$, $C(O)NR^7R^8$, $C(S)NR^7R^8$, $S(O)R^7$, $S(O)_2R^7$, $C_{1-8}$ alkyl optionally substituted with up to 5 fluoro, $C_{1-8}$ alkoxy optionally substituted with up to 5 fluoro, $C_{1-8}$ alkylthio group optionally substituted with up to 5 fluoro, or $C_{1-8}$ alkylamino optionally substituted with up to 5 fluoro;
$R^7$ and $R^8$ are independently optionally substituted alkyl, optionally substituted aryl, or optionally substituted heteroaryl;
$R^{5a}$ and $R^{5b}$ are independently hydrogen, $C_{1-8}$ alkyl optionally substituted with up to 5 fluoro, $C_{1-8}$ cycloalkyl-alkyl, $C_{2-8}$ alkenyl, $C_{3-7}$ cycloalkyl optionally substituted with up to 5 fluoro, optionally substituted aryl, optionally substituted heteroaryl, optionally substituted $C_{7-10}$ aralkyl, or optionally substituted $C_{6-12}$ heteroaryl-alkyl; alternatively $R^{5a}$ and $R^{5b}$ are taken together to form a three to six-membered carbocyclic or heterocyclic ring system optionally substituted by 1-3 substituents selected from the group consisting of $C_{1-6}$ alkyl, $C_{2-6}$ alkenyl, and optionally substituted $C_{3-7}$ cycloalkyl;
$R^{6a}$ and $R^{6b}$ are independently hydrogen, $C_{1-8}$ alkyl optionally substituted with up to 5 fluoro, $C_{2-8}$ alkenyl, $C_{3-7}$ cycloalkyl optionally substituted with up to 5 fluoro, $C_{4-7}$ cycloalkyl-alkyl, optionally substituted aryl, optionally substituted heteroaryl, optionally substituted $C_{7-10}$ aralkyl, or optionally substituted $C_{6-12}$ heteroaryl-alkyl; alternatively $R^{6a}$ and $R^{6b}$ are taken together to form an optionally substituted three to six-membered carbocyclic or heterocyclic ring system;
$R^{8a}$ and $R^{8b}$ are independently hydrogen, optionally substituted alkyl, optionally substituted aryl, optionally substituted heteroaryl, or optionally substituted $C_{3-8}$ heterocyclic;
Y is selected from the group consisting of $-C(O)NHS(O)_2R^{9a}$, $-C(O)NHS(O)_2NR^{9a}R^{9b}$, $-C(O)NHS(O)R^{9a}$, $-C(O)NHS(O)NR^{9a}R^{9b}$, $-C(O)C(O)OH$, $-C(O)NHR^{9a}$, $-C(O)R^{9a}$, $-C(O)OR^{9a}$, $-C(O)NHC(O)R^{9a}$, $-C(O)OH$, $-C(O)C(O)NR^{9a}R^{9b}$, and $-C(O)NHOR^{9a}$; and
$R^{9a}$ and $R^{9b}$ are independently hydrogen, optionally substituted $C_{1-6}$ alkyl, optionally substituted $C_{3-7}$ cycloalkyl, optionally substituted $C_{4-9}$ cycloalkyl-alkyl, optionally substituted aryl, optionally substituted heteroaryl, $C_{7-9}$ aralkyl, or optionally substituted $C_{6-12}$ heteroaryl-alkyl, or $NR^{9a}R^{9b}$ forms a substituted or unsubstituted three-to six-membered heterocyclic ring;

$R^{10}$ is an aryl or heteroaryl optionally substituted by 1-3 substituents selected from the group consisting of halogen, hydroxy, nitro, amino, cyano, $C(O)R^{8a}$, $C(O)OR^{8a}$, $C(O)NR^{8a}R^{8b}$, $C(S)NR^{8a}R^{8b}$, $OR^{8a}$, $S(O)_2R^{8a}$, $C_{3-8}$ heterocyclic, $C_{1-8}$ alkoxy optionally substituted with up to 5 fluoro, $C_{1-8}$ alkylthio group optionally substituted with up to 5 fluoro, and $C_{1-8}$ alkylamino optionally substituted with up to 5 fluoro, and $C_{1-8}$ alkyl optionally substituted with up to 5 fluoro or cyano;

with the provisos that:
if B is

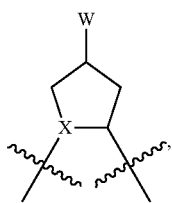

X is N, and W is $OR^{3a}$, then $R^{3a}$ is not optionally substituted quinazolinyl, optionally substituted quinolinyl, or optionally substituted napthalenyl, or naphthalenyl-methyl; and if B is

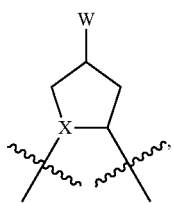

X is N, W is H, and Y is —C(O)OH then $R^7$ is not optionally substituted acridinyl or optionally substituted 1,3,5-triazinyl.

The present embodiments provide for a method of inhibiting NS3/NS4 protease activity comprising contacting a NS3/NS4 protease with a compound disclosed herein.

The present embodiments provide for a method of treating hepatitis by modulating NS3/NS4 protease comprising contacting a NS3/NS4 protease with a compound disclosed herein.

The embodiments provide compounds having the general Formula II:

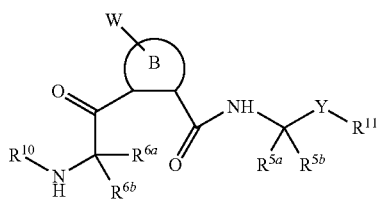

(II)

or a pharmaceutically acceptable salt, prodrug, or ester thereof, wherein:

$R^{5a}$ and $R^{5b}$ are independently hydrogen, $C_{1-8}$ alkyl optionally substituted with up to 5 fluoro, $C_{1-8}$ cycloalkyl-alkyl, $C_{2-8}$ alkenyl, $C_{3-7}$ cycloalkyl optionally substituted with up to 5 fluoro, optionally substituted aryl, optionally substituted heteroaryl, optionally substituted $C_{7-10}$ aralkyl, or optionally substituted $C_{6-12}$ heteroaryl-alkyl; alternatively $R^{5a}$ and $R^{5b}$ are taken together to form a three to six-membered carbocyclic or heterocyclic ring system optionally substituted by 1-3 substituents selected from the group consisting of $C_{1-6}$ alkyl, $C_{2-6}$ alkenyl, and optionally substituted $C_{3-7}$ cycloalkyl;

$R^{6a}$ and $R^{6b}$ are independently hydrogen, $C_{1-8}$ alkyl optionally substituted with up to 5 fluoro, $C_{2-8}$ alkenyl, $C_{3-7}$ cycloalkyl optionally substituted with up to 5 fluoro, $C_{4-7}$ cycloalkyl-alkyl, optionally substituted aryl, optionally substituted heteroaryl, optionally substituted $C_{7-10}$ aralkyl, or optionally substituted $C_{6-12}$ heteroaryl-alkyl; alternatively $R^{6a}$ and $R^{6b}$ are taken together to form an optionally substituted three to six-membered carbocyclic or heterocyclic ring system;

$R^{10}$ is an aryl or heteroaryl optionally substituted by 1-3 substituents selected from the group consisting of halogen, hydroxy, nitro, amino, cyano, $C(O)R^{8a}$, $C(O)OR^{8a}$, $C(O)NR^{8a}R^{8b}$, $C(S)NR^{8a}R^{8b}$, $OR^{8a}$, $S(O)_2R^{8a}$, $C_{3-8}$ heterocyclic, $C_{1-8}$ alkoxy optionally substituted with up to 5 fluoro, $C_{1-8}$ alkylthio group optionally substituted with up to 5 fluoro, $C_{1-8}$ alkylamino optionally substituted with up to 5 fluoro, and $C_{1-8}$ alkyl optionally substituted with up to 5 fluoro or cyano;

$R^{8a}$ and $R^{8b}$ are independently hydrogen, optionally substituted alkyl, optionally substituted aryl, optionally substituted heteroaryl, or optionally substituted $C_{3-8}$ heterocyclic;

B is a ring system selected from the group consisting of:

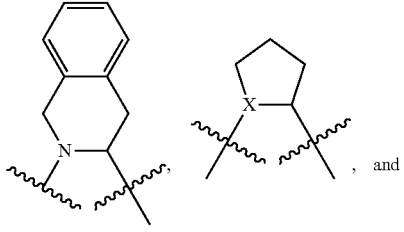, and

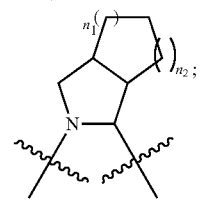;

$n_1$ is 0, 1, 2 or 3;
$n_2$ is 0 or 1;
X is N or CH;
Y is a group configured to hydrogen bond to an NS3 protease His57 imidazole moiety and to hydrogen bond to a NS3 protease Gly137 nitrogen atom;
$R^{11}$ is a group configured to form a non-polar interaction with at least one NS3 protease S1' pocket moiety selected from the group consisting of Lys136, Gly137, Ser138, His57, Gly58, Gln41, Gly42, and Phe43; and
W is a group configured to form a non-polar interaction with at least one NS3 protease S2 pocket moiety selected from the group consisting of His57, Arg155, Val78, Asp79, and Gln80.

Also provided herein are compounds containing moieties configured to interact with particular regions, particular amino acid residues, or particular atoms of NS3 protease. Some compounds provided herein contain one or more moieties configured to form a hydrogen bond with NS3 protease at a particular region, amino acid residue, or atom. Some compounds provided herein contain one or more moieties configured to form a non-polar interaction with NS3 protease at a particular region, amino acid residue, or atom. For example, the compound having the general Formula II may contain one or more moieties that form a hydrogen bond with a peptide backbone atom or side chain moiety located in the substrate binding pocket of NS3 protease. In another example, the compound having the general Formula II may contain one or more moieties that form non-polar interactions with peptide backbone or side chain atom or atoms located in the substrate binding pocket of NS3 protease.

As provided in the compound having the general formula II, Y may be configured to form a hydrogen bond with a peptide backbone atom or side chain moiety located in the substrate binding pocket of NS3 protease, including, but not limited to, NS3 protease His57 imidazole moiety and NS3 protease Gly137 nitrogen atom. In some instances, Y may be configured to form a hydrogen bond with both the NS3 protease His57 imidazole moiety and the NS3 protease Gly137 nitrogen atom.

The $R^{11}$ group of the compound having the general formula II may be configured to form a non-polar interaction with peptide backbone or side chain atom or atoms located in the substrate binding pocket of NS3 protease, including, but not limited to amino acid residues that form the NS3 protease S1' pocket. For example the $R^{11}$ group may form a non-polar interaction with at least one amino acid selected from Lys136, Gly137, Ser139, His 57, Gly58, Gln41, Ser42, and Phe43.

The W group of the compound having the general formula II may be configured to form a non-polar interaction with peptide backbone or side chain atom or atoms located in the substrate binding pocket of NS3 protease, including, but not limited to amino acid residues that form the NS3 protease S2 pocket. For example the W group may form a non-polar interaction with at least one amino acid selected from His57, Arg155, Val78, Asp79, Gln80 and Asp81. The W group also may be configured to form a hydrogen bond with peptide backbone or side chain atom or atoms located in the substrate binding pocket of NS3 protease, including, but not limited to amino acid residues that form the NS3 protease S2 pocket. For example the W group may form a hydrogen bond with at least one amino acid selected from His57, Arg155, Val78, Asp79, Gln80 and Asp81. In some instances, W may form both a non-polar interaction and a hydrogen bond with peptide backbone or side chain moieties or atoms located in the substrate binding pocket of NS3 protease, such amino acids selected from His57, Arg155, Val78, Asp79, Gln80 and Asp81. Such hydrogen bond and non-polar interactions may occur with the same amino acid residue or with different amino acid residues in the NS3 protease S2 pocket. In some embodiments, W may be selected from the group consisting of unsubstituted aryl, substituted aryl, unsubstituted heteroaryl, substituted heteroaryl, unsubstituted heterocyclic and substituted heterocyclic.

In some embodiments of the compound of formula (II), B and W taken together form a ring having the structure:

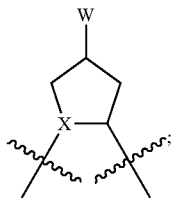

where W is

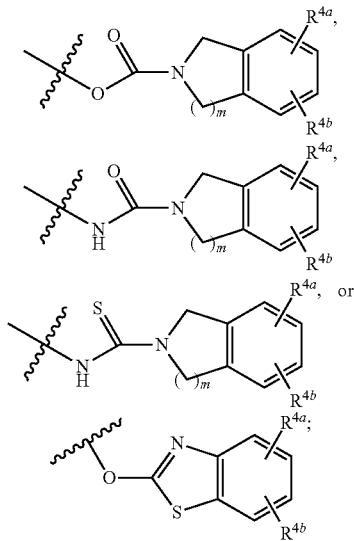

$R^{4a}$ and $R^{4b}$ are independently hydrogen, halogen, hydroxy, nitro, amino, cyano, $C(O)R^7$, $C(O)OR^7$, $C(O)NR^7R^8$, $C(S)NR^7R^8$, $S(O)R^7$, $S(O)_2R^7$, $C_{1-8}$ alkyl optionally substituted with up to 5 fluoro, $C_{1-8}$ alkoxy optionally substituted with up to 5 fluoro, $C_{1-8}$ alkylthio group optionally substituted with up to 5 fluoro, or $C_{1-8}$ alkylamino optionally substituted with up to 5 fluoro; and $R^7$ and $R^8$ are independently optionally substituted alkyl, optionally substituted aryl, or optionally substituted heteroaryl.

In some embodiments, several atoms of the compound of formula II may have a particular chirality.

Exemplary compounds of Formula I are set forth in Table 1 and compounds therein below.

Preferred embodiments provide a method of treating a hepatitis C virus infection in an individual, the method comprising administering to the individual an effective amount of a composition comprising a preferred compound.

Preferred embodiments provide a method of treating liver fibrosis in an individual, the method comprising administering to the individual an effective amount of a composition comprising a preferred compound.

Preferred embodiments provide a method of increasing liver function in an individual having a hepatitis C virus infection, the method comprising administering to the individual an effective amount of a composition comprising a preferred compound.

Preferred embodiments of compounds of Formula II provide compounds in which W has the structure:

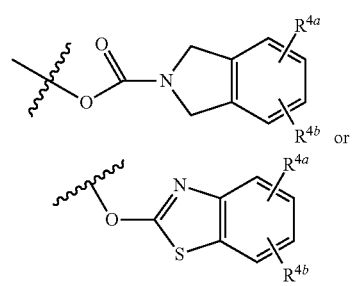

positioned to form a hydrogen bonding interaction with at least one NS3 protease S2 pocket moiety selected from the group consisting of His57, Arg155, Val78, Asp79, Gln80 and Asp81.

The present embodiments further provide compositions, including pharmaceutical compositions, comprising compounds of the general Formula I, including salts, esters, or other derivatives thereof. The present embodiments further provide compositions, including pharmaceutical compositions, comprising compounds of the general Formula II, including salts, esters, or other derivatives thereof. A subject pharmaceutical composition comprises a subject compound; and a pharmaceutically acceptable excipient. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In many embodiments, a subject compound inhibits the enzymatic activity of a hepatitis virus C(HCV) NS3 protease. Whether a subject compound inhibits HCV NS3 protease can be readily determined using any known method. Typical methods involve a determination of whether an HCV polyprotein or other polypeptide comprising an NS3 recognition site is cleaved by NS3 in the presence of the agent. In many embodiments, a subject compound inhibits NS3 enzymatic activity by at least about 10%, at least about 15%, at least about 20%, at least about 25%, at least about 30%, at least about 40%, at least about 50%, at least about 60%, at least about 70%, at least about 80%, or at least about 90%, or more, compared to the enzymatic activity of NS3 in the absence of the compound.

In many embodiments, a subject compound inhibits enzymatic activity of an HCV NS3 protease with an $IC_{50}$ of less than about 50 µM, e.g., a subject compound inhibits an HCV NS3 protease with an $IC_{50}$ of less than about 40 µM, less than about 25 µM, less than about 10 µM, less than about 1 µM, less than about 100 nM, less than about 80 nM, less than about 60 nM, less than about 50 nM, less than about 25 nM, less than about 10 nM, or less than about 1 nM, or less.

In many embodiments, a subject compound inhibits the enzymatic activity of a hepatitis virus C(HCV) NS3 helicase. Whether a subject compound inhibits HCV NS3 helicase can be readily determined using any known method. In many embodiments, a subject compound inhibits NS3 enzymatic activity by at least about 10%, at least about 15%, at least about 20%, at least about 25%, at least about 30%, at least about 40%, at least about 50%, at least about 60%, at least about 70%, at least about 80%, or at least about 90%, or more, compared to the enzymatic activity of NS3 in the absence of the compound.

In many embodiments, a subject compound inhibits HCV viral replication. For example, a subject compound inhibits HCV viral replication by at least about 10%, at least about 15%, at least about 20%, at least about 25%, at least about 30%, at least about 40%, at least about 50%, at least about 60%, at least about 70%, at least about 80%, or at least about 90%, or more, compared to HCV viral replication in the absence of the compound. Whether a subject compound inhibits HCV viral replication can be determined using methods known in the art, including an in vitro viral replication assay.

Treating a Hepatitis Virus Infection

The methods and compositions described herein are generally useful in treatment of an of HCV infection.

Whether a subject method is effective in treating an HCV infection can be determined by a reduction in viral load, a reduction in time to seroconversion (virus undetectable in patient serum), an increase in the rate of sustained viral response to therapy, a reduction of morbidity or mortality in clinical outcomes, or other indicator of disease response.

In general, an effective amount of a compound of Formula I or Formula II, and optionally one or more additional antiviral agents, is an amount that is effective to reduce viral load or achieve a sustained viral response to therapy.

Whether a subject method is effective in treating an HCV infection can be determined by measuring viral load, or by measuring a parameter associated with HCV infection, including, but not limited to, liver fibrosis, elevations in serum transaminase levels, and necroinflammatory activity in the liver. Indicators of liver fibrosis are discussed in detail below.

The method involves administering an effective amount of a compound of Formula I or Formula II, optionally in combination with an effective amount of one or more additional antiviral agents. In some embodiments, an effective amount of a compound of Formula I or Formula II, and optionally one or more additional antiviral agents, is an amount that is effective to reduce viral titers to undetectable levels, e.g., to about 1000 to about 5000, to about 500 to about 1000, or to about 100 to about 500 genome copies/mL serum. In some embodiments, an effective amount of a compound of Formula I or Formula II, and optionally one or more additional antiviral agents, is an amount that is effective to reduce viral load to lower than 100 genome copies/mL serum.

In some embodiments, an effective amount of a compound of Formula I or Formula II, and optionally one or more additional antiviral agents, is an amount that is effective to achieve a 1.5-log, a 2-log, a 2.5-log, a 3-log, a 3.5-log, a 4-log, a 4.5-log, or a 5-log reduction in viral titer in the serum of the individual.

In many embodiments, an effective amount of a compound of Formula I or Formula II, and optionally one or more additional antiviral agents, is an amount that is effective to achieve a sustained viral response, e.g., non-detectable or substantially non-detectable HCV RNA (e.g., less than about 500, less than about 400, less than about 200, or less than about 100 genome copies per milliliter serum) is found in the patient's serum for a period of at least about one month, at least about two months, at least about three months, at least about four months, at least about five months, or at least about six months following cessation of therapy.

As noted above, whether a subject method is effective in treating an HCV infection can be determined by measuring a parameter associated with HCV infection, such as liver fibrosis. Methods of determining the extent of liver fibrosis are discussed in detail below. In some embodiments, the level of a serum marker of liver fibrosis indicates the degree of liver fibrosis.

As one non-limiting example, levels of serum alanine aminotransferase (ALT) are measured, using standard assays. In general, an ALT level of less than about 45 international units is considered normal. In some embodiments, an effective amount of a compound of Formula I or Formula II, and optionally one or more additional antiviral agents, is an amount effective to reduce ALT levels to less than about 45 IU/mL serum.

A therapeutically effective amount of a compound of Formula I or Formula II, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Methods of measuring serum markers include immunological-based methods, e.g., enzyme-linked immunosorbent assays (ELISA), radioimmunoassays, and the like, using antibody specific for a given serum marker.

In many embodiments, an effective amount of a compound of Formula I or Formula II and an additional antiviral agent is a synergistic amount. As used herein, a "synergistic combination" or a "synergistic amount" of a compound of Formula I or Formula II and an additional antiviral agent is a combined dosage that is more effective in the therapeutic or prophylactic treatment of an HCV infection than the incremental improvement in treatment outcome that could be predicted or expected from a merely additive combination of (i) the therapeutic or prophylactic benefit of the compound of Formula I or Formula II when administered at that same dosage as a monotherapy and (ii) the therapeutic or prophylactic benefit of the additional antiviral agent when administered at the same dosage as a monotherapy.

In some embodiments, a selected amount of a compound of Formula I or Formula II and a selected amount of an additional antiviral agent are effective when used in combination therapy for a disease, but the selected amount of the compound of Formula I or Formula II and/or the selected amount of the additional antiviral agent is ineffective when used in monotherapy for the disease. Thus, the embodiments encompass (1) regimens in which a selected amount of the additional antiviral agent enhances the therapeutic benefit of a selected amount of the compound of Formula I or Formula II when used in combination therapy for a disease, where the selected amount of the additional antiviral agent provides no therapeutic benefit when used in monotherapy for the disease (2) regimens in which a selected amount of the compound of Formula I or Formula II enhances the therapeutic benefit of a selected amount of the additional antiviral agent when used in combination therapy for a disease, where the selected amount of the compound of Formula I or Formula II provides no therapeutic benefit when used in monotherapy for the disease and (3) regimens in which a selected amount of the compound of Formula I or Formula II and a selected amount of the additional antiviral agent provide a therapeutic benefit when used in combination therapy for a disease, where each of the selected amounts of the compound of Formula I or Formula II and the additional antiviral agent, respectively, provides no therapeutic benefit when used in monotherapy for the disease. As used herein, a "synergistically effective amount" of a compound of Formula I or Formula II and an additional antiviral agent, and its grammatical equivalents, shall be understood to include any regimen encompassed by any of (1)-(3) above.

Fibrosis

The embodiments provides methods for treating liver fibrosis (including forms of liver fibrosis resulting from, or associated with, HCV infection), generally involving administering a therapeutic amount of a compound of Formula I or Formula II, and optionally one or more additional antiviral agents. Effective amounts of compounds of Formula I or Formula II, with and without one or more additional antiviral agents, as well as dosing regimens, are as discussed below.

Whether treatment with a compound of Formula I or Formula II, and optionally one or more additional antiviral agents, is effective in reducing liver fibrosis is determined by any of a number of well-established techniques for measuring liver fibrosis and liver function. Liver fibrosis reduction is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of anti-fibrotic therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

In some embodiments, a therapeutically effective amount of a compound of Formula I or Formula II, and optionally one or more additional antiviral agents, is an amount that effects a change of one unit or more in the fibrosis stage based on pre-and post-therapy liver biopsies. In particular embodiments, a therapeutically effective amount of a compound of Formula I or Formula II, and optionally one or more additional antiviral agents, reduces liver fibrosis by at least one unit in the METAVIR, the Knodell, the Scheuer, the Ludwig, or the Ishak scoring system.

Secondary, or indirect, indices of liver function can also be used to evaluate the efficacy of treatment with a compound of Formula I or Formula II. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score.

An effective amount of a compound of Formula I or Formula II, and optionally one or more additional antiviral agents, is an amount that is effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

A therapeutically effective amount of a compound of Formula I or Formula II, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Quantitative tests of functional liver reserve can also be used to assess the efficacy of treatment with an interferon receptor agonist and pirfenidone (or a pirfenidone analog). These include: indocyanine green clearance (ICG), galactose elimination capacity (GEC), aminopyrine breath test (ABT), antipyrine clearance, monoethylglycine-xylidide (MEG-X) clearance, and caffeine clearance.

As used herein, a "complication associated with cirrhosis of the liver" refers to a disorder that is a sequellae of decompensated liver disease, i.e., or occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

A therapeutically effective amount of a compound of Formula I or Formula II, and optionally one or more additional antiviral agents, is an amount that is effective in reducing the incidence (e.g., the likelihood that an individual will develop) of a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with a compound of Formula I or Formula II, and optionally one or more additional antiviral agents, is effective in reducing the incidence of a disorder associated with cirrhosis of the liver can readily be determined by those skilled in the art.

Reduction in liver fibrosis increases liver function. Thus, the embodiments provide methods for increasing liver function, generally involving administering a therapeutically effective amount of a compound of Formula I or Formula II, and optionally one or more additional antiviral agents. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splancnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splancnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Those skilled in the art know the normal ranges for such serum proteins. The following are non-limiting examples. The normal level of alanine transaminase is about 45 IU per milliliter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

A therapeutically effective amount of a compound of Formula I or Formula II, and optionally one or more additional antiviral agents, is one that is effective to increase liver function by at least about 10%, at least about 20%, at least about 30%, at least about 40%, at least about 50%, at least about 60%, at least about 70%, at least about 80%, or more. For example, a therapeutically effective amount of a compound of Formula I or Formula II, and optionally one or more additional antiviral agents, is an amount effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. A therapeutically effective amount of a compound of Formula I or Formula II, and optionally one or more additional antiviral agents, is also an amount effective to increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

Dosages, Formulations and Routes of Administration

In the subject methods, the active agent(s) (e.g., compound of Formula I or Formula II, and optionally one or more additional antiviral agents) may be administered to the host using any convenient means capable of resulting in the desired therapeutic effect. Thus, the agent can be incorporated into a variety of formulations for therapeutic administration. More particularly, the agents of the embodiments can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations

The above-discussed active agent(s) can be formulated using well-known reagents and methods. Compositions are provided in formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, an agent is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

As such, administration of the agents can be achieved in various ways, including oral, buccal, rectal, parenteral, intraperitoneal, intradermal, subcutaneous, intramuscular, transdermal, intratracheal, etc., administration. In many embodiments, administration is by bolus injection, e.g., subcutaneous bolus injection, intramuscular bolus injection, and the like.

The pharmaceutical compositions of the embodiments can be administered orally, parenterally or via an implanted reservoir. Oral administration or administration by injection is preferred.

Subcutaneous administration of a pharmaceutical composition of the embodiments is accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a pharmaceutical composition of the embodiments to a patient through the port is referred to herein as "a subcutaneous injection port delivery system." In many embodiments, subcutaneous administration is achieved by bolus delivery by needle and syringe.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents can be made into suppositories by mixing with a variety of bases such as emulsifying bases or water-soluble bases. The compounds of the embodiments can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the embodiments calculated in an amount sufficient to produce the desired effect in association with a pharmaceutically acceptable diluent, carrier or vehicle. The specifications for the novel unit dosage forms of the embodiments depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Other Antiviral or Antifibrotic Agents

As discussed above, a subject method will in some embodiments be carried out by administering an NS3 inhibitor that is a compound of Formula I or Formula II, and optionally one or more additional antiviral agent(s).

In some embodiments, the method further includes administration of one or more interferon receptor agonist(s). Interferon receptor agonists are described herein.

In other embodiments, the method further includes administration of pirfenidone or a pirfenidone analog. Pirfenidone and pirfenidone analogs are described herein.

Additional antiviral agents that are suitable for use in combination therapy include, but are not limited to, nucleotide and nucleoside analogs. Non-limiting examples include azidothymidine (AZT) (zidovudine), and analogs and derivatives thereof, 2',3'-dideoxyinosine (DDI) (didanosine), and analogs and derivatives thereof, 2',3'-dideoxycytidine (DDC) (dideoxycytidine), and analogs and derivatives thereof, 2',3'-didehydro-2',3'-dideoxythymidine (D4T) (stavudine), and analogs and derivatives thereof, combivir; abacavir; adefovir dipoxil; cidofovir; ribavirin; ribavirin analogs; and the like.

In some embodiments, the method further includes administration of ribavirin. Ribavirin, 1-β-D-ribofuranosyl-1H-1,2, 4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. Some embodiments also involve use of derivatives of ribavirin (see, e.g. U.S. Pat. No. 6,277,830). The ribavirin may be administered orally in capsule or tablet form, or in the same or different administration form and in the same or different route as the NS-3 inhibitor compound. Of course, other types of administration of both medicaments, as they become available are contemplated, such as by nasal spray, transdermally, intravenously, by suppository, by sustained release dosage form, etc. Any form of administration will work so long as the proper dosages are delivered without destroying the active ingredient.

In some embodiments, the method further includes administration of ritonavir. Ritonavir, 10-hydroxy-2-methyl-5-(1-methylethyl)-1-[2-(1-methylethyl)-4-thiazolyl]-3,6-dioxo-8,11-bis(phenylmethyl)-2,4,7,12-tetraazamidecan-13-oic acid, 5-thiazolylmethyl ester[5S-(5R*,8R*,10R*,11R*)], available from Abbott Laboratories, is an inhibitor of the protease of the human immunodeficiency virus and also of the cytochrome P450 3A and P450 2D6 liver enzymes frequently involved in hepatic metabolism of therapeutic molecules in man. Because of its strong inhibitory effect on cytochrome P450 3A and the inhibitory effect on cytochrome P450 2D6, ritonavir at doses below the normal therapeutic dosage may be combined with other protease inhibitors to achieve therapeutic levels of the second protease inhibitor while reducing the number of dosage units required, the dosing frequency, or both.

Coadministration of low-dose ritonavir may also be used to compensate for drug interactions that tend to decrease levels of a protease inhibitor metabolized by CYP3A. Its structure, synthesis, manufacture and formulation are described in U.S. Pat. Nos. 5,541,206 5,635,523 5,648,497 5,846,987 and 6,232,333. The ritonavir may be administered orally in capsule or tablet or oral solution form, or in the same or different administration form and in the same or different route as the NS-3 inhibitor compound. Of course, other types of administration of both medicaments, as they become available are contemplated, such as by nasal spray, transdermally, intravenously, by suppository, by sustained release dosage form, etc. Any form of administration will work so long as the proper dosages are delivered without destroying the active ingredient.

In some embodiments, an additional antiviral agent is administered during the entire course of NS3 inhibitor compound treatment. In other embodiments, an additional antiviral agent is administered for a period of time that is overlapping with that of the NS3 inhibitor compound treatment, e.g., the additional antiviral agent treatment can begin before the NS3 inhibitor compound treatment begins and end before the NS3 inhibitor compound treatment ends; the additional antiviral agent treatment can begin after the NS3 inhibitor compound treatment begins and end after the NS3 inhibitor compound treatment ends; the additional antiviral agent treatment can begin after the NS3 inhibitor compound treatment begins and end before the NS3 inhibitor compound treatment ends; or the additional antiviral agent treatment can begin before the NS3 inhibitor compound treatment begins and end after the NS3 inhibitor compound treatment ends.

Methods of Treatment

Monotherapies

The NS3 inhibitor compounds described herein may be used in acute or chronic therapy for HCV disease. In many embodiments, the NS3 inhibitor compound is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The NS3 inhibitor compound can be administered 5 times per day, 4 times per day, tid, bid, qd, qod, biw, tiw, qw, qow, three times per month, or once monthly. In other embodiments, the NS3 inhibitor compound is administered as a continuous infusion.

In many embodiments, an NS3 inhibitor compound of the embodiments is administered orally.

In connection with the above-described methods for the treatment of HCV disease in a patient, an NS3 inhibitor compound as described herein may be administered to the patient at a dosage from about 0.01 mg to about 100 mg/kg patient bodyweight per day, in 1 to 5 divided doses per day. In some embodiments, the NS3 inhibitor compound is administered at a dosage of about 0.5 mg to about 75 mg/kg patient bodyweight per day, in 1 to 5 divided doses per day.

The amount of active ingredient that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific NS3 inhibitor compound, the severity of the symptoms and the susceptibility of the subject to side effects. Preferred dosages for a given NS3 inhibitor compound are readily determinable by those of skill in the art by a variety of means. A preferred means is to measure the physiological potency of a given interferon receptor agonist.

In many embodiments, multiple doses of NS3 inhibitor compound are administered. For example, an NS3 inhibitor compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapies with Ribavirin

In some embodiments, the methods provide for combination therapy comprising administering an NS3 inhibitor compound as described above, and an effective amount of ribavirin. Ribavirin can be administered in dosages of about 400 mg, about 800 mg, about 1000 mg, or about 1200 mg per day.

One embodiment provides any of the above-described methods modified to include co-administering to the patient a therapeutically effective amount of ribavirin for the duration of the desired course of NS3 inhibitor compound treatment.

Another embodiment provides any of the above-described methods modified to include co-administering to the patient about 800 mg to about 1200 mg ribavirin orally per day for the duration of the desired course of NS3 inhibitor compound treatment. In another embodiment, any of the above-described methods may be modified to include co-administering to the patient (a) 1000 mg ribavirin orally per day if the patient has a body weight less than 75 kg or (b) 1200 mg ribavirin orally per day if the patient has a body weight greater than or equal to 75 kg, where the daily dosage of ribavirin is optionally divided into to 2 doses for the duration of the desired course of NS3 inhibitor compound treatment.

Combination Therapies with Levovirin

In some embodiments, the methods provide for combination therapy comprising administering an NS3 inhibitor compound as described above, and an effective amount of levovirin. Levovirin is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, levovirin is administered orally in dosages of about 400, about 800, about 1000, or about 1200 mg per day for the desired course of NS3 inhibitor compound treatment.

Combination Therapies with Viramidine

In some embodiments, the methods provide for combination therapy comprising administering an NS3 inhibitor compound as described above, and an effective amount of viramidine. Viramidine is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, viramidine is administered orally in dosages of about 800, or about 1600 mg per day for the desired course of NS3 inhibitor compound treatment.

Combination Therapies with Ritonavir

In some embodiments, the methods provide for combination therapy comprising administering an NS3 inhibitor compound as described above, and an effective amount of ritonavir. Ritonavir is generally administered in an amount ranging from about 50 mg to about 100 mg, from about 100 mg to about 200 mg, from about 200 mg to about 300 mg, from about 300 mg to about 400 mg, from about 400 mg to about 500 mg, or from about 500 mg to about 600 mg, twice per day. In some embodiments, ritonavir is administered orally in dosages of about 300 mg, or about 400 mg, or about 600 mg twice per day for the desired course of NS3 inhibitor compound treatment.

Combination Therapies with Alpha-Glucosidase Inhibitors

Suitable α-glucosidase inhibitors include any of the above-described imino-sugars, including long-alkyl chain derivatives of imino sugars as disclosed in U.S. Patent Publication No. 2004/0110795; inhibitors of endoplasmic reticulum-associated α-glucosidases; inhibitors of membrane bound α-glucosidase; miglitol (Glyset®), and active derivatives, and analogs thereof, and acarbose (Precose®), and active derivatives, and analogs thereof.

In many embodiments, the methods provide for combination therapy comprising administering an NS3 inhibitor compound as described above, and an effective amount of an α-glucosidase inhibitor administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

An α-glucosidase inhibitor can be administered 5 times per day, 4 times per day, tid (three times daily), bid, qd, qod, biw, tiw, qw, qow, three times per month, or once monthly. In other embodiments, an α-glucosidase inhibitor is administered as a continuous infusion.

In many embodiments, an α-glucosidase inhibitor is administered orally.

In connection with the above-described methods for the treatment of a flavivirus infection, treatment of HCV infection, and treatment of liver fibrosis that occurs as a result of an HCV infection, the methods provide for combination therapy comprising administering an NS3 inhibitor compound as described above, and an effective amount of α-glucosidase inhibitor administered to the patient at a dosage of from about 10 mg per day to about 600 mg per day in divided doses, e.g., from about 10 mg per day to about 30 mg per day, from about 30 mg per day to about 60 mg per day, from about 60 mg per day to about 75 mg per day, from about 75 mg per day to about 90 mg per day, from about 90 mg per day to about 120 mg per day, from about 120 mg per day to about 150 mg per day, from about 150 mg per day to about 180 mg per day, from about 180 mg per day to about 210 mg per day, from about 210 mg per day to about 240 mg per day, from about 240 mg per day to about 270 mg per day, from about 270 mg per day to about 300 mg per day, from about 300 mg per day to about 360 mg per day, from about 360 mg per day to about 420 mg per day, from about 420 mg per day to about 480 mg per day, or from about 480 mg to about 600 mg per day.

In some embodiments, the methods provide for combination therapy comprising administering an NS3 inhibitor compound as described above, and an effective amount of α-glucosidase inhibitor administered in a dosage of about 10 mg three times daily. In some embodiments, an α-glucosidase inhibitor is administered in a dosage of about 15 mg three times daily. In some embodiments, an α-glucosidase inhibitor is administered in a dosage of about 20 mg three times daily. In some embodiments, an α-glucosidase inhibitor is administered in a dosage of about 25 mg three times daily. In some embodiments, an α-glucosidase inhibitor is administered in a dosage of about 30 mg three times daily. In some embodiments, an α-glucosidase inhibitor is administered in a dosage of about 40 mg three times daily. In some embodiments, an α-glucosidase inhibitor is administered in a dosage of about 50 mg three times daily. In some embodiments, an α-glucosidase inhibitor is administered in a dosage of about 100 mg three times daily. In some embodiments, an α-glucosidase inhibitor is administered in a dosage of about 75 mg per day to about 150 mg per day in two or three divided doses, where the individual weighs 60 kg or less. In some embodiments, an α-glucosidase inhibitor is administered in a dosage of about 75 mg per day to about 300 mg per day in two or three divided doses, where the individual weighs 60 kg or more.

The amount of active ingredient (e.g., α-glucosidase inhibitor) that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific α-glucosidase inhibitor, the severity of the symptoms and the susceptibility of the subject to side effects. Preferred dosages for a given α-glucosidase inhibitor are readily determinable by those of skill in the art by a variety of means. A typical means is to measure the physiological potency of a given active agent.

In many embodiments, multiple doses of an α-glucosidase inhibitor are administered. For example, the methods provide for combination therapy comprising administering an NS3 inhibitor compound as described above, and an effective amount of α-glucosidase inhibitor administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapies with Thymosin-α

In some embodiments, the methods provide for combination therapy comprising administering an NS3 inhibitor compound as described above, and an effective amount of thymosin-α. Thymosin-α (Zadaxin™) is generally administered by subcutaneous injection. Thymosin-α can be administered tid, bid, qd, qod, biw, tiw, qw, qow, three times per month, once monthly, substantially continuously, or continuously for the desired course of NS3 inhibitor compound treatment. In many embodiments, thymosin-α is administered twice per week for the desired course of NS3 inhibitor compound treatment. Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

Thymosin-α can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In one embodiment, thymosin-α is administered for the desired course of NS3 inhibitor compound treatment.

Combination Therapies with Interferon(s)

In many embodiments, the methods provide for combination therapy comprising administering an NS3 inhibitor compound as described above, and an effective amount of an interferon receptor agonist. In some embodiments, a compound of Formula I or Formula II and a Type I or III interferon receptor agonist are co-administered in the treatment methods described herein. Type I interferon receptor agonists suitable for use herein include any interferon-α (IFN-α). In certain embodiments, the interferon-α is a PEGylated interferon-α. In certain other embodiments, the interferon-α is a consensus interferon, such as INFERGEN® interferon alfacon-1. In still other embodiments, the interferon-α is a monoPEG (30 kD, linear)-ylated consensus interferon.

Effective dosages of an IFN-α range from about 3 μg to about 27 μg, from about 3 MU to about 10 MU, from about 90 μg to about 180 μg, or from about 18 μg to about 90 μg. Effective dosages of Infergen® consensus IFN-α include about 3 μg, about 6 μg, about 9 μg, about 12 μg, about 15 μg, about 18 μg, about 21 μg, about 24 μg, about 27 μg, or about 30 μg, of drug per dose. Effective dosages of IFN-α2a and IFN-α2b range from 3 million Units (MU) to 10 MU per dose. Effective dosages of PEGASYS®PEGylated IFN-α2a contain an amount of about 90 μg to 270 μg, or about 180 μg, of drug per dose. Effective dosages of PEG-INTRON®PEGylated IFN-α2b contain an amount of about 0.5 μg to 3.0 μg of drug per kg of body weight per dose. Effective dosages of PEGylated consensus interferon (PEG-CIFN) contain an amount of about 18 μg to about 90 μg, or from about 27 μg to about 60 μg, or about 45 μg, of CIFN amino acid weight per dose of PEG-CIFN. Effective dosages of monoPEG (30 kD, linear)-ylated CIFN contain an amount of about 45 μg to about 270 μg, or about 60 μg to about 180 μg, or about 90 μg to about 120 μg, of drug per dose. IFN-α can be administered daily, every other day, once a week, three times a week, every other week, three times per month, once monthly, substantially continuously or continuously.

In many embodiments, the Type I or Type III interferon receptor agonist and/or the Type II interferon receptor agonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. Dosage regimens can include tid, bid, qd, qod, biw, tiw, qw, qow, three times per month, or monthly administrations. Some embodiments provide any of the above-described methods in which the desired dosage of IFN-α is administered subcutaneously to the patient by bolus delivery qd, qod, tiw, biw, qw, qow, three times per month, or monthly, or is administered subcutaneously to the patient per day by substantially continuous or continuous delivery, for the desired treatment duration. In other embodiments, any of the above-described methods may be practiced in which the desired dosage of PEGylated IFN-α (PEG-IFN-α) is administered subcutaneously to the patient by bolus delivery qw, qow, three times per month, or monthly for the desired treatment duration.

In other embodiments, an NS3 inhibitor compound and a Type II interferon receptor agonist are co-administered in the treatment methods of the embodiments. Type II interferon receptor agonists suitable for use herein include any interferon-γ (IFN-γ).

Effective dosages of IFN-γ can range from about 0.5 μg/m$^2$ to about 500 μg/m$^2$, usually from about 1.5 μg/m$^2$ to 200 μg/m$^2$, depending on the size of the patient. This activity is based on $10^6$ international units (U) per 50 μg of protein. IFN-γ can be administered daily, every other day, three times a week, or substantially continuously or continuously.

In specific embodiments of interest, IFN-γ is administered to an individual in a unit dosage form of from about 25 μg to about 500 μg, from about 50 μg to about 400 μg, or from about 100 μg to about 300 μg. In particular embodiments of interest, the dose is about 200 μg IFN-γ. In many embodiments of interest, IFN-γ1b is administered.

Where the dosage is 200 μg IFN-γ per dose, the amount of IFN-γ per body weight (assuming a range of body weights of from about 45 kg to about 135 kg) is in the range of from about 4.4 μg IFN-γ per kg body weight to about 1.48 μg IFN-γ per kg body weight.

The body surface area of subject individuals generally ranges from about 1.33 m$^2$ to about 2.50 m$^2$. Thus, in many embodiments, an IFN-γ dosage ranges from about 150 μg/m$^2$ to about 20 μg/m$^2$. For example, an IFN-γ dosage ranges from about 20 μg/m$^2$ to about 30 μg/m$^2$, from about 30 μg/m$^2$ to about 40 μg/m$^2$, from about 40 μg/m$^2$ to about 50 μg/m$^2$, from about 50 μg/m$^2$ to about 60 μg/m$^2$, from about 60 μg/m$^2$ to about 70 μg/m$^2$, from about 70 μg/m$^2$ to about 80 μg/m$^2$, from about 80 μg/m$^2$ to about 90 μg/m$^2$, from about 90 μg/m$^2$ to about 100 μg/m$^2$, from about 100 μg/m$^2$ to about 110 μg/m$^2$, from about 110 μg/m$^2$ to about 120 μg/m$^2$, from about 120 μg/m$^2$ to about 130 μg/m$^2$, from about 130 μg/m$^2$ to about 140 μg/m$^2$, or from about 140 μg/m$^2$ to about 150 μg/m$^2$. In some embodiments, the dosage groups range from about 25 μg/m$^2$ to about 100 μg/m$^2$. In other embodiments, the dosage groups range from about 25 μg/m$^2$ to about 50 μg/m$^2$.

In some embodiments, a Type I or a Type III interferon receptor agonist is administered in a first dosing regimen, followed by a second dosing regimen. The first dosing regimen of Type I or a Type III interferon receptor agonist (also referred to as "the induction regimen") generally involves administration of a higher dosage of the Type I or Type III interferon receptor agonist. For example, in the case of Infergen® consensus IFN-α (CIFN), the first dosing regimen comprises administering CIFN at about 9 μg, about 15 μg, about 18 μg, or about 27 μg. The first dosing regimen can encompass a single dosing event, or at least two or more dosing events. The first dosing regimen of the Type I or Type III interferon receptor agonist can be administered daily, every other day, three times a week, every other week, three times per month, once monthly, substantially continuously or continuously.

The first dosing regimen of the Type I or Type III interferon receptor agonist is administered for a first period of time, which time period can be at least about 4 weeks, at least about 8 weeks, or at least about 12 weeks.

The second dosing regimen of the Type I or Type III interferon receptor agonist (also referred to as "the maintenance dose") generally involves administration of a lower amount of the Type I or Type III interferon receptor agonist. For example, in the case of CIFN, the second dosing regimen comprises administering CIFN at a dose of at least about 3 μg, at least about 9 μg, at least about 15 μg, or at least about 18 μg. The second dosing regimen can encompass a single dosing event, or at least two or more dosing events.

The second dosing regimen of the Type I or Type III interferon receptor agonist can be administered daily, every other day, three times a week, every other week, three times per month, once monthly, substantially continuously or continuously.

In some embodiments, where an "induction"/"maintenance" dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase.

In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, the Type II interferon receptor agonist treatment is discontinued once Type I or a Type III interferon receptor agonist treatment begins.

In other embodiments, the Type I or Type III interferon receptor agonist is administered in single dosing regimen. For example, in the case of CIFN, the dose of CIFN is generally in a range of from about 3 μg to about 15 μg, or from about 9 μg to about 15 μg. The dose of Type I or a Type III interferon receptor agonist is generally administered daily, every other day, three times a week, every other week, three times per month, once monthly, or substantially continuously. The dose of the Type I or Type III interferon receptor agonist is administered for a period of time, which period can be, for example, from at least about 24 weeks to at least about 48 weeks, or longer.

In some embodiments, where a single dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase. In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with the Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, Type II interferon receptor agonist treatment is discontinued once Type I or a Type III interferon receptor agonist treatment begins.

In additional embodiments, an NS3 inhibitor compound, a Type I or III interferon receptor agonist, and a Type II interferon receptor agonist are co-administered for the desired duration of treatment in the methods described herein. In some embodiments, an NS3 inhibitor compound, an interferon-α, and an interferon-γ are co-administered for the desired duration of treatment in the methods described herein.

In some embodiments, the invention provides methods using an amount of a Type I or Type III interferon receptor agonist, a Type II interferon receptor agonist, and an NS3 inhibitor compound, effective for the treatment of HCV infection in a patient. Some embodiments provide methods using an effective amount of an IFN-α, IFN-γ, and an NS3 inhibitor compound in the treatment of HCV infection in a patient. One embodiment provides a method using an effective amount of a consensus IFN-α, IFN-γ and an NS3 inhibitor compound in the treatment of HCV infection in a patient.

In general, an effective amount of a consensus interferon (CIFN) and IFN-γ suitable for use in the methods of the embodiments is provided by a dosage ratio of 1 μg CIFN:10 μg IFN-γ, where both CIFN and IFN-γ are unPEGylated and unglycosylated species.

In one embodiment, the invention provides any of the above-described methods modified to use an effective amount of INFERGEN®consensus IFN-α and IFN-γ in the treatment of HCV infection in a patient comprising administering to the patient a dosage of INFERGEN® containing an amount of about 1 μg to about 30 μg, of drug per dose of INFERGEN®, subcutaneously qd, qod, tiw, biw, qw, qow, three times per month, once monthly, or per day substantially continuously or continuously, in combination with a dosage of IFN-γ containing an amount of about 10 μg to about 300 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN®consensus IFN-α and IFN-γ in the treatment of virus infection in a patient comprising administering to the patient a dosage of INFERGEN® containing an amount of about 1 μg to about 9 μg, of drug per dose of INFERGEN®, subcutaneously qd, qod, tiw, biw, qw, qow, three times per month, once monthly, or per day substantially continuously or continuously, in combination with a dosage of IFN-γ containing an amount of about 10 μg to about 100 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN®consensus IFN-α and IFN-γ in the treatment of virus infection in a patient comprising administering to the patient a dosage of INFERGEN® containing an amount of about 1 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 10 μg to about 50 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN®consensus IFN-α and IFN-γ in the treatment of a virus infection in a patient comprising administering to the patient a dosage of INFERGEN® containing an amount of about 9 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 90 μg to about 100 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN®consensus IFN-α and IFN-γ in the treatment of a virus infection in a patient comprising administering to the patient a dosage of INFERGEN® containing an amount of about 30 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 200 μg to about 300 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of PEGylated consensus IFN-α and IFN-γ in the treatment of a virus infection in a patient comprising administering to the patient a dosage of PEGylated consensus IFN-α (PEG-CIFN) containing an amount of about 4 μg to about 60 μg of CIFN amino acid weight per dose of PEG-CIFN, subcutaneously qw, qow, three times per month, or monthly, in combination with a total weekly dosage of IFN-γ containing an amount of about 30 μg to about 1,000 μg of drug per week in divided doses administered subcutaneously qd, qod, tiw, biw, or administered substantially continuously or continuously, for the desired duration of treatment with an NS3 inhibitor compound.

Another embodiment provides any of the above-described methods modified to use an effective amount of PEGylated consensus IFN-α and IFN-γ in the treatment of a virus infection in a patient comprising administering to the patient a dosage of PEGylated consensus IFN-α (PEG-CIFN) containing an amount of about 18 μg to about 24 μg of CIFN amino acid weight per dose of PEG-CIFN, subcutaneously qw, qow, three times per month, or monthly, in combination with a total weekly dosage of IFN-γ containing an amount of about 100 μg to about 300 μg of drug per week in divided doses administered subcutaneously qd, qod, tiw, biw, or substantially continuously or continuously, for the desired duration of treatment with an NS3 inhibitor compound.

In general, an effective amount of IFN-α 2a or 2b or 2c and IFN-γ suitable for use in the methods of the embodiments is provided by a dosage ratio of 1 million Units (MU) IFN-α 2a or 2b or 2c: 30 μg IFN-γ, where both IFN-α 2a or 2b or 2c and IFN-γ are unPEGylated and unglycosylated species.

Another embodiment provides any of the above-described methods modified to use an effective amount of IFN-α 2a or 2b or 2c and IFN-γ in the treatment of a virus infection in a patient comprising administering to the patient a dosage of IFN-α 2a, 2b or 2c containing an amount of about 1 MU to about 20 MU of drug per dose of IFN-α 2a, 2b or 2c subcutaneously qd, qod, tiw, biw, or per day substantially continuously or continuously, in combination with a dosage of IFN-γ containing an amount of about 30 μg to about 600 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of IFN-α 2a or 2b or 2c and IFN-γ in the treatment of a virus infection in a patient comprising administering to the patient a dosage of IFN-α 2a, 2b or 2c containing an amount of about 3 MU of drug per dose of IFN-α 2a, 2b or 2c subcutaneously qd, qod, tiw, biw, or per day substantially continuously or continuously, in combination with a dosage of IFN-γ containing an amount of about 100 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of IFN-α 2a or 2b or 2c and IFN-γ in the treatment of a virus infection in a patient comprising administering to the patient a dosage of IFN-α 2a, 2b or 2c containing an amount of about 10 MU of drug per dose of IFN-α 2a, 2b or 2c subcutaneously qd, qod, tiw, biw, or per day substantially continuously or continuously, in combination with a dosage of IFN-γ containing an amount of about 300 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of PEGASYS®PEGylated IFN-α2a and IFN-γ in the treatment of a virus infection in a patient comprising administering to the patient a dosage of PEGASYS® containing an amount of about 90 μg to about 360 μg, of drug per dose of PEGASYS®, subcutaneously qw, qow, three times per month, or monthly, in combination with a total weekly dosage of IFN-γ containing an amount of about 30 μg to about 1,000 μg, of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEGASYS®PEGylated IFN-α2a and IFN-γ in the treatment of a virus infection in a patient comprising administering to the patient a dosage of PEGASYS® containing an amount of about 180 μg of drug per dose of PEGASYS®, subcutaneously qw, qow, three times per month, or monthly, in combination with a total weekly dosage of IFN-γ containing an amount of about 100 μg to about 300 μg, of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEG-INTRON®PEGylated IFN-α2b and IFN-γ in the treatment of a virus infection in a patient comprising administering to the patient a dosage of PEG-INTRON® containing an amount of about 0.75 μg to about 3.0 μg of drug per kilogram of body weight per dose of PEG-INTRON®, subcutaneously qw, qow, three times per month, or monthly, in combination with a total weekly dosage of IFN-γ containing an amount of about 30 μg to about 1,000 μg of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEG-INTRON®PEGylated IFN-α2b and IFN-γ in the treatment of a virus infection in a patient comprising administering to the patient a dosage of PEG-INTRON® containing an amount of about 1.5 μg of drug per kilogram of body weight per dose of PEG-INTRON®, subcutaneously qw, qow, three times per month, or monthly, in combination with a total weekly dosage of IFN-γ containing an amount of about 100 μg to about 300 μg of drug per week administered in divided doses subcutaneously qd, qod, tiw, or biw, or administered substantially continuously or continuously, for the desired duration of treatment with an NS3 inhibitor compound.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 9 μg INFERGEN® consensus IFN-α administered subcutaneously qd or tiw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 9 μg INFERGEN® consensus IFN-α administered subcutaneously qd or tiw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an inhibitor; and a regimen of 9 µg INFERGEN® consensus IFN-α administered subcutaneously qd or tiw; and 100 µg Actimmune® human IFN-γ1b administered subcutaneously tiw, where the duration of therapy is 48 weeks.

One embodiment provides any of the above-described methods modified to comprise administering to an individual having an HCV infection an effective amount of an inhibitor; and a regimen of 9 µg INFERGEN® consensus IFN-α administered subcutaneously qd or tiw; 25 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 9 µg INFERGEN® consensus IFN-α administered subcutaneously qd or tiw; 200 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 9 µg INFERGEN® consensus IFN-α administered subcutaneously qd or tiw; and 25 µg Actimmune® human IFN-γ1b administered subcutaneously tiw, where the duration of therapy is 48 weeks.

One embodiment provides any of the above-described methods modified to comprise administering to an individual having an HCV infection an effective amount of an inhibitor; and a regimen of 9 µg INFERGEN® consensus IFN-α administered subcutaneously qd or tiw; and 200 µg Actimmune® human IFN-γ1b administered subcutaneously tiw, where the duration of therapy is 48 weeks.

One embodiment provides any of the above-described methods modified to comprise administering to an individual having an HCV infection an effective amount of an inhibitor; and a regimen of 100 µg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 100 µg monoPEG(30 kD, linear)-ylated consensus IFN-α administered subcutaneously every 10 days or qw; 50 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 100 µg monoPEG(30 kD, linear)-ylated consensus IFN-α administered subcutaneously every 10 days or qw; 100 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 100 µg monoPEG(30 kD, linear)-ylated consensus IFN-α administered subcutaneously every 10 days or qw; and 50 µg Actimmune® human IFN-γ1b administered subcutaneously tiw, where the duration of therapy is 48 weeks.

One embodiment provides any of the above-described methods modified to comprise administering to an individual having an HCV infection an effective amount of an inhibitor; and a regimen of 100 µg monoPEG(30 kD, linear)-ylated consensus IFN-α administered subcutaneously every 10 days or qw; and 100 µg Actimmune® human IFN-γ1b administered subcutaneously tiw, where the duration of therapy is 48 weeks.

One embodiment provides any of the above-described methods modified to comprise administering to an individual having an HCV infection an effective amount of an inhibitor; and a regimen of 150 µg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 150 µg monoPEG(30 kD, linear)-ylated consensus IFN-α administered subcutaneously every 10 days or qw; 50 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 150 µg monoPEG(30 kD, linear)-ylated consensus IFN-α administered subcutaneously every 10 days or qw; 100 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 150 µg monoPEG(30 kD, linear)-ylated consensus IFN-α administered subcutaneously every 10 days or qw; and 50 µg Actimmune® human IFN-γ1b administered subcutaneously tiw, where the duration of therapy is 48 weeks.

One embodiment provides any of the above-described methods modified to comprise administering to an individual having an HCV infection an effective amount of an inhibitor; and a regimen of 150 µg monoPEG(30 kD, linear)-ylated consensus IFN-α administered subcutaneously every 10 days or qw; and 100 µg Actimmune® human IFN-γ1b administered subcutaneously tiw, where the duration of therapy is 48 weeks.

One embodiment provides any of the above-described methods modified to comprise administering to an individual having an HCV infection an effective amount of an inhibitor; and a regimen of 200 µg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an inhibitor; and a regimen of 200 µg monoPEG(30 kD, linear)-ylated consensus IFN-α administered subcutaneously every 10 days or qw; 50 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 µg monoPEG(30 kD, linear)-ylated consensus IFN-α administered subcutaneously every 10 days or qw; 100 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 µg monoPEG(30 kD, linear)-ylated consensus IFN-α administered subcutaneously every 10 days or qw; and 50 µg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 200 µg monoPEG(30 kD, linear)-ylated consensus IFN-α administered subcutaneously every 10 days or qw; and 100 µg Actimmune® human IFN-γ1b administered subcutaneously tiw, where the duration of therapy is 48 weeks.

Any of the above-described methods involving administering an NS3 inhibitor, a Type I interferon receptor agonist (e.g., an IFN-α), and a Type II interferon receptor agonist (e.g., an IFN-γ), can be augmented by administration of an effective amount of a TNF-α antagonist (e.g., a TNF-α antagonist other than pirfenidone or a pirfenidone analog). Exemplary, non-limiting TNF-α antagonists that are suitable for use in such combination therapies include ENBREL®, REMICADE®, and HUMIRA™.

One embodiment provides a method using an effective amount of ENBREL®; an effective amount of IFN-α; an effective amount of IFN-γ; and an effective amount of an NS3 inhibitor in the treatment of an HCV infection in a patient, comprising administering to the patient a dosage ENBREL® containing an amount of from about 0.1 µg to about 23 mg per dose, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, or from about 20 mg to about 23 mg of ENBREL®, subcutaneously qd, qod, tiw, biw, qw, qow, three times per month, once monthly, or once every other month, or per day substantially continuously or continuously, for the desired duration of treatment.

One embodiment provides a method using an effective amount of REMICADE®, an effective amount of IFN-α; an effective amount of IFN-γ; and an effective amount of an NS3 inhibitor in the treatment of an HCV infection in a patient, comprising administering to the patient a dosage of REMICADE® containing an amount of from about 0.1 mg/kg to about 4.5 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, or from about 4.0 mg/kg to about 4.5 mg/kg per dose of REMICADE®, intravenously qd, qod, tiw, biw, qw, qow, three times per month, once monthly, or once every other month, or per day substantially continuously or continuously, for the desired duration of treatment.

One embodiment provides a method using an effective amount of HUMIRA™, an effective amount of IFN-α; an effective amount of IFN-γ; and an effective amount of an NS3 inhibitor in the treatment of an HCV infection in a patient, comprising administering to the patient a dosage of HUMIRA™ containing an amount of from about 0.1 µg to about 35 mg, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, or from about 30 mg to about 35 mg per dose of a HUMIRA™, subcutaneously qd, qod, tiw, biw, qw, qow, three times per month, once monthly, or once every other month, or per day substantially continuously or continuously, for the desired duration of treatment.

Combination Therapies with Pirfenidone

In many embodiments, the methods provide for combination therapy comprising administering an NS3 inhibitor compound as described above, and an effective amount of pirfenidone or a pirfenidone analog. In some embodiments, an NS3 inhibitor compound, one or more interferon receptor agonist(s), and pirfenidone or pirfenidone analog are co-administered in the treatment methods of the embodiments. In certain embodiments, an NS3 inhibitor compound, a Type I interferon receptor agonist, and pirfenidone (or a pirfenidone analog) are co-administered. In other embodiments, an NS3 inhibitor compound, a Type I interferon receptor agonist, a Type II interferon receptor agonist, and pirfenidone (or a pirfenidone analog) are co-administered. Type I interferon receptor agonists suitable for use herein include any IFN-α, such as interferon alfa-2a, interferon alfa-2b, interferon alfacon-1, and PEGylated IFN-α's, such as peginterferon alfa-2a, peginterferon alfa-2b, and PEGylated consensus interferons, such as monoPEG (30 kD, linear)-ylated consensus interferon. Type II interferon receptor agonists suitable for use herein include any interferon-γ.

Pirfenidone or a pirfenidone analog can be administered once per month, twice per month, three times per month, once per week, twice per week, three times per week, four times per week, five times per week, six times per week, daily, or in divided daily doses ranging from once daily to 5 times daily over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Effective dosages of pirfenidone or a specific pirfenidone analog include a weight-based dosage in the range from about 5 mg/kg/day to about 125 mg/kg/day, or a fixed dosage of about 400 mg to about 3600 mg per day, or about 800 mg to about 2400 mg per day, or about 1000 mg to about 1800 mg per day, or about 1200 mg to about 1600 mg per day, administered orally in one to five divided doses per day. Other doses and formulations of pirfenidone and specific pirfenidone analogs suitable for use in the treatment of fibrotic diseases are described in U.S. Pat. Nos. 5,310,562; 5,518,729; 5,716,632; and 6,090,822.

One embodiment provides any of the above-described methods modified to include co-administering to the patient a therapeutically effective amount of pirfenidone or a pirfenidone analog for the duration of the desired course of NS3 inhibitor compound treatment.

Combination Therapies with TNF-α Antagonists

In many embodiments, the methods provide for combination therapy comprising administering an effective amount of an NS3 inhibitor compound as described above, and an effective amount of TNF-α antagonist, in combination therapy for treatment of an HCV infection.

Effective dosages of a TNF-α antagonist range from 0.1 µg to 40 mg per dose, e.g., from about 0.1 µg to about 0.5 µg per dose, from about 0.5 µg to about 1.0 µg per dose, from about 1.0 µg per dose to about 5.0 µg per dose, from about 5.0 µg to about 10 µg per dose, from about 10 µg to about 20 µg per dose, from about 20 µg per dose to about 30 µg per dose, from about 30 µg per dose to about 40 µg per dose, from about 40 µg per dose to about 50 µg per dose, from about 50 µg per dose to about 60 µg per dose, from about 60 µg per dose to about 70 µg per dose, from about 70 µg to about 80 µg per dose, from about 80 µg per dose to about 100 µg per dose, from about 100 µg to about 150 µg per dose, from about 150 µg to about 200 µg per dose, from about 200 µg per dose to about 250 µg per dose, from about 250 µg to about 300 µg per dose, from about 300 µg to about 400 µg per dose, from about 400 µg to about 500 µg per dose, from about 500 µg to about 600 µg per dose, from about 600 µg to about 700 µg per dose, from about 700 µg to about 800 µg per dose, from about 800 µg to about 900 µg per dose, from about 900 µg to about 1000 µg per dose, from about 1 mg to about 10 mg per dose, from about 10 mg to about 15 mg per dose, from about 15 mg to about 20 mg per dose, from about 20 mg to about 25 mg per dose, from about 25 mg to about 30 mg per dose, from about 30 mg to about 35 mg per dose, or from about 35 mg to about 40 mg per dose.

In some embodiments, effective dosages of a TNF-α antagonist are expressed as mg/kg body weight. In these embodiments, effective dosages of a TNF-α antagonist are from about 0.1 mg/kg body weight to about 10 mg/kg body weight, e.g., from about 0.1 mg/kg body weight to about 0.5 mg/kg body weight, from about 0.5 mg/kg body weight to about 1.0 mg/kg body weight, from about 1.0 mg/kg body weight to about 2.5 mg/kg body weight, from about 2.5 mg/kg body weight to about 5.0 mg/kg body weight, from about 5.0 mg/kg body weight to about 7.5 mg/kg body weight, or from about 7.5 mg/kg body weight to about 10 mg/kg body weight.

In many embodiments, a TNF-α antagonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The TNF-α antagonist can be administered tid, bid, qd, qod, biw, tiw, qw, qow, three times per month, once monthly, substantially continuously, or continuously.

In many embodiments, multiple doses of a TNF-α antagonist are administered. For example, a TNF-α antagonist is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A TNF-α antagonist and an NS3 inhibitor are generally administered in separate formulations. A TNF-α antagonist and an NS3 inhibitor may be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

One embodiment provides a method using an effective amount of a TNF-α antagonist and an effective amount of an NS3 inhibitor in the treatment of an HCV infection in a patient, comprising administering to the patient a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides a method using an effective amount of ENBREL® and an effective amount of an NS3 inhibitor in the treatment of an HCV infection in a patient, comprising administering to the patient a dosage ENBREL® containing an amount of from about 0.1 µg to about 23 mg per dose, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, or from about 20 mg to about 23 mg of ENBREL®, subcutaneously qd, qod, tiw, biw, qw, qow, three times per month, once monthly, or once every other month, or per day substantially continuously or continuously, for the desired duration of treatment with an NS3 inhibitor compound.

One embodiment provides a method using an effective amount of REMICADE® and an effective amount of an NS3 inhibitor in the treatment of an HCV infection in a patient, comprising administering to the patient a dosage of REMICADE® containing an amount of from about 0.1 mg/kg to about 4.5 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, or from about 4.0 mg/kg to about 4.5 mg/kg per dose of REMICADE®, intravenously qd, qod, tiw, biw, qw, qow, three times per month, once monthly, or once every other month, or per day substantially continuously or continuously, for the desired duration of treatment with an NS3 inhibitor compound.

One embodiment provides a method using an effective amount of HUMIRA™ and an effective amount of an NS3 inhibitor in the treatment of an HCV infection in a patient, comprising administering to the patient a dosage of HUMIRA™ containing an amount of from about 0.1 µg to about 35 mg, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, or from about 30 mg to about 35 mg per dose of a HUMIRA™, subcutaneously qd, qod, tiw, biw, qw, qow, three times per month, once monthly, or once every other month, or per day substantially continuously or continuously, for the desired duration of treatment with an NS3 inhibitor compound.

Combination Therapies with Thymosin-α

In many embodiments, the methods provide for combination therapy comprising administering an effective amount of an NS3 inhibitor compound as described above, and an effective amount of thymosin-α, in combination therapy for treatment of an HCV infection.

Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

One embodiment provides a method using an effective amount of ZADAXIN™ thymosin-α and an effective amount of an NS3 inhibitor in the treatment of an HCV infection in a patient, comprising administering to the patient a dosage of ZADAXIN™ containing an amount of from about 1.0 mg to about 1.6 mg per dose, subcutaneously twice per week for the desired duration of treatment with the NS3 inhibitor compound.

Combination Therapies with a TNF-α Antagonist and an Interferon

Some embodiments provide a method of treating an HCV infection in an individual having an HCV infection, the method comprising administering an effective amount of an NS3 inhibitor, and effective amount of a TNF-α antagonist, and an effective amount of one or more interferons.

One embodiment provides any of the above-described methods modified to use an effective amount of IFN-γ and an effective amount of a TNF-α antagonist in the treatment of HCV infection in a patient comprising administering to the patient a dosage of IFN-γ containing an amount of about 10 µg to about 300 µg of drug per dose of IFN-γ, subcutaneously qd, qod, tiw, biw, qw, qow, three times per month, once monthly, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of IFN-γ and an effective amount of a TNF-α antagonist in the treatment of HCV infection in a patient comprising administering to the patient a dosage of IFN-γ containing an amount of about 10 µg to about 100 µg of drug per dose of IFN-γ, subcutaneously qd, qod, tiw, biw, qw, qow, three times per month, once monthly, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-γ and an effective amount of a TNF-α antagonist in the treatment of a virus infection in a patient comprising administering to the patient a total weekly dosage of IFN-γ containing an amount of about 30 µg to about 1,000 µg of drug per week in divided doses administered subcutaneously qd, qod, tiw, biw, or administered substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-γ and an effective amount of a TNF-α antagonist in the treatment of a virus infection in a patient comprising administering to the patient a total weekly dosage of IFN-γ containing an amount of about 100 µg to about 300 µg of drug per week in divided doses administered subcutaneously qd, qod, tiw, biw, or administered substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of INFERGEN® consensus IFN-α and a TNF-α antagonist in the treatment of HCV infection in a patient comprising administering to the patient a dosage of INFERGEN® containing an amount of about 1 µg to about 30 µg, of drug per dose of INFERGEN®, subcutaneously qd, qod, tiw, biw, qw, qow, three times per month, once monthly, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of INFERGEN® consensus IFN-α and a TNF-α antagonist in the treatment of HCV infection in a patient comprising administering to the patient a dosage of INFERGEN® containing an amount of about 1 µg to about 9 µg, of drug per dose of INFERGEN®, subcutaneously qd, qod, tiw, biw, qw, qow, three times per month, once monthly, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGylated consensus IFN-α and an effective amount of a TNF-α antagonist in the treatment of a virus infection in a patient comprising administering to the patient a dosage of PEGylated consensus IFN-α (PEG-CIFN) containing an amount of about 4 µg to about 60 µg of CIFN amino acid weight per dose of PEG-CIFN, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGylated consensus IFN-α and an effective amount of a TNF-α antagonist in the treatment of a virus infection in a patient comprising administering to the patient a dosage of PEGylated consensus IFN-α (PEG-CIFN) containing an amount of about 18 µg to about 24 µg of CIFN amino acid weight per dose of PEG-CIFN, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α 2a or 2b or 2c and an effective amount of a TNF-α antagonist in the treatment of a virus infection in a patient comprising administering to the patient a dosage of IFN-α 2a, 2b or 2c containing an amount of about 1 MU to about 20 MU of drug per dose of IFN-α 2a, 2b or 2c subcutaneously qd, qod, tiw, biw, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α 2a or 2b or 2c and an effective amount of a TNF-α antagonist in the treatment of a virus infection in a patient comprising administering to the patient a dosage of IFN-α 2a, 2b or 2c containing an amount of about 3 MU of drug per dose of IFN-α 2a, 2b or 2c subcutaneously qd, qod, tiw, biw, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α 2a or 2b or 2c and an effective amount of a TNF-α antagonist in the treatment of a virus infection in a patient comprising administering to the patient a dosage of IFN-α 2a, 2b or 2c containing an amount of about 10 MU of drug per dose of IFN-α 2a, 2b or 2c subcutaneously qd, qod, tiw, biw, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGASYS®PEGylated IFN-α2a and an effective amount of a TNF-α antagonist in the treatment of a virus infection in a patient comprising administering to the patient a dosage of PEGASYS® containing an amount of about 90 µg to about 360 µg, of drug per dose of PEGASYS®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGASYS®PEGylated IFN-α2a and an effective amount of a TNF-α antagonist in the treatment of a virus infection in a patient comprising administering to the patient a dosage of PEGASYS® containing an amount of about 180 µg, of drug per dose of PEGASYS®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEG-INTRON®PEGylated IFN-α2b and an effective amount of a TNF-α antagonist in the treatment of a virus infection in a patient comprising administering to the patient a dosage of PEG-INTRON® containing an amount of about 0.75 µg to about 3.0 µg of drug per kilogram of body weight per dose of PEG-INTRON®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEG-INTRON®PEGylated IFN-α2b and an effective amount of a TNF-α antagonist in the treatment of a virus infection in a patient comprising administering to the patient a dosage of PEG-INTRON® containing an amount of about 1.5 µg of drug per kilogram of body weight per dose of PEG-INTRON®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Combination Therapies with Other Antiviral Agents

Other agents such as inhibitors of HCV NS3 helicase are also attractive drugs for combinational therapy, and are contemplated for use in combination therapies described herein. Ribozymes such as Heptazyme™ and phosphorothioate oligonucleotides which are complementary to HCV protein sequences and which inhibit the expression of viral core proteins are also suitable for use in combination therapies described herein.

In some embodiments, the additional antiviral agent(s) is administered during the entire course of treatment with the NS3 inhibitor compound described herein, and the beginning and end of the treatment periods coincide. In other embodiments, the additional antiviral agent(s) is administered for a period of time that is overlapping with that of the NS3 inhibitor compound treatment, e.g., treatment with the additional antiviral agent(s) begins before the NS3 inhibitor compound treatment begins and ends before the NS3 inhibitor compound treatment ends; treatment with the additional antiviral agent(s) begins after the NS3 inhibitor compound treatment begins and ends after the NS3 inhibitor compound treatment ends; treatment with the additional antiviral agent(s) begins after the NS3 inhibitor compound treatment begins and ends before the NS3 inhibitor compound treatment ends; or treatment with the additional antiviral agent(s) begins before the NS3 inhibitor compound treatment begins and ends after the NS3 inhibitor compound treatment ends.

The NS3 inhibitor compound can be administered together with (i.e., simultaneously in separate formulations; simultaneously in the same formulation; administered in separate formulations and within about 48 hours, within about 36 hours, within about 24 hours, within about 16 hours, within about 12 hours, within about 8 hours, within about 4 hours, within about 2 hours, within about 1 hour, within about 30 minutes, or within about 15 minutes or less) one or more additional antiviral agents.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 100 μg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 150 μg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 200 μg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 9 μg of drug per dose, subcutaneously once daily or three times per week for the desired treatment duration with an NS3 inhibitor compound.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 15 μg of drug per dose, subcutaneously once daily or three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 25 μg of drug per dose, subcutaneously three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 50 μg of drug per dose, subcutaneously three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 100 μg of drug per dose, subcutaneously three times per week for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring a TNF antagonist regimen can be modified to replace the subject TNF antagonist regimen with a TNF antagonist regimen comprising administering a dosage of a TNF antagonist selected from the group of: (a) etanercept in an amount of 25 mg of drug per dose subcutaneously twice per week, (b) infliximab in an amount of 3 mg of drug per kilogram of body weight per dose intravenously at weeks 0, 2 and 6, and every 8 weeks thereafter, or (c) adalimumab in an amount of 40 mg of drug per dose subcutaneously once weekly or once every 2 weeks; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b)

administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 100

μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of INFERGEN® interferon alfacon-1 containing an amount of 9 μg of drug per dose, subcutaneously once daily or three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of INFERGEN® interferon alfacon-1 containing an amount of 15 μg of drug per dose, subcutaneously once daily or three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 25 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 50 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 100 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods that includes a regimen of monoPEG (30 kD, linear)-ylated consensus IFN-α can be modified to replace the regimen of monoPEG (30 kD, linear)-ylated consensus IFN-α with a regimen of peginterferon alfa-2a comprising administering a dosage of peginterferon alfa-2a containing an amount of 180 μg of drug per dose, subcutaneously once weekly for the desired treatment duration with an NS3 inhibitor compound.

As non-limiting examples, any of the above-described methods that includes a regimen of monoPEG (30 kD, linear)-ylated consensus IFN-α can be modified to replace the regimen of monoPEG (30 kD, linear)-ylated consensus IFN-α with a regimen of peginterferon alfa-2b comprising administering a dosage of peginterferon alfa-2b containing an amount of 1.0 μg to 1.5 μg of drug per kilogram of body weight per dose, subcutaneously once or twice weekly for the desired treatment duration with an NS3 inhibitor compound.

As non-limiting examples, any of the above-described methods can be modified to include administering a dosage of ribavirin containing an amount of 400 mg, 800 mg, 1000 mg or 1200 mg of drug orally per day, optionally in two or more divided doses per day, for the desired treatment duration with an NS3 inhibitor compound.

As non-limiting examples, any of the above-described methods can be modified to include administering a dosage of ribavirin containing (i) an amount of 1000 mg of drug orally per day for patients having a body weight of less than 75 kg or (ii) an amount of 1200 mg of drug orally per day for patients having a body weight of greater than or equal to 75 kg, optionally in two or more divided doses per day, for the desired treatment duration with an NS3 inhibitor compound.

As non-limiting examples, any of the above-described methods can be modified to replace the subject NS3 inhibitor regimen with an NS3 inhibitor regimen comprising administering a dosage of 0.01 mg to 0.1 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 0.1 mg to 1 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 1 mg to 10 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 10 mg to 100 mg of drug per kilogram of body weight orally daily, optionally in two or more divided doses per day, for the desired treatment duration with the NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 0.01 mg to 0.1 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 0.1 mg to 1 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 1 mg to 10 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 10 mg to 100 mg of drug per kilogram of body weight orally daily, optionally in two or more divided doses per day, for the desired treatment duration with an NS3 inhibitor compound.

Patient Identification

In certain embodiments, the specific regimen of drug therapy used in treatment of the HCV patient is selected according to certain disease parameters exhibited by the patient, such as the initial viral load, genotype of the HCV infection in the patient, liver histology and/or stage of liver fibrosis in the patient.

Thus, some embodiments provide any of the above-described methods for the treatment of HCV infection in which the subject method is modified to treat a treatment failure patient for a duration of 48 weeks.

Other embodiments provide any of the above-described methods for HCV in which the subject method is modified to treat a non-responder patient, where the patient receives a 48 week course of therapy.

Other embodiments provide any of the above-described methods for the treatment of HCV infection in which the subject method is modified to treat a relapser patient, where the patient receives a 48 week course of therapy.

Other embodiments provide any of the above-described methods for the treatment of HCV infection in which the subject method is modified to treat a naïve patient infected with HCV genotype 1, where the patient receives a 48 week course of therapy.

Other embodiments provide any of the above-described methods for the treatment of HCV infection in which the subject method is modified to treat a naïve patient infected with HCV genotype 4, where the patient receives a 48 week course of therapy.

Other embodiments provide any of the above-described methods for the treatment of HCV infection in which the subject method is modified to treat a naïve patient infected with HCV genotype 1, where the patient has a high viral load (HVL), where "HVL" refers to an HCV viral load of greater than $2 \times 10^6$ HCV genome copies per mL serum, and where the patient receives a 48 week course of therapy.

One embodiment provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and no or early stage liver fibrosis as measured by a Knodell score of 0, 1, or 2 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and no or early stage liver fibrosis as measured by a Knodell score of 0, 1, or 2 and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 20 weeks to about 24 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 24 weeks to about 48 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 24 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of at least about 24 weeks.

Another embodiment provides any of the above-described methods for the treatment of an HCV infection, where the subject method is modified to include the steps of (1) identifying a patient having an HCV genotype 1 or 4 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of about 20 weeks to about 50 weeks.

Another embodiment provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of at least about 24 weeks and up to about 48 weeks.

Subjects Suitable for Treatment

Any of the above treatment regimens can be administered to individuals who have been diagnosed with an HCV infection. Any of the above treatment regimens can be administered to individuals who have failed previous treatment for HCV infection ("treatment failure patients," including non-responders and relapsers).

Individuals who have been clinically diagnosed as infected with HCV are of particular interest in many embodiments. Individuals who are infected with HCV are identified as having HCV RNA in their blood, and/or having anti-HCV antibody in their serum. Such individuals include anti-HCV ELISA-positive individuals, and individuals with a positive recombinant immunoblot assay (RIBA). Such individuals may also, but need not, have elevated serum ALT levels.

Individuals who are clinically diagnosed as infected with HCV include naïve individuals (e.g., individuals not previously treated for HCV, particularly those who have not previously received IFN-α-based and/or ribavirin-based therapy) and individuals who have failed prior treatment for HCV ("treatment failure" patients). Treatment failure patients include non-responders (i.e., individuals in whom the HCV titer was not significantly or sufficiently reduced by a previous treatment for HCV, e.g., a previous IFN-α monotherapy, a previous IFN-α and ribavirin combination therapy, or a previous pegylated IFN-α and ribavirin combination therapy); and relapsers (i.e., individuals who were previously treated for HCV, e.g., who received a previous IFN-α monotherapy, a previous IFN-α and ribavirin combination therapy, or a previous pegylated IFN-α and ribavirin combination therapy, whose HCV titer decreased, and subsequently increased).

In particular embodiments of interest, individuals have an HCV titer of at least about $10^5$, at least about $5 \times 10^5$, or at least about $10^6$, or at least about $2 \times 10^6$, genome copies of HCV per milliliter of serum. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

Also of interest are HCV-positive individuals (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment with IFN-α-based therapies or who cannot tolerate IFN-α-based therapies, or who have a contraindication to such therapies. In particular embodiments of interest, HCV-positive individuals with stage 3 or 4 liver fibrosis according to the METAVIR scoring system are suitable for treatment with the methods described herein. In other embodiments, individuals suitable for treatment with the methods of the embodiments are patients with decompensated cirrhosis with clinical manifestations, including patients with far-advanced liver cirrhosis, including those awaiting liver transplantation. In still other embodiments, individuals suitable for treatment with the methods described herein include patients with milder degrees of fibrosis including those with early fibrosis (stages 1 and 2 in the METAVIR, Ludwig, and Scheuer scoring systems; or stages 1, 2, or 3 in the Ishak scoring system.).

Preparation of NS3 Inhibitors

Methodology

The HCV protease inhibitors in the following sections can be prepared according to the procedures and schemes shown in each section. The numberings in each of the following Preparation of NS3 Inhibitor sections are meant for that specific section only, and should not be construed or confused with the same numberings in other sections.

Preparation of NS3 Inhibitors: Section I

One method used in preparing compounds with general Formula I utilized intermediates 1, 2, 4 and 9. Intermediate 1 was prepared according to the procedures disclosed in International Application PCT/CA00/00353 (Publication No. WO 00/59929), which is incorporated herein by reference in its entirety. Intermediate 4 was synthesized using the following procedure (Ma, D; Zhang, Y; Yao, J; Wu, S; Tao, F. *J. Am. Chem. Soc.* 1998, 120, 12459-12467, which is incorporated herein by reference in its entirety). Intermediate 9 was prepared according to procedures disclosed in (1. Khan et al, *Bioorg. & Med. Chem. Lett.,* 1997, 7 (23), 3017-3022. 2. International Application PCT/US02/39926, WO 03/053349), both of which are incorporated herein by reference in their entirety. Intermediate 2 was synthesized using the following procedure: McKenna, J. M. *Tetrahedron Letters* 2001 42, 5795-5800 and Ullman Chemistry, both of which are incorporated herein by reference in their entirety and will be described in the following procedures.

Method:

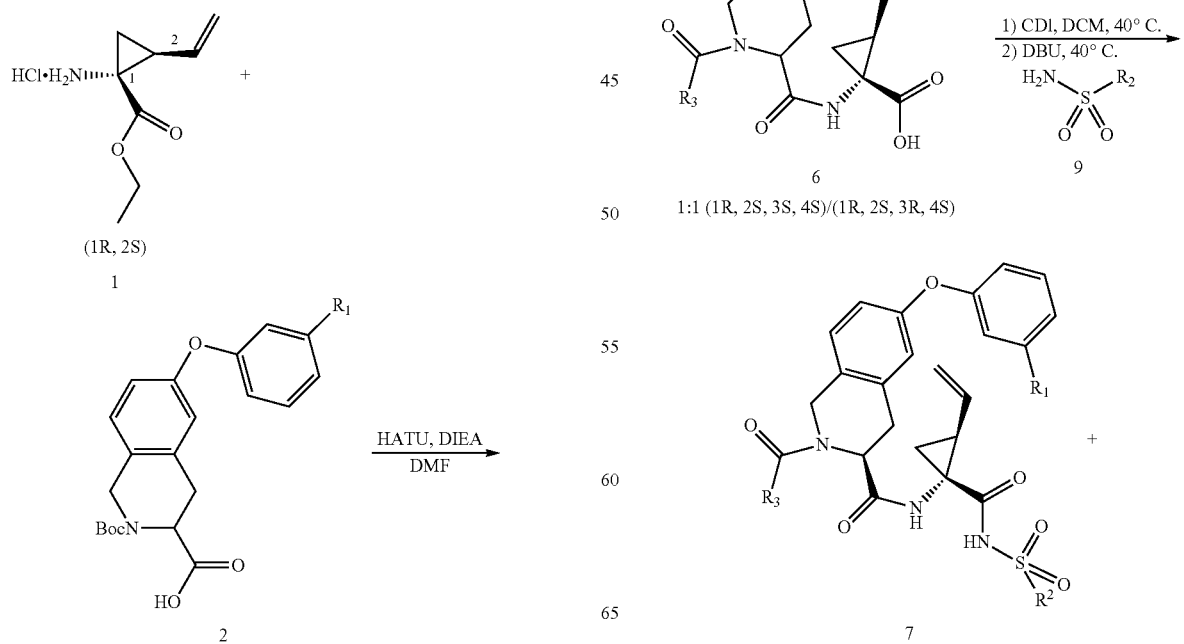

-continued

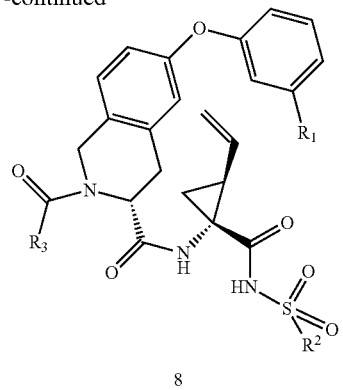

8

EXAMPLE 1-1

Compound 10

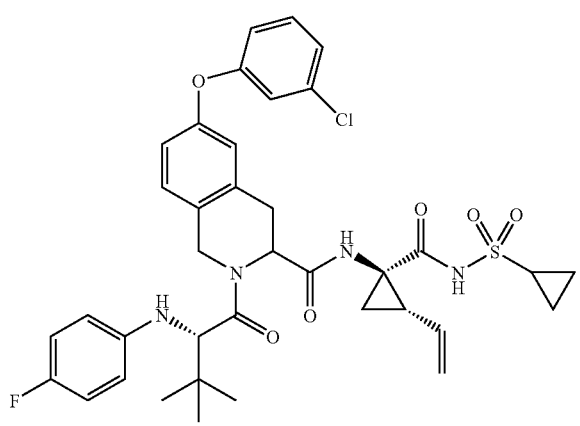

6-(3-chlorophenoxy)-N-((1R,2S)-1-(cyclopropylsulfonylcarbamoyl)-2-vinylcyclopropyl)-2-((S)-2-(4-fluorophenylamino)-3,3-dimethylbutanoyl)-1,2,3,4-tetrahydroisoquinoline-3-carboxamide

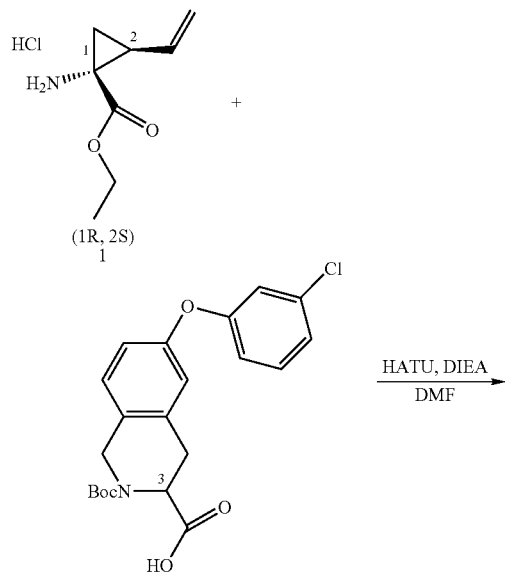

-continued

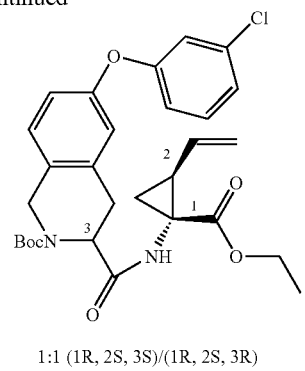

1:1 (1R, 2S, 3S)/(1R, 2S, 3R)

Step 1: Synthesis of tert-butyl 3-(((1R,2S)-1-(ethoxycarbonyl)-2-vinylcyclopropyl)carbamoyl)-6-(3-chlorophenoxy)-3,4-dihydroisoquinoline-2(1H)-carboxylate To a flask charged with ethyl-(1R,2S)-1-amino-2-vinylcyclopropyl carboxylate (1, 1.0 g, 5.2 mmol), 2-(tert-butoxycarbonyl)-6-(3-chlorophenoxy)-1,2,3,4-tetrahydroisoquinoline-3-carboxylic acid (2.31 g, 1.1 equiv), and O-(7-Azabenzotriazol-1-yl)-N,N,N',N'-tetramethyluronium hexafluorophosphate (HATU) (2.7 g, 1.1 equiv) were added 30 mL DMF to make a solution. It was cooled to 0° C. in an ice-water bath, followed by slow addition of a solution of N,N-Diisopropylethylamine (DIEA) (4.4 mL, 4 equiv) in DMF (15 mL) while stirring. The reaction was allowed to warm up to rt and stirred overnight After 16 h, the reaction was complete as monitored by HPLC. It was diluted with EtOAc (100 mL), washed with water (3×40 mL), sat. NaHCO$_3$ (2×40 mL), and brine (2×40 mL), then dried over Na$_2$SO$_4$ and concentrated down to give a dark copper colored oil. The crude was purified on the Horizon Biotage instrument using a C-18 column (eluent: acetonitrile/water; gradient of 20% Acetonitrile to 80% Acetonitrile over 168-6 mL fractions), giving pure 3 as a mixture of diasteriomers (647 mg, 23%). MS m/e 442.1 (M$^+$–Boc).

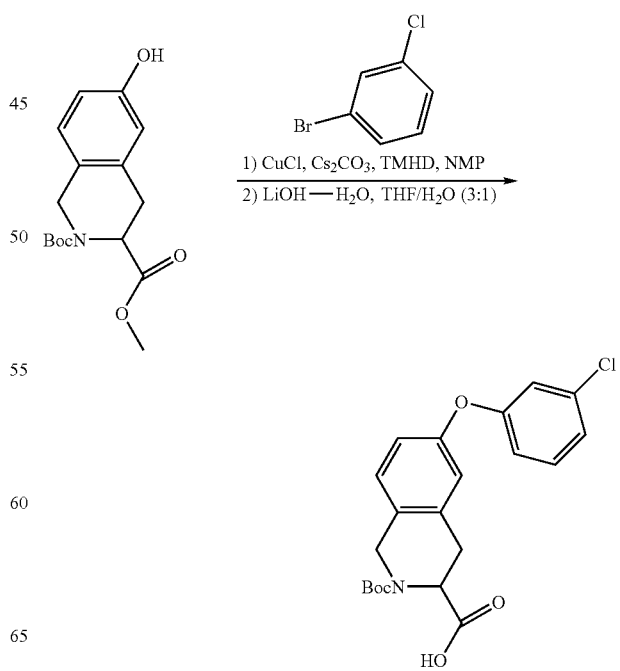

Step 1a: Synthesis of 2-(tert-butoxycarbonyl)-6-(3-chlorophenoxy)-1,2,3,4-tetrahydroisoquinoline-3-carboxylic acid 2-Tert-butyl 3-methyl 6-hydroxy-3,4-dihydroisoquinoline-2, 3(1H)-dicarboxylate (200 mg, 0.65 mmol), m-chlorophenyl bromide (103 mg, 0.54 mmol), 2,2,6,6-tetramethyl-3,5-heptanedione (TMHD, 10 mg, 0.054 mmol), $Cs_2CO_3$ (326 mg, 1.00 mmol), and CuCl (27 mg, 0.27 mmol) were mixed together in NMP (1 mL) and heated to 120° C. for 6 h. The reaction was then diluted with methyl tert-butyl ether (MTBE) and filtered over celite. The filtrate was washed with 1 N HCl, 1 N NaOH, and brine. The organic was dried over $Na_2SO_4$ and concentrated before loading on a Biotage silica column (12 m) and eluting with 10% Acetone/Hexanes to give 2-tert-butyl 3-methyl 6-(3-chlorophenoxy)-3,4-dihydroisoquinoline-2,3(1H)-dicarboxylate as a pale yellow oil (113 mg, 50%). This material was then taken up in 1 mL of a mixture of THF/$H_2O$ (3:1) and LiOH (70 mg, 1.62 mmol) was added. The reaction stirred overnight at rt, before it was concentrated and quenched with 1 N HCl. The product was then extracted with EtOAc (3×). The combined extracts were dried over $Na_2SO_4$ and concentrated to give a pale yellow foam (100 mg, 92%). MS m/e 402.9 (M$^-$–H), concentrated down again twice. To this yellow oil was added 4 (297 mg, 1.1 equiv) and HATU (502 mg, 1.1 equiv), followed by DMF (5 mL). The reaction was cooled on ice-water bath for 15 min, after which DIEA (0.84 mL, 4 equiv) was added to the reaction slowly while stirring. The ice bath was left to slowly rise to rt and the reaction stirred overnight. After 24 h, the reaction had a dark brownish color and its aliquot TLC showed product formation. The reaction mixture was diluted with EtOAc (100 mL) and washed with water (3×120 mL), sat. $NaHCO_3$ (2×120 mL), brine (120 mL), dried ($Na_2SO_4$), and concentrated to give (1R,2S)-ethyl 1-(6-(3-chlorophenoxy)-2-((S)-2-(4-fluorophenylamino)-3,3-dimethylbutanoyl)-1,2,3,4-tetrahydroisoquinoline-3-carboxamido)-2-vinylcyclopropanecarboxylate as an orange oil (500 mg). The crude product was purified on the Horizon Biotage instrument using a C-18 column (eluent: acetonitrile/water; gradient of 0% Acetonitrile to 100% Acetonitrile over 40-6 mL fractions), giving pure (1R,2S)-ethyl 1-(6-(3-chlorophenoxy)-2-((S)-2-(4-fluorophenylamino)-3,3-dimethylbutanoyl)-1,2,3,4-tetrahydroisoquinoline-3-carboxamido)-2-vinylcyclopropanecarboxylate as a white foam (622 mg, 80%).

MS m/e 649.2 (M$^+$+H).

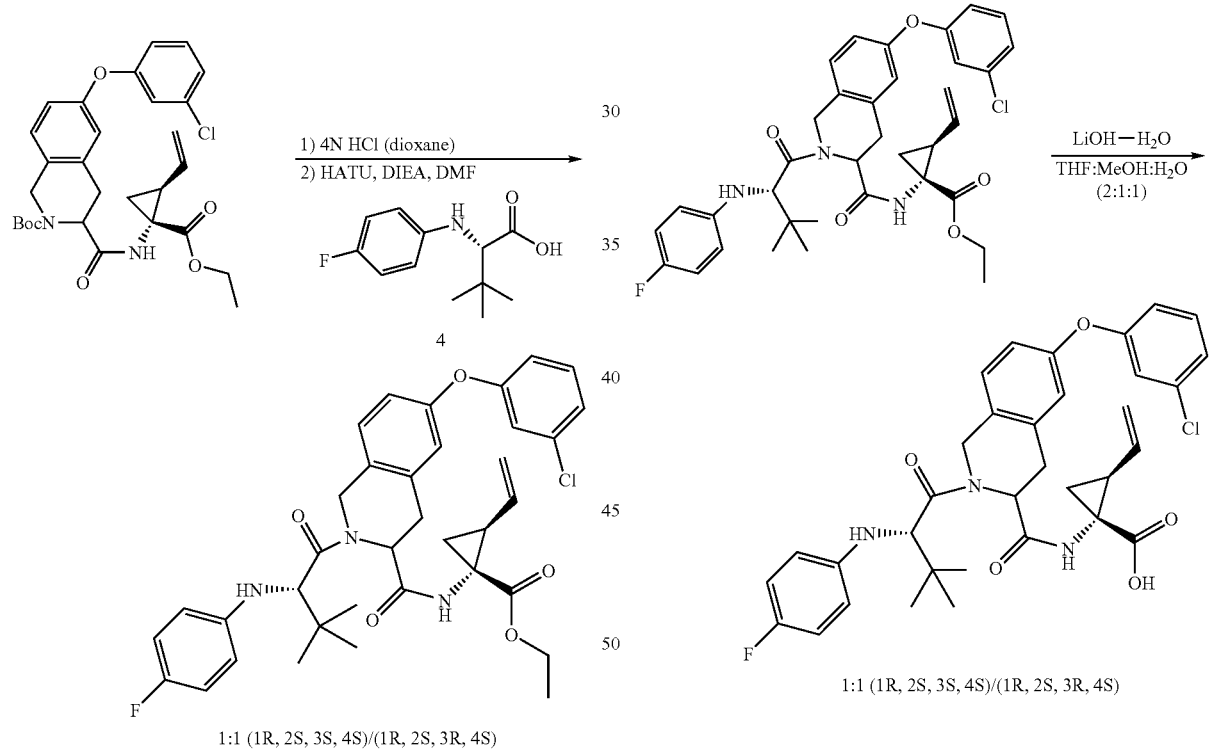

Step 2: Synthesis of (1R,2S)-ethyl 1-(6-(3-chlorophenoxy)-2-((S)-2-(4-fluorophenylamino)-3,3-dimethylbutanoyl)-1,2,3,4-tetrahydroisoquinoline-3-carboxamido)-2-vinylcyclopropanecarboxylate Tert-butyl 3-(((1R,2S)-1-(ethoxycarbonyl)-2-vinylcyclopropyl) carbamoyl)-6-(3-chlorophenoxy)-3,4-dihydroisoquinoline-2(1H)-carboxylate (647 mg, 1.20 mmol) was dissolved in 4 N HCl (dioxane, 8 mL) and left at rt for 90 min to remove the tert-butyloxycarbonyl (Boc) protective group. It was then concentrated down, taken up in acetonitrile and

Step 3: Synthesis of (1R,2S)-1-(6-(3-chlorophenoxy)-2-((S)-2-(4-fluorophenylamino)-3,3-dimethylbutanoyl)-1,2,3,4-tetrahydroisoquinoline-3-carboxamido)-2-vinylcyclopropanecarboxylic acid The crude (1R,2S)-ethyl 1-(6-(3-chlorophenoxy)-2-((S)-2-(4-fluorophenylamino)-3,3-dimethylbutanoyl)-1,2,3,4-tetrahydroisoquinoline-3-carboxamido)-2-vinylcyclopropanecarboxylate (130 mg, 0.20 mmol) was dissolved in 1.0 mL of a mixture of THF:MeOH:$H_2O$ (2:1:1). Lithium hydroxide monohydrate (0.050 g, 1.2 mmol) was added and reaction stirred at rt overnight. The reaction was then concentrated under vacuum and quenched with 5 mL of 1 N HCl. The product precipitated and could be filtered off giving an off-white powder (110 mg). It was directly used in the next step without further purification. MS m/e 619 (M⁻–H).

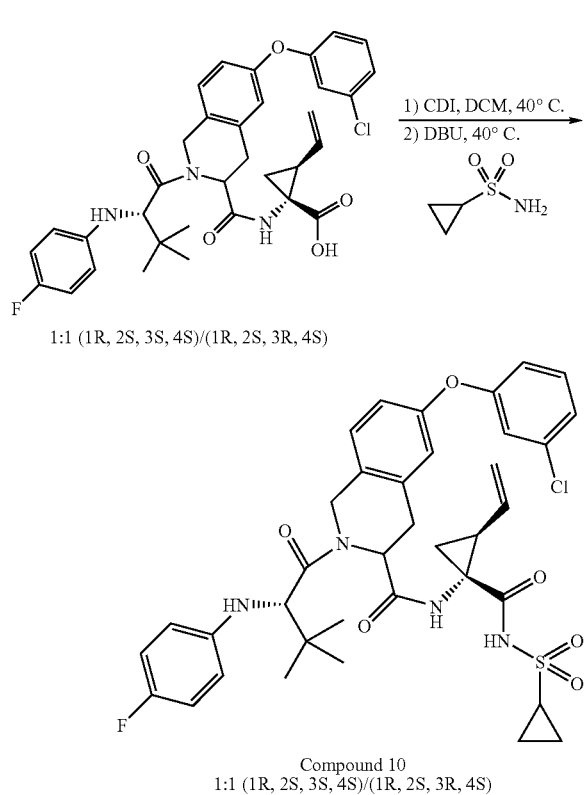

Compound 10
1:1 (1R, 2S, 3S, 4S)/(1R, 2S, 3R, 4S)

Step 4: Synthesis of 6-(3-chlorophenoxy)-N-((1R, 2S)-1-(cyclopropylsulfonylcarbamoyl)-2-vinylcyclopropyl)-2-((S)-2-(4-fluorophenylamino)-3,3-dimethylbutanoyl)-1,2,3,4-tetrahydroisoquinoline-3-carboxamide The crude (1R,2S)-1-(6-(3-chlorophenoxy)-2-((S)-2-(4-fluorophenylamino)-3,3-dimethylbutanoyl)-1,2,3,4-tetrahydroisoquinoline-3-carboxamido)-2-vinylcyclopropanecarboxylic acid (112 mg, 0.180 mmol) was dissolved in 1.0 mL of 1,2-dichloroethane (DCE) and 1,1'-carbonyldiimidazole (CDI, 88 mg, 0.54 mmol) was added. The reaction was heated to 40° C. for 4 h. TLC run in 10% MeOH/CHCl₃ showed conversion to a higher R_f spot. Cyclopropyl sulfonamide (65 mg, 0.54 mmol) and 1,8-diazabicyclo[5.4.0]undec-7-ene (DBU, 81 μL, 0.54 mmol) were added and the reaction heated to 50° C. and stirred overnight. The reaction was concentrated to 400 μL volume and loaded on a Biotage size 12, C-18 samplet for purification using the Horizon LC (12 m, C-18 column) eluting with a gradient from 0% acetonitrile/water to 100% acetonitrile/water over 40-6 mL fractions. Upon concentration product is a white solid. Compound 10 (26 mg, 20%) ¹H NMR (CDCl₃, 500 MHz): δ 9.72 (br s, 1H), 7.32-7.22 (m, 1H), 7.20-7.07 (m, 2H), 7.02-6.68 (m, 7H), 6.58 (br s, 1H), 5.85-5.49 (m, 2H), 5.31-5.03 (m, 2H), 4.83-4.67 (m, 2H), 4.54-4.42 (m, 1H), 4.32 (br s, 1H), 4.18 (br s, 1H), 3.24-2.76 (m, 3H), 1.94 (br s, 1H), 1.86-1.18 (m, 5H), 1.17-0.95 (m, 10H); MS m/e 722 (M⁻–H).

EXAMPLE 1-2

Compound 11

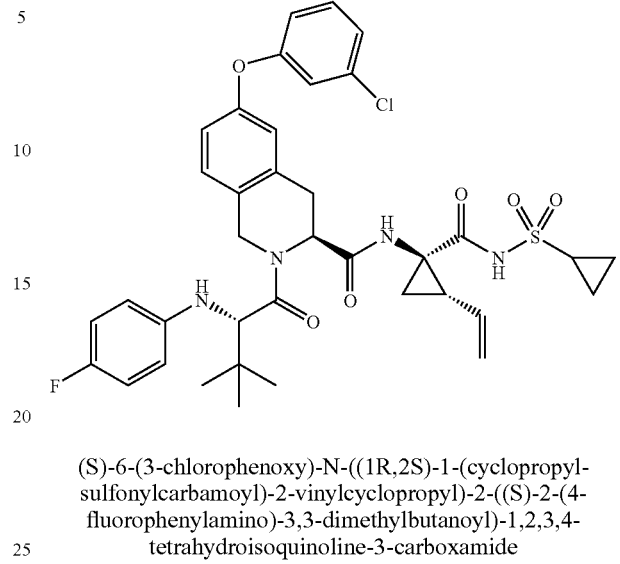

(S)-6-(3-chlorophenoxy)-N-((1R,2S)-1-(cyclopropylsulfonylcarbamoyl)-2-vinylcyclopropyl)-2-((S)-2-(4-fluorophenylamino)-3,3-dimethylbutanoyl)-1,2,3,4-tetrahydroisoquinoline-3-carboxamide Compound II was synthesized according to the procedure described in Example 1-1 and separated as a diasteriomer, (2.3 mg, 4%) MS m/e 722 (M⁻–H), using the following preparative HPLC conditions (Biotage SP4 system using SPX software; version 2: Column: Biotage, KP-C18-HS, 12+M1296-1, 35-70 micron particle size, 90-angstrom pore size
Mobile Phase Gradient: 0-95% B in 40-6 mL fractions
A: water
B: MeCN
Flow rate: 15 mL/min
Temperature: 25 C
Wavelength: 220 nm

EXAMPLE 1-3

Compound 12

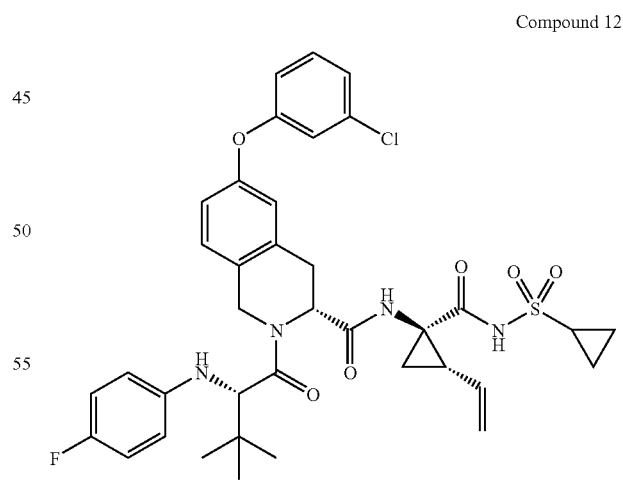

(R)-6-(3-chlorophenoxy)-N-((1R,2S)-1-(cyclopropylsulfonylcarbamoyl)-2-vinylcyclopropyl)-2-((S)-2-(4-fluorophenylamino)-3,3-dimethylbutanoyl)-1,2,3,4-tetrahydroisoquinoline-3-carboxamide Compound 12 was synthesized according to the procedure described in Example 1-1 and separated as a diasteriomer, (3.2 mg, 6%) MS m/e 722 (M⁻–H), using the following preparative HPLC conditions (Biotage SP4 system using SPX software; version 2: Column: Biotage, KP-C18-HS, 12+M1296-1, 35-70 micron particle size, 90-angstrom pore size Mobile Phase Gradient: 0-95% B in 40-6 mL fractions
A: water
B: MeCN
Flow rate: 15 mL/min
Temperature: 25 C
Wavelength: 220 nm

EXAMPLE 1-4

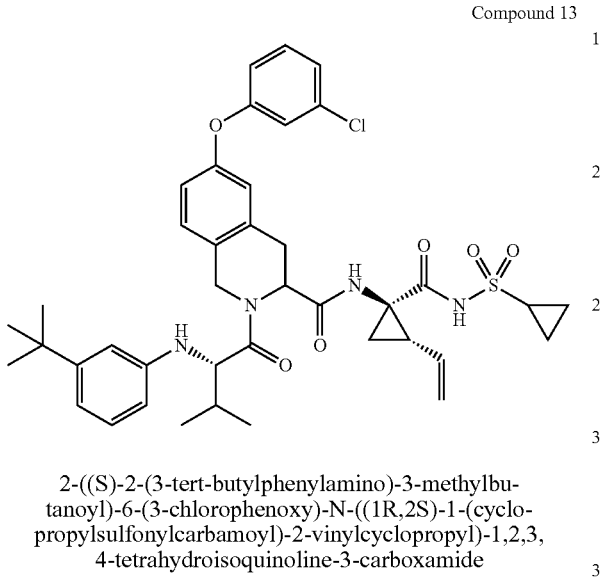

Compound 13

2-((S)-2-(3-tert-butylphenylamino)-3-methylbutanoyl)-6-(3-chlorophenoxy)-N-((1R,2S)-1-(cyclopropylsulfonylcarbamoyl)-2-vinylcyclopropyl)-1,2,3,4-tetrahydroisoquinoline-3-carboxamide Compound 13 was synthesized according to the procedure described in Example 1-1. Purification by loading crude material on a Biotage SP4 using a size 12, C-18 samplet and column for purification. Eluting with a gradient from 5% acetonitrile/water to 100% acetonitrile/water over 40-6 mL fractions. Product was a white solid upon concentration. MS m/e 747 (M⁻).

EXAMPLE 1-5

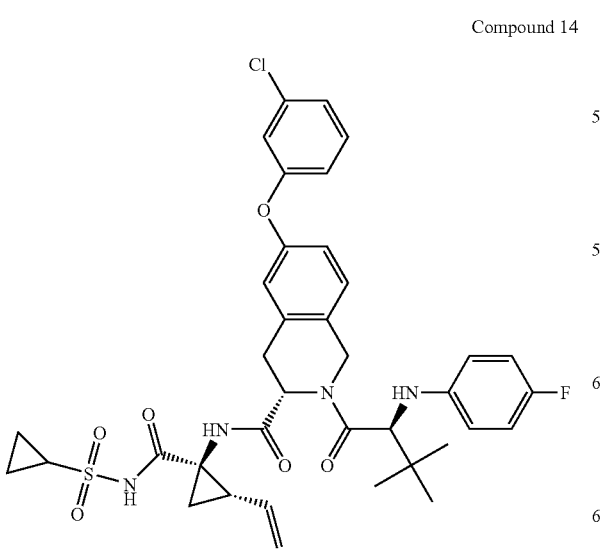

Compound 14

(S)-6-(3-chlorophenoxy)-N-((1R,2S)-1-(cyclopropylsulfonylcarbamoyl)-2-vinylcyclopropyl)-2-((S)-2-(4-fluorophenylamino)-3,3-dimethylbutanoyl)-1,2,3,4-tetrahydroisoquinoline-3-carboxamide Compound 14 was synthesized according to the procedure described in Example 1-1 and separated as a diasteriomer, (2.5 mg, 5%) MS m/e 729 (M⁻), using the following preparative HPLC conditions (Biotage SP4 system using SPX software; version 2: Column: Biotage, KP-C18-HS, 12+M1296-1, 35-70 micron particle size, 90-angstrom pore size Mobile Phase Gradient: 0-95% B in 40-6 mL fractions
A: water
B: MeCN
Flow rate: 15 mL/min
Temperature: 25 C
Wavelength: 220 nm Another method used in preparing compounds with general Formula I is shown below.

Method:

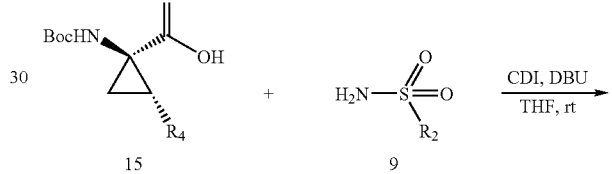

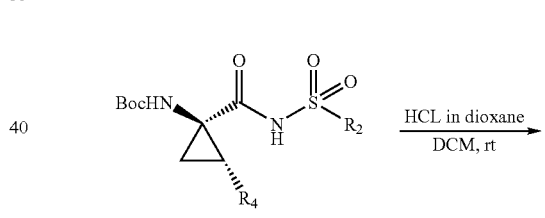

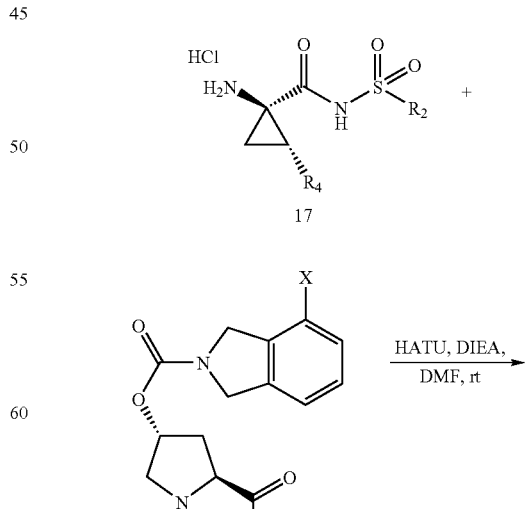

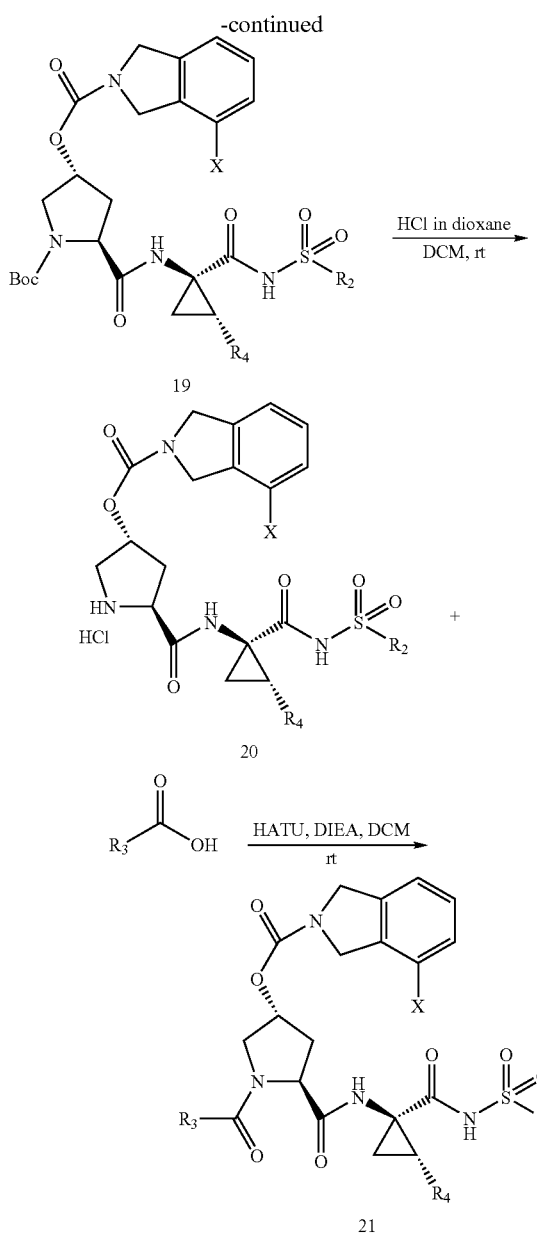

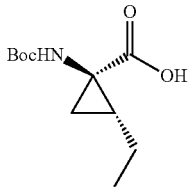

The following intermediates were prepared as described herein:

Compound 22

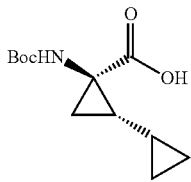

(1R,2S)-1-(tert-butoxycarbonylamino)-2-cyclopropylcyclopropane carboxylic acid

A 30 mL ether solution of (1R,2S)-ethyl 1-(tert-butoxycarbonylamino)-2-vinylcyclopropanecarboxylate (1.0 g, 3.9 mmol, prepared as described in WO2005037214) in a 500 mL round-bottomed flask equipped with a stir bar was first cooled in an acetone-ice bath to approx. −15° C., then an ether solution of diazomethane (33 ml, 20 mmol) was added in one portion to the above solution. While stirring vigorously and keeping the reaction open to air, Pd(OAc)$_2$ (0.088 g, 0.39 mmol) was added to in one portion to the reaction at −15° C. After the active effervescence subsided, the reaction was allowed to stir for another 5 min at −15° C. and concentrated down to fairly clean crude product. The crude could be further purified with flash chromatography on silica (eluent=hexanes/EtOAc 5:1), giving the titled compound as a colorless thick oil (1.0 g, 95% yield). $^1$H-NMR (400 MHz, CDCl$_3$) δ 5.10 (br s, 1 H), 4.18-4.24 (m, 2 H), 1.60-1.64 (m, 2 H), 1.44 (s, 9 H), 1.27 (t, 3 H), 1.05-1.11 (m, 1 H), 0.83-0.89 (m, 1H), 0.47-0.58 (m, 2 H), 0.30-0.34 (m, 2 H). LCMS (APCI+) 170.0 (MH$^+$−Boc).

(1R,2S)-ethyl 1-(tert-butoxycarbonylamino)-2-cyclopropylcyclopropanecarboxylate (0.578 g, 2.15 mmol), was dissolved in 10 mL mixed solvent of THF:MeOH:water (2:2:1 v/v), followed by addition of LiOH—H$_2$O (0.270 g, 6.44 mmol) in one portion at rt. Stirred it at rt over 2 days. After removal of most solvent, the white solid reaction residue was taken up in water (30 mL) and washed with ether (30 mL). The aqueous layer was then acidified with 1N HCl until pH reached 2. It was then extracted with EtOAc (2×50 mL), and the combined organic extract was washed with brine and dried over Na$_2$SO$_4$, giving the acid, (1R,2S)-1-(tert-butoxycarbonylamino)-2-cyclopropylcyclopropane carboxylic acid, as a white fluffy solid (0.48 g, 93%).

Compound 23

(1R,2R)-1-(tert-butoxycarbonylamino)-2-ethylcyclopropanecarboxylic acid (1R,2S)-1-(tert-butoxycarbonyl)-2-vinylcyclopropanecarboxylic acid (10.0 g, 44.0 mmol, prepared as described in WO2005037214) was dissolved in MTBE (250 mL) and hydrogenated (1 atm H$_2$) over Pd(OH)$_2$/C (1.24 g, 8.80 mmol) for 5 h at rt. The reaction was then stopped, filtered and concentrated down to 30 mL, followed by addition of 300 mL hexanes while stirring vigorously. After 60 min, the fine white precipitate was filtered, yielding the titled compound as a fine off-white powder (4.2 g, 42% yield). $^1$H-NMR (400 MHz, d$^6$-DMSO) δ 12.2 (s, 1 H), 7.41 (s, 1 H), 1.29-1.54 (m, 3 H), 1.36 (s, 9 H), 1.18-1.21 (m, 1 H), 0.96-0.98 (m, 1 H), 0.90 (t, 3 H).

EXAMPLE 2-1

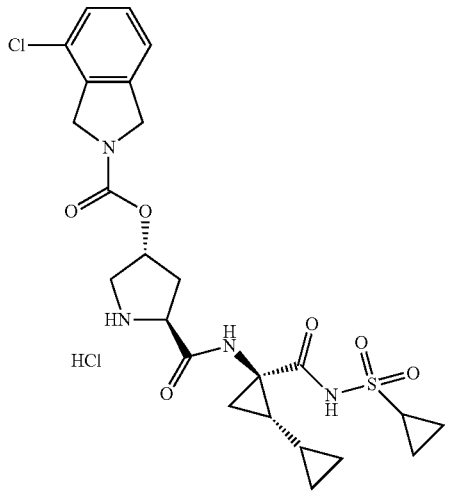

Compound 24

[(3R,5S)-5-((1R,2S)-1-(cyclopropylsulfonylcarbamoyl)-2-cyclopropylcyclopropylcarbamoyl)pyrrolidin-3-yl]4-chloroisoindoline-2-carboxylate hydrochloride

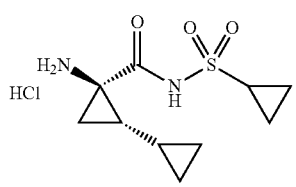

Compound 25

Step 1: Synthesis of (1R,2S)-1-amino-N-(cyclopropylsulfonyl) 2-cyclopropylcyclopropane carboxamide hydrochloride (Compound 25)

(1R,2S)-1-(tert-butoxycarbonylamino)-2-cyclopropylcyclopropane carboxylic acid (484 mg, 2.01 mmol), was dissolved in 20 mL THF, followed by addition of CDI (390 mg, 2.41 mmol) in one portion at rt. The reaction was stirred in a 60° C. sandbath for 4 h, cooled to rt, and cyclopropanesulfonamide (292 mg, 2.41 mmol) and DBU (366 mg, 2.41 mmol) were added. The reaction was stirred at rt for overnight. The reaction was then diluted with 300 mL EtOAc and washed with 1 N HCl (2×15 mL), water, brine (10 mL each), and dried (Na$_2$SO$_4$), giving a white solid after removal of solvent (0.63 g, 91% yield). This crude product was determined to be fairly clean by $^1$H-NMR and LCMS (APCI+, 245.0, MH$^+$–Boc), hence was directly used for the next deprotection step without further purification.

The N-protected acylsulfonamide product from the previous step, (1R,2S)-1-(tert-butoxycarbonylamino)-2-cyclopropylcyclopropane carboxylic acid (0.63 g, 1.8 mmol), was dissolved in 20 mL 4 N HCl (dioxane) and stirred at rt for 150 min. Removal of solvent gave the product as a white foamy solid. It was used directly in the next coupling step without further purification.

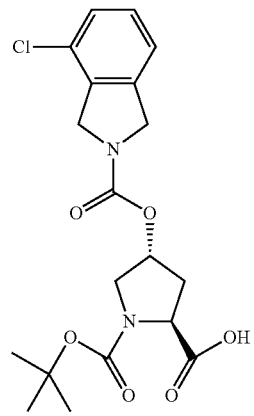

Compound 26

Step 2: Synthesis of (2S,4R)-1-(tert-butoxycarbonyl)-4-(4-chloroisoindoline-2-carbonyloxy)pyrrolidine-2-carboxylic acid To a solution of (2S,4R)-1-tert-butyl 2-methyl 4-hydroxypyrrolidine-1,2-dicarboxylate (500 mg, 2.04 mmol) in dry THF (6 mL) was added CDI (430 mg, 2.65 mmol) in one portion and the mixture was stirred at rt for 6 h. The amine, 4-chloroisoindoline hydrochloride (0.89 g, 4.7 mmol) was then added in portions, followed by slow addition of DIEA (1.07 mL, 6.12 mmol). The reaction was stirred at rt for overnight. The reaction was diluted with 120 mL EtOAc, washed with 1N HCl (2×50 mL), water and brine (50 mL each), and dried over Na$_2$SO$_4$ and concentrated down to a thick brownish oil. The crude was purified by silica chromatography (eluent=hexanes/EtOAc 2:1), giving the ester product, (2S,4R)-1-tert-butyl 2-methyl 4-(4-chloroisoindoline-2-carbonyloxy)pyrrolidine-1,2-dicarboxylate, as a light pinkish foamy solid (0.79 g, 91% yield).

This ester product, (2S,4R)-1-tert-butyl 2-methyl 4-(4-chloroisoindoline-2-carbonyloxy)pyrrolidine-1,2-dicarboxylate (0.78 g, 1.8 mmol) was then dissolved in a mixture of solvent THF:MeOH:water 2:2:1 (v/v) (5.4 mL), followed by addition of LiOH—H$_2$O (0.15 g, 3.7 mmol). After stirring at rt for overnight, the reaction was concentrated to near dryness. The resulting solid residue was re-dissolved in water (40 mL) and washed with ether (2×30 mL). The aqueous layer was acidified with 1N HCl to pH ~2 and the combined EtOAc extracts (3×30 mL) was washed with brine and dried (Na$_2$SO$_4$), giving the titled product as a white foamy solid after evaporation of solvent.

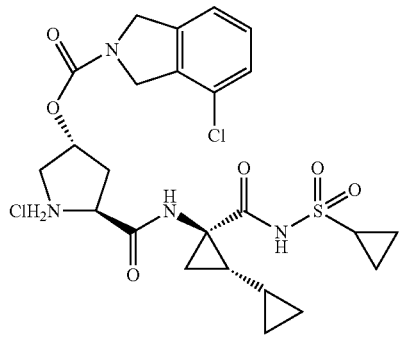

Compound 27

Step 3: Synthesis of (3R,5S)-5-((1R,2S)-1-(cyclopropylsulfonylcarbamoyl)-2-cyclopropylcyclopropylcarbamoyl)pyrrolidin-3-yl]4-chloroisoindoline-2-carboxylate hydrochloride (2S,4R)-1-(tert-butoxycarbonyl)-4-(4-chloroisoindoline-2-carbonyloxy)pyrrolidine-2-carboxylic acid 26 (0.35 g, 0.852 mmol), (1R,2S)-1-amino-2-cyclopropyl-N-(cyclopropylsulfonyl)cyclopropanecarboxamide hydrochloride 25 (0.287 g, 1.02 mmol) and HATU (0.389 g, 1.02 mmol) were dissolved in DriSolve DMF (8.5 mL), and cooled in an ice bath. DIEA (d 0.742) (0.445 ml, 2.56 mmol) was then added to reaction drop-wise. The reaction was allowed to warm up to rt slowly and stirred overnight. After reaching completion, the reaction was diluted with water (120 mL) and extracted with EtOAc (3×150 mL). The combined organic extract was washed with 0.5 N HCl (200 mL), brine (150 mL) and dried over Na$_2$SO$_4$. Removal of solvent yielded the crude product as a light yellowish foamy solid, which was purified by reverse phase chromatography (eluent: 5 to 95% MeCN/water), giving pure desired product as a white solid (0.40 g, 70% yield). LCMS (APCI+): 537.2 (MH$^+$–Boc).

This product was then treated with 4N HCl (dioxane) for 6 h at rt to remove the Boc protective group and yield the titled compound, [(3R,5S)-5-((1R,2S)-1-(cyclopropylsulfonylcarbamoyl)-2-cyclopropylcyclopropylcarbamoyl)pyrrolidin-3-yl]4-chloroisoindoline-2-carboxylate, as its HCl salt.

EXAMPLE 2-2

Compound 28

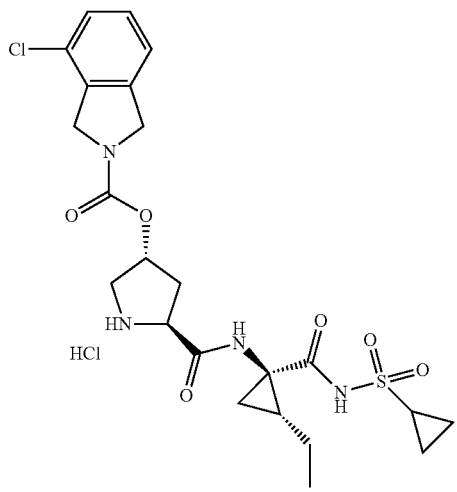

[(3R,5S)-5-((1R,2R)-1-(cyclopropylsulfonylcarbamoyl)-2-ethylcyclopropylcarbamoyl)pyrrolidin-3-yl]4-chloroisoindoline-2-carboxylate hydrochloride Compound 28 was prepared in a similar fashion as described for compound [(3R,5S)-5-((1R,2S)-2-(cyclopropylsulfonylcarbamoyl)-2-cyclopropylcyclopropylcarbamoyl)pyrrolidin-3-yl]4-chloroisoindoline-2-carboxylate hydrochloride 27 in other parts of this application, except that (1R,2R)-1-(tert-butoxycarbonylamino)-2-ethylcyclopropane carboxylic acid P1 intermediate was used in lieu of (1R,2S)-1-(tert-butoxycarbonylamino)-2-cyclopropylcyclopropane carboxylic acid.

EXAMPLE 2-3

Compound 29

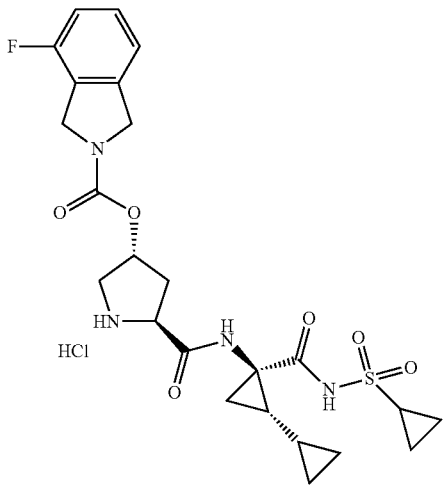

[(3R,5S)-5-((1R,2S)-1-(cyclopropylsulfonylcarbamoyl)-2-cyclopropylcyclopropylcarbamoyl)pyrrolidin-3-yl]4-fluoroisoindoline-2-carboxylate hydrochloride Compound 29 was prepared in a similar fashion as described for compound [(3R,5S)-5-((1R,2S)-1-(cyclopropylsulfonylcarbamoyl)-2-cyclopropylcyclopropylcarbamoyl)pyrrolidin-3-yl]4-chloroisoindoline-2-carboxylate hydrochloride 27 in other parts of this application, except that 4-fluoroisoindoline hydrochloride P2 intermediate was used in lieu of 4-chloroisoindoline hydrochloride in the coupling step with (2S,4R)-1-tert-butyl 2-methyl 4-hydroxypyrrolidine-1,2-dicarboxylate.

EXAMPLE 2-4

Compound 30

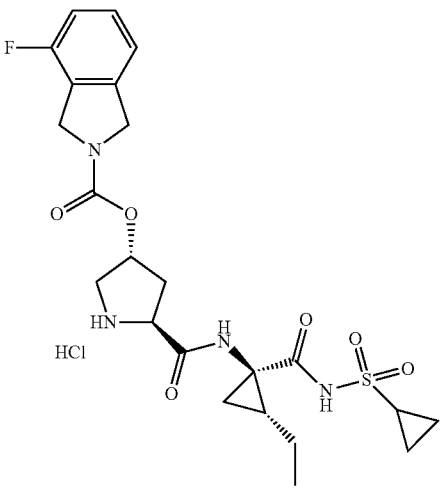

[(3R,5S)-5-((1R,2R)-1-(cyclopropylsulfonylcarbamoyl)-2-ethylcyclopropylcarbamoyl)pyrrolidin-3-yl]4-fluoroisoindoline-2-carboxylate hydrochloride Compound 30 was prepared in a similar fashion as described for compound [(3R,5S)-5-((1R,2R)-1-(cyclopropylsulfonylcarbamoyl)-2-ethylcyclopropylcarbamoyl)pyrrolidin-3-yl]4-chloroisoindoline-2-carboxylate hydrochloride 28 in other parts of this application, except that 4-fluoroisoindoline hydrochloride P2 intermediate was used in lieu of 4-chloroisoindoline hydrochloride in the coupling step with (2S,4R)-1-tert-butyl 2-methyl 4-hydroxypyrrolidine-1,2-dicarboxylate.

EXAMPLE 2-5

Compound 31

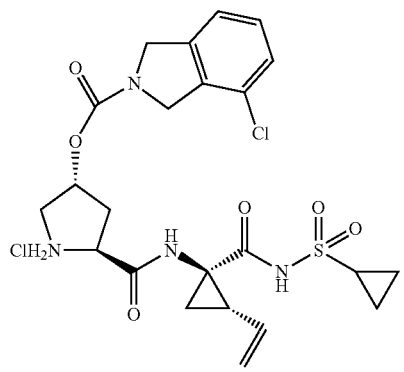

[(3R,5S)-5-((1R,2S)-1-(cyclopropylsulfonylcarbamoyl)-2-vinylcyclopropylcarbamoyl)pyrrolidin-3-yl]4-chloroisoindoline-2-carboxylate hydrochloride Compound 31 was prepared in a similar fashion as described for compound [(3R,5S)-5-((1R,2S)-1-(cyclopropylsulfonylcarbamoyl)-2-cyclopropylcyclopropylcarbamoyl)pyrrolidin-3-yl]4-chloroisoindoline-2-carboxylate hydrochloride 27 in other parts of this application, except that (1R,2S)-1-(tert-butoxycarbonylamino)-2-vinylcyclopropanecarboxylic acid PI intermediate was used in lieu of (1R,2S)-1-(tert-butoxycarbonylamino)-2-cyclopropylcyclopropane carboxylic acid.

EXAMPLE 2-6

Compound 32

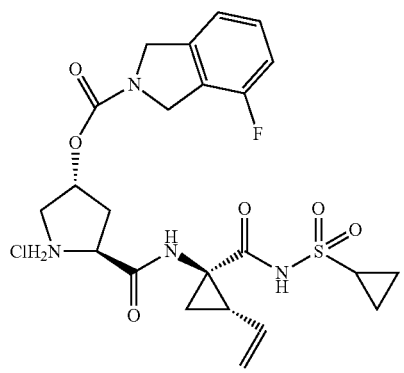

[(3R,5S)-5-((1R,2S)-1-(cyclopropylsulfonylcarbamoyl)-2-vinylcyclopropylcarbamoyl)pyrrolidin-3-yl]4-fluoroisoindoline-2-carboxylate hydrochloride Compound 32 was prepared in a similar fashion as described for compound [(3R,5S)-5-((1R,2S)-1-(cyclopropylsulfonylcarbamoyl)-2-vinylcyclopropylcarbamoyl)pyrrolidin-3-yl]4-chloroisoindoline-2-carboxylate hydrochloride 31 in other parts of this application, except that 4-fluoroisoindoline hydrochloride P2 intermediate was used in lieu of 4-chloroisoindoline hydrochloride in the coupling step with (2S,4R)-1-tert-butyl 2-methyl 4-hydroxypyrrolidine-1,2-dicarboxylate.

EXAMPLE 2-7

Compound 33

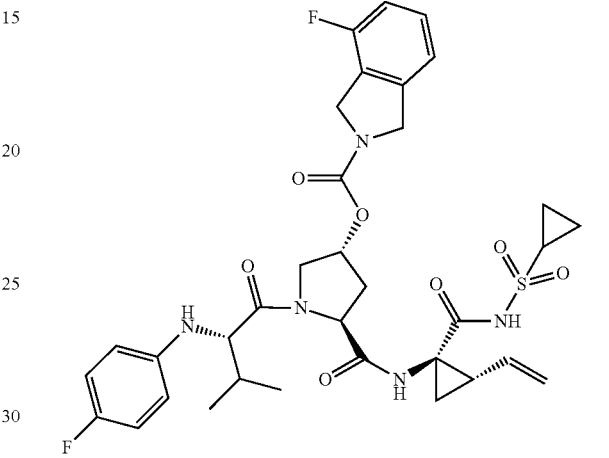

(3R,5S)-5-((1R,2S)-1-(cyclopropylsulfonylcarbamoyl)-2-vinylcyclopropylcarbamoyl)-1-((S)-2-(4-fluorophenylamino)-3-methylbutanoyl)pyrrolidin-3-yl 4-fluoroisoindoline-2-carboxylate

[(3R,5S)-5-((1R,2S)-1-(cyclopropylsulfonylcarbamoyl)-2-vinylcyclopropylcarbamoyl)pyrrolidin-3-yl]4-fluoroisoindoline-2-carboxylate hydrochloride (0.050 g, 0.092 mmol), (S)-2-(4-fluorophenylamino)-3-methylbutanoic acid (0.021 g, 0.10 mmol) and HATU (0.042 g, 0.11 mmol) in DCM (3 mL) was added DIEA (0.048 mL, 0.28 mmol) and the reaction was stirred at rt for 5 hr. $H_2O$ (5 mL) and saturated $KHSO_4$ solution (3 mL) was added. The mixture was extracted with ether (15 mL), washed with brine (10 mL) and dried over sodium sulfate. After removal of solvent, the residue was purified by chromatography (hexane:Ethyl acetate=1:2) to give the (3R,5S)-5-((1R,2S)-1-(cyclopropylsulfonylcarbamoyl)-2-vinylcyclopropylcarbamoyl)-1-((S)-2-(4-fluorophenylamino)-3-methylbutanoyl)pyrrolidin-3-yl 4-fluoroisoindoline-2-carboxylate (0.042 g, 65%) as white solid. MS: Calcd.: 699; Found: [M+H]$^+$ 700. $^1$H NMR (400 MHz, d$^6$-DMSO) δ 10.91, 10.85 & 10.58 (s, 1H), 9.16, 9.05 & 8.84 (s, 1H), 7.40 (m, 1H), 7.04-7.21 (m, 2H), 6.71 (m, 2H), 6.60 (m, 2H), 5.62 (m, 1H), 5.10-5.17 (m, 4H), 4.68 (s, 2H), 4.41-4.60 (m, 2H), 4.32 (m, 1H), 4.09 (m, 1H), 3.97 (m, 1H), 3.80 (m, 1H), 2.94 (m, 1H), 2.22 (m 1H), 2.00-2.18 (m, 3H), 1.71 (m, 1H), 1.20-1.31 (m, 2H), 0.87-1.10 (m, 9H).

EXAMPLE 2-8

Compounds 34-60 were prepared in a similar fashion as described for compound [(3R,5S)-5-((1R,2S)-1-(cyclopropylsulfonylcarbamoyl)-2-vinylcyclopropylcarbamoyl)-1-

((S)-2-(4-fluorophenylamino)-3-methylbutanoyl)pyrrolidin-3-yl]4-fluoroisoindoline-2-carboxylate 33 in other parts of this application.

Compound 34

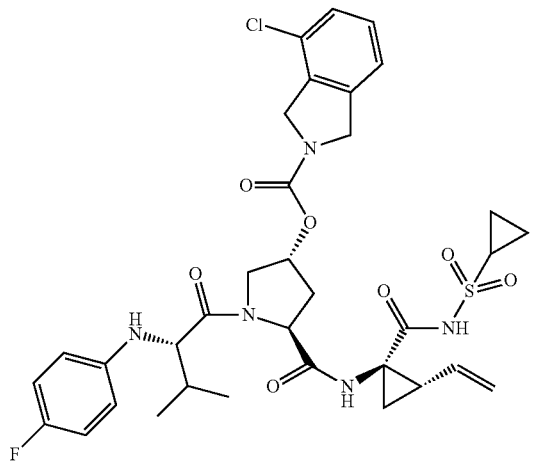

[(3R,5S)-5-((1R,2S)-1-(cyclopropylsulfonylcarbamoyl)-2-vinylcyclopropylcarbamoyl)-1-((S)-2-(4-fluorophenylamino)-3-methylbutanoyl)pyrrolidin-3-yl]4-chloroisoindoline-2-carboxylate 39% yield; MS: Calcd.: 715; Found: [M+H]+ 716. $^1$H NMR (400 MHz, d$^6$-DMSO) δ 10.88, 10.83 & 10.58 (s, 1H), 9.17, 9.08 & 8.83 (s, 1H), 7.21-7.40 (m, 3H), 6.72 (m, 2H), 6.61 (m, 2H), 5.60 (m, 1H), 5.35 (m, 1H), 5.20-5.28 (m, 2H), 5.12 (m, 1H), 4.68 (s, 1H), 4.41-4.62 (m, 3H), 4.30 (m, 1H), 4.12 (m, 1H), 3.98 (m, 1H), 3.81 (m, 1H), 2.93 (m, 1H), 2.25 (m 1H), 2.00-2.20 (m, 3H), 1.68 (m, 1H), 1.20-1.35 (m, 2H), 0.87-1.10 (m, 9H).

Compound 35

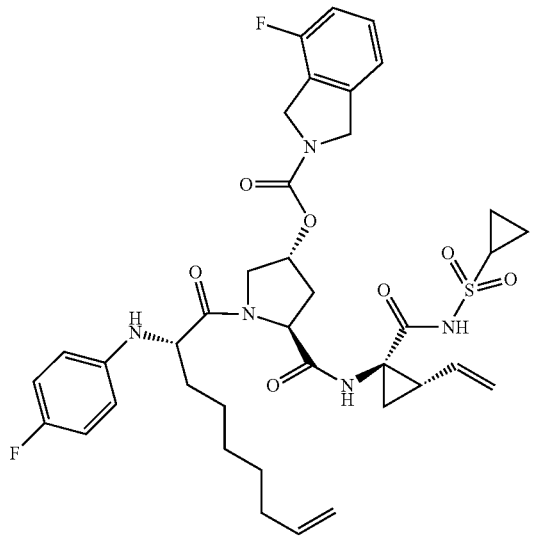

[(3R,5S)-5-((1R,2S)-1-(cyclopropylsulfonylcarbamoyl)-2-vinylcyclopropylcarbamoyl)-1-((S)-2-(4-fluorophenylamino)non-8-enoyl)pyrrolidin-3-yl]4-floroisoindoline-2-carboxylate 39% yield; MS: Calcd.: 753; Found: [M+H]+ 754.

Compound 36

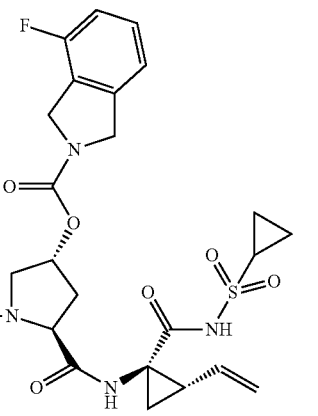

[(3R,5S)-5-((1R,2S)-1-(cyclopropylsulfonylcarbamoyl)-2-vinylcyclopropylcarbamoyl)-1-((S)-2-(4-bromophenylamino)-3-methylbutanoyl)pyrrolidin-3-yl] 4-fluoroisoindoline-2-carboxylate 72% yield; MS: Calcd.: 761; Found: [M+H]+ 762. $^1$H NMR (400 MHz, d$^6$-DMSO) δ 10.83, 10.80 & 10.52 (s, 1H), 9.04, 9.00 & 8.80 (s, 1H), 7.38 (m, 1H), 7.16-7.20 (m, 2H), 6.98 (m, 2H), 6.52 (m, 2H), 5.60 (m, 2H), 5.28 (m, 1H), 5.22 (m, 1H), 5.08 (m, 1H), 4.63 (s, 2H), 4.40-4.60 (m, 2H), 4.32 (m, 1H), 4.09 (m, 1H), 3.95 (m, 1H), 3.78 (m, 1H), 2.96 (m, 1H), 2.23 (m 1H), 2.00-2.18 (m, 3H), 1.67 (m, 1H), 1.21-1.31 (m, 2H), 0.93-1.10 (m, 9H).

Compound 37

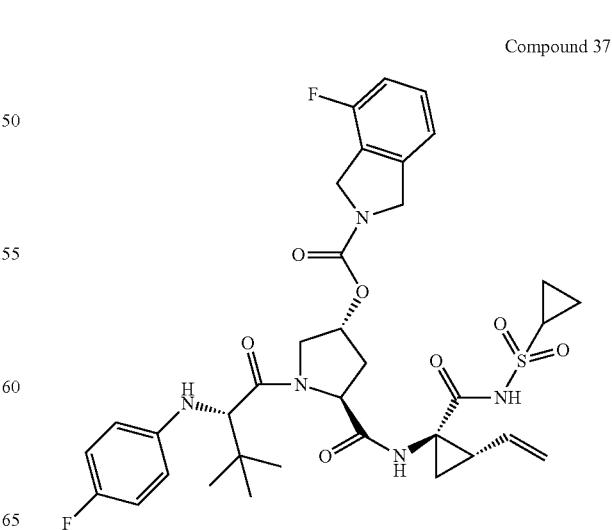

[(3R,5S)-5-((1R,2S)-1-(cyclopropylsulfonylcarbamoyl)-2-vinylcyclopropylcarbamoyl)-1-((S)-2-(4-fluorophenylamino)-3,3-methylbutanoyl)pyrrolidin-3-yl] 4-fluoroisoindoline-2-carboxylate 38% yield; MS: Calcd.: 713; Found: [M+H]⁺ 714. ¹H NMR (400 MHz, d⁶-DMSO) δ 10.98, 10.96 & 10.57 (s, 1H), 8.94, 8.85 & 8.75 (s, 1H), 7.38 (m, 1H), 7.04-7.21 (m, 2H), 6.71 (m, 2H), 6.63 (m, 2H), 5.60 (m, 1H), 5.20-5.33 (m, 2H), 5.11 (m, 1H), 5.04 (m, 1H), 4.64 (m, 2H), 4.2-4.36 (m, 1H), 4.29 (m, 2H), 4.10 (m, 1H), 4.01 (m, 1H), 3.79 (m, 1H), 2.92 (m, 1H), 2.25 (m 1H), 2.17 (m, 1H), 2.04 (m, 1H), 1.70 (m, 1H), 1.27 (m, 1H), 1.22 (m, 1H), 0.98-1.08 (m, 12H).

Compound 37

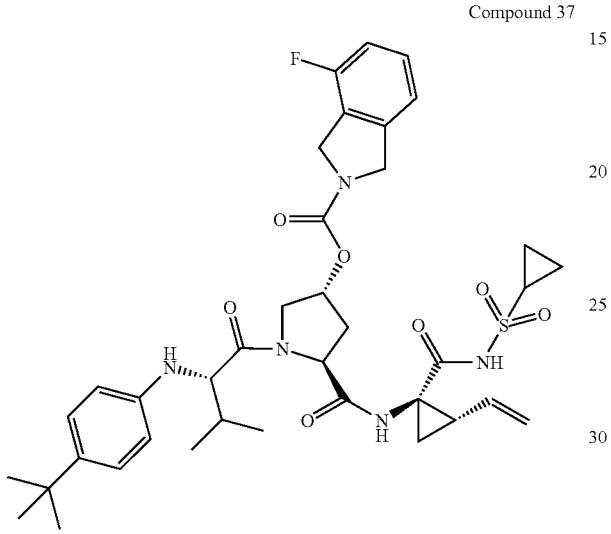

[(3R,5S)-1-((S)-2-(4-tert-butylphenylamino)-3-methylbutanoyl)-5-((1R,2S)-1-(cyclopropylsulfonylcarbamoyl)-2-vinylcyclopropylcarbamoyl)pyrrolidin-3-yl]4-fluoroisoindoline-2-carboxylate 46% yield; MS: Calcd.: 737; Found: [M+H]⁺ 738. ¹H NMR (400 MHz, d⁶-DMSO) δ 10.92, 10.84 & 10.58 (s, 1H), 9.17, 9.08 & 8.86 (s, 1H), 7.38 (m, 1H), 7.16-7.22 (m, 2H), 6.90 (m, 2H), 6.45 (m, 2H), 5.62 (m, 1H), 5.36 (m, 1H), 5.08-5.27 (m, 3H), 4.62-4.67 (m, 3H), 4.47 (m, 1H), 4.36 (m, 1H), 4.17 (m, 1H), 3.80-3.93 (m, 2H), 2.94 (m, 1H), 2.25 (m 1H), 1.96-2.18 (m, 3H), 1.74 (m, 1H), 1.23 (m, 1H), 0.98-1.13 (m, 19H).

Compound 39

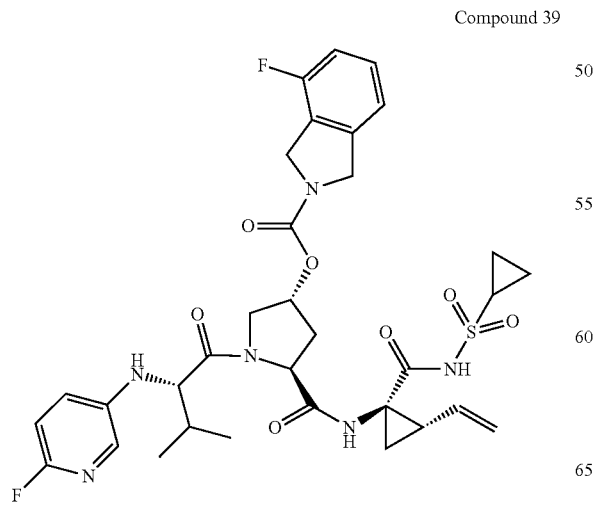

[(3R,5S)-5-((1R,2S)-1-(cyclopropylsulfonylcarbamoyl)-2-vinylcyclopropylcarbamoyl)-1-((S)-2-(6-fluoropyridin-3-ylamino)-3-methylbutanoyl)pyrrolidin-3-yl]4-fluoroisoindoline-2-carboxylate 49% yield; MS: Calcd.: 700; Found: [M+H]⁺ 701.

Compound 40

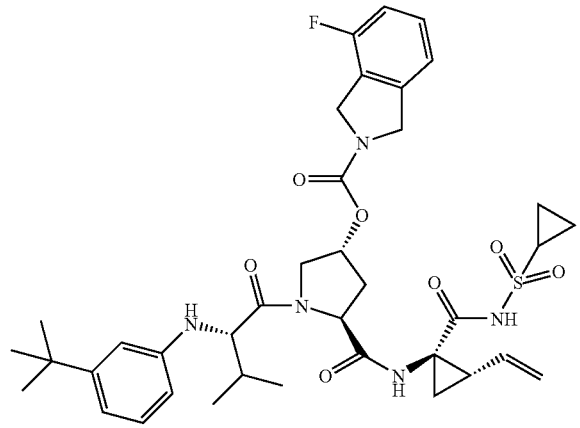

[(3R,5S)-1-((S)-2-(3-tert-butylphenylamino)-3-methylbutanoyl)-5-((1R,2S)-1-(cyclopropylsulfonylcarbamoyl)-2-vinylcyclopropylcarbamoyl)pyrrolidin-3-yl]4-fluoroisoindoline-2-carboxylate 61% yield; MS: Calcd.: 737; Found: [M+H]⁺ 738. ¹H NMR (400 MHz, d⁶-DMSO) δ 10.94, 10.85 & 10.60 (s, 1H), 9.18, 9.09 & 8.88 (s, 1H), 7.39 (m, 1H), 7.08-7.24 (m, 2H), 6.92 (m, 1H), 6.72 (s, 1H), 6.33-6.46 (m, 2H), 5.64 (m, 1H), 5.37 (s, 1H), 5.23 (m, 1H), 5.12 (m, 2H), 4.71 (s, 2H), 4.60 (m, 1H), 4.44 (m, 1H), 4.35 (m, 1H), 4.02-4.16 (m, 2H), 3.85 (m, 1H), 2.94 (m, 1H), 2.24 (m 1H), 2.02-2.17 (m, 3H), 1.74 (m, 1H), 1.34 (m, 1H), 0.95-1.15 (m, 19H).

Compound 41

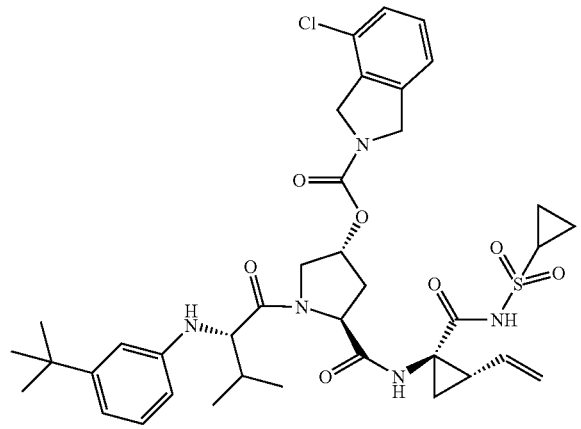

[(3R,5S)-1-((S)-2-(3-tert-butylphenylamino)-3-methylbutanoyl)-5-((1R,2S)-1-(cyclopropylsulfonylcarbamoyl)-2-vinylcyclopropylcarbamoyl)pyrrolidin-3-yl]4-chloroisoindoline-2-carboxylate 55% yield; MS: Calcd.: 753; Found: [M+H]⁺ 754. ¹H NMR (400 MHz, d⁶-DMSO) δ 10.92, 10.84 & 10.60 (s, 1H), 9.18, 9.10 & 8.90 (s, 1H), 7.22-7.38 (m, 3H), 6.80 (m, 1H), 6.73 (m, 1H), 6.29-6.46 (m, 2H), 5.62 (m, 1H), 5.38 (s, 1H), 5.24 (m, 1H), 5.15 (m, 2H), 4.72 (s, 1H), 4.40-4.62 (m, 3H), 4.33 (m, 1H), 4.13 (m, 1H), 4.05 (m, 1H), 3.86 (m, 1H), 2.93 (m, 1H), 2.22 (m 1H), 2.00-2.19 (m, 3H), 1.72 (m, 1H), 1.20-1.36 (m, 2H), 0.93-1.18 (m, 18H).

Compound 42

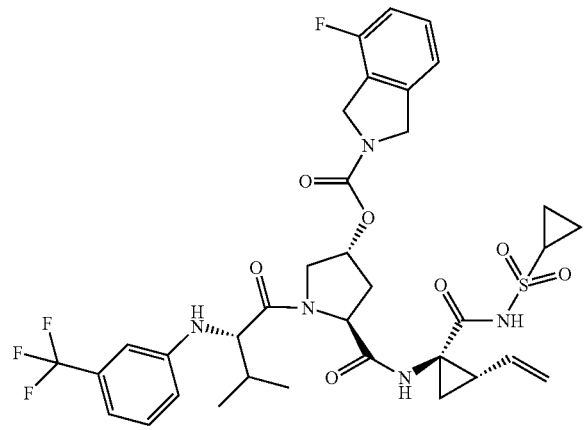

[(3R,5S)-5-((1R,2S)-1-(cyclopropylsulfonylcarbamoyl)-2-vinylcyclopropylcarbamoyl)-1-((S)-3-methyl-2-(3-(trifluoromethyl)phenylamino)butanoyl)pyrrolidin-3-yl]4-fluoroisoindoline-2-carboxylate 58% yield; MS: Calcd.: 749; Found: [M+H]⁺ 750. ¹H NMR (400 MHz, d⁶-DMSO) δ 10.94, 10.88 & 10.58 (s, 1H), 9.09, 9.04 & 8.83 (s, 1H), 7.38 (m, 1H), 7.06-7.23 (m, 3H), 6.97 (s, 1H), 6.82 (m, 1H), 6.60-6.68 (m, 1H), 5.83 (m, 1H), 5.60 (m, 1H), 5.38 (s, 1H), 5.24 (m, 1H), 5.14 (m, 1H), 4.68 (s, 2H), 4.40-4.62 (m, 2H), 4.35 (m, 1H), 4.16 (m, 2H), 3.83 (m, 1H), 2.93 (m, 1H), 2.25 (m 1H), 2.03-2.18 (m, 3H), 1.70 (m, 1H), 1.28 (m, 1H), 0.93-1.18 (m, 10H).

Compound 43

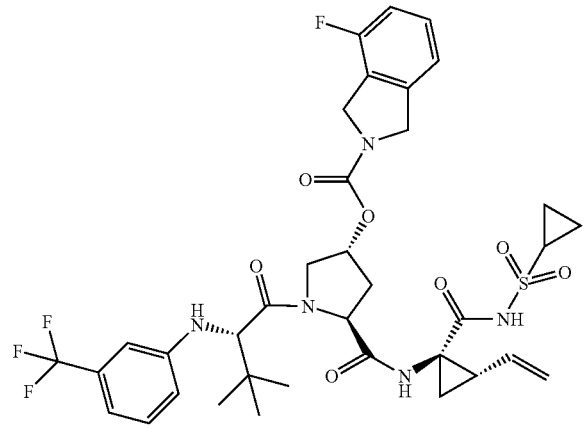

[(3R,5S)-5-((1R,2S)-1-(cyclopropylsulfonylcarbamoyl)-2-vinylcyclopropylcarbamoyl)-1-((S)-3,3-dimethyl-2-(3-(trifluoromethyl)phenylamino)butanoyl)pyrrolidin-3-yl]4-fluoroisoindoline-2-carboxylate 33% yield; MS: Calcd.: 763; Found: [M+H]⁺ 764.

Compound 44

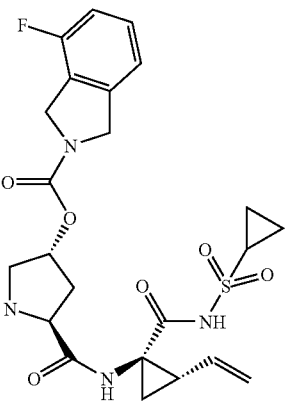

[(3R,5S)-5-((1R,2S)-1-(cyclopropylsulfonylcarbamoyl)-2-vinylcyclopropylcarbamoyl)-1-((S)-3-methyl-2-(5-(trifluoromethyl)pyridin-3-ylamino)butanoyl)pyrrolidin-3-yl]4-fluoroisoindoline-2-carboxylate 66% yield; MS: Calcd.: 750; Found: [M+H]⁺ 751.

Compound 45

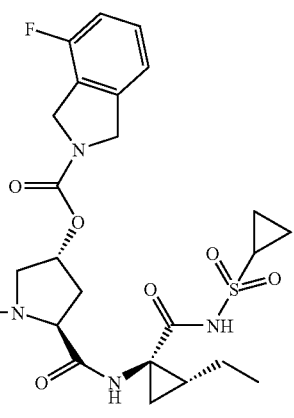

[(3R,5S)-1-((S)-2-(3-tert-butylphenylamino)-3-methylbutanoyl)-5-((1R,2R)-1-(cyclopropylsulfonylcarbamoyl)-2-ethylcyclopropylcarbamoyl)pyrrolidin-3-yl]4-fluoroisoindoline-2-carboxylate 66% yield; MS: Calcd.: 739; Found: [M+H]⁺ 740. ¹H NMR (400 MHz, d⁶-DMSO) δ 10.55 (s, 1H), 9.08 & 9.00 (s, 1H), 7.38 (m, 1H), 7.06-7.23 (m, 2H), 6.79 (m, 1H), 6.73 (s, 1H), 6.30-6.44 (m, 2H), 5.38 (s, 1H), 5.06 (m, 1H), 4.69 (s, 2H), 4.57 (m, 1H), 4.44 (m, 1H), 4.33 (m, 1H), 4.12 (m, 1H), 4.06 (m, 1H), 3.85 (m, 1H), 2.96 (m, 1H), 2.22 (m, 1H), 2.07 (m, 2H), 1.57 (m, 1H), 0.96-1.40 (m, 26H).

Compound 46

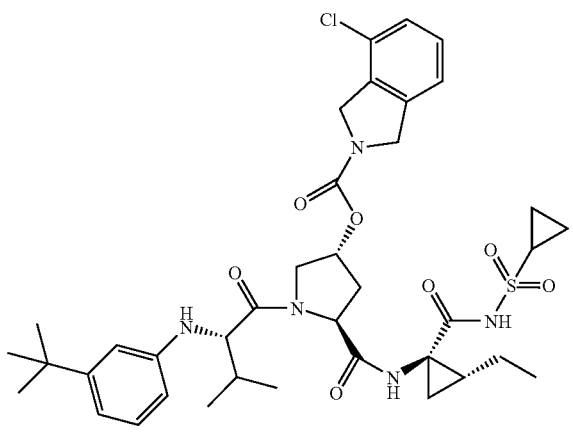

[(3R,5S)-1-((S)-2-(3-tert-butylphenylamino)-3-methylbutanoyl)-5-((1R,2R)-1-(cyclopropylsulfonylcarbamoyl)-2-ethylcyclopropylcarbamoyl)pyrrolidin-3-yl]4-chloroisoindoline-2-carboxylate 61% yield; MS: Calcd.: 755; Found: [M+H]+ 756. $^1$H NMR (400 MHz, d$^6$-DMSO) δ 10.57 (s, 1H), 9.08 & 9.01 (s, 1H), 7.21-7.38 (m, 3H), 6.80 (m, 1H), 6.72 (m, 1H), 6.34-6.44 (m, 2H), 5.36 (s, 1H), 5.04 (m, 1H), 4.73 (s, 1H), 4.38-4.62 (m, 3H), 4.31 (m, 1H), 4.10 (m, 1H), 4.05 (m, 1H), 3.84 (m, 1H), 2.96 (m, 1H), 2.22 (m, 1H), 2.08 (m, 2H), 1.58 (m, 1H), 0.94-1.42 (m, 26H).

Compound 48

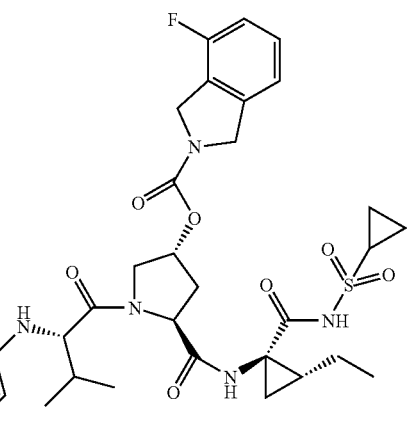

[(3R,5S)-5-((1R,2R)-1-(cyclopropylsulfonylcarbamoyl)-2-ethylcyclopropylcarbamoyl)-1-((S)-3-methyl-2-(5-(trifluoromethyl)pyridin-3-ylamino)butanoyl)pyrrolidin-3-yl]4-fluoroisoindoline-2-carboxylate 66% yield; MS: Calcd.: 752; Found: [M+H]+ 753. $^1$H NMR (400 MHz, d$^6$-DMSO) δ 10.42 (s, 1H), 8.99 & 8.96 (s, 1H), 8.20 (m, 1H), 7.82 & 7.92 (s, 1H), 7.38 (m, 2H), 7.12-7.21 (m, 2H), 6.15 (m, 1H), 5.36 (m, 1H), 4.68 (m, 2H), 4.48-4.60 (m, 2H), 4.22-4.37 (m, 3H), 3.82 (m, 1H), 2.95 (m, 1H), 2.24 (m, 1H), 2.10 (m, 2H), 0.94-1.55 (m, 18H).

Compound 47

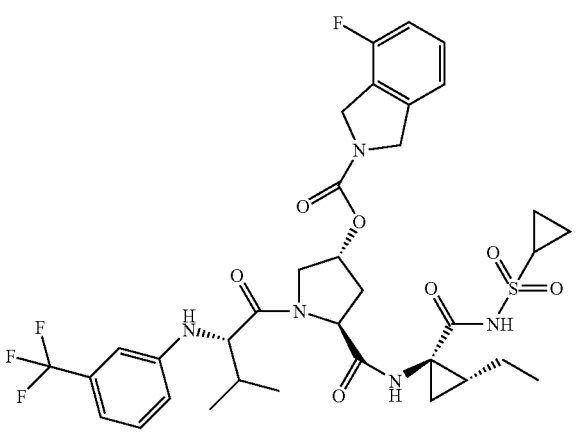

[(3R,5S)-5-((1R,2R)-1-(cyclopropylsulfonylcarbamoyl)-2-ethylcyclopropylcarbamoyl)-1-((S)-3-methyl-2-(3-(trifluoromethyl)phenylamino)butanoyl)pyrrolidin-3-yl]4-fluoroisoindoline-2-carboxylate 50% yield; MS: Calcd.: 751; Found: [M+H]+ 752.

Compound 49

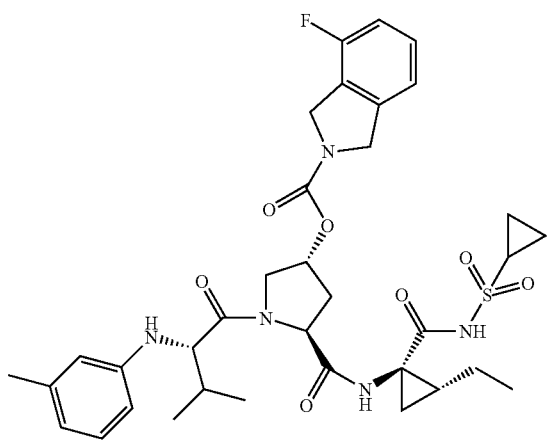

[(3R,5S)-5-((1R,2R)-1-(cyclopropylsulfonylcarbamoyl)-2-ethylcyclopropylcarbamoyl)-1-((S)-3-methyl-2-(m-tolylamino)butanoyl)pyrrolidin-3-yl]4-fluoroisoindoline-2-carboxylate 52% yield; MS: Calcd.: 697; Found: [M+H]+ 698.

Compound 50

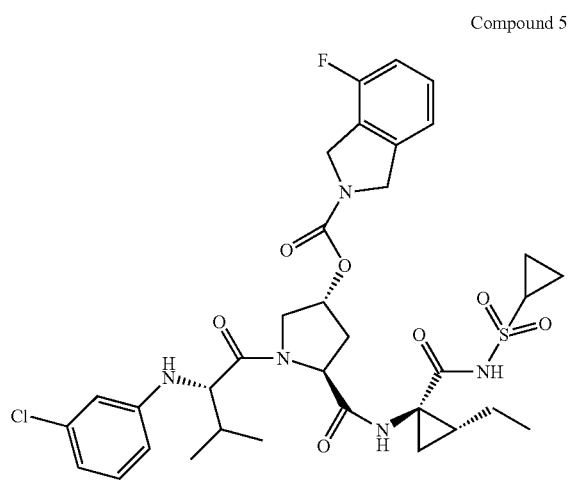

[(3R,5S)-1-((S)-2-(3-chlorophenylamino)-3-methylbutanoyl)-5-((1R,2R)-1-(cyclopropylsulfonylcarbamoyl)-2-ethylcyclopropylcarbamoyl)pyrrolidin-3-yl]4-fluoroisoindoline-2-carboxylate 56% yield; MS: Calcd.: 717; Found: [M+H]$^+$ 718.

Compound 51

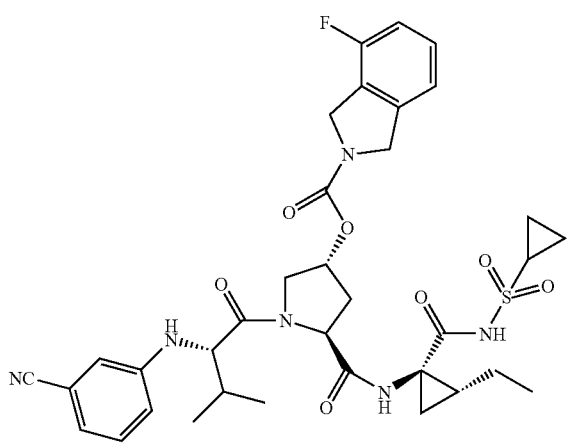

[(3R,5S)-1-((S)-2-(3-cyanophenylamino)-3-methylbutanoyl)-5-((1R,2R)-1-(cyclopropylsulfonylcarbamoyl)-2-ethylcyclopropylcarbamoyl)pyrrolidin-3-yl]4-fluoroisoindoline-2-carboxylate 59% yield; MS: Calcd.: 708; Found: [M+H]$^+$ 709

Compound 52

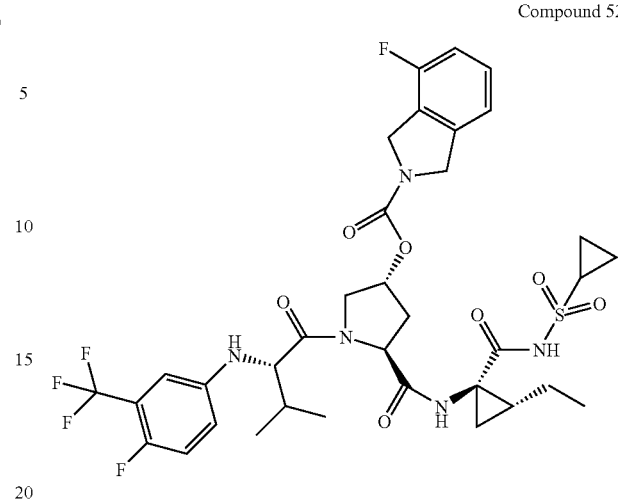

[(3R,5S)-5-((1R,2R)-1-(cyclopropylsulfonylcarbamoyl)-2-ethylcyclopropylcarbamoyl)-1-((S)-2-(4-fluoro-3-(trifluoromethyl)phenylamino)-3-methylbutanoyl)pyrrolidin-3-yl]4-fluoroisoindoline-2-carboxylate 64% yield; MS: Calcd.: 769; Found: [M+H]$^+$ 770. $^1$H NMR (400 MHz, d$^6$-DMSO) δ 10.49 (s, 1H), 8.99 & 8.95 (s, 1H), 7.41 (m, 1H), 7.07-7.37 (m, 2H), 7.04 (m, 2H), 6.89 (m, 1H), 5.73 (m, 1H), 5.36 (s, 1H), 4.68 (s, 2H), 4.58 (m, 1H), 4.45 (m, 1H), 4.31 (m, 1H), 4.12 (m, 2H), 3.83 (m, 1H), 2.94 (m, 1H), 2.24 (m, 1H), 2.08 (m, 2H), 1.54 (m, 1H), 0.82-1.42 (m, 17H).

Compound 53

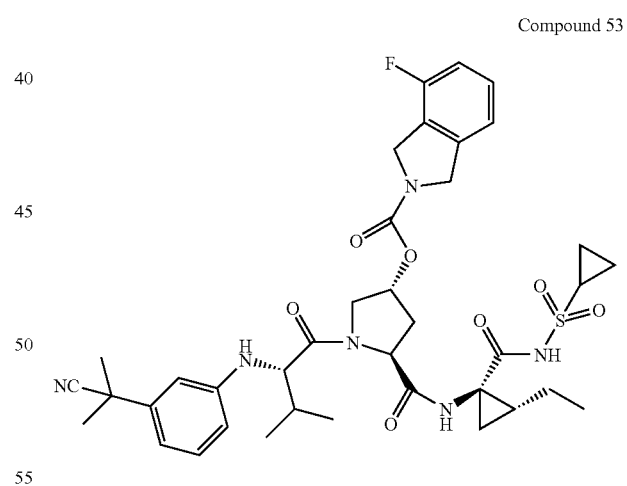

[(3R,5S)-1-((S)-2-(3-(2-cyanopropan-2-yl)phenylamino)-3-methylbutanoyl)-5-((1R,2R)-1-(cyclopropylsulfonylcarbamoyl)-2-ethylcyclopropylcarbamoyl)-pyrrolidin-3-yl]4-fluoroisoindoline-2-carboxylate 65% yield; MS: Calcd.: 750; Found: [M+H]$^+$ 751. $^1$H NMR (400 MHz, d$^6$-DMSO) δ 10.51 (s, 1H), 9.02 & 8.98 (s, 1H), 7.39 (m, 1H), 7.10-7.24 (m, 2H), 6.87-6.93 (m, 2H), 6.46-6.56 (m, 2H), 5.47 (m, 1H), 5.36 (s, 1H), 4.69 (m, 2H), 4.59 (m, 1H), 4.46 (m, 1H), 4.32 (m 1H), 4.05-4.15 (m, 2H), 3.86 (m, 1H), 2.96 (m, 1H), 2.24 (m, 1H), 2.08 (m, 2H), 0.82-1.56 (m, 24H).

(m, 1H), 4.46-4.60 (m, 2H), 4.32 (m 1H), 4.10-4.22 (m, 3H), 3.83 (m, 1H), 2.96 (m, 1H), 2.25 (m, 1H), 2.05 (m, 1H), 0.88-1.53 (m, 21H).

Compound 54

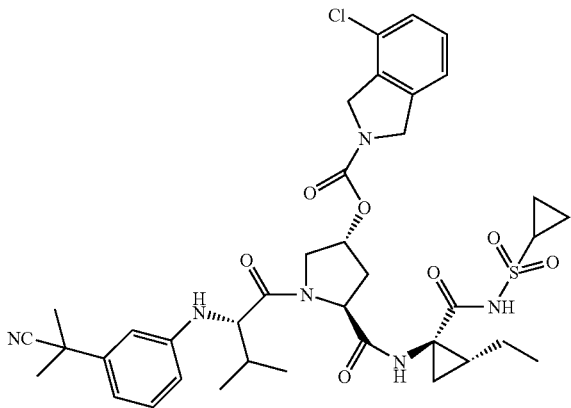

[(3R,5S)-1-((S)-2-(3-(2-cyanopropan-2-yl)phenylamino)-3-methylbutanoyl)-5-((1R,2R)-1-(cyclopropylsulfonylcarbamoyl)-2-ethylcyclopropylcarbamoyl)-pyrrolidin-3-yl]4-chloroisoindoline-2-carboxylate 61% yield; MS: Calcd.: 766; Found: [M+H]$^+$ 767. $^1$H NMR (400 MHz, d$^6$-DMSO) δ 10.51 (s, 1H), 9.04 & 8.98 (s, 1H), 7.38 & 6.98 (m, 3H), 6.56-6.91 (m, 2H), 6.47-6.56 (m, 2H), 5.49 (m, 1H), 5.37 (s, 1H), 4.73 (m, 1H), 4.41-4.63 (m, 3H), 4.32 (m 1H), 4.03-4.15 (m, 2H), 3.87 (m, 1H), 2.96 (m, 1H), 2.23 (m, 1H), 2.09 (m, 2H), 0.83-1.55 (m, 24H).

Compound 55

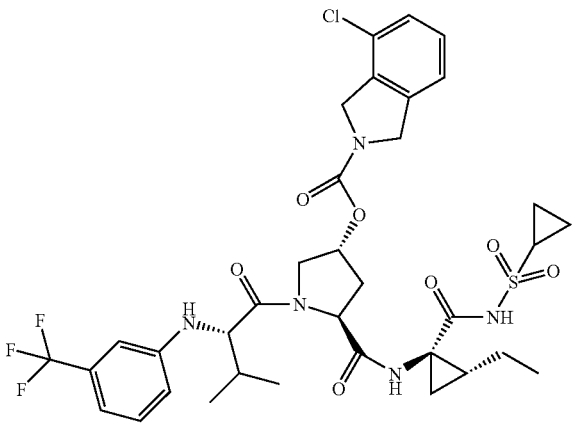

[(3R,5S)-5-((1R,2R)-1-(cyclopropylsulfonylcarbamoyl)-2-ethylcyclopropylcarbamoyl)-1-((S)-3,3-dimethyl-2-(3-(trifluoromethyl)phenylamino)butanoyl)pyrrolidin-3-yl]4-chloroisoindoline-2-carboxylate 59% yield; MS: Calcd.: 781; Found: [M+H]$^+$ 782. $^1$H NMR (400 MHz, d$^6$-DMSO) δ 10.43 (s, 1H), 8.84 & 8.77 (s, 1H), 7.37 (m, 3H), 7.14 (m, 1H), 7.04 (m, 1H), 6.85 (m, 1H), 6.56 & 6.45 (d, J=7.6 Hz, 1H), 5.71 (m, 1H), 5.34 (s, 1H), 4.71

Compound 56

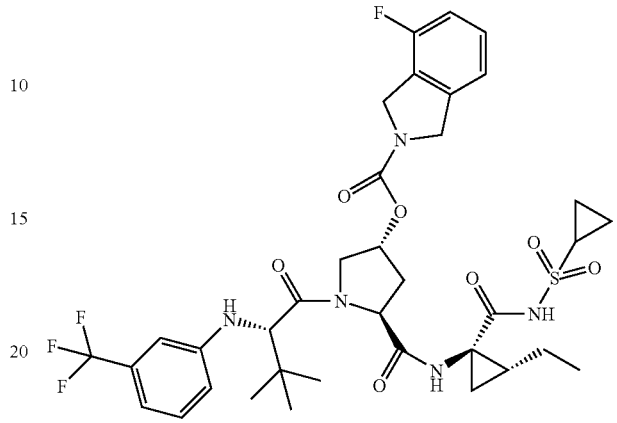

[(3R,5S)-5-((1R,2R)-1-(cyclopropylsulfonylcarbamoyl)-2-ethylcyclopropylcarbamoyl)-1-((S)-3,3-dimethyl-2-(3-(trifluoromethyl)phenylamino)butanoyl)pyrrolidin-3-yl]4-fluoroisoindoline-2-carboxylate 62% yield; MS: Calcd.: 765; Found: [M+H]$^+$ 766. $^1$H NMR (400 MHz, d$^6$-DMSO) δ 10.43 (s, 1H), 8.82 & 8.78 (s, 1H), 7.37 (m, 1H), 7.00-7.23 (m, 4H), 6.86 (m, 1H), 6.56 & 6.45 (d, J=7.6 Hz, 1H), 5.69 (m, 1H), 5.33 (s, 1H), 4.66 (m, 2H), 4.49 (m, 1H), 4.29 (m, 1H), 4.13-4.26 (m, 3H), 3.83 (m, 1H), 2.96 (m, 1H), 2.24 (m, 1H), 2.04 (m, 1H), 0.88-1.52 (m, 21H).

Compound 57

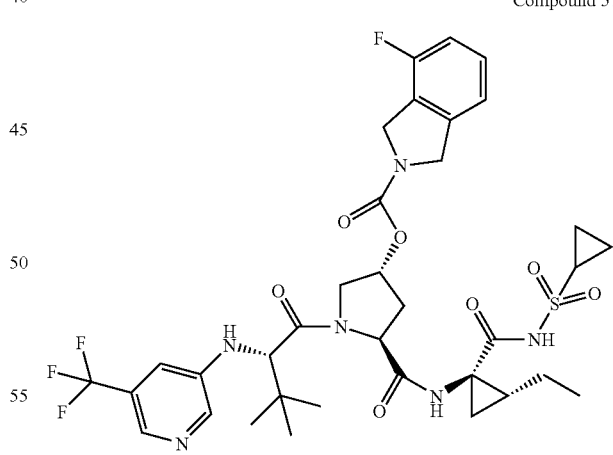

[(3R,5S)-5-((1R,2R)-1-(cyclopropylsulfonylcarbamoyl)-2-ethylcyclopropylcarbamoyl)-1-((S)-3,3-dimethyl-2-(5-(trifluoromethyl)pyridin-3-ylamino)butanoyl)pyrrolidin-3-yl]4-fluoroisoindoline-2-carboxylate 59% yield; MS: Calcd.: 766; Found: [M+H]$^+$ 767.

Compound 58

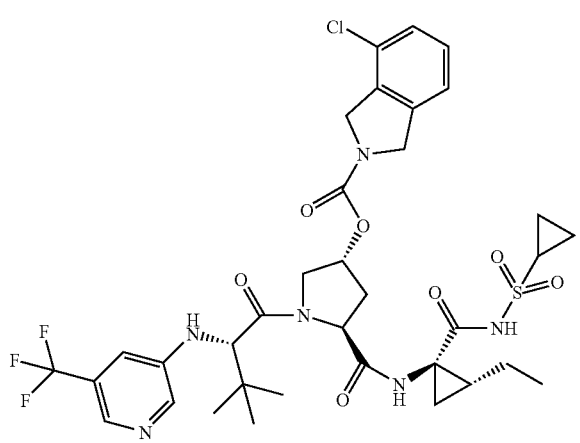

[(3R,5S)-5-(((1R,2R)-1-(cyclopropylsulfonylcarbamoyl)-2-ethylcyclopropylcarbamoyl)-1-((S)-3,3-dimethyl-2-(5-(trifluoromethyl)pyridin-3-ylamino)butanoyl)pyrrolidin-3-yl]4-chloroisoindoline-2-carboxylate 50% yield; MS: Calcd.: 782; Found: [M+H]+ 783.

Compound 59

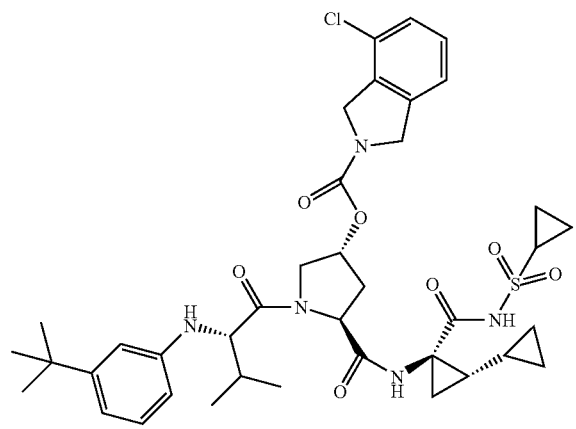

[(3R,5S)-1-((S)-2-(3-tert-butylphenylamino)-3-methylbutanoyl)-5-((1R,2S)-1-(cyclopropylsulfonylcarbamoyl)-2-cyclopropylcyclopropylcarbamoyl)pyrrolidin-3-yl]4-chloroisoindoline-2-carboxylate 75% yield; MS: Calcd.: 767; Found: [M+H]+ 768. $^1$H NMR (400 MHz, d$^6$-DMSO) δ 10.57 (s, 1H), 8.96 and 8.90 (s, 1H), 7.37 & 7.24 (m, 3H), 6.79 (m, 1H), 6.71 (m, 1H), 6.33-6.46 (m, 2H), 5.36 (m, 1H), 5.09 (m, 1H), 4.73 (s, 1H), 4.37-4.62 (m, 3H), 4.28 (m, 1H), 4.10 (m, 1H), 4.01 (m, 1H), 3.87 (m, 1H), 2.96 (m, 1H), 2.22 (m, 1H), 2.08 (m, 2H), 1.59 (m, 1H), 0.83-1.26 (m, 21H), 0.71 (m, 1H), 0.45-0.52 (m, 2H), 0.26 (m, 2H).

Compound 60

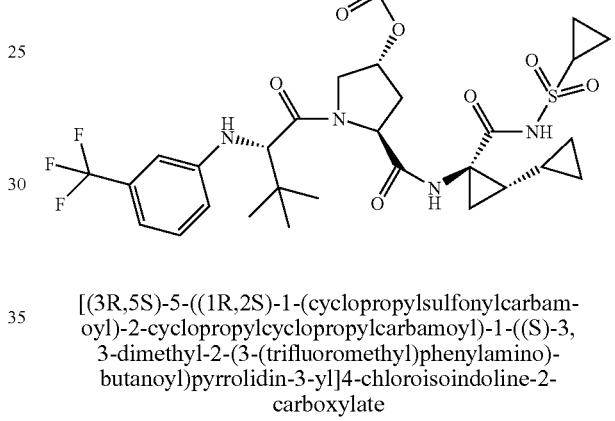

[(3R,5S)-5-(((1R,2S)-1-(cyclopropylsulfonylcarbamoyl)-2-cyclopropylcyclopropylcarbamoyl)-1-((S)-3,3-dimethyl-2-(3-(trifluoromethyl)phenylamino)butanoyl)pyrrolidin-3-yl]4-chloroisoindoline-2-carboxylate 43% yield; MS: Calcd.: 793; Found: [M+H]+ 794. $^1$H NMR (400 MHz, d$^6$-DMSO) δ 10.53 (s, 1H), 8.79 and 8.73 (s, 1H), 7.37 (m, 3H), 7.14 (m, 1H), 7.03 (m, 1H), 6.85 (m, 1H), 6.54 & 6.44 (d, J=7.6 Hz, 1H), 5.72 (m, 1H), 5.34 (m, 1H), 4.71 (s, 2H), 4.45-4.60 (m, 2H), 4.27 (m, 1H), 4.10-4.20 (m, 2H), 3.83 (m, 1H), 2.97 (m, 1H), 2.27 (m, 1H), 2.04 (m, 1H), 1.56 (m, 1H), 1.01-1.13 (m, 15H), 0.74 (m, 1H), 0.49 (m, 2H), 0.29 (m, 2H).

Another method used in preparing compounds with general Formula I is shown below.

Method:

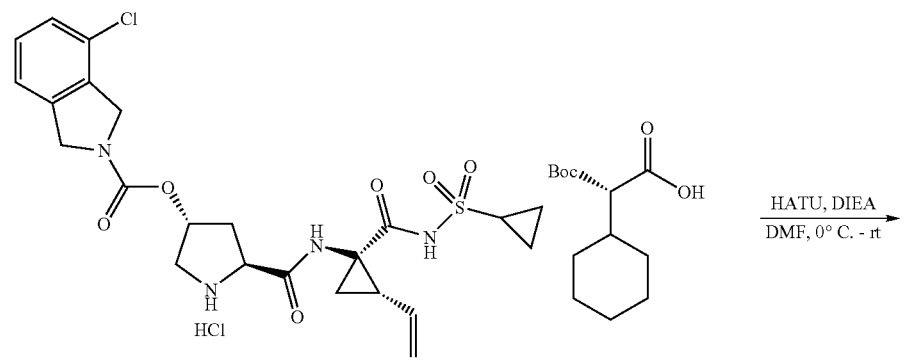

-continued
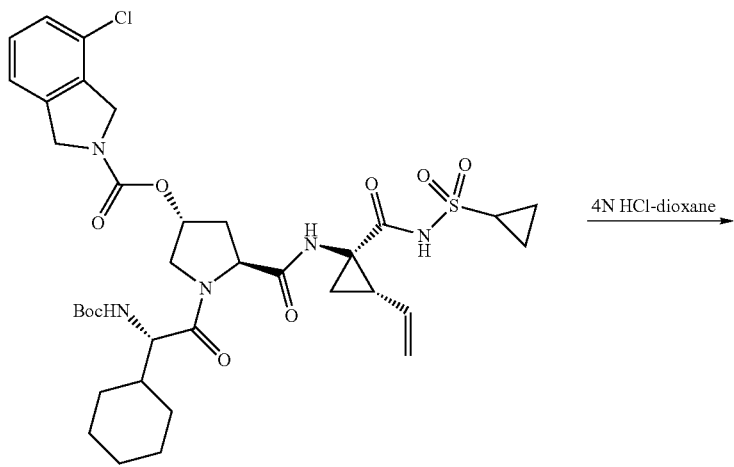
4N HCl-dioxane
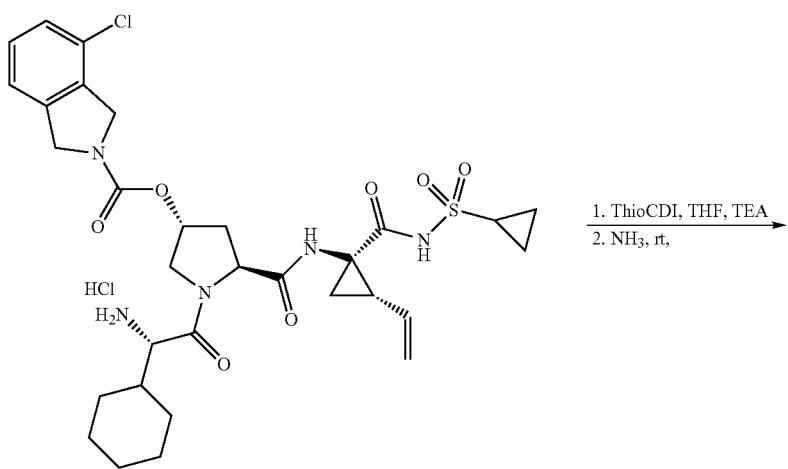
1. ThioCDI, THF, TEA
2. NH₃, rt,
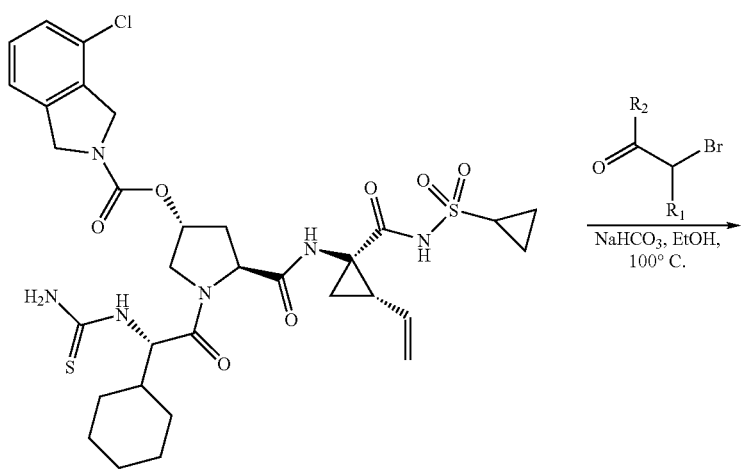
NaHCO₃, EtOH,
100° C.

-continued

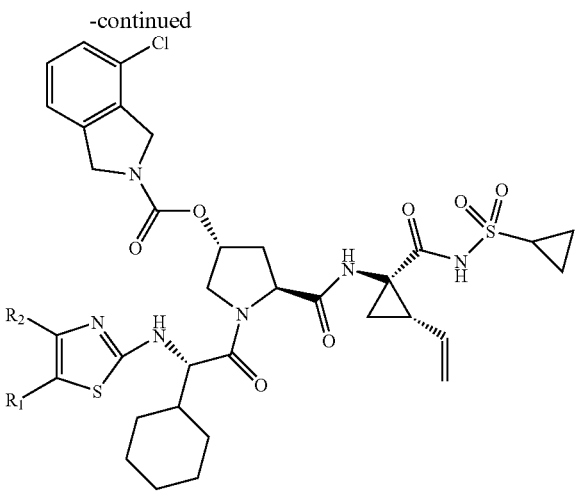

The following tripeptides were prepared using method above:

EXAMPLE 3-1

Compound 61

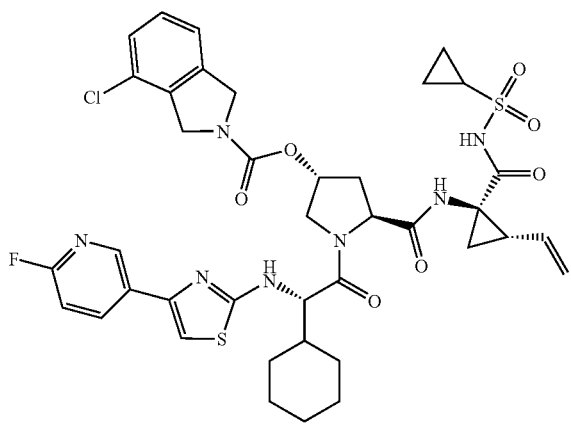

[(3R,5S)-5-(((1R,2S)-1-(cyclopropylsulfonylcarbamoyl)-2-vinylcyclopropyl)carbamoyl)-1-((S)-2-cyclohexyl-2-(4-(6-fluoropyridin-3-yl)thiazol-2-ylamino)acetyl)pyrrolidin-3-yl]-4-chloroisoindoline-2-carboxylate Step 1: Synthesis of [(3R,5S)-5-(((1R,2S)-1-(Cyclopropylsulfonylcarbamoyl)-2-vinylcyclopropyl)carbamoyl)-1-((S)-2-(tert-butoxycarbonyl)-2-cyclohexylacetyl)pyrrolidin-3-yl]4-chloroisoindoline-2-carboxylate A 25 mL round-bottomed flask was charged with (3R,5S)-5-(((1R,2S)-1-(cyclopropylsulfonylcarbamoyl)-2-vinylcyclopropyl)carbamoyl)pyrrolidin-3-yl 4-chloroisoindoline-2-carboxylate hydrochloride (0.500 g, 0.894 mmol), (S)-2-(tert-butoxycarbonyl)-2-cyclohexylacetic acid (276 mg, 1.07 mmol) and HATU (408 mg, 1.07 mmol) in dry DMF (9 mL). The solution was cooled on an ice-water bath and treated with DIEA (0.467 mL, 2.68 mmol) by dropwise addition. The mixture was stirred at 0° C. for 1 h, then allowed to warm up and stirred at room temperature for 16 h. The mixture was diluted with water (50 mL) and the pH adjusted to 3 with 1N HCl, the mixture was extracted with Et$_2$O (3×20 mL). The combined organic extracts were then washed with 1N HCl (3×20 mL), water (3×20 mL) and brine (3×20 mL). The organic extract was then dried over MgSO$_4$, filtered and concentrated. The crude material was the purified by chromatography (Biotage) eluting with 1-3% MeOH—CH$_2$Cl$_2$ to give the product as a white foam, (394 mg, 59%). MS m/e 662 (M$^+$–Boc).

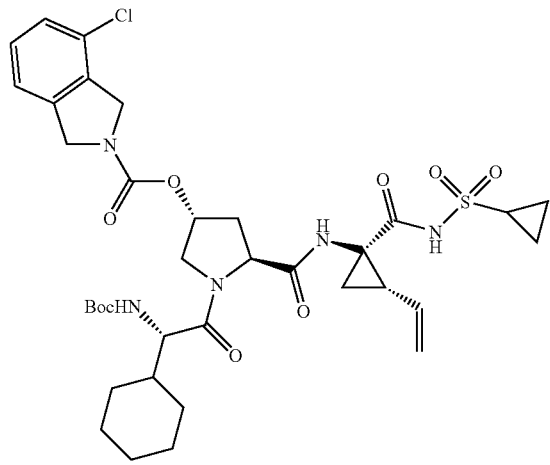

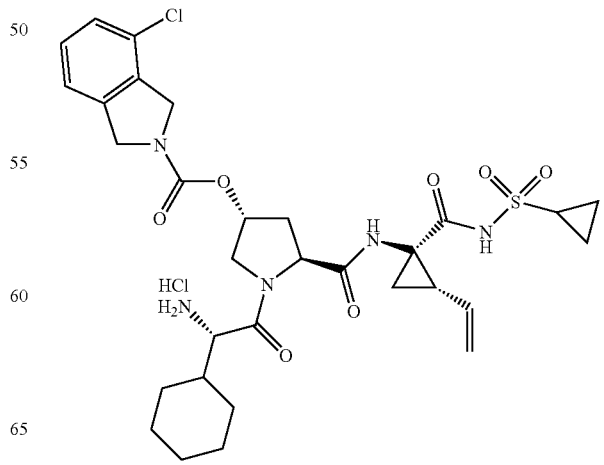

Step 2: Synthesis of [(3R,5S)-5-(((1R,2S)-1-(Cyclopropylsulfonylcarbamoyl)-2-vinylcyclopropyl)carbamoyl)-1-((S)-2-amino-2-cyclohexylacetyl)pyrrolidin-3-yl]4-chloroisoindoline-2-carboxylate hydrochloride A 25 mL round-bottomed flask was charged with (3R,5S)-5-(((1R,2S)-1-(cyclopropylsulfonylcarbamoyl)-2-vinylcyclopropyl)carbamoyl)-1-((S)-2-(tert-butoxycarbonyl)-2-cyclohexylacetyl)pyrrolidin-3-yl 4-chloroisoindoline-2-carboxylate (267 mg, 0.350 mmol), to which was added 4N HCl-dioxane (4 mL) and the resulting solution was stirred at room temperature for 4 h. The reaction mixture was then concentrated and the product triturated with Et$_2$O to give the hydrochloride salt as a cream colored foam, (245 mg, 100%). MS m/e 662 (M$^+$).

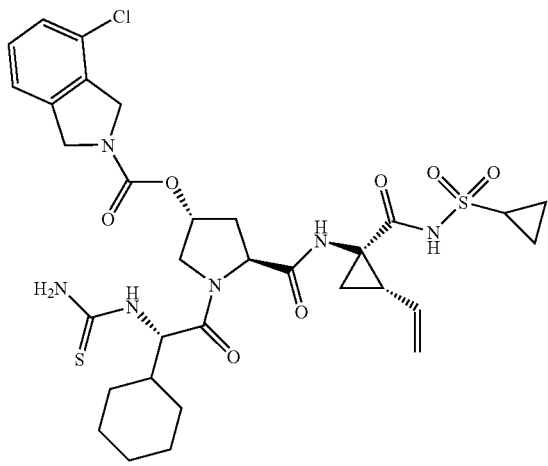

Step 3: Synthesis of [(3R,5S)-5-(((1R,2S)-1-(Cyclopropylsulfonylcarbamoyl)-2-vinylcyclopropyl)carbamoyl)-1-((S)-2-cyclohexyl-2-thioureidoacetyl)pyrrolidin-3-yl]4-chloroisoindoline-2-carboxylate A 10 mL round-bottomed flask was charged with [(3R,5S)-5-(((1R,2S)-1-(cyclopropylsulfonylcarbamoyl)-2-vinylcyclopropyl)carbamoyl)-1-((S)-2-amino-2-cyclohexylacetyl)pyrrolidin-3-yl]4-chloroisoindoline-2-carboxylate hydrochloride (268 mg, 0.383 mmol) and stirred in dry THF (2.0 mL). To this solution was added TEA (0.267 mL, 1.91 mmol) with vigorous stirring to prevent clumping. After stirring at room temperature for 5 minutes, di(1H-imidazol-1-yl)methanethione (102 mg, 0.574 mmol) was added and the resulting mixture stirred at room temperature for 1 h. HPLC of reaction mixture indicated consumption of the starting hydrochloride salt. Ammonia was then bubbled into the reaction mixture for 8 minutes, and the resulting mixture then stirred at room temperature for an additional 1 h. HPLC indicated formation of the desired thiourea. The reaction mixture was concentrated to an orange colored foam and was purified by using the following preparative HPLC conditions (Biotage SP4 system using SPX software; version 2:
Column: Biotage, KP-C18-HS 25+M2436-1, 35-70 micron particle size, 90-angstrom pore size
  Mobile Phase Gradient: 0-95% B in 40-6 mL fractions
  A: water
  B: MeCN
  Flow rate: 15 mL/min
  Temperature: 25 C
  Wavelength: 220 nm
to yield the thiourea as a cream colored foam, (174 mg, 63%). MS m/e 719 (M$^-$−2H).

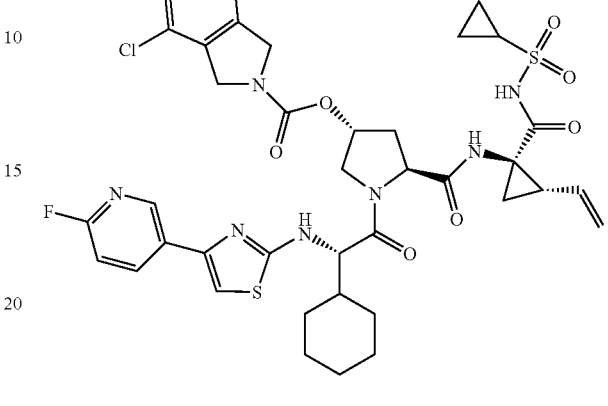

Step 4: Synthesis of [(3R,5S)-5-(((1R,2S)-1-(cyclopropylsulfonylcarbamoyl)-2-vinylcyclopropyl)carbamoyl)-1-((S)-2-cyclohexyl-2-(4-(6-fluoropyridin-3-yl)thiazol-2-ylamino)acetyl)pyrrolidin-3-yl]4-chloroisoindoline-2-carboxylate A 10 mL round-bottomed flask was charged with [(3R,5S)-5-(((1R,2S)-1-(cyclopropylsulfonylcarbamoyl)-2-vinylcyclopropyl)carbamoyl)-1-((S)-2-cyclohexyl-2-thioureidoacetyl)pyrrolidin-3-yl]4-chloroisoindoline-2-carboxylate (56 mg, 0.078 mmol) and stirred in ethanol (1.0 mL). To this solution was added 2-bromo-1-(6-fluoropyridin-3-yl)ethanone (31 mg, 0.14 mmol) and sodium bicarbonate (66 mg, 0.78 mmol) and the resulting mixture heated at 100° C. After 25 minutes heating was discontinued and the reaction mixture was cooled to room temperature and purified by preparative HPLC conditions (Biotage SP4 system using SPX software; version 2)
Column: Biotage, KP-C18-HS, 25+M2436-1, 35-70 micron particle size, 90-angstrom pore size
  Mobile Phase Gradient: 0-95% B in 40-6 mL fractions
  A: water
  B: MeCN
  Flow rate: 15 mL/min
  Temperature: 25 C
  Wavelength: 220 nm
to give the product as a cream colored solid, (14 mg, 21%). MS m/e 838 (M$^-$−2H).

EXAMPLE 3-2

Compounds 62 and 63 were prepared in a similar fashion as described for compound [(3R,5S)-5-(((1R,2S)-1-(cyclopropylsulfonylcarbamoyl)-2-vinylcyclopropyl)carbamoyl)-1-((S)-2-cyclohexyl-2-(4-(6-fluoropyridin-3-yl)thiazol-2-ylamino)acetyl)pyrrolidin-3-yl]4-chloroisoindoline-2-carboxylate 61 in other parts of this application.

EXAMPLE 3-3

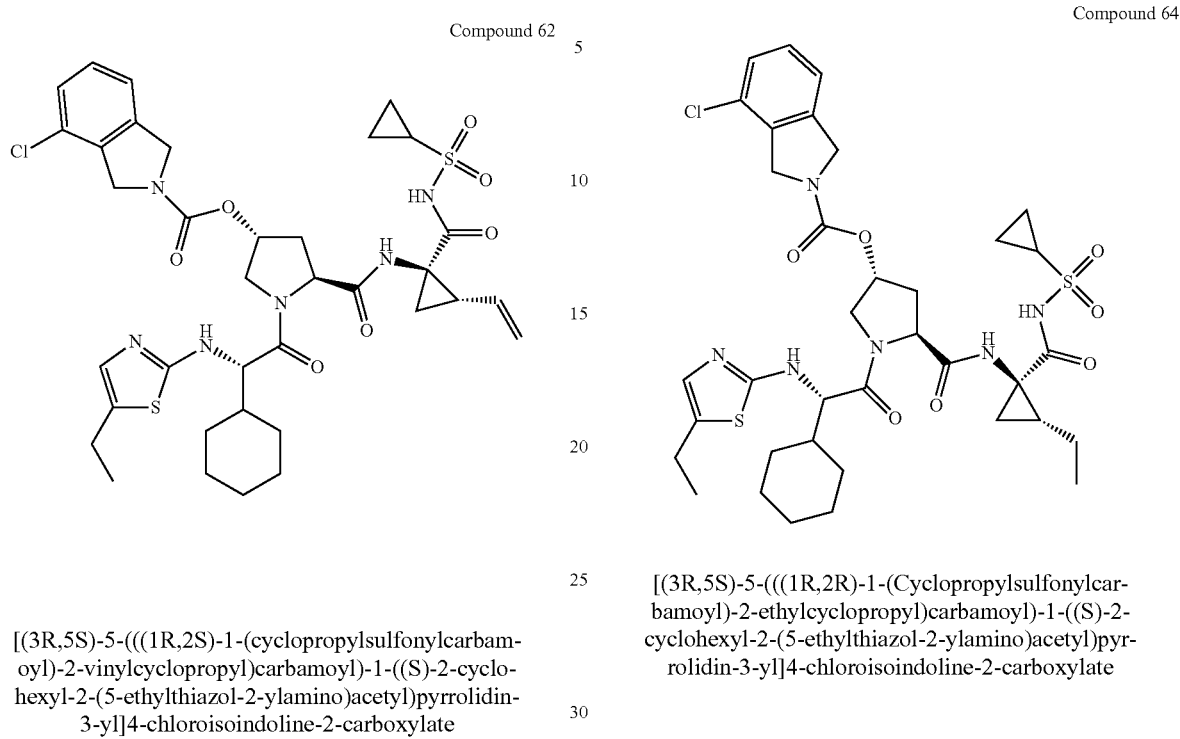

Compound 62

[(3R,5S)-5-(((1R,2S)-1-(cyclopropylsulfonylcarbamoyl)-2-vinylcyclopropyl)carbamoyl)-1-((S)-2-cyclohexyl-2-(5-ethylthiazol-2-ylamino)acetyl)pyrrolidin-3-yl]4-chloroisoindoline-2-carboxylate 18% yield. MS m/e 773 (M+).

Compound 63

[(3R,5S)-5-(((1R,2S)-1-(Cyclopropylsulfonylcarbamoyl)-2-vinylcyclopropyl)carbamoyl)-1-((S)-2-cyclohexyl-2-(4-(trifluoromethyl)thiazol-2-ylamino)acetyl)pyrrolidin-3-yl]4-chloroisoindoline-2-carboxylate 7.5% yield. MS m/e 811 (M−−2H).

Compound 64

[(3R,5S)-5-(((1R,2R)-1-(Cyclopropylsulfonylcarbamoyl)-2-ethylcyclopropyl)carbamoyl)-1-((S)-2-cyclohexyl-2-(5-ethylthiazol-2-ylamino)acetyl)pyrrolidin-3-yl]4-chloroisoindoline-2-carboxylate

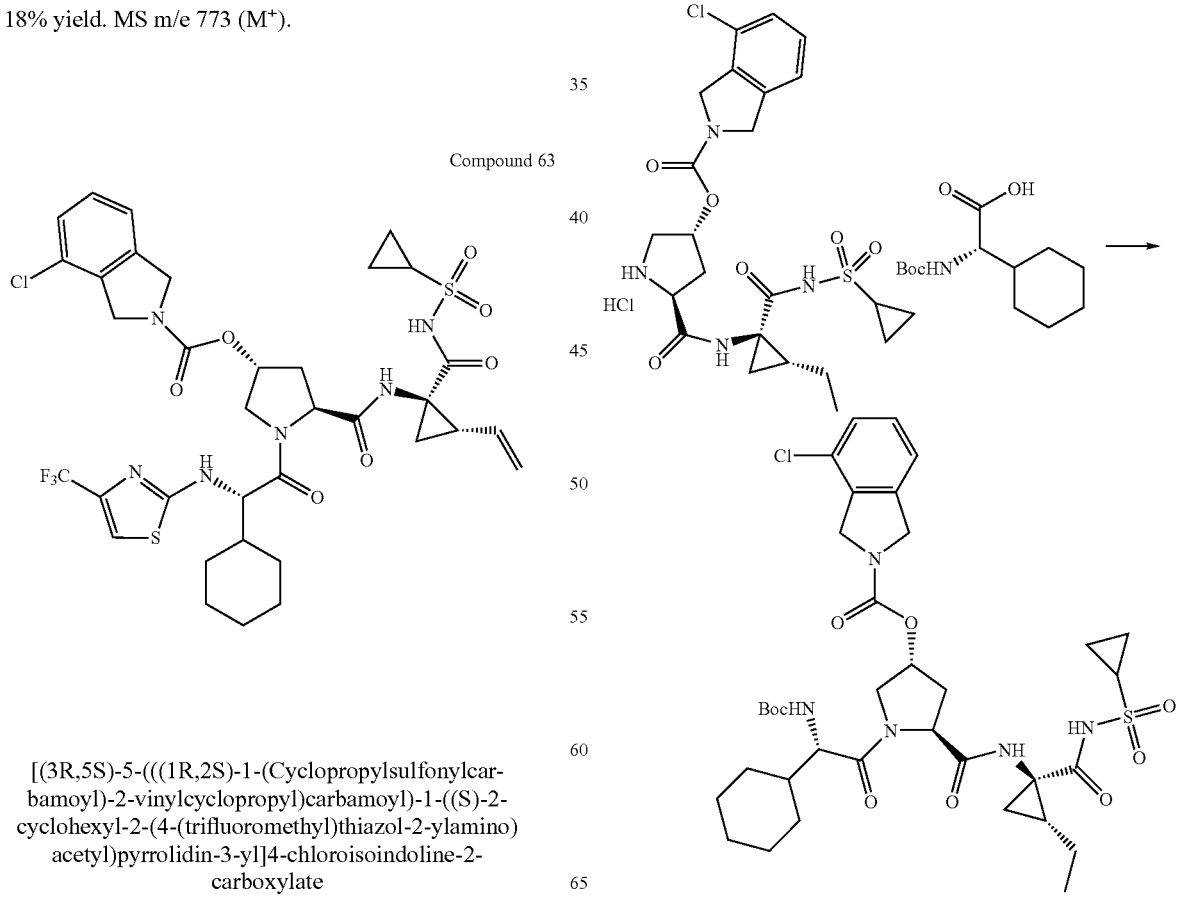

Step 1: Synthesis of [(3R,5S)-5-(((1R,2R)-1-(Cyclopropylsulfonylcarbamoyl)-2-ethylcyclopropyl)carbamoyl)-1-((S)-2-(tert-butoxycarbonyl)-2-cyclohexylacetyl)pyrrolidin-3-yl]4-chloroisoindoline-2-carboxylate A 10 mL round-bottomed flask was charged with (3R,5S)-5-(((1R,2R)-1-(cyclopropylsulfonylcarbamoyl)-2-ethylcyclopropyl)carbamoyl)pyrrolidin-3-yl 4-chloroisoindoline-2-carboxylate hydrochloride (0.150 g, 0.267 mmol), (S)-2-(tert-butoxycarbonyl)-2-cyclohexylacetic acid (82 mg, 0.32 mmol) and HATU (122 mg, 0.321 mmol) and stirred in dry DMF (1.5 mL). The solution was cooled on an ice-water bath and then treated with DIEA (0.140 mL, 0.802 mmol) by dropwise addition. The mixture was stirred at 0° C. for 1 h, then allowed to warm up and stirred at room temperature for 16 h. The reaction mixture was diluted with water (5.0 mL) resulting in the separation of a precipitate. After stirring at room temperature for about 1 hour the precipitate was collected by filtration, washed with water and dried to a cream colored solid, (195 mg, 95%). MS m/e 664 (M$^+$–Boc).

Step 2: Synthesis of [(3R,5S)-5-(((1R,2R)-1-(Cyclopropylsulfonylcarbamoyl)-2-ethylcyclopropyl)carbamoyl)-1-((S)-2-amino-2-cyclohexylacetyl)pyrrolidin-3-yl]4-chloroisoindoline-2-carboxylate hydrochloride

[(3R,5S)-5-(((1R,2R)-1-(Cyclopropylsulfonylcarbamoyl)-2-ethylcyclopropyl)carbamoyl)-1-((S)-2-(tert-butoxycarbonyl)-2-cyclohexylacetyl)pyrrolidin-3-yl]4-chloroisoindoline-2-carboxylate (205 mg, 0.268 mmol) was stirred in 4M HCl-dioxane (3 mL) at room temperature for 2.5 h. The reaction mixture was then concentrated and the product triturated with 40% Et$_2$O-hexanes to give the hydrochloride salt as a cream colored powder, 189 mg. MS m/e 664 (M$^+$).

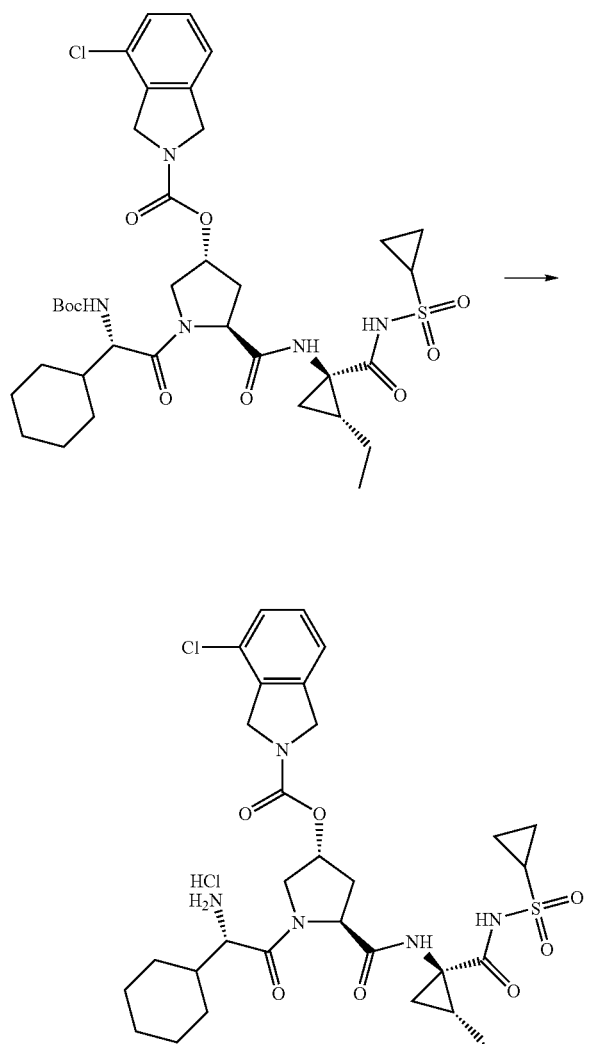

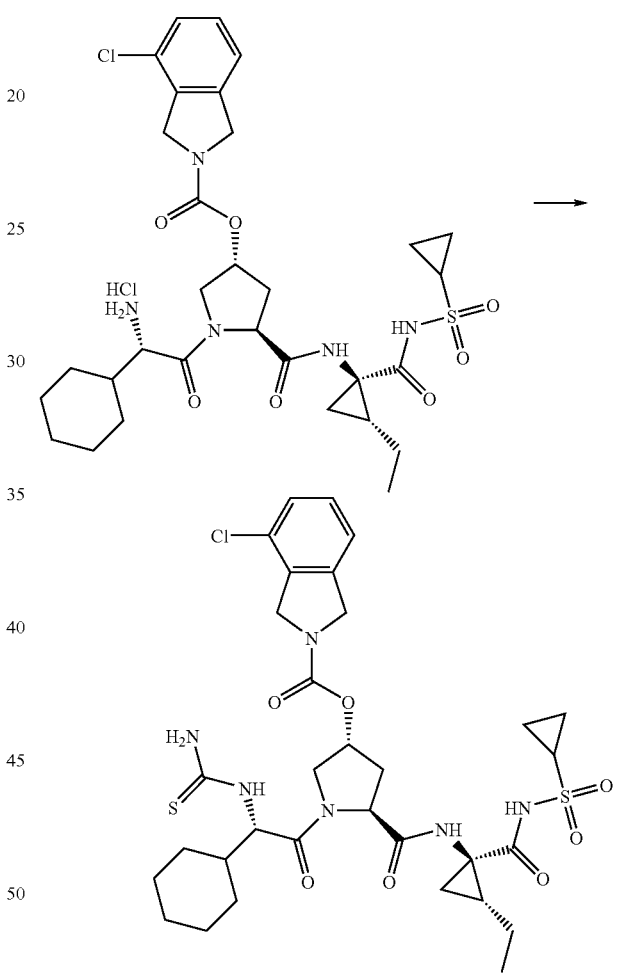

Step 3: Synthesis of [(3R,5S)-5-(((1R,2R)-1-(Cyclopropylsulfonylcarbamoyl)-2-ethylcyclopropyl)carbamoyl)-1-((S)-2-cyclohexyl-2-thioureidoacetyl)pyrrolidin-3-yl]4-chloroisoindoline-2-carboxylate The intermediate thiourea was prepared according to the procedure disclosed in International Application PCT/US04/022599 (Publication No. WO 05/007601).
A 10 mL round-bottomed flask was charged with [(3R,5S)-5-(((1R,2R)-1-(cyclopropylsulfonylcarbamoyl)-2-ethylcyclopropyl)carbamoyl)-1-((S)-2-amino-2-cyclohexylacetyl)pyrrolidin-3-yl]4-chloroisoindoline-2-carboxylate hydrochloride (189 mg, 0.270 mmol) and stirred in dry THF (1.0 mL). To this suspension was added TEA (0.094 mL, 0.67 mmol) with vigorous stirring to prevent clumping. After stirring at room temperature for 15 minutes, di(1H-imidazol-1-yl)methanethione (74 mg, 0.41 mmol) was added and the resulting mixture stirred for 1 h. 2M Ammonia in methanol solution (0.539 mL, 1.08 mmol) was then added and the resulting mixture stirred at room temperature for 2 h. The solvent was then evaporated and the crude thiourea was purified by chromatography (Biotage) eluting with 0.5-1.5% MeOH—CH$_2$Cl$_2$ to give the product as a light yellow foam, 52.6 mg, 27%. MS m/e 721 (M$^-$–2H).

the residue was suspended in EtOAc (10 mL) and washed with water. The aqueous was extracted with EtOAc (10 mL) and the combined organic layers dried over MgSO$_4$, filtered and concentrated. The crude material was purified by column chromatography (Silica gel) eluting with 2.5% MeOH—CH$_2$Cl$_2$ to give the product as a cream colored powder, 4.6 mg, 10%. MS m/e 775 (M$^+$).

Another method used in preparing compounds with general Formula I is shown below.

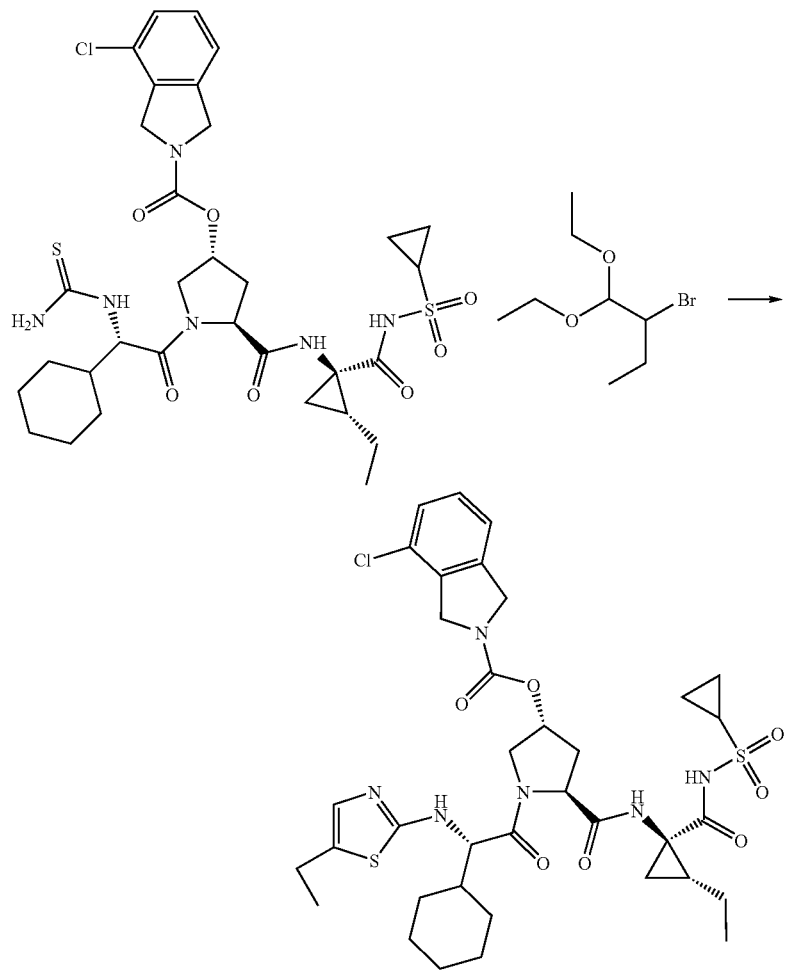

Step 4: Synthesis of [(3R,5S)-5-(((1R,2R)-1-(Cyclopropylsulfonylcarbamoyl)-2-ethylcyclopropyl)carbamoyl)-1-((S)-2-cyclohexyl-2-(5-ethylthiazol-2-ylamino)acetyl)pyrrolidin-3-yl]4-chloroisoindoline-2-carboxylate A 10 mL round-bottomed flask was charged with [(3R,5S)-5-(((1R,2R)-1-(cyclopropylsulfonylcarbamoyl)-2-ethylcyclopropyl)carbamoyl)-1-((S)-2-cyclohexyl-2-thioureidoacetyl)pyrrolidin-3-yl]4-chloroisoindoline-2-carboxylate (41 mg, 0.057 mmol) and stirred in ethanol (1.0 mL). To this solution was added 2-bromo-1,1-diethoxybutane (0.129 mL, 0.571 mmol) and sodium bicarbonate (48 mg, 0.57 mmol) and the resulting mixture heated at 100° C. for 16 h. The mixture was cooled to room temperature and evaporated and Method:

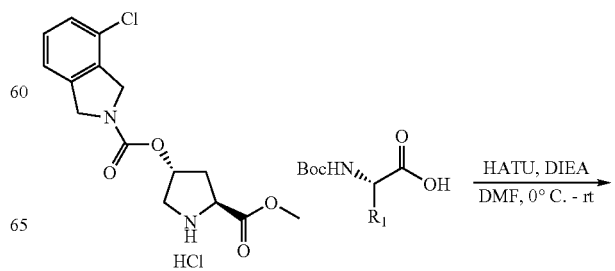

109
-continued
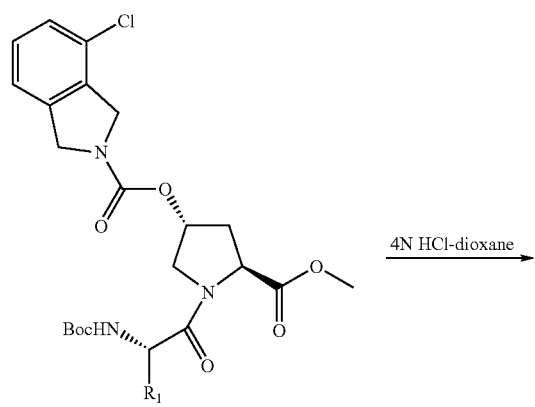
4N HCl-dioxane →
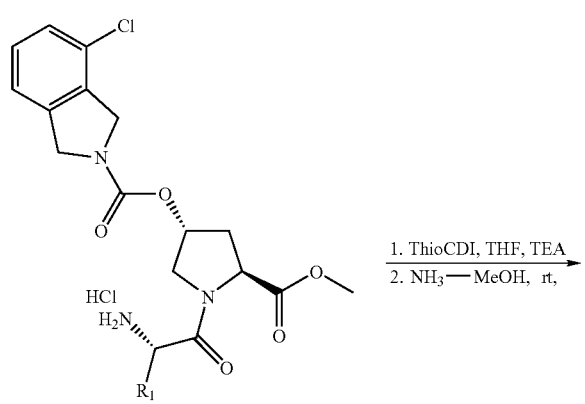
1. ThioCDI, THF, TEA
2. NH₃—MeOH, rt,
→
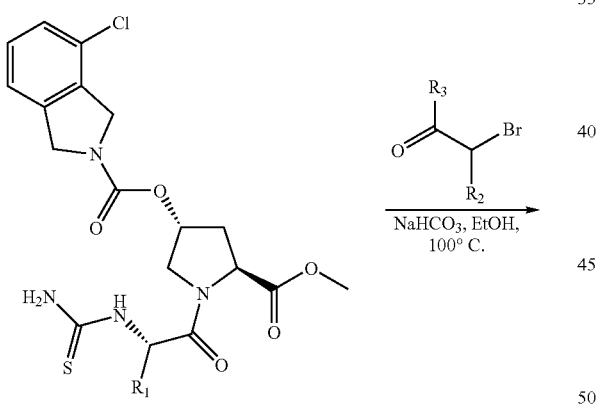
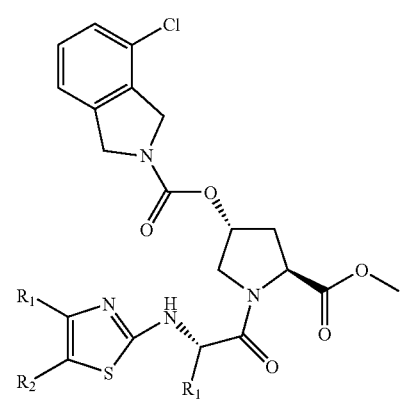
LiOH·H₂O, H₂O
THF, MeOH, rt
→
110
-continued
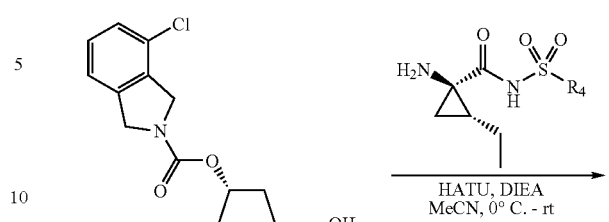
HATU, DIEA
MeCN, 0° C. - rt
→
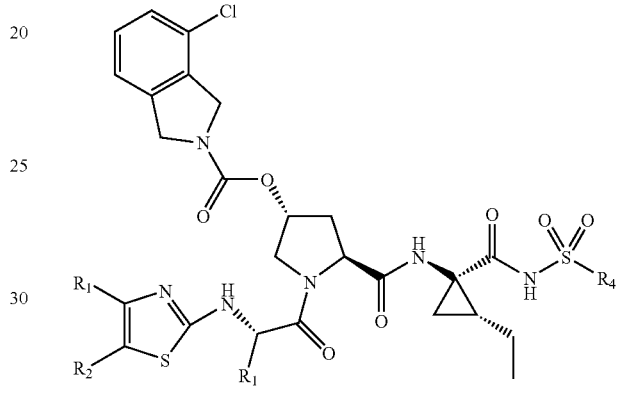
The following tripeptides were prepared using method above:
EXAMPLE 4-1
Compound 65
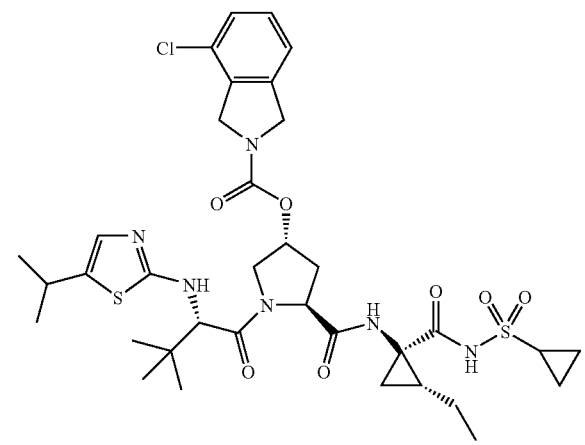

111

[(3R,5S)-5-(((1R,2R)-1-(Cyclopropylsulfonylcarbamoyl)-2-ethylcyclopropyl)carbamoyl)-1-((S)-2-(5-isopropylthiazol-2-ylamino)-3,3-dimethylbutanoyl)pyrrolidin-3-yl]4-chloroisoindoline-2-carboxylate

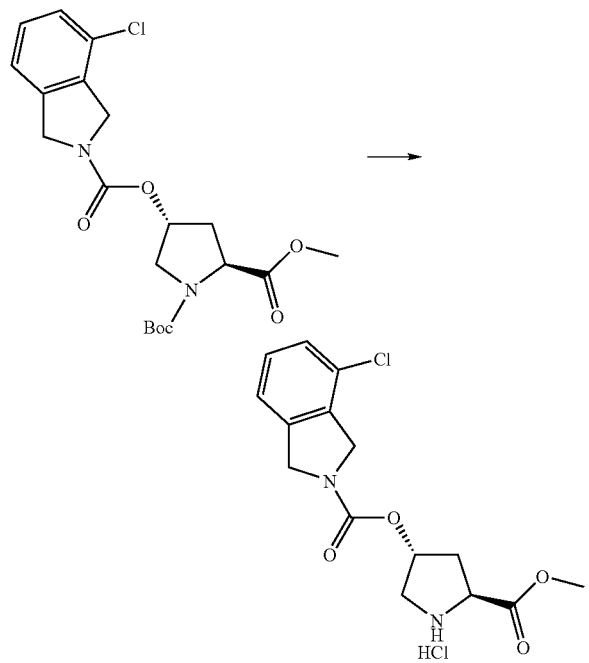

Step 1: Synthesis of (3R,5S)-5-(Methoxycarbonyl)pyrrolidin-3-yl 4-chloroisoindoline-2-carboxylate hydrochloride (2S,4R)-1-tert-butyl 2-methyl 4-(4-chloroisoindoline-2-carbonyloxy)pyrrolidine-1,2-dicarboxylate (4.95 g, 11.7 mmol) was stirred at room temperature in 4M HCl-dioxane (50 mL) for 5 h. The reaction mixture was then concentrated to dryness and the resulting powder was triturated with 50% EtOAc-hexanes to give the hydrochloride salt as a white powder 4.2 g, 99%. MS m/e 325 (M+). $^1$H NMR (400 MHz, d$^6$-DMSO) δ 7.27-7.42 (m, 3H), 5.30 (m, 1H), 4.8-4.92 (m, 5H), 3.79 (d, 3H), 3.54-3.62 (m, 1H), 3.30-3.45 (m, 2H), 2.43-2.49 (m, 1H), 2.31-2.40 (m, 1H).

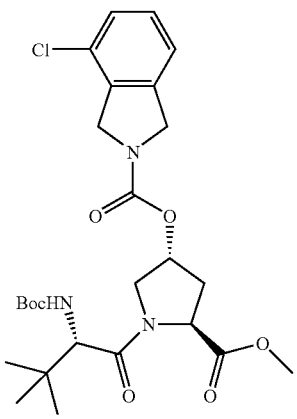

Step 2: Synthesis of (3R,5S)-1-((S)-2-(tert-Butoxycarbonyl)-3,3-dimethylbutanoyl)-5-(methoxycarbonyl)pyrrolidin-3-yl 4-chloroisoindoline-2-carboxylate A 200 mL round-bottomed flask was charged with (3R,5S)-5-(methoxycarbonyl)pyrrolidin-3-yl 4-chloroisoindoline-2-carboxylate hydrochloride (1.20 g, 3.32 mmol), (S)-2-(tert-butoxycarbonyl)-3,3-dimethylbutanoic acid (807 mg, 3.49 mmol) and HATU (1.90 g, 4.98 mmol) in dry MeCN (30 mL). The solution was then cooled on an ethanol-ice bath and treated with DIEA (1.74 mL, 9.97 mmol) by dropwise addition. The mixture was stirred at 0° C. for 1 h, then allowed to warm up and stirred at room temperature for 16 h. The mixture was then concentrated and the residue dissolved in EtOAc (100 mL) and washed with iced 5% citric acid (aq.) (3×30 mL), 1M NaOH (3×30 mL), water (3×30 mL) and brine (3×30 mL). The organic layer was dried over MgSO$_4$, filtered and concentrated to an oil. The oil was purified by chromatography (Biotage) eluting with 35% EtOAc-hexanes to give the product as a white foam, 1.27 g, 71%. MS m/e 438 (M+H)+–Boc. $^1$H NMR (400 MHz, d$^6$-DMSO) δ 7.3-7.4 (m, 3H), 6.7-6.76 (m, 1H), 5.24 (bs, 1H), 4.4-4.76 (m, 4H), 4.12-4.2 (m, 1H), 3.96-4.3 (m, 1H), 3.7-3.78 (m, 1H), 3.64 (d, 3H), 2.38-2.48 (m, 1H), 2.07-2.16 (m, 1H), 1.14 (d, 9H), 0.98 (s, 9H).

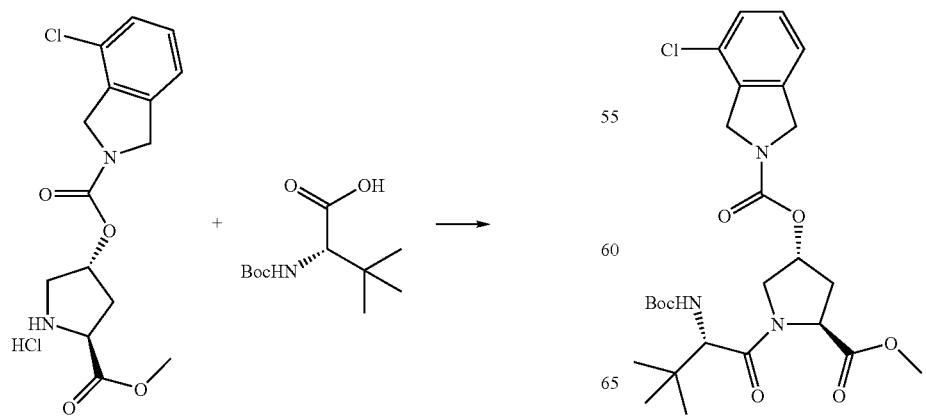

Step 3: Synthesis of (3R,5S)-1-((S)-2-Amino-3,3-dimethylbutanoyl)-5-(methoxycarbonyl)pyrrolidin-3-yl 4-chloroisoindoline-2-carboxylate hydrochloride (3R,5S)-1-((S)-2-(tert-butoxycarbonyl)-3,3-dimethylbutanoyl)-5-(methoxycarbonyl)pyrrolidin-3-yl 4-chloroisoindoline-2-carboxylate (2.93 g, 5.45 mmol) was stirred at room temperature in 4M HCl-dioxane (25 mL) for 5 h. The reaction mixture was then concentrated to dryness and the resulting solid was triturated with 50% EtOAc-hexanes to give the hydrochloride salt as a white powder, 2.43 g, 94%. MS m/e 438 (M+). $^1$H NMR (400 MHz, d$^6$-DMSO) δ 8.16 (bs, 2H), 7.28-7.4 (m, 3H), 5.30 (m, 1H), 4.48-4.80 (m, 4H), 3.95-4.12 (m, 2H), 3.76-3.86 (m, 1H), 3.75 (d, 3H), 2.4-2.48 (m, 1H), 2.12-2.24 (m, 1H), 1.04 (d, 9H).

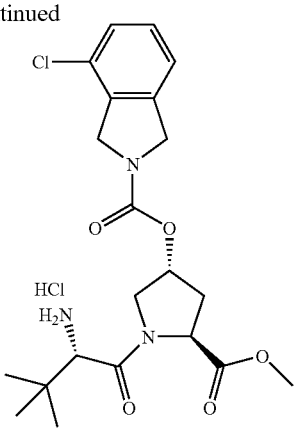

Step 4: (3R,5S)-1-((S)-3,3-Dimethyl-2-thioureidobutanoyl)-5-(methoxycarbonyl)pyrrolidin-3-yl 4-chloroisoindoline-2-carboxylate A 200 mL round-bottomed flask was charged with [(3R,5S)-1-((S)-2-amino-3,3-dimethylbutanoyl)-5-(methoxycarbonyl)pyrrolidin-3-yl]4-chloroisoindoline-2-carboxylate hydrochloride (2.43 g, 5.12 mmol) and stirred in dry THF (25 mL). To this suspension was added TEA (1.75 mL, 12.8 mmol) with vigorous stirring to prevent clumping. After stirring at room temperature for 15 minutes, di(1H-imidazol-1-yl)methanethione (1.41 g, 7.68 mmol) was added and the resulting yellow-orange suspension stirred for 1 h. 2M Ammonia in methanol solution (10.2 mL, 20.5 mmol) was then added and the resulting mixture stirred at room temperature for 2 h. The solvent was then evaporated and the residue re-suspended in EtOAc (50 mL) and stirred with water (20 mL). The layers were separated and the aqueous layer was extracted with EtOAc (2×15 mL). The combined organic layers were dried over MgSO$_4$, filtered and concentrated to a yellow-orange oil. The crude thiourea was purified by chromatography (Biotage) eluting with a gradient of 0.5-1.5% MeOH—CH$_2$Cl$_2$ to give the product as a light-yellow colored foam, 2.29 g, 90%. MS m/e 495 (M$^-$−2H). $^1$H NMR (400 MHz, CDCl$_3$) δ 7.16-7.25 (m, 3H), 7.08-7.14 (m, 1H), 6.17 (d, 2H), 5.42 (bs, 1H), 5.12-5.21 (m, 1H), 4.5-4.81 (m, 6H), 3.89-3.91 (m, 1H), 3.75 (d, 3H), 2.51-2.59 (m, 1H), 2.17-2.26 (m, 1H), 1.08 (d, 9H).

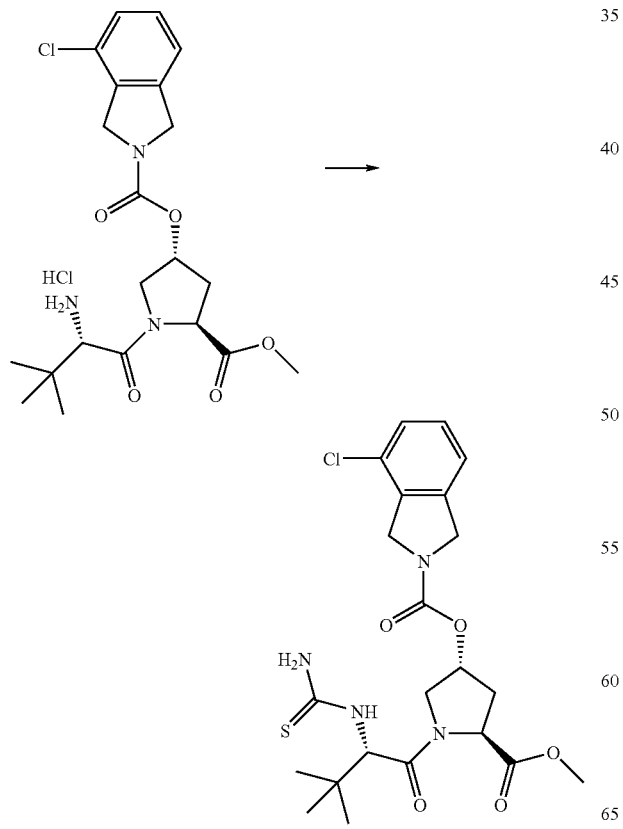

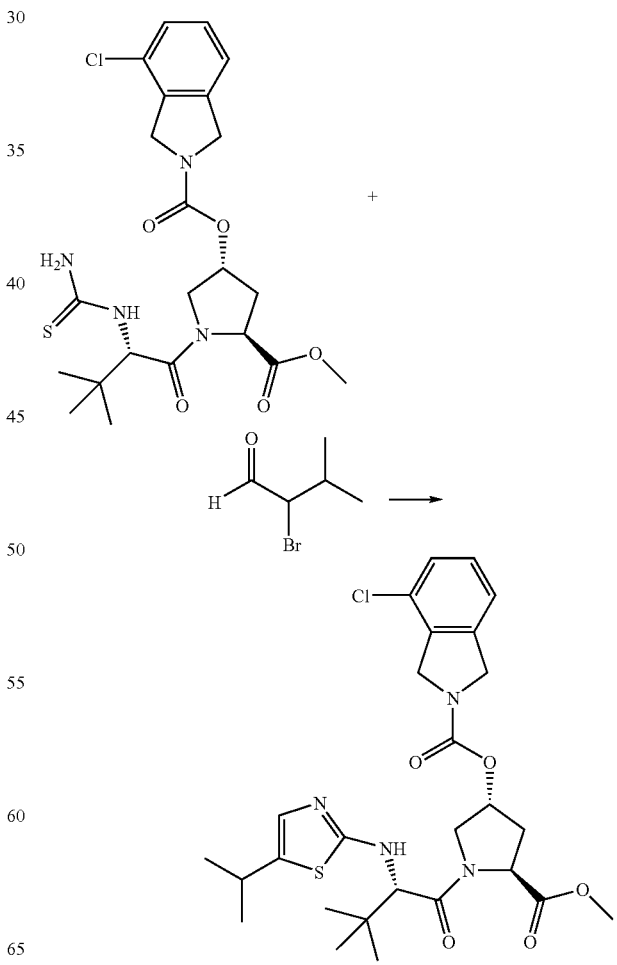

Step 5: Synthesis of [(3R,5S)-1-((S)-2-(5-isopropylthiazol-2-ylamino)-3,3-dimethylbutanoyl)-5-(methoxycarbonyl)pyrrolidin-3-yl]4-chloroisoindoline-2-carboxylate To a solution of [(3R,5S)-1-((S)-3,3-dimethyl-2-thioureidobutanoyl)-5-(methoxycarbonyl)pyrrolidin-3-yl]4-chloroisoindoline-2-carboxylate (1.0 g, 2.0 mmol) in ethanol (8 mL) was added 2-bromo-3-methylbutanal (1.66 mL, 10.1 mmol) and sodium bicarbonate (1.69 g, 20.1 mmol) and the resulting suspension heated at 100° C. After 30 minutes LC-MS of the reaction mixture showed about 50% consumption of the thiourea. An additional (1.66 mL, 10.1 mmol) of 2-bromo-3-methylbutanal was added and heating with stirring was continued. Heating was stopped after 1.5 h, the mixture cooled and concentrated. The residue was stirred in EtOAc (25 mL) and treated with water (10 mL). The layers were then separated and the aqueous extracted with EtOAc (2×10 mL). The combined organic layers were then washed with water (3×15 mL) and brine (3×15 mL), dried over MgSO$_4$, filtered and concentrated to a reddish-brown oil. The oil was then purified by chromatography (Biotage) eluting with 10-40% EtOAc-hexanes to give the product as a white foam, 893 mg, 79%. MS m/e 563 (M$^+$). $^1$H NMR (400 MHz, d$^6$-DMSO) δ 7.44-7.49 (m, 1H), 7.30-7.40 (m, 3H), 6.16 (bs, 1H), 5.30 (m, 1H), 4.24-4.80 (m, 6H), 3.75-3.85 (m, 1H), 3.64 (s, 3H), 2.35-2.48 (m, 2H), 2.05-2.17 (m, 1H), 1.03 (d, 9H), 0.77-0.85 (m, 6H).

mixture of THF (3 mL) and MeOH (2 mL). To the solution was added a solution of LiOH—H$_2$O (91 mg, 2.1 mmol) in water (2 mL). The resulting mixture was stirred at room temperature. After 75 minutes LC-MS of reaction mixture shows complete consumption of the starting ester, with the only peak consistent with that of the desired acid. The reaction was stopped after 105 minutes and the reaction mixture was diluted with EtOAc (10 mL) and stirred with 1N HCl (5 mL) for 20 minutes. The layers were then separated and the acidic aqueous layer extracted with EtOAc (10 mL). The combined organic layers were then washed with water (3×15 mL) and brine (3×15 mL), then dried over MgSO$_4$, filtered and concentrated to a white foam, 380 mg, 97%. MS m/e 549 (M$^+$).

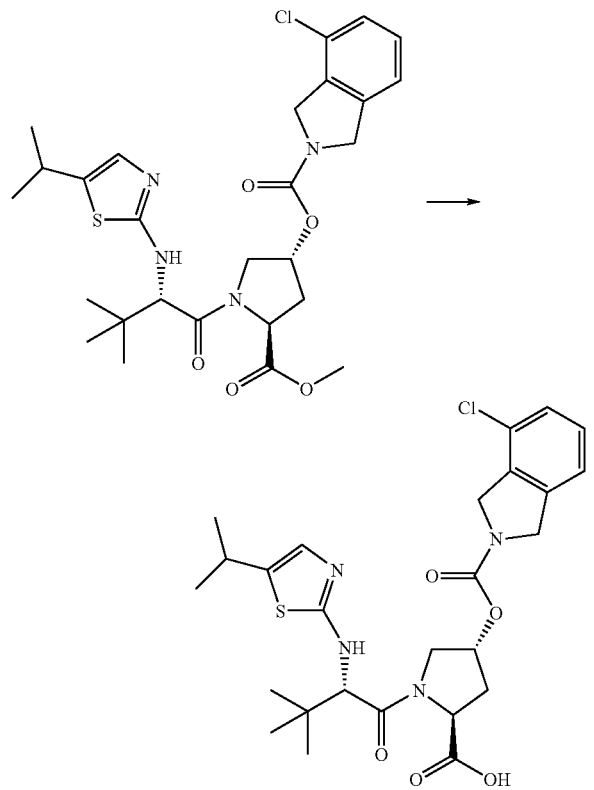

Step 6: (2S,4R)-4-(4-Chloroisoindoline-2-carbonyloxy)-1-((S)-2-(5-isopropylthiazol-2-ylamino)-3,3-dimethylbutanoyl)pyrrolidine-2-carboxylic acid A 25 mL round-bottomed flask was charged with (3R,5S)-1-((S)-2-(5-isopropylthiazol-2-ylamino)-3,3-dimethylbutanoyl)-5-(methoxycarbonyl)pyrrolidin-3-yl-4-chloroisoindoline-2-carboxylate (0.40 g, 0.71 mmol) and stirred in a

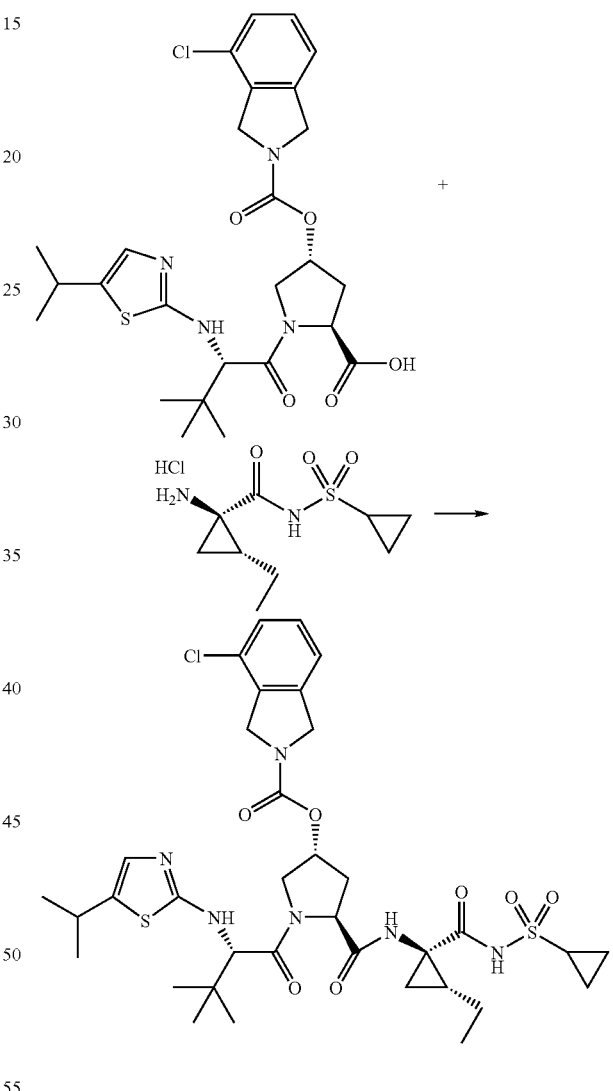

Step 7: [(3R,5S)-5-(((1R,2R)-1-(Cyclopropylsulfonylcarbamoyl)-2-ethylcyclopropyl)carbamoyl)-1-((S)-2-(5-isopropylthiazol-2-ylamino)-3,3-dimethylbutanoyl)pyrrolidin-3-yl]4-chloroisoindoline-2-carboxylate A solution of (2S,4R)-4-(4-chloroisoindoline-2-carbonyloxy)-1-((S)-2-(5-isopropylthiazol-2-ylamino)-3,3-dimethylbutanoyl)pyrrolidine-2-carboxylic acid (0.080 g, 0.15 mmol), (1R,2R)-1-amino-N-(cyclopropylsulfanyl)-2-ethylcyclopropanecarboxamide hydrochloride (42.2 mg, 0.157 mmol) and HATU (85.3 mg, 0.224 mmol) in dry MeCN (1 mL) stirred under nitrogen, was cooled on an ethanol-ice bath. The solution was treated with DIEA (0.078 mL, 0.449 mmol) by dropwise addition and the resulting mixture was stirred at 0° C. for 1 h, then allowed to warm to room temperature and stirred for 16 h. The mixture was concentrated and the residue dissolved in EtOAc (10 mL), washed with 1N HCl (3×5 mL) water (3×5 mL) and brine (3×5 mL), dried over MgSO$_4$, filtered and concentrated to an oil. The oil was purified by chromatography (Biotage) eluting with 0.5-1.5% MeOH—CH$_2$Cl$_2$ to give the product as a white solid, 74 mg, 67%. MS m/e 763 (M$^+$).

EXAMPLE 4-2

Compounds 66 and 67 were prepared in a similar fashion as described for compound [(3R,5S)-5-(((1R,2R)-1-(Cyclopropylsulfonylcarbamoyl)-2-ethylcyclopropyl)carbamoyl)-1-((S)-2-(5-isopropylthiazol-2-ylamino)-3,3-dimethylbutanoyl)pyrrolidin-3-yl]4-chloroisoindoline-2-carboxylate 65 in other parts of this application.

Compound 66

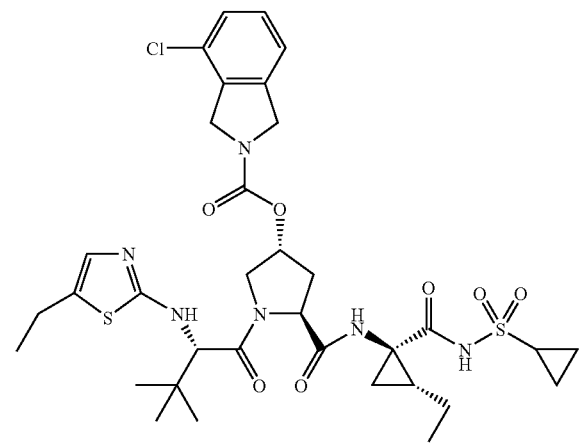

[(3R,5S)-5-(((1R,2R)-1-(Cyclopropylsulfonylcarbamoyl)-2-ethylcyclopropyl)carbamoyl)-1-((S)-2-(5-ethylthiazol-2-ylamino)-3,3-dimethylbutanoyl)pyrrolidin-3-yl]4-chloroisoindoline-2-carboxylate Compound 66 was synthesized according to procedure described for compound 65 and purified by chromatography (Biotage) eluting with a gradient of 0.5-1.5% MeOH—CH$_2$Cl$_2$ to yield the product as a white powder, 63 mg, 57%. MS m/e 749 (M$^+$).

Compound 67

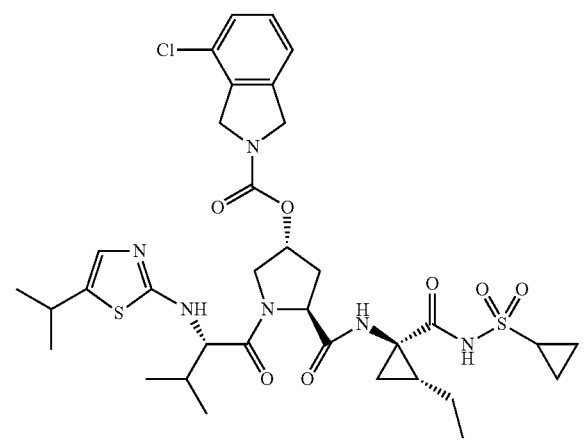

[(3R,5S)-5-(((1R,2R)-1-(Cyclopropylsulfonylcarbamoyl)-2-ethylcyclopropyl)carbamoyl)-1-((S)-2-(5-isopropylthiazol-2-ylamino)-3-methylbutanoyl)pyrrolidin-3-yl]4-chloroisoindoline-2-carboxylate Compound 67 was synthesized according to procedure described for compound 65 and purified by chromatography (Biotage) eluting with a gradient of 0.5-1.5% MeOH—CH$_2$Cl$_2$ to yield the product as a white powder, 75 mg, 63%. MS m/e 749 (M$^+$).

EXAMPLE 5

The following tripeptide was prepared as described below:

Compound 68

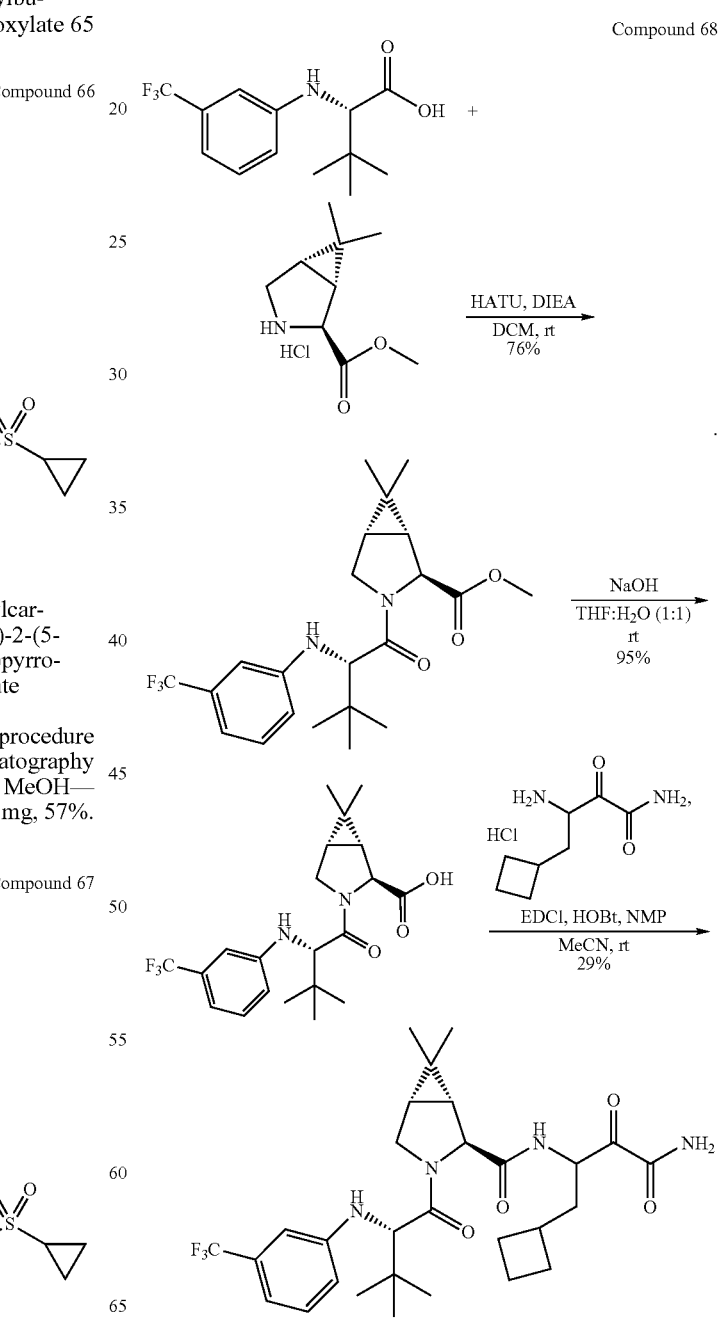

(1R,2S,5S)—N-(4-amino-1-cyclobutyl-3,4-dioxobutan-2-yl)-3-((S)-3,3-dimethyl-2-(3-trifluoromethyl)phenylamino)butanoyl)-6,6-dimethyl-3-azabicyclo[3.1.0]hexane-2-carboxamide

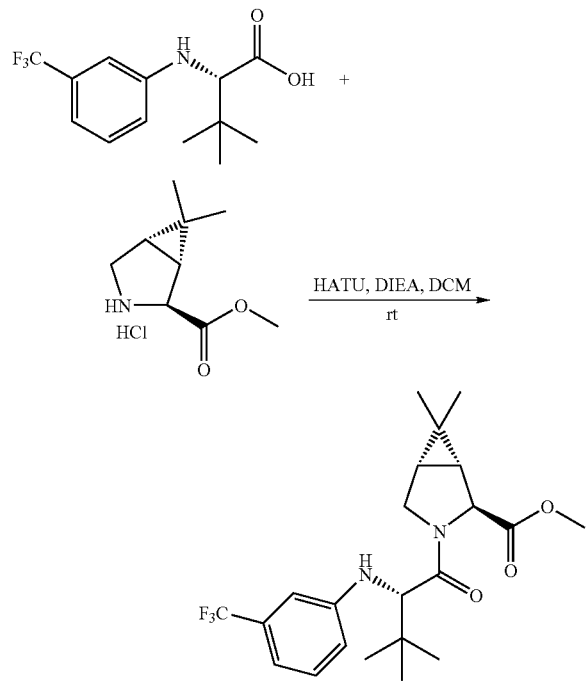

Step 1: Synthesis of (1R,2S,5S)-methyl 3-((S)-3,3-dimethyl-2-(3-trifluoromethyl)phenylamino)butanoyl)-6,6-dimethyl-3-azabicyclo[3.1.0]hexane-2-carboxylate (1R,2S,5S)-methyl-6,6-dimethyl-3-azabicyclo[3.1.0]hexane-2-carboxylate hydrochloride (0.030 g, 0.15 mmol), (S)-3,3-dimethyl-2-(3-(trifluoromethyl)phenylamino)butanoic acid (0.044 g, 0.16 mmol) and HATU (0.067 g, 0.18 mmol) in DCM (5 mL) was added DIEA (d 0.742) (0.080 mL, 0.44 mmol) and the reaction was stirred at rt for 18 hr. H$_2$O (5 mL) was added and the mixture was extracted with ether (10 mL), washed with brine and dried over sodium sulfate. After removal of solvent, the residue was purified by chromatography (Hexane:Ethyl acetate=1:5) to give the (1R,2S,5S)-methyl 3-((S)-3,3-dimethyl-2-(3-trifluoromethyl)phenylamino)butanoyl)-6,6-dimethyl-3-azabicyclo[3.1.0]hexane-2-carboxylate (0.047 g, 76%) as white solid. MS: Calcd.: 426; Found: [M+H]$^+$ 427.

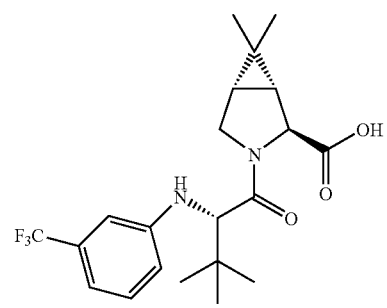

Step 2: Synthesis of (1R,2S,5S)-3-((S)-3,3-dimethyl-2-(3-trifluoromethyl)phenylamino)butanoyl)-6,6-dimethyl-3-azabicyclo[3.1.0]hexane-2-carboxylic acid (1R,2S,5S)-methyl 3-((S)-3,3-dimethyl-2-(3-(trifluoromethyl)phenylamino)butanoyl)-6,6-dimethyl-3-aza-bicyclo[3.1.0]hexane-2-carboxylate (0.047 g, 0.11 mmol) in THF (1 mL) was added 0.4 N NaOH solution (0.69 mL, 0.28 mmol) and the reaction was stirred at rt for 3 hrs. THF was removed and acidified with saturated KHSO$_4$ until PH=3~4. The mixture was extracted with Ether (15 mL), washed with brine and dried over sodium sulfate. After removal of solvent, it gave the (1R,2S,5S)-3-((S)-3,3-dimethyl-2-(3-trifluoromethyl)phenylamino)butanoyl)-6,6-dimethyl-3-azabicyclo[3.1.0]hexane-2-carboxylic acid (0.043 g, 95%) as white solid. MS: Calcd.: 412; Found: [M−H]$^+$ 411.

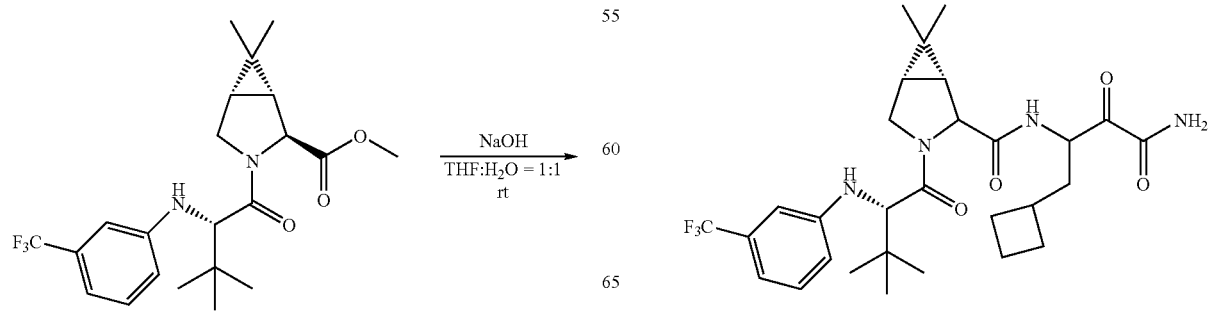

Step 3: Synthesis of (1R,2S,5S)—N-(4-amino-1-cyclobutyl-3,4-dioxobutan-2-yl)-3-((S)-3,3-dimethyl-2-(3-trifluoromethyl)phenylamino)butanoyl)-6,6-dimethyl-3-azabicyclo[3.1.0]hexane-2-carboxamide (1R,2S,5S)-3-((S)-3,3-dimethyl-2-(3-(trifluoromethyl)phenylamino)butanoyl)-6,6-dimethyl-3-aza-bicyclo[3.1.0]hexane-2-carboxylic acid (0.043 g, 0.10 mmol), 3-(chloroamino)-4-cyclobutyl-2-oxobutanamide (0.031 g, 0.14 mmol), 1-ethyl-3-[3-dimethylaminopropyl]carbodiimide hydrochloride (EDCI, 0.030 g, 0.16 mmol), 1-hydroxybenzotriazole hydrate (HOBt-H$_2$O, 0.005 g, 0.03 mmol) in MeCN (3 mL) was added N-Methylmorpholine (d=0.920) (0.015 ml, 0.14 mmol) in MeCN (1 mL) dropwise over 40 minutes. The mixture was stirred at rt for 2 hrs and saturated KHSO$_4$ (3 mL) was added, extracted with EtOAc (2×10 mL). The combined EtOAc extracts was washed with brine (10 mL), dried over sodium sulfate. After removal of solvent, the residue was purified by chromatography (Hexane:Ethyl acetate=1:1) to give the (1R,2S,5S)—N-(4-amino-1-cyclobutyl-3,4-dioxobutan-2-yl)-3-((S)-3,3-dimethyl-2-(3-trifluoromethyl)phenylamino)butanoyl)-6,6-dimethyl-3-azabicyclo[3.1.0]hexane-2-carboxamide (0.017 g, 29%) as white solid. MS: Calcd.: 564; Found: [M+H]$^+$ 565. $^1$H NMR (400 MHz, d$^6$-DMSO) δ 8.23 (m, 1H), 7.96 & 7.89 (s, 1H), 7.71 & 7.67 (s, 1H), 7.17 (m, 1H), 7.06 (s, 1H), 6.92 (m, 1H), 6.76 (m, 1H), 5.67 (d, J=10.8 Hz, 1H), 4.93 & 4.75 (m, 1H), 4.17 (s, 1H), 3.99 (m, 1H), 3.82 (m, 1H), 3.68 (m, 1H), 2.29 (m, 1H), 1.91 (m, 2H), 1.70 (m, 3H), 1.58 (m, 2H), 1.43 (m, 1H), 1.20 (m, 1H), 0.92-1.00 (m, 14H), 0.61 (s, 1H), 0.57 (s, 1H).

EXAMPLE 6

The following tripeptides were prepared as presented in the scheme below.

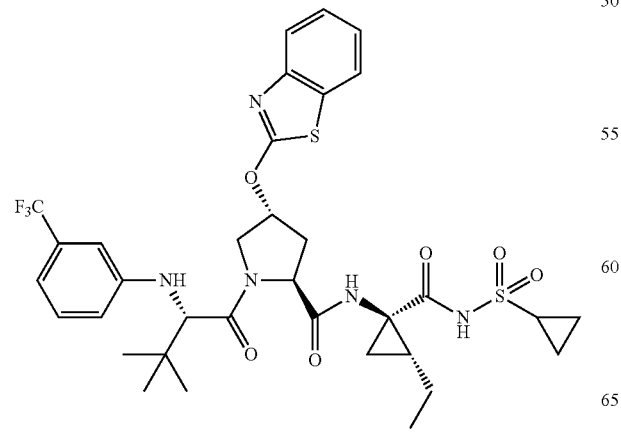

Compound 69

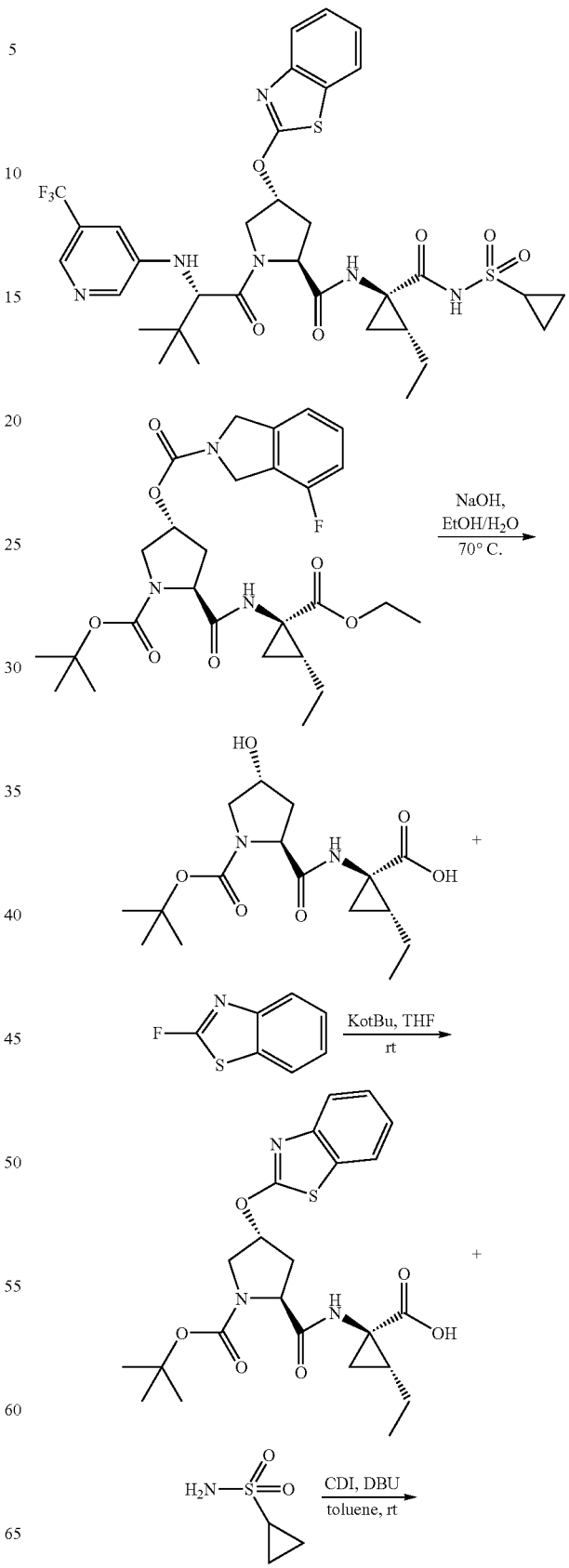

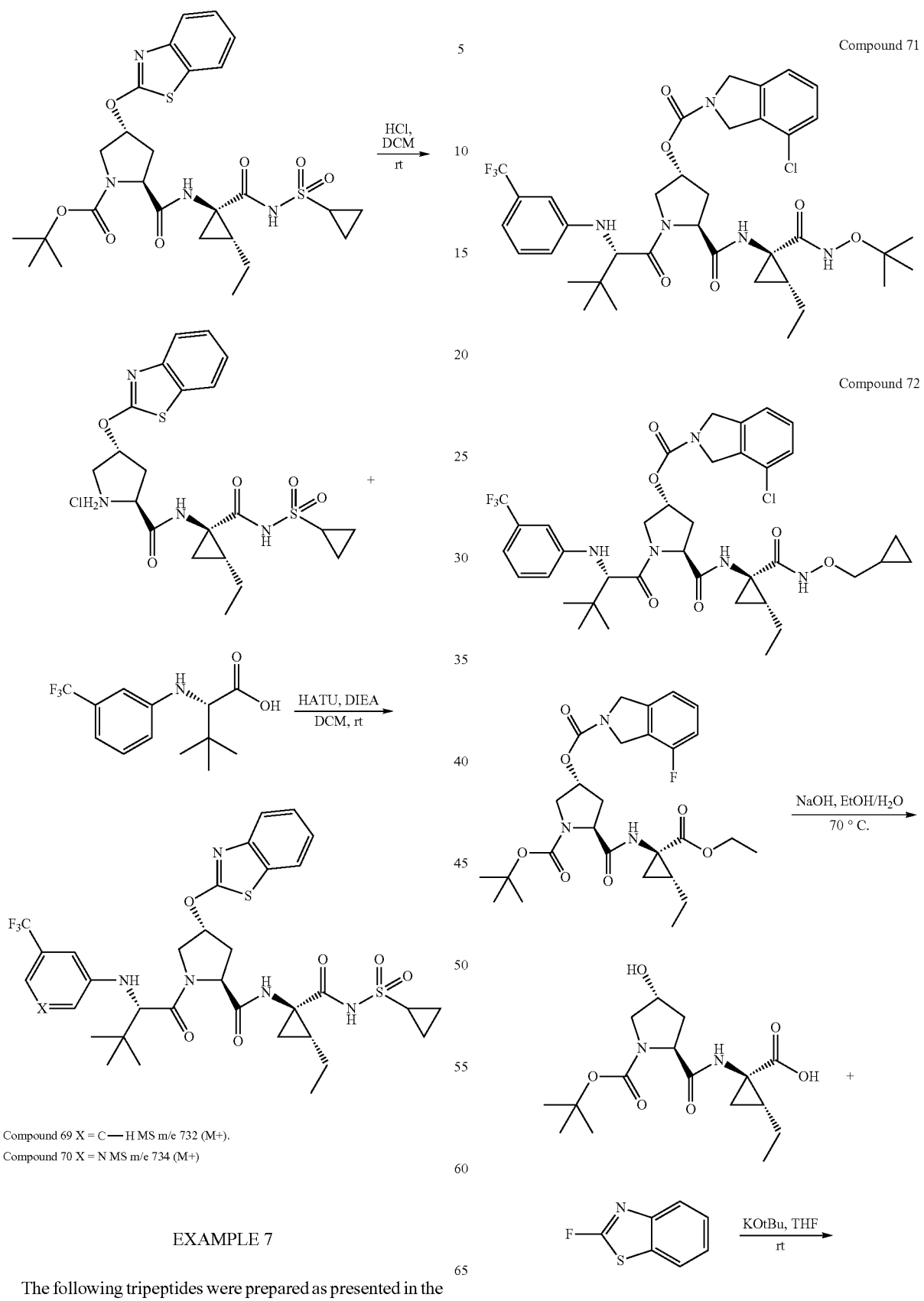
EXAMPLE 7
The following tripeptides were prepared as presented in the scheme below.

125
-continued
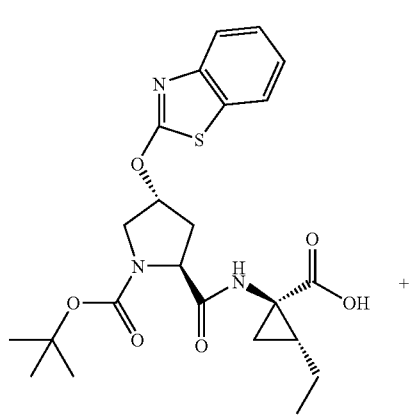
126
-continued
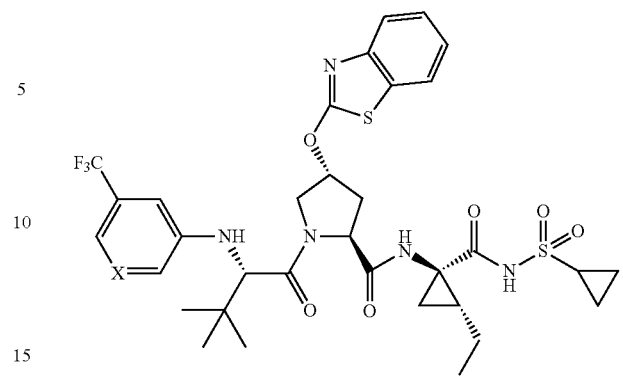
Compound 69 X = C—H MS m/e 732 (M+).
Compound 70 X = N MS m/e 734 (M+)
EXAMPLE 8
Scheme 8-1
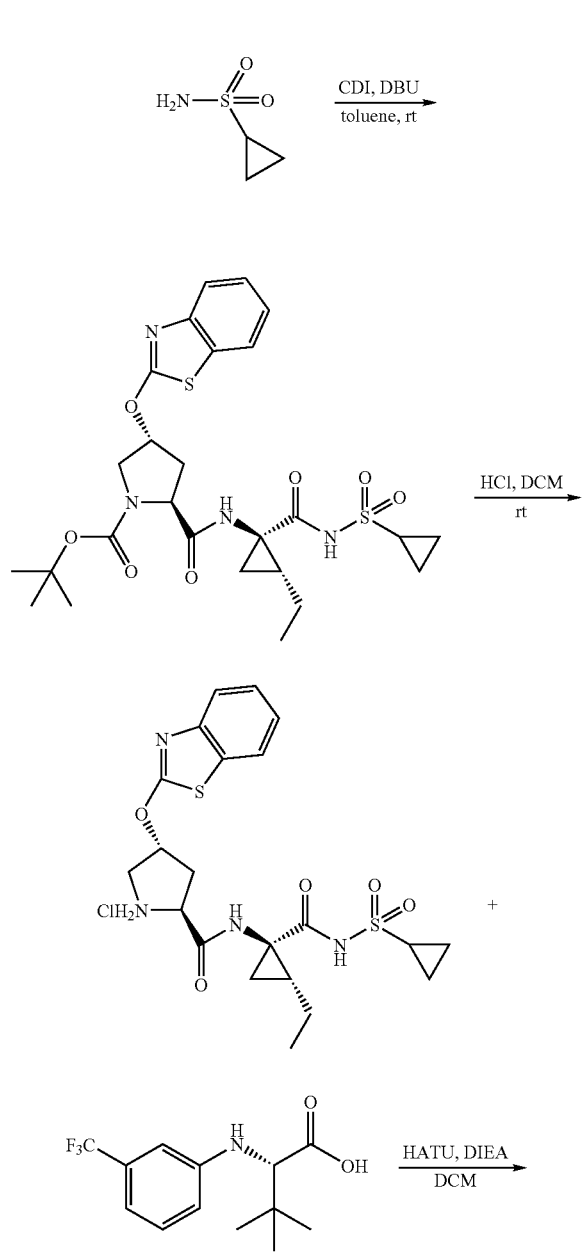
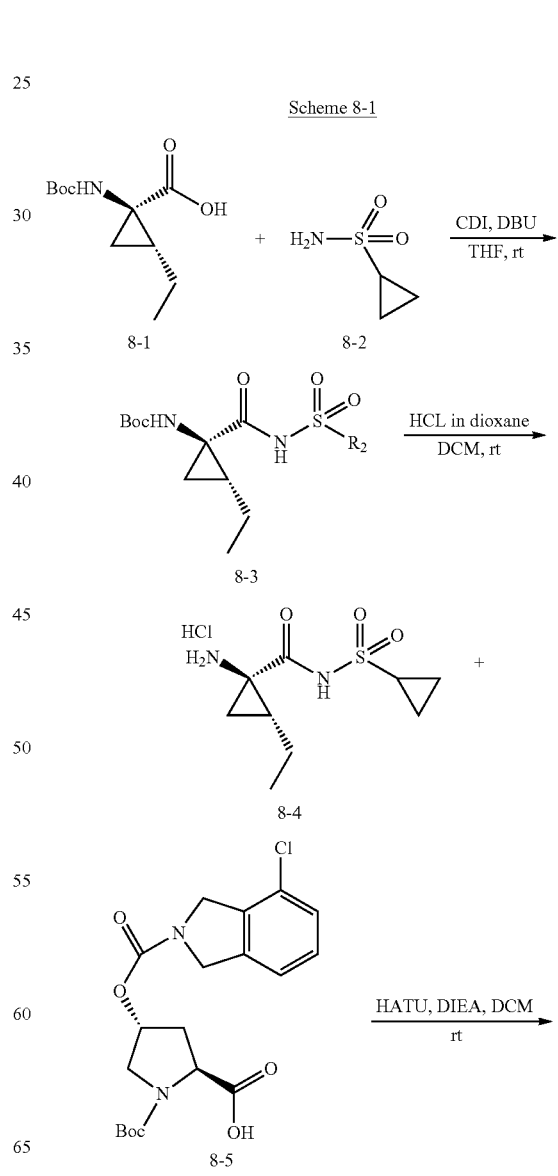

-continued

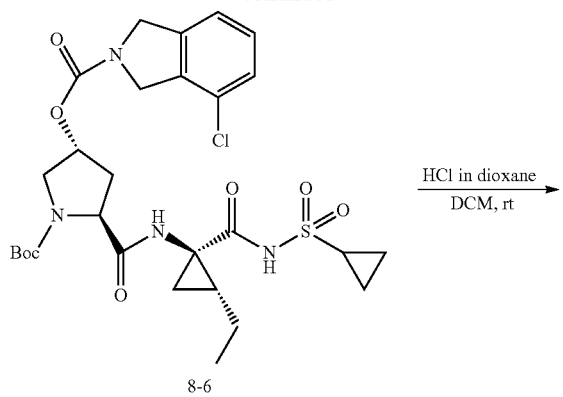

8-6

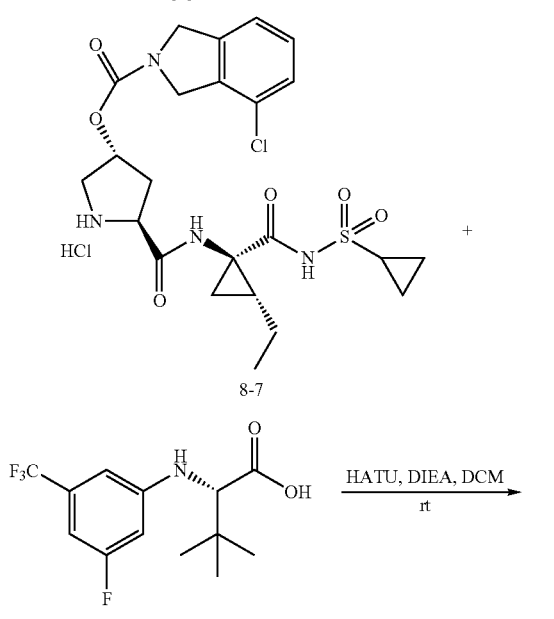

8-7

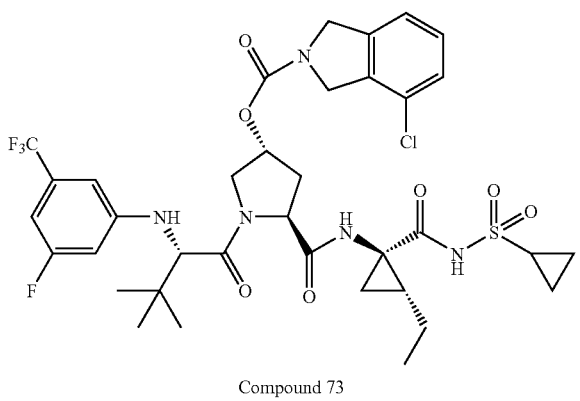

8-8

Compound 73

The following intermediates were prepared as described herein:

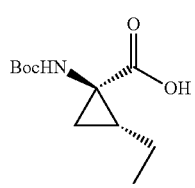

8-1

(1R,2R)-1-(tert-butoxycarbonylamino)-2-ethylcyclopropanecarboxylic acid (1R,2S)-1-(tert-butoxycarbonyl)-2-vinylcyclopropanecarboxylic acid (10.0 g, 44.0 mmol, prepared as described in WO2005037214) was dissolved in MTBE (250 mL) and hydrogenated (1 atm $H_2$) over Pd(OH)$_2$/C (1.24 g, 8.80 mmol) for 5 h at rt. The reaction was then stopped, filtered and concentrated down to 30 mL, followed by addition of 300 mL hexanes while stirring vigorously. After 60 min, the fine white precipitate was filtered, yielding the titled compound as a fine off-white powder (4.2 g, 42% yield). $^1$H-NMR (400 MHz, d$^6$-DMSO) δ 12.2 (s, 1 H), 7.41 (s, 1 H), 1.29-1.54 (m, 3 H), 1.36 (s, 9 H), 1.18-1.21 (m, 1 H), 0.96-0.98 (m, 1 H), 0.90 (t, 3 H).

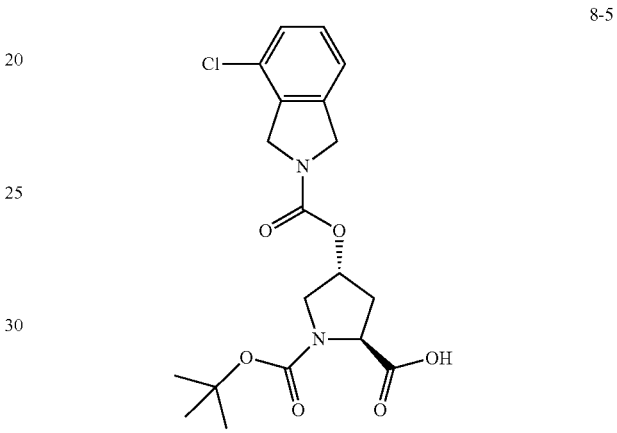

8-5

(2S,4R)-1-(tert-butoxycarbonyl)-4-(4-chloroisoindoline-2-carbonyloxy)pyrrolidine-2-carboxylic acid To a solution of (2S,4R)-1-tert-butyl 2-methyl 4-hydroxypyrrolidine-1,2-dicarboxylate (0.50 g, 2.04 mmol) in dry THF (6 mL) was added CDI (430 mg, 2.65 mmol) in one portion and the mixture was stirred at rt for 6 h. 4-chloroisoindoline hydrochloride (0.89 g, 4.69 mmol) was then added in portions, followed by slow addition of DIEA (1.07 mL, 6.12 mmol). The reaction was stirred at rt for overnight. The reaction was diluted with 120 mL EtOAc, washed with 1N HCl (2×50 mL), water and brine (50 mL each), and dried over Na$_2$SO$_4$ and concentrated down to a thick brownish oil. The crude was purified by silica chromatography (eluent=hexanes/EtOAc 2:1), giving (2S,4R)-1-tert-butyl 2-methyl 4-(4-chloroisoindoline-2-carbonyloxy)pyrrolidine-1,2-dicarboxylate as a light pinkish foamy solid (0.79 g, 91% yield).

(2S,4R)-1-tert-butyl 2-methyl 4-(4-chloroisoindoline-2-carbonyloxy)pyrrolidine-1,2-dicarboxylate (0.78 g, 1.8 mmol) was dissolved in a mixture of solvent THF:MeOH:water 2:2:1 (v/v) (5.4 mL), followed by addition of LiOH—H$_2$O (0.15 g, 3.7 mmol). After stirring at rt for overnight, the reaction was concentrated to near dryness. The resulting solid residue was re-dissolved in water (40 mL) and washed with ether (2×30 mL). The aqueous layer was acidified with 1N HCl to pH~2 and the combined EtOAc extracts (3×30 mL) was washed with brine and dried (Na$_2$SO$_4$), giving (2S,4R)-1-(tert-butoxycarbonyl)-4-(4-chloroisoindoline-2-carbonyloxy)pyrrolidine-2-carboxylic acid as a white foamy solid after evaporation of solvent.

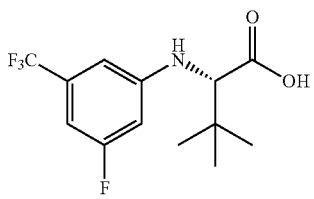

8-8

(S)-2-(3-fluoro-5-(trifluoromethyl)phenylamino)-3,3-dimethylbutanoic acid (S)-2-amino-3,3-dimethylbutanoic acid (0.50 g, 3.81 mmol), $K_2CO_3$ (1.580 g, 11.44 mmol), copper(I) iodide (0.073 g, 0.38 mmol) and 1-bromo-3-fluoro-5-(trifluoromethyl)benzene (2.32 g, 9.53 mmol) in DMA (4 mL) was heated at 95° C. for 32 hrs. $H_2O$ (15 mL) and ethyl ether (20 ml) was added. The aqueous phase was isolated and acidified with saturated $KHSO_4$ solution, extracted with ether, dried over sodium sulfate. After removal of solvent, it gave (S)-2-(3-fluoro-5-(trifluoromethyl)phenylamino)-3,3-dimethylbutanoic acid (0.78 g, 70%) as white solid. LCMS (APCI−): 292.2. $^1$H NMR (400 MHz, $d^6$-DMSO) δ 12.63 (s, 1H), 6.88 (s, 1H), 6.66 (d, J=12.4 Hz, 1H), 6.61 (d, J=8.8 Hz, 1H), 6.40 (d, J=9.2 Hz, 1H), 3.71 (d, J=9.6 Hz, 1H), 0.98 (s, 9H).

Compound 73

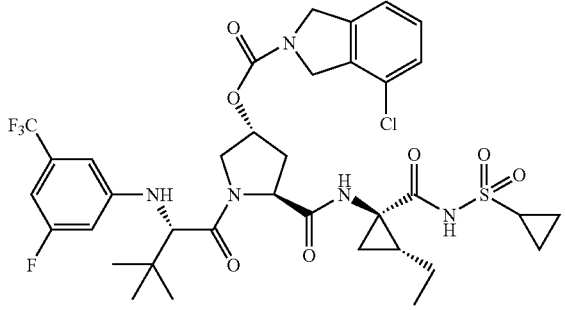

Compound 73 was prepared as described herein

Step 1: Synthesis of tert-butyl (1R,2R)-1-(cyclopropylsulfonylcarbamoyl)-2-ethylcyclopropylcarbamate (1R,2R)-1-(tert-butoxycarbonyl)-2-ethylcyclopropanecarboxylic acid (0.5 g, 2.18 mmol) was dissolved in THF (20 mL), followed by addition of CDI (390 mg, 2.41 mmol) in one portion at rt. The reaction was stirred in a 60° C. sandbath for 4 h, cooled to rt, and cyclopropanesulfonamide (292 mg, 2.41 mmol) and DBU (366 mg, 2.41 mmol) were added. The reaction was stirred at rt for overnight. The reaction was then diluted with EtOAc (30 mL) and washed with 1 N HCl (2×15 mL), water (10 mL), brine (10 mL), and dried ($Na_2SO_4$), giving tert-butyl (1R,2R)-1-(cyclopropylsulfonylcarbamoyl)-2-ethylcyclopropylcarbamate (0.53 g, 73% yield) as a white solid after removal of solvent. This crude product was directly used for the next without further purification.

Step 2: Synthesis of (1R,2R)-1-amino-N-(cyclopropylsulfonyl)-2-ethylcyclopropanecarboxamide dihydrochloride Tert-butyl (1R,2R)-1-(cyclopropylsulfonylcarbamoyl)-2-ethylcyclopropylcarbamate (0.53 g, 1.60 mmol) was dissolved in 4 N HCl in dioxane (20 mL) and stirred at rt for 5 hour. Removal of solvent gave (1R,2R)-1-amino-N-(cyclopropylsulfonyl)-2-ethylcyclopropanecarboxamide dihydrchloride as a white foamy solid. It was used directly in the next step without further purification.

Step 3: Synthesis of (3R,5S)-1-(tert-butoxycarbonyl)-5-((1R,2R)-1-(cyclopropylsulfonylcarbamoyl)-2-ethylcyclopropylcarbamoyl)pyrrolidin-3-yl 4-chloroisoindoline-2-carboxylate (2S,4R)-1-(tert-butoxycarbonyl)-4-(4-chloroisoindoline-2-carbonyloxy)pyrrolidine-2-carboxylic acid (0.93 g, 2.26 mmol), (1R,2R)-1-amino-N-(cyclopropylsulfonyl)-2-ethylcyclopropanecarboxamide dihydrochloride (0.64 g, 2.38 mmol) and HATU (0.79 g, 2.078 mmol) in DCM (20 mL) was added DIEA (1.18 ml, 6.79 mmol) and the reaction was stirred at rt for 18 hours. $H_2O$ (10 mL) was added and acidified with saturated $KHSO_4$ until PH=3~4. The mixture was extracted with ether (30 mL), washed with brine and dried over sodium sulfate. After removal of solvent, it gave (3R,5S)-1-(tert-butoxycarbonyl)-5-((1R,2R)-1-(cyclopropylsulfonylcarbamoyl)-2-ethylcyclopropylcarbamoyl)pyrrolidin-3-yl 4-chloroisoindoline-2-carboxylate (1.36 g, 96%) as a white solid, which was used directly for the next step without purification. LCMS (APCI+): 525.1 (MH$^+$−Boc).

Step 4: Synthesis of (3R,5S)-5-((1R,2R)-1-(cyclopropylsulfonylcarbamoyl)-2-ethylcyclopropylcarbamoyl)pyrrolidin-3-yl 4-chloroisoindoline-2-carboxylate dihydrochloride (3R,5S)-1-(tert-butoxycarbonyl)-5-((1R,2R)-1-(cyclopropylsulfonylcarbamoyl)-2-ethylcyclopropylcarbamoyl)pyrrolidin-3-yl 4-chloroisoindoline-2-carboxylate (1.35 g, 2.16 mmol) in DCM (5 mL) was added 4 N HCl in dioxane (4.32 ml, 17.3 mmol). The reaction mixture was stirred at rt for 2 hours. The solvent was removed and the residue was suspended in ethyl ether (30 mL) and stirred for 30 min. The solid was collected by filtration to give (3R,5S)-5-((1R,2R)-1-(cyclopropylsulfonylcarbamoyl)-2-ethylcyclopropylcarbamoyl)pyrrolidin-3-yl 4-chloroisoindoline-2-carboxylate dihydrochloride (1.10 g, 91%) as white solid. LCMS (APCI+): 525.2.

Step 5: Synthesis of (3R,5S)-5-((1R,2R)-1-(cyclopropylsulfonylcarbamoyl)-2-ethylcyclopropylcarbamoyl)-1-((S)-2-(3-fluoro-5-(trifluoromethyl)phenylamino)-3,3-dimethylbutanoyl)pyrrolidin-3-yl 4-chloroisoindoline-2-carboxylate (3R,5S)-5-((1R,2R)-1-(cyclopropylsulfonylcarbamoyl)-2-ethylcyclopropylcarbamoyl)pyrrolidin-3-yl 4-chloroisoindoline-2-carboxylate dihydrochloride (0.040 g, 0.071 mmol), (S)-2-(3-fluoro-5-(trifluoromethyl)phenylamino)-3,3-dimethylbutanoic acid (0.023 g, 0.079 mmol) and HATU (0.042 g, 0.11 mmol) in DCM (3 mL) was added DIEA (0.048 mL, 0.28 mmol) and the reaction was stirred at rt for 5 hr. $H_2O$ (5 mL) and saturated $KHSO_4$ solution (3 mL) was added. The mixture was extracted with ether (15 mL), washed with brine (10 mL) and dried over sodium sulfate. After removal of solvent, the residue was purified by chromatography (hexane:Ethyl acetate=1:2) to give the (3R,5S)-5-((1R,2R)-1-(cyclopropylsulfonylcarbamoyl)-2-ethylcyclopropylcarbamoyl)-1-((S)-2-(3-fluoro-5-(trifluoromethyl)phenylamino)-3,3-dimethylbutanoyl)pyrrolidin-3-yl 4-chloroisoindoline-2-carboxylate (0.037 g, 65%) as white solid. MS: Calcd.: 799.2;

Found: [M+H]+ 800.1. ¹H NMR (400 MHz, d⁶-DMSO). 10.44 (s, 1H), 8.80 & 8.74 (s, 1H), 7.34 (m, 3H), 7.14 & 7.02 (m, 1H), 6.73 (m, 1H), 6.35 & 6.26 (d, J=8.4 Hz, 1H), 6.15 (m, 1H), 5.35 (m, 1H), 4.50-4.72 (m, 3H), 4.20-4.46 (m, 4H), 3.82 (m, 1H), 2.94 (m, 1H), 2.31 (m, 1H), 2.04 (m, 1H), 0.84-1.49 (m, 21H).

EXAMPLE 9

Example A

NS3-NS4 Protease Assay

NS3 Complex Formation with NS4A-2.

Recombinant *E. coli* or Baculovirus full-length NS3 was diluted to 3.33 µM with assay buffer and transferred material to an eppendorf tube and place in water bath in 4° C. refrigerator. The appropriate amount of NS4A-2 to 8.3 mM in assay buffer was added to equal the volume of NS3 in step 2.1.1 (conversion factor ~3.8 mg/272 µL assay buffer). The material was transferred to an eppendorf tube and place in water bath in 4° C. refrigerator.

After equilibration to 4° C., equal volumes of NS3 and NS4A-2 solutions were combined in an eppendorf tube, mix gently with a manual pipettor, and incubate mixture for 15 minutes in the 4° C. water bath. Final concentrations in the mixture are 1.67 µM NS3, 4.15 mM NS4A-2 (2485-fold molar excess NS4A-2).

After 15 minutes at 4° C., the NS3/NS4A-2 eppendorf tube was removed and place it in a room temperature water bath for 10 minutes. NS3/NS4A-2 was aliquoted at appropriate volumes and store at −80° C. (*E. coli* NS3 run at 2 nM in assay, aliquot at 25 µL. BV NS3 run at 3 nM in assay, aliquot at 30 µL).

Example B

NS3 Inhibition Assay

Sample compounds were dissolved to 10 mM in DMSO then diluted to 2.5 mM (1:4) in DMSO. Typically, compounds were added to an assay plate at 2.5 mM concentration, yielding upon dilution a starting concentration of 50 microM in the assay inhibition curve. Compounds were serial diluted in assay buffer to provide test solutions at lower concentrations.

The *E. coli*. NS3/NS4A-2 was diluted to 4 nM NS3 (1:417.5 of 1.67 µM stock−18 µL1.67 µM stock+7497 µL assay buffer). The BV NS3/NS4A-2 was diluted to 6 nM NS3 (1:278.3 of 1.67 µM stock−24 µL1.67 µM stock+6655 µL assay buffer). Using the manual multichannel pipettor, careful not to introduce bubbles into the plate, add 50 µL assay buffer to wells A01-H01 of a black Costar 96-well polypropylene storage plate.

Using the manual multichannel pipettor, careful not to introduce bubbles into the plate, add 50 µL of diluted NS3/NS4A-2 from step 2.2.6 to wells A02-H12 of plate in step 2.2.7. Using the manual multichannel pipettor, careful not to introduce bubbles into the plate, transfer 25 µL of the wells in drug dilution plate in step 2.2.5 to corresponding wells in assay plate in step 2.2.8. Change tips on multichannel pipettor for each row of compounds transferred. Using the manual multichannel pipettor, careful not to introduce bubbles into the plate, mix the wells from the assay plate in step 2.2.9 by aspirating and dispensing 35 µL of the 75 µL in each well five times. Change tips on multichannel pipettor for each row of wells mixed. Cover plate with a polystyrene plate lid and pre-incubate the plate from step 2.2.10 containing NS3 protease and sample compounds 10 minutes at room temperature. While plate from step 2.2.11 is pre-incubating, dilute RETS1 substrate in a 15 mL polypropylene centrifuge tube. Dilute RETS1 substrate to 8 µM (1:80.75 of 646 µM stock−65 µL 646 µM stock+5184 µL assay buffer).

After the plate in step is done pre-incubating, and using the manual multichannel, add 25 µL of substrate to all wells on the plate. Quickly mix the plate as in step 2.2.10, mixing 65 µL of the 100 µL in the wells.

Read the plate in kinetic mode on the Molecular Devices SpectraMax Gemini XS plate reader. Reader settings: Read time: 30 minutes, Interval: 36 seconds, Reads: 51, Excitation λ: 335 nm, Emission λ: 495 nm, cutoff: 475 nm, Automix: off, Calibrate: once, PMT: high, Reads/well: 6, Vmax pts: 21 or 28/51 depending on length of linearity of reaction $IC_{50}$s are determined using a four parameter curve fit equation, and converted to Ki's using the following Km's:

Full-length *E. coli* NS3–2.03 µM
Full-length BV NS3–1.74 µM
where $Ki=IC_{50}/(1+[S]/Km)$ Quantitation by ELISA of the Selectable Marker Protein, Neomycin Phosphotransferase II (NPTII) in the HCV Sub-Genomic Replicon, GS4.3

The HCV sub-genomic replicon (1377/NS3-3', accession No. AJ242652), stably maintained in HuH-7 hepatoma cells, was created by Lohmann et al. *Science* 285: 110-113 (1999). The replicon-containing cell culture, designated GS4.3, was obtained from Dr. Christoph Seeger of the Institute for Cancer Research, Fox Chase Cancer Center, Philadelphia, Pa.

GS4.3 cells were maintained at 37° C., 5% $CO_2$, in DMEM (Gibco 11965-092) supplemented with L-glutamine 200 mM (100x) (Gibco25030-081), non-essential amino acids (NEAA) (Biowhittaker 13-114E), heat-inactivated (HI) Fetal Bovine Serum (FBS) (Hyclone SH3007.03) and 750 µg/mL geneticin (G418)(Gibco 10131-035). Cells were sub-divided 1:3 or 4 every 2-3 days.

24 h prior to the assay, GS4.3 cells were collected, counted, and plated in 96-well plates (Costar 3585) at 7500 cells/well in 100 µL standard maintenance medium (above) and incubated in the conditions above. To initiate the assay, culture medium was removed, cells were washed once with PBS (Gibco 10010-023) and 90 µl Assay Medium (DMEM, L-glutamine, NEAA, 10% HI FBS, no G418) was added. Inhibitors were made as a 10x stock in Assay Medium, (3-fold dilutions from 10 µM to 56 pM final concentration, final DMSO concentration 1%), 10 µL were added to duplicate wells, plates were rocked to mix, and incubated as above for 72 h.

An NPTII Elisa kit was obtained from AGDIA, Inc. (Compound direct ELISA test system for Neomycin Phosphotransferase II, PSP 73000/4800). Manufacturer's instructions were followed, with some modifications. 10xPEB-1 lysis buffer was made up to include 500 µM PMSF (Sigma P7626, 50 mM stock in isopropanol). After 72 h incubation, cells were washed once with PBS and 150 µL PEB-1 with PMSF was added per well. Plates were agitated vigorously for 15 minutes, room temperature, then frozen at −70° C. Plates were thawed, lysates were mixed thoroughly, and 100 µl were applied to an NPTII Elisa plate. A standard curve was made. Lysate from DMSO-treated control cells was pooled, serially diluted with PEB-1 with PMSF, and applied to duplicate wells of the ELISA plate, in a range of initial lysate amount of 150 µL-2.5 µL. In addition, 100 µL buffer alone was applied in duplicate as a blank. Plates were sealed and gently agitated at room temperature for 2 h. Following capture incubation, the plates were washed 5×300 µL with PBS-T (0.5% Tween-20, PBS-T was supplied in the ELISA kit). For detection, a 1x dilution of enzyme conjugate diluent MRS-2 (5x) was made in PBS-T, into which 1:100 dilutions of enzyme conjugates A and B were added, as per instructions. Plates were resealed, and incubated with agitation, covered, room temperature, for 2 h. The washing was then repeated and 100 µL of room temperature TMB substrate was added. After approximately 30 minutes incubation (room temperature, agitation, covered), the reaction was stopped with 50 μL 3M sulfuric acid. Plates were read at 450 nm on a Molecular Devices Versamax plate reader.

Inhibitor effect was expressed as a percentage of DMSO-treated control signal, and inhibition curves were calculated using a 4-parameter equation: $y=A+((B-A)/(1+((C/x)^D)))$, where C is half-maximal activity or $EC_{50}$.

Examples of Activity

TABLE 1

| Compound # | Structure | NS3-NS4 $IC_{50}$ | Replicon $EC_{50}$ |
|---|---|---|---|
| 10 | 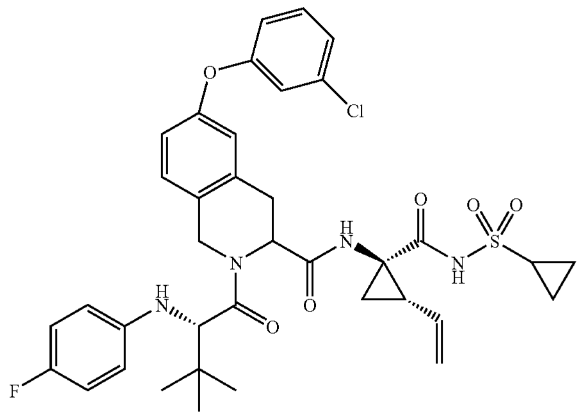 | D | B |
| 11 | 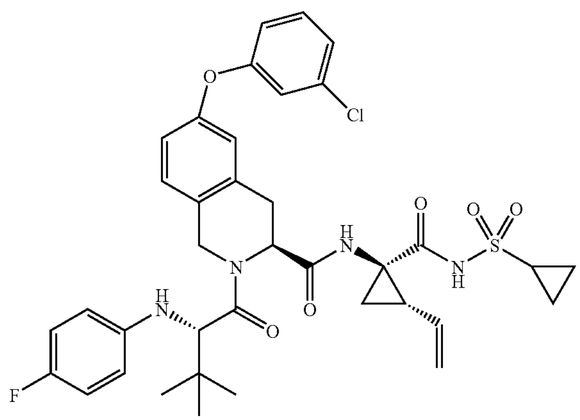 | D | A |
| 12 | 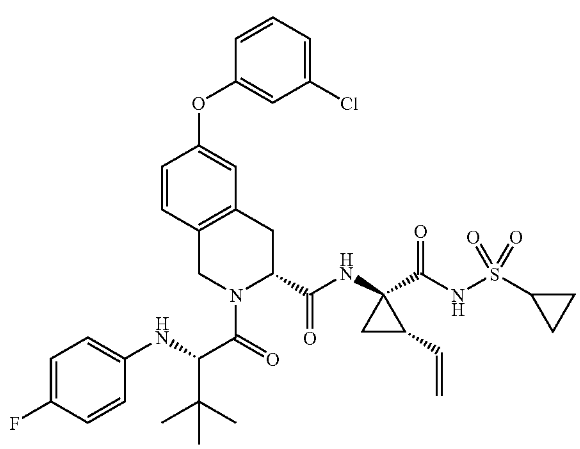 | C | A |

TABLE 1-continued
| Compound # | Structure | NS3-NS4 IC$_{50}$ | Replicon EC$_{50}$ |
|---|---|---|---|
| 13 | 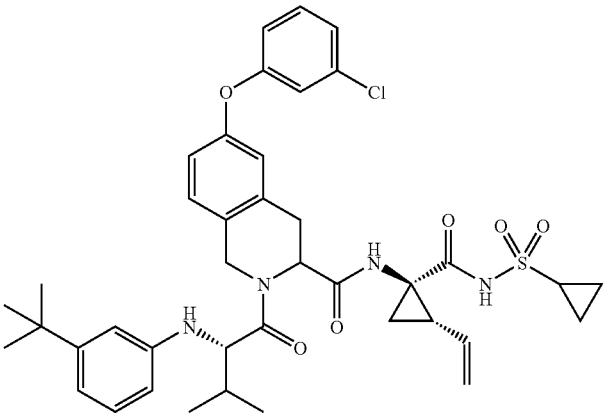 | D | A |
| 33 | 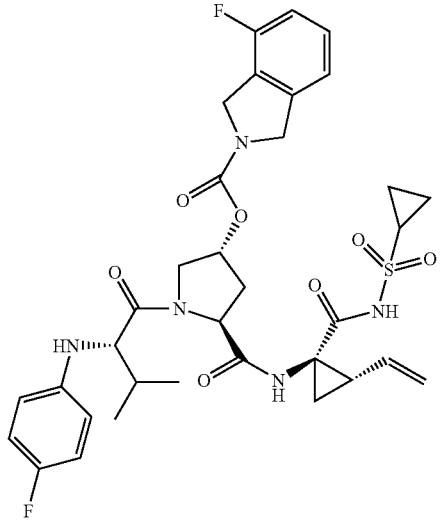 | D | C |
| 34 | 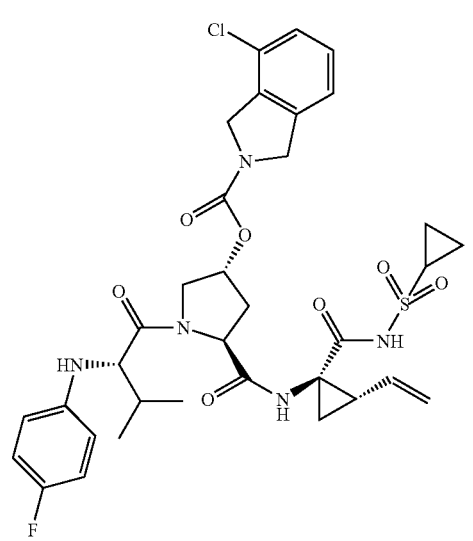 | D | D |

US 7,932,277 B2
137                                                                                                   138
TABLE 1-continued
| Compound # | Structure | NS3-NS4 IC$_{50}$ | Replicon EC$_{50}$ |
|---|---|---|---|
| 35 | 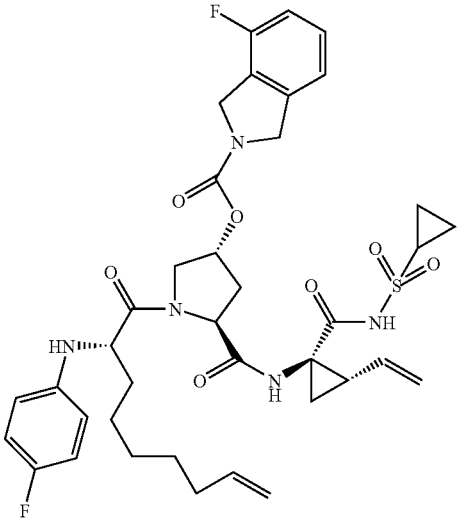 | D | B |
| 36 | 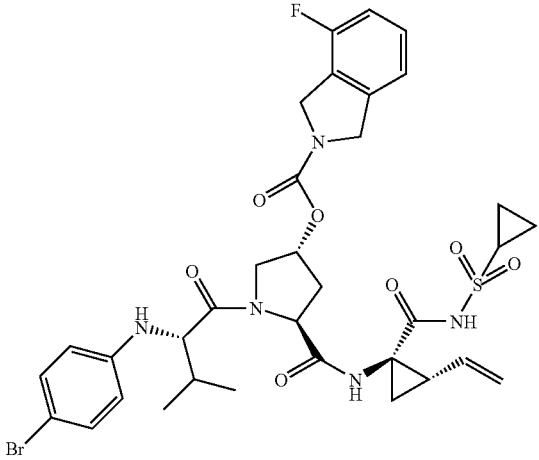 | D | C |
| 37 | 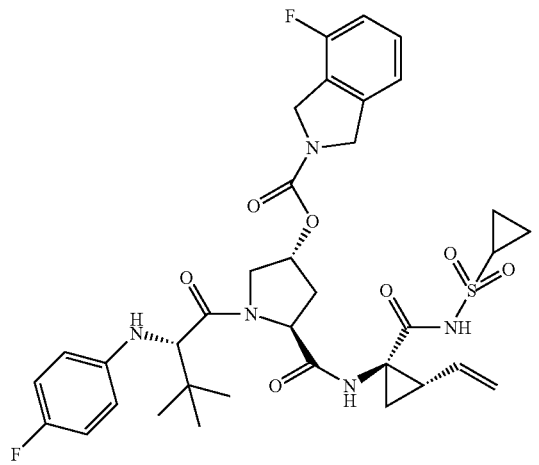 | D | D |

| Compound # | Structure | NS3-NS4 IC$_{50}$ | Replicon EC$_{50}$ |
|---|---|---|---|
| 38 | 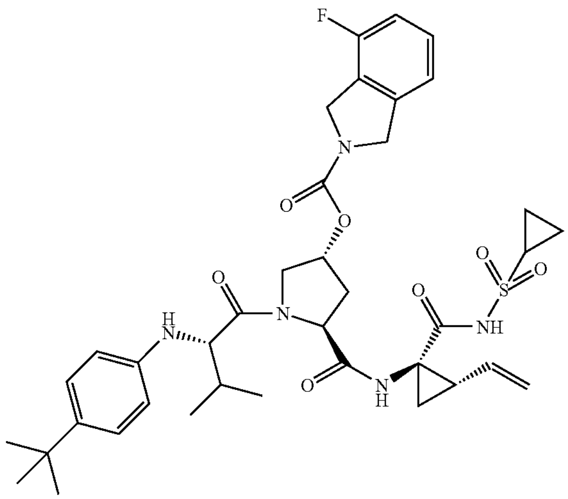 | D | C |
| 39 | 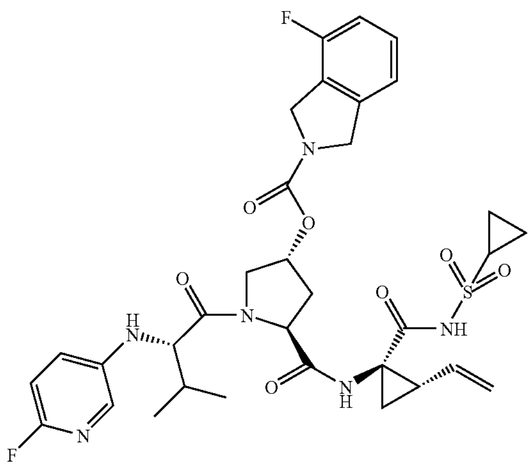 | D | C |
| 40 | 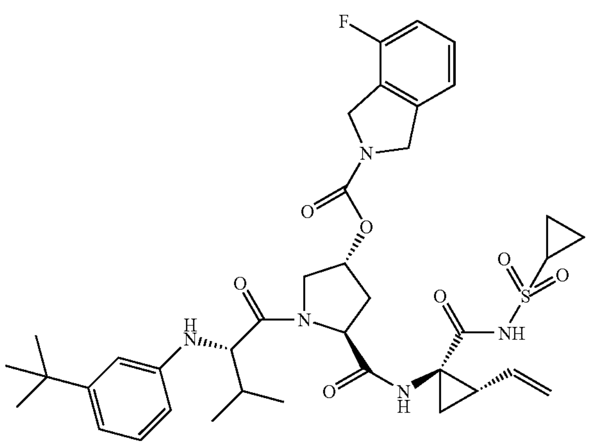 | D | D |

TABLE 1-continued
| Compound # | Structure | NS3-NS4 IC$_{50}$ | Replicon EC$_{50}$ |
|---|---|---|---|
| 41 | 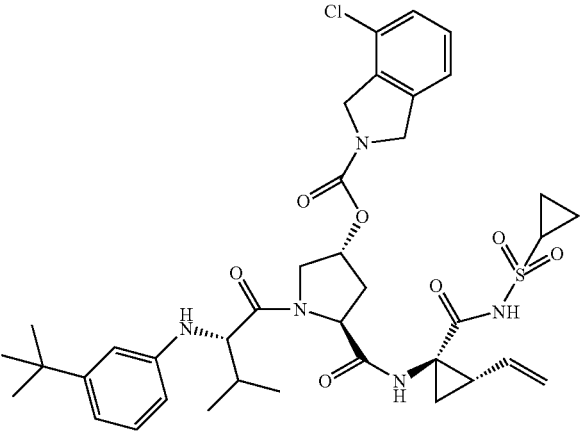 | D | D |
| 42 | 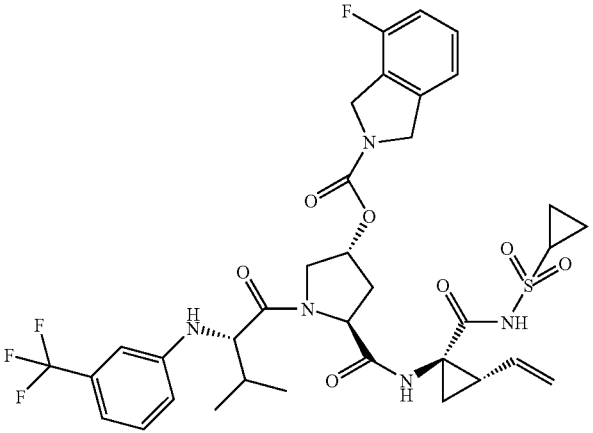 | D | D |
| 43 | 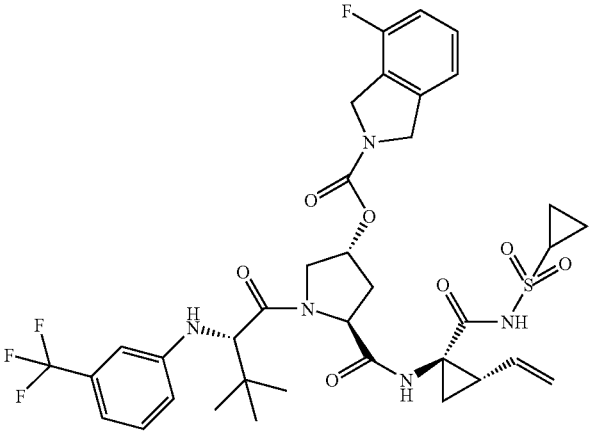 | D | D |

TABLE 1-continued

| Compound # | Structure | NS3-NS4 IC$_{50}$ | Replicon EC$_{50}$ |
|---|---|---|---|
| 44 | 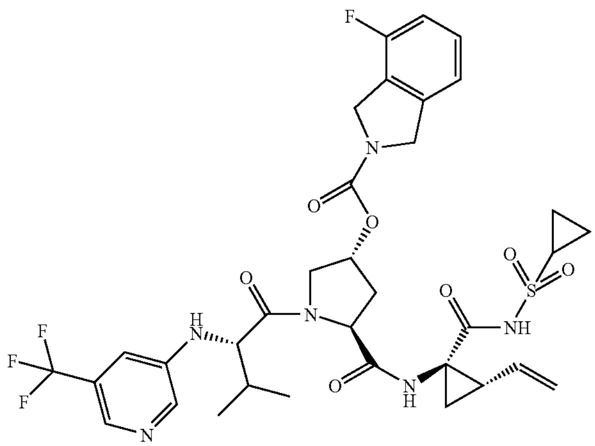 | D | C |
| 45 | 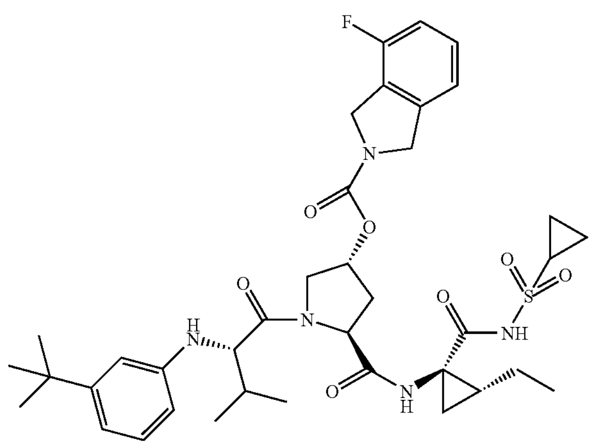 | D | D |
| 46 | 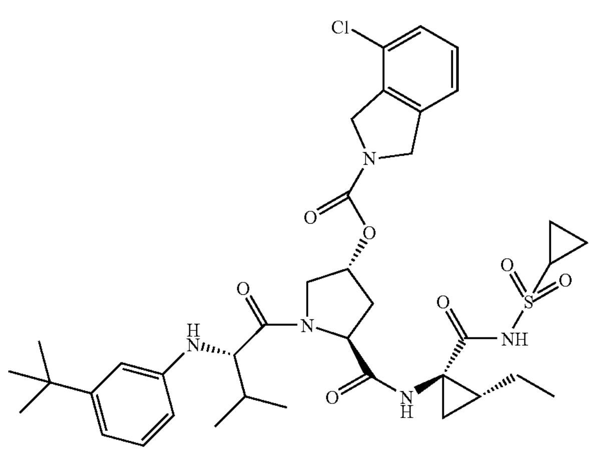 | D | D |

TABLE 1-continued

| Compound # | Structure | NS3-NS4 IC$_{50}$ | Replicon EC$_{50}$ |
|---|---|---|---|
| 47 | 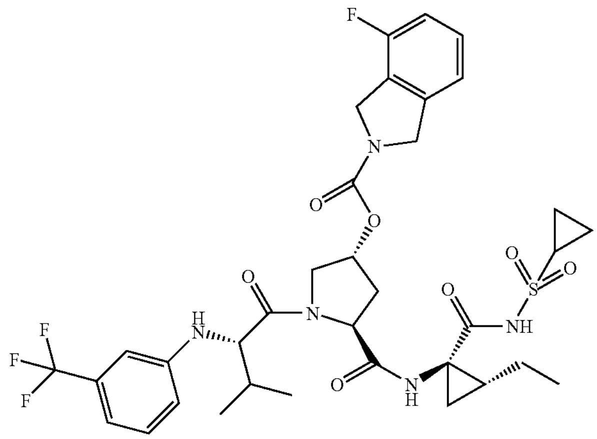 | D | D |
| 48 | 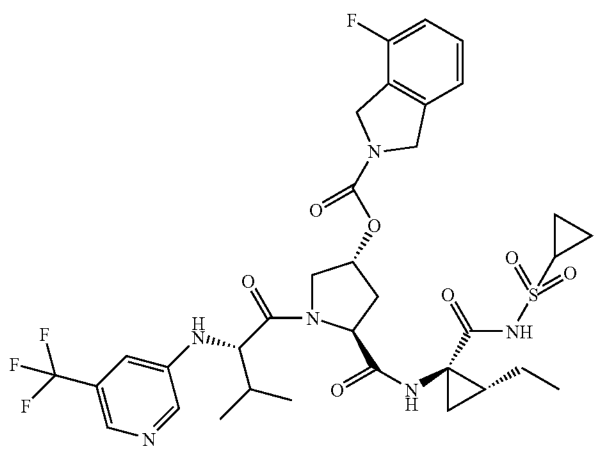 | D | C |
| 49 | 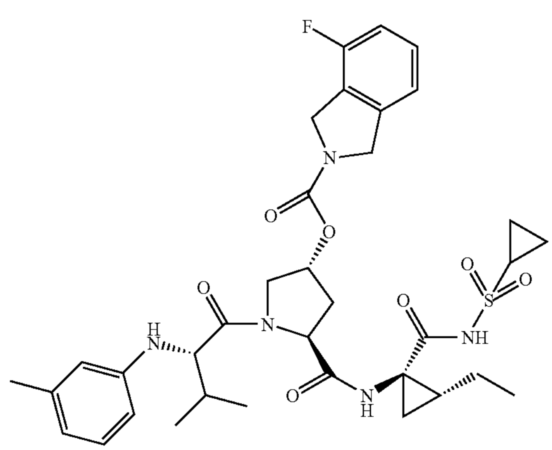 | D | C |

TABLE 1-continued
| Compound # | Structure | NS3-NS4 IC$_{50}$ | Replicon EC$_{50}$ |
|---|---|---|---|
| 50 | 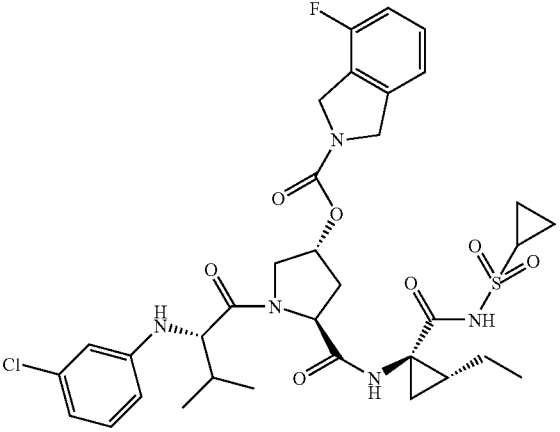 | D | D |
| 51 | 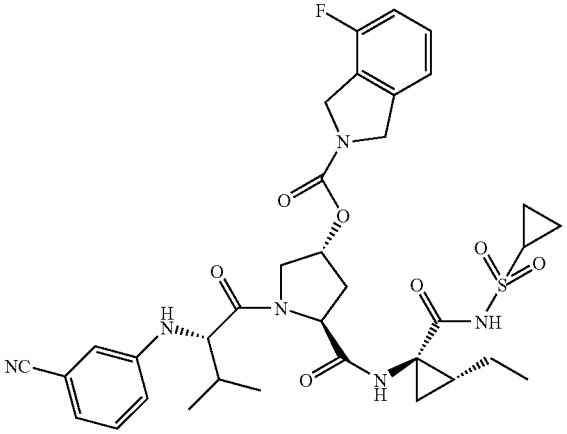 | D | C |
| 52 | 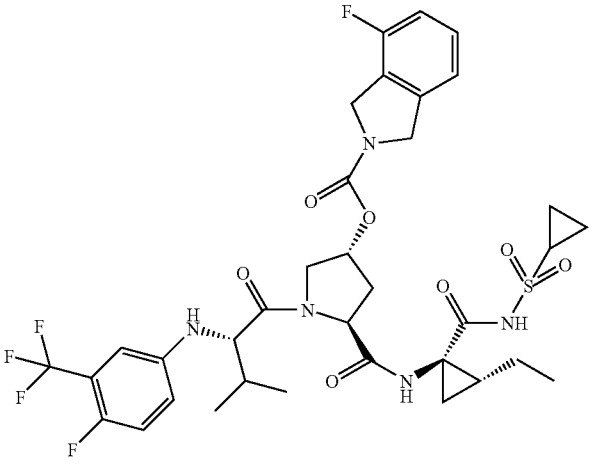 | D | D |

TABLE 1-continued
| Compound # | Structure | NS3-NS4 IC$_{50}$ | Replicon EC$_{50}$ |
|---|---|---|---|
| 53 | 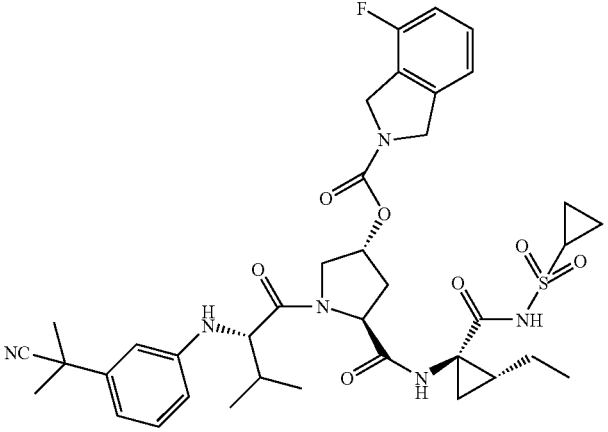 | D | D |
| 54 | 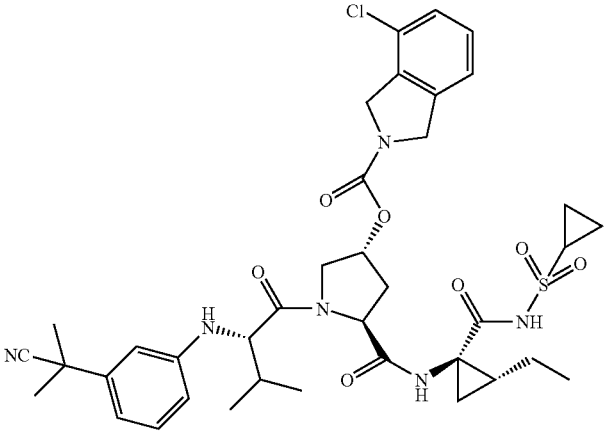 | D | D |
| 55 | 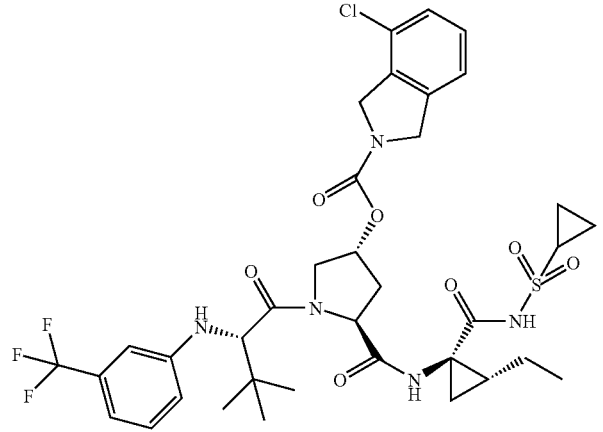 | D | D |

TABLE 1-continued

| Compound # | Structure | NS3-NS4 IC$_{50}$ | Replicon EC$_{50}$ |
|---|---|---|---|
| 56 | 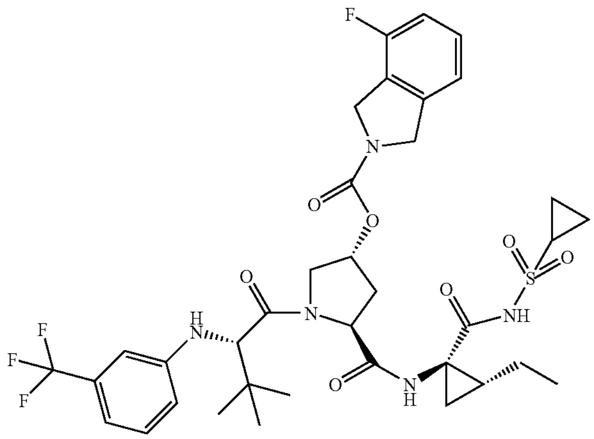 | D | D |
| 57 | 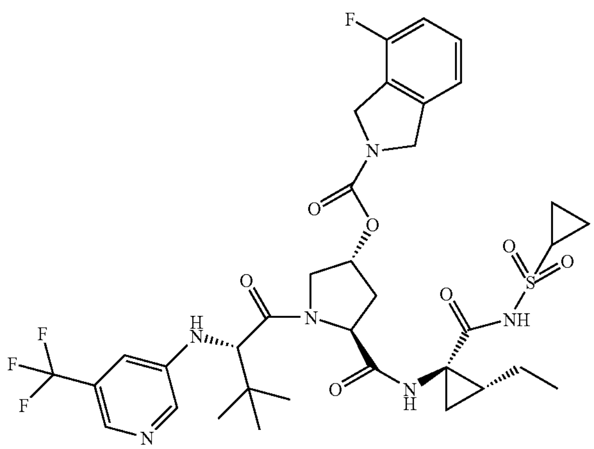 | D | D |
| 58 | 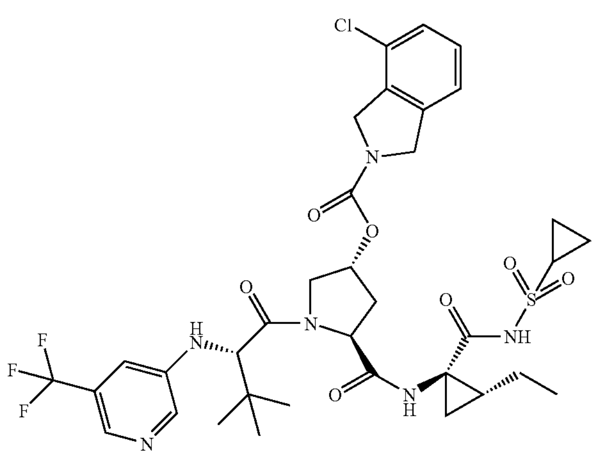 | D | D |

TABLE 1-continued

| Compound # | Structure | NS3-NS4 IC$_{50}$ | Replicon EC$_{50}$ |
| --- | --- | --- | --- |
| 59 | 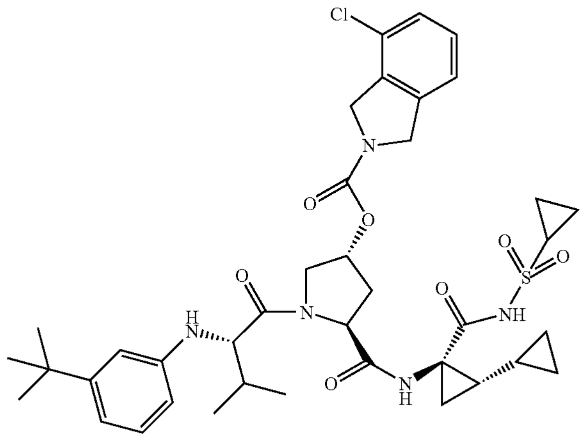 | D | D |
| 60 | 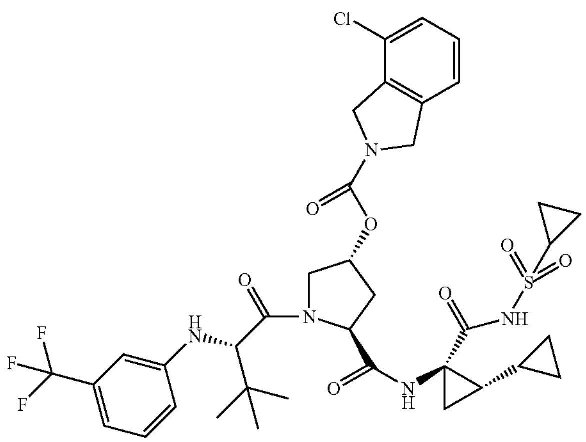 | D | D |
| 61 | 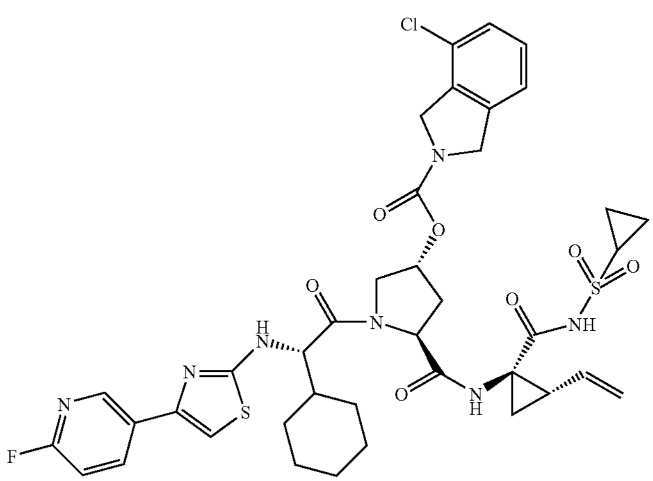 | D | D |

TABLE 1-continued

| Compound # | Structure | NS3-NS4 IC$_{50}$ | Replicon EC$_{50}$ |
|---|---|---|---|
| 62 | 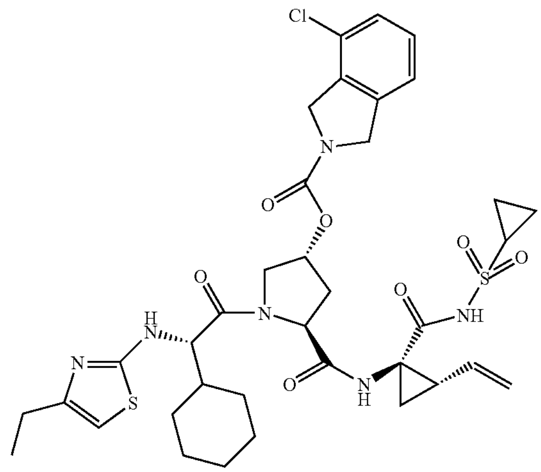 | D | D |
| 63 | 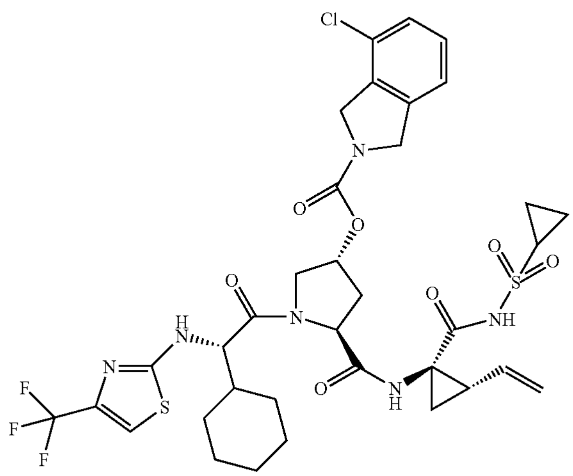 | D | D |
| 64 | 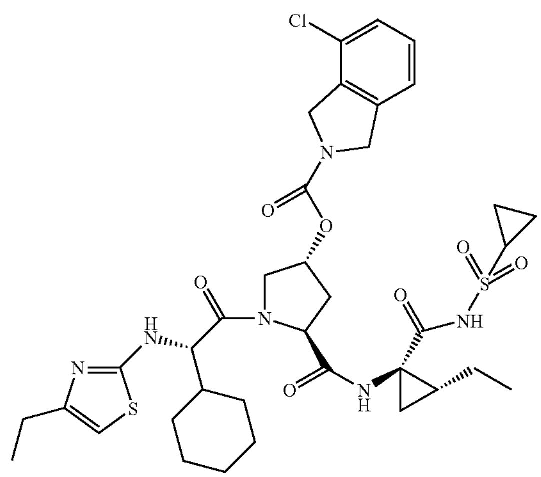 | D | D |

TABLE 1-continued
| Compound # | Structure | NS3-NS4 IC$_{50}$ | Replicon EC$_{50}$ |
|---|---|---|---|
| 65 | 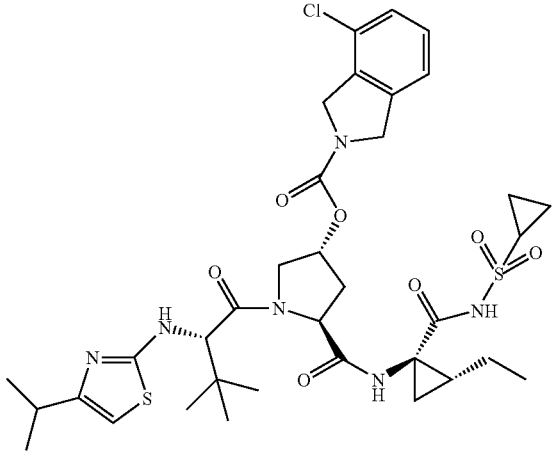 | D | n.a. |
| 66 | 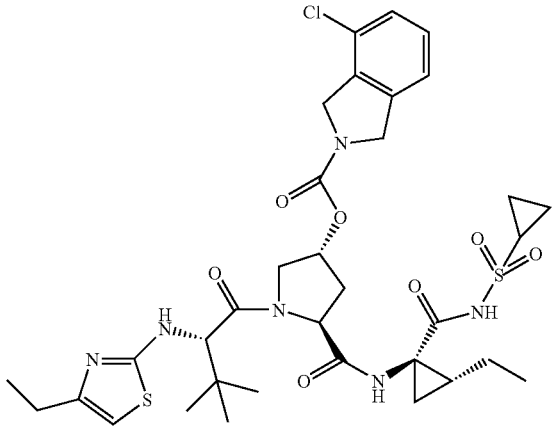 | D | D |
| 67 | 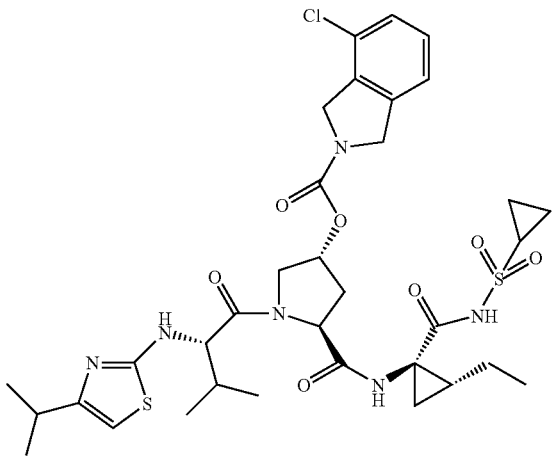 | D | D |

TABLE 1-continued

| Compound # | Structure | NS3-NS4 IC$_{50}$ | Replicon EC$_{50}$ |
| --- | --- | --- | --- |
| 68 | 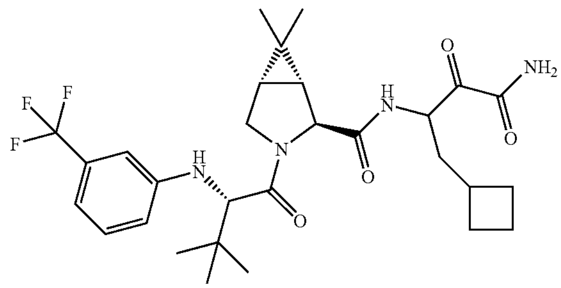 | C | A |
| 69 | 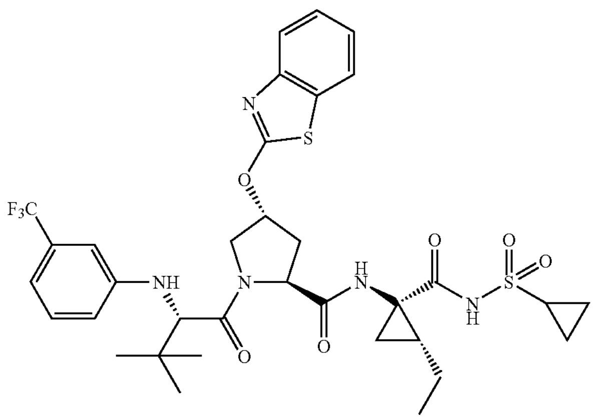 | D | D |
| 70 | 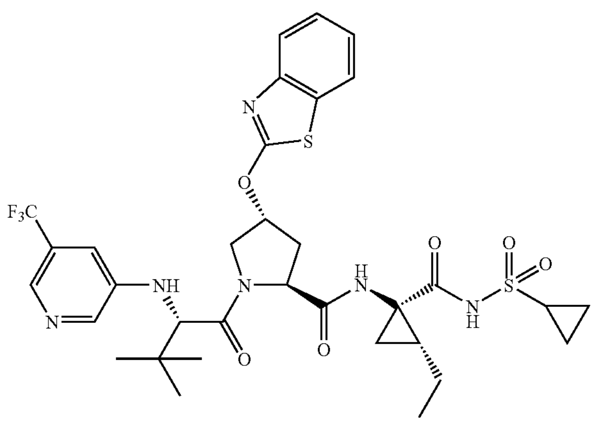 | D | D |
| 71 | 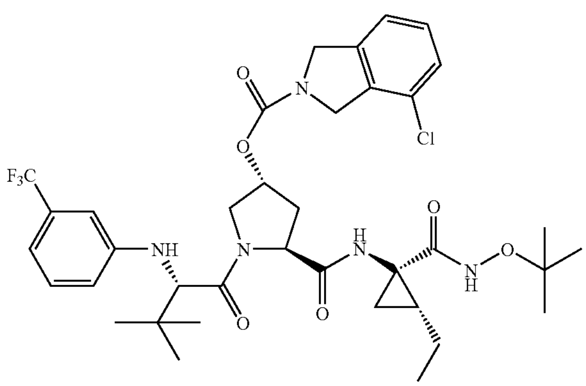 | C | C |

TABLE 1-continued

| Compound # | Structure | NS3-NS4 IC$_{50}$ | Replicon EC$_{50}$ |
| --- | --- | --- | --- |
| 72 | 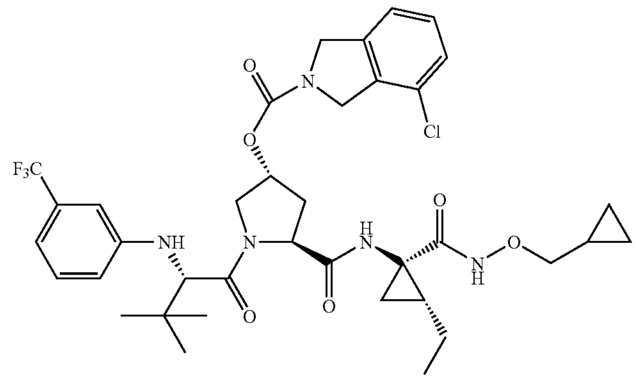 | C | C |
| 73 | 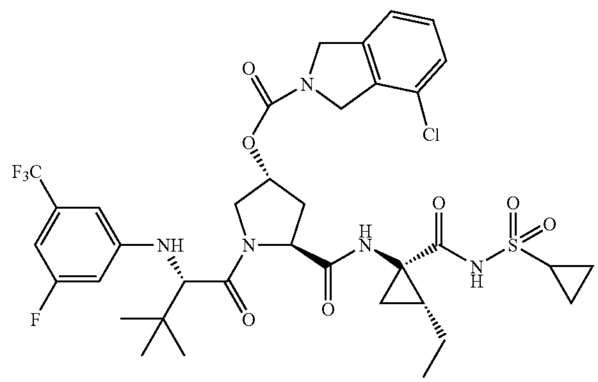 | D | D |
| 74 | 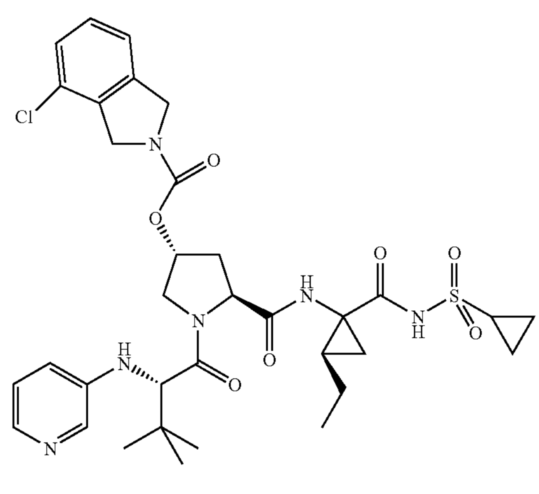 | D | D |

163 164

TABLE 1-continued

| Compound # | Structure | NS3-NS4 IC$_{50}$ | Replicon EC$_{50}$ |
|---|---|---|---|
| 75 | 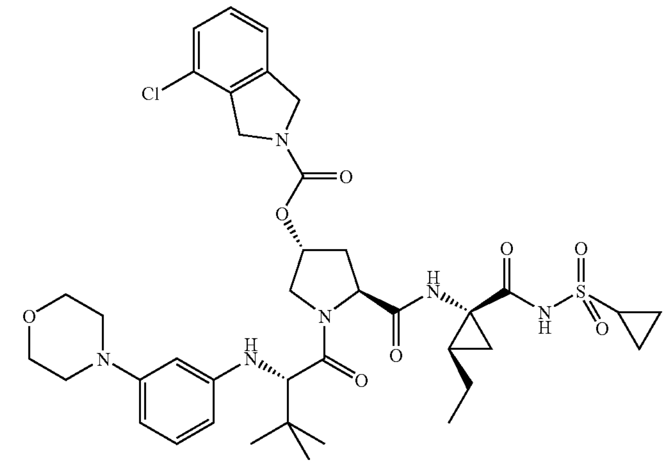 | D | D |
| 76 | 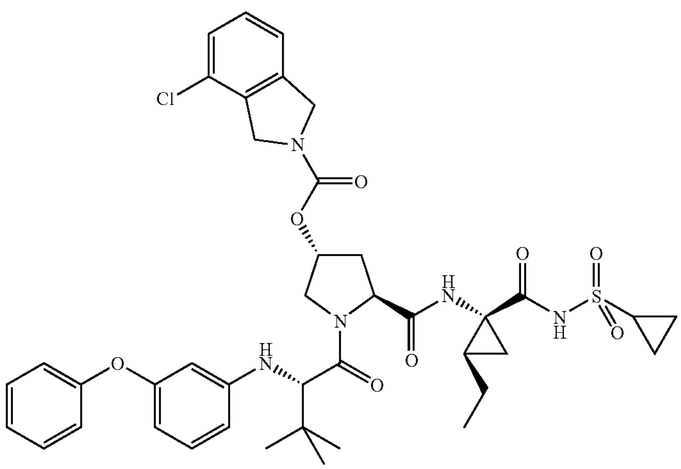 | D | D |
| 77 | 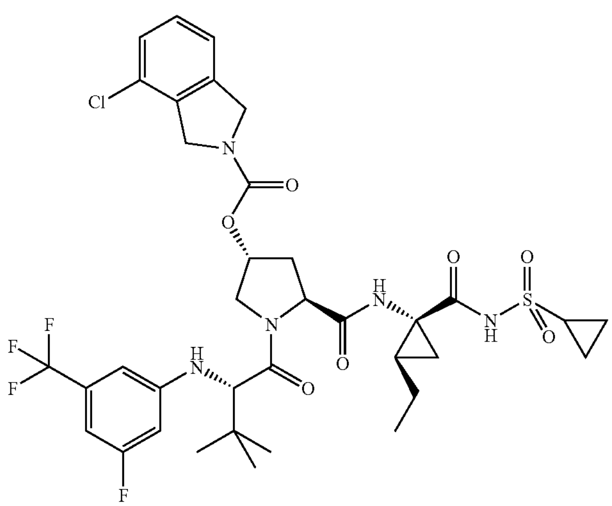 | n.a. | D |

TABLE 1-continued
| Compound # | Structure | NS3-NS4 IC$_{50}$ | Replicon EC$_{50}$ |
|---|---|---|---|
| 78 | 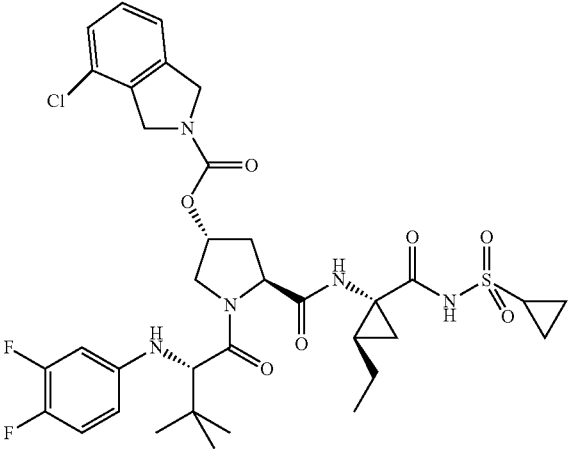 | n.a. | n.a. |
| 79 | 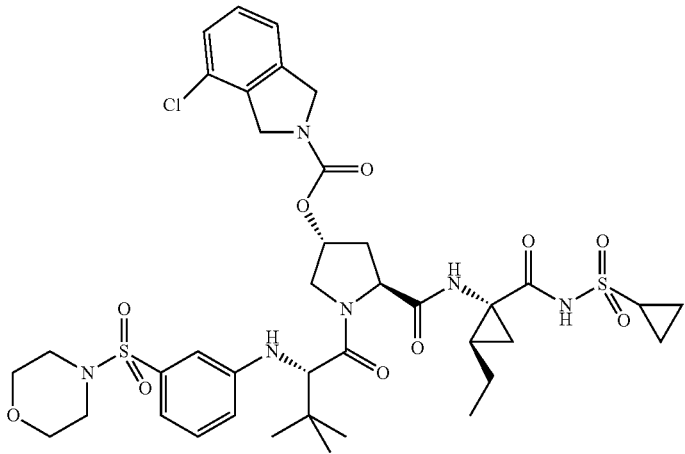 | n.a. | n.a. |
| 80 | 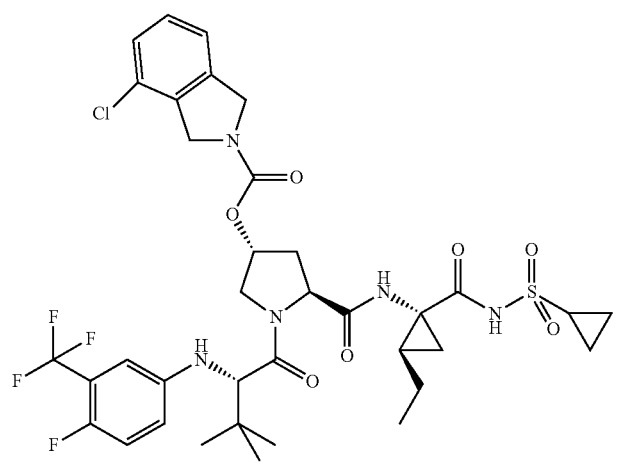 | n.a. | n.a. |

TABLE 1-continued

| Compound # | Structure | NS3-NS4 IC$_{50}$ | Replicon EC$_{50}$ |
|---|---|---|---|
| 81 | 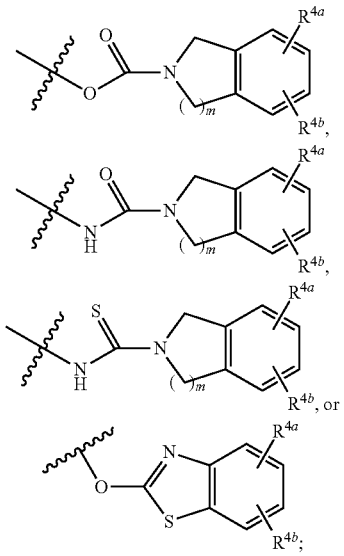 | D | D |

A indicates an EC$_{50}$ or IC$_{50}$ between 10 and 50 μM
B indicates an EC$_{50}$ or IC$_{50}$ between 1 and 10 μM
C indicates an EC$_{50}$ or IC$_{50}$ between 0.1 and 1 μM
D indicates an EC$_{50}$ or IC$_{50}$ of less than 0.1 μM

CONCLUSION

Potent small molecule inhibitors of the HCV NS3 protease have been developed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the Formula I:

(I)

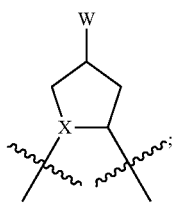

or a pharmaceutically acceptable salt, prodrug, or ester thereof wherein:

B is

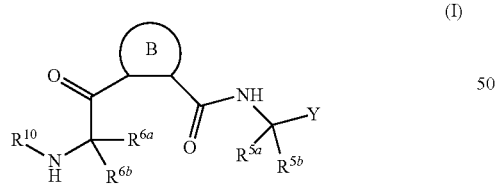

X is N or CH;

W is OR$^{3a}$, O(CO)R$^{3a}$, O(CO)NR$^{3a}$R$^{3b}$, SR$^{3a}$, NHR$^{3a}$, NH(CO)R$^{3a}$, CHR$^{3a}$R$^{3b}$, NH(CS)R$^{3a}$, optionally substituted heterocycle, optionally substituted phenyl, R$^{3a}$ and R$^{3b}$ are independently hydrogen, C$_{1-8}$ alkyl, C$_{3-7}$ cycloalkyl, C$_{4-10}$ cycloalkyl-alkyl, optionally substituted C$_{6-10}$ aryl, optionally substituted benzothiazyl optionally substituted benzoxazyl, optionally substituted isoquinolinyl, optionally substituted pyridinyl, optionally substituted pyrrolyl, optionally substituted oxazolyl, optionally substituted indolyl, optionally substituted C$_{7-10}$ aralkyl, optionally substituted C$_{6-12}$ heteroaryl-alkyl, optionally substituted heterocycle, optionally substituted phenyl, optionally substituted bicyclic ring system, or optionally substituted benzyl;

m is 1 or 2;

$R^{4a}$ and $R^{4b}$ are independently hydrogen, halogen, hydroxy, nitro, amino, cyano, $C_{1-8}$ alkyl optionally substituted with up to 5 fluoro, $C_{1-8}$ alkoxy optionally substituted with up to 5 fluoro, $C_{1-8}$ alkylthio group optionally substituted with up to 5 fluoro, $C_{1-8}$ alkylamino optionally substituted with up to 5 fluoro, $C(O)R^7$, $C(O)OR^7$, $C(O)NR^7R^8$, $C(S)NR^7R^8$, $S(O)R^7$ or $S(O)_2R^7$;

$R^7$ and $R^8$ are independently optionally substituted alkyl, optionally substituted aryl, or optionally substituted heteroaryl;

$R^{5a}$ and $R^{5b}$ are independently hydrogen, $C_{1-8}$ alkyl optionally substituted with up to 5 fluoro, $C_{1-8}$ cycloalkyl-alkyl, $C_{2-8}$ alkenyl, $C_{3-7}$ cycloalkyl optionally substituted with up to 5 fluoro, optionally substituted aryl, optionally substituted heteroaryl, optionally substituted $C_{7-10}$ aralkyl, or optionally substituted $C_{6-12}$ heteroaryl-alkyl; alternatively $R^{5a}$ and $R^{5b}$ are taken together to form a three to six- membered carbocyclic or heterocyclic ring system optionally substituted by 1-3 substituents selected from the group consisting of $C_{1-6}$ alkyl, $C_{2-6}$ alkenyl, and optionally substituted $C_{3-7}$ cycloalkyl;

$R^{6a}$ and $R^{6b}$ are independently hydrogen, $C_{1-8}$ alkyl optionally substituted with up to 5 fluoro, $C_{2-8}$ alkenyl, $C_{3-7}$ cycloalkyl optionally substituted with up to 5 fluoro, $C_{4-7}$ cycloalkyl-alkyl, optionally substituted aryl, optionally substituted heteroaryl, optionally substituted $C_{7-10}$ aralkyl, or optionally substituted $C_{6-12}$ heteroaryl-alkyl; alternatively $R^{6a}$ and $R^{6b}$ are taken together to form a optionally substituted three to six- membered carbocyclic or heterocyclic ring system;

Y is selected from the group consisting of —C(O)NHS(O)$_2R^{9a}$, —C(O)NHS(O)$_2NR^{9a}R^{9b}$, —C(O)NHS(O)$R^{9a}$, —C(O)NHS(O)NR$^{9a}R^{9b}$, —C(O)C(O)OH, —C(O)NHR$^{9a}$, —C(O)R$^{9a}$, —C(O)OR$^{9a}$, —C(O)NHC(O)R$^{9a}$, —C(O)OH, —C(O)C(O)NR$^{9a}R^{9b}$, and —C(O)NHOR$^{9a}$;

$R^{9a}$ and $R^{9b}$ are independently hydrogen, optionally substituted $C_{1-6}$ alkyl, optionally substituted $C_{3-7}$ cycloalkyl, optionally substituted $C_{4-9}$ cycloalkyl-alkyl, optionally substituted aryl, optionally substituted heteroaryl, $C_{7-9}$ aralkyl, or optionally substituted $C_{6-12}$ heteroaryl-alkyl, or $NR^{9a}R^{9b}$ forms a substituted or unsubstituted three- to six- membered heterocyclic ring;

$R^{10}$ is an aryl or heteroaryl optionally substituted by 1-3 substituents selected from the group consisting of halogen, hydroxy, nitro, amino, cyano, $C_{1-8}$ alkyl optionally substituted with up to 5 fluoro or cyano, $C_{1-8}$ alkoxy optionally substituted with up to 5 fluoro, $C_{1-8}$ alkylthio group optionally substituted with up to 5 fluoro, $C_{1-8}$ alkylamino optionally substituted with up to 5 fluoro, $C_{3-8}$ heterocyclic, $C(O)R^{8a}$, $C(O)OR^{8a}$, $C(O)NR^{8a}R^{8b}$, $C(S)NR^{8a}R^{8b}$, $OR^{8a}$, and $S(O)_2R^{8a}$;

$R^{8a}$ and $R^{8b}$ are independently hydrogen, optionally substituted alkyl, optionally substituted aryl, optionally substituted heteroaryl, or optionally substituted $C_{3-8}$ heterocyclic; and with the provisos that:
if B is

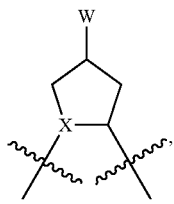

X is N, and W is $OR^{3a}$, then $R^{3a}$ is not optionally substituted napthalenyl or naphthalenylmethyl.

2. The compound of claim 1, wherein X is N.

3. The compound of claim 1, wherein W is $OR^{3a}$, $O(CO)R^{3a}$, $O(CO)NR^{3a}R^{3b}$, or $SR^{3a}$.

4. The compound of claim 1, wherein W is $O(CO)R^{3a}$ or $O(CO)NR^{3a}R^{3b}$.

5. The compound of claim 1, wherein W is

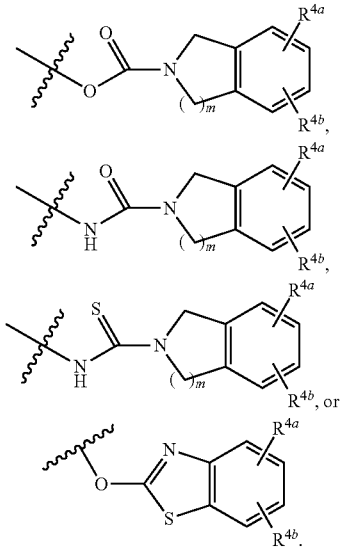

6. The compound of claim 1, wherein W is

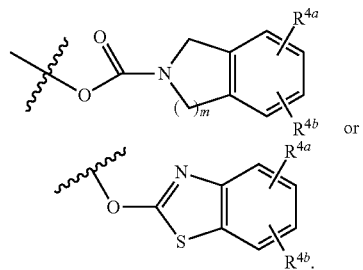

7. The compound of claim 6, wherein m is 1.

8. The compound of claim 6, wherein $R^{4a}$ and $R^{4b}$ are independently hydrogen or halogen.

9. The compound of claim 1, wherein W is $O(CO)R^{3a}$, $O(CO)NR^{3a}R^{3b}$, $NH(CO)R^{3a}$, or $NH(CS)R^{3a}$.

10. The compound of claim 1, wherein B is

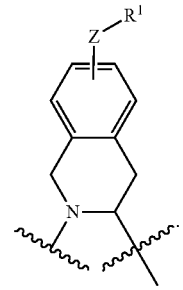

11. The compound of claim 10, wherein Z is O, NH, or S.

12. The compound of claim 10, wherein $R^1$ is selected from the group consisting of optionally substituted heterocycle, optionally substituted phenyl, benzyloxy, and substituted benzyl.

13. The compound of claim 12, wherein $R^1$ optionally substituted phenyl.

14. The compound of claim 10, wherein Z is O.

15. The compound of claim 1, wherein B is

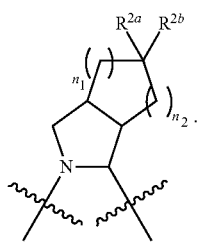

16. The compound of claim 15, wherein $R^{2a}$ and $R^{2b}$ are $C_{1-3}$ alkyl.

17. The compound of claim 16, wherein $R^{2a}$ and $R^{2b}$ are methyl.

18. The compound of claim 15, wherein $n_1$ is 0 and $n_2$ is 0.

19. The compound of claim 15, wherein Y is —C(O)C(O)OH or —C(O)C(O)NR$^{9a}$R$^{9b}$.

20. The compound of claim 19, wherein Y is —C(O)C(O)NH$_2$.

21. The compound of claim 15, wherein at least one of $R^{5a}$ and $R^{5b}$ is $C_{1-8}$ cycloalkyl-alkyl.

22. The compound of claim 21, wherein at least one of $R^{5a}$ and $R^{5b}$ is cyclobutyl-methyl.

23. The compound of claim 15, wherein $R^7$ is aryl optionally substituted by 1-3 substituents selected from the group consisting of halogen, hydroxy, nitro, amino, cyano, $C_{1-8}$ alkyl optionally substituted with up to 5 fluoro, $C_{1-8}$ alkoxy optionally substituted with up to 5 fluoro, $C_{1-8}$ alkylthio group optionally substituted with up to 5 fluoro, $C_{1-8}$alkylamino optionally substituted with up to 5 fluoro, C(O)R$^{8a}$, C(O)OR$^{8a}$, C(O)NR$^{8a}$R$^{8b}$, C(S)NR$^{8a}$R$^{8b}$, and S(O)$_2$R$^{8a}$.

24. The compound of claim 1, wherein Y is selected from the group consisting of —C(O)NHS(O)$_2$R$^{9a}$, —C(O)NHS(O)$_2$NR$^{9a}$R$^{9b}$, —C(O)NHS(O)R$^{9a}$, —C(O)NHS(O)NR$^{9a}$R$^{9b}$, —C(O)C(O)OH, —C(O)NHR$^{9a}$, —C(O)R$^{9a}$, —C(O)NHC(O)R$^{9a}$, —C(O)C(O)NR$^{9a}$R$^{9b}$, and —C(O)NHOR$^{9a}$.

25. The compound of claim 1, wherein Y is selected from the group consisting of —C(O)NHS(O)$_2$R$^{9a}$, —C(O)NHS(O)$_2$NR$^{9a}$R$^{9b}$, —C(O)NHS(O)R$^{9a}$, and —C(O)NHS(O)NR$^{9a}$R$^{9b}$.

26. The compound of claim 1, wherein Y is selected from the group consisting of —C(O)NHS(O)$_2$R$^{9a}$ and —C(O)NHS(O)NR$^{9a}$R$^{9b}$.

27. The compound of claim 1, wherein Y is —C(O)NHS(O)$_2$R$^{9a}$.

28. The compound of claim 24, wherein R$^{9a}$ is selected from the group consisting of optionally substituted $C_{3-7}$ cycloalkyl, optionally substituted $C_{4-9}$ cycloalkyl-alkyl, optionally substituted aryl, optionally substituted heteroaryl, optionally substituted $C_{7-9}$ aralkyl, and optionally substituted $C_{6-12}$ heteroaryl-alkyl.

29. The compound of claim 28, wherein R$^{9a}$ is $C_{3-7}$ cycloalkyl.

30. The compound of claim 29, wherein R$^{9a}$ is cyclopropyl.

31. The compound of claim 1, wherein $R^{5a}$ and $R^{5b}$ are taken together to form a three- to six- membered carbocyclic or heterocyclic ring system optionally substituted by 1-3 substituents selected from the group consisting of $C_{1-6}$ alkyl, $C_{2-6}$ alkenyl, and optionally substituted $C_{3-7}$ cycloalkyl.

32. The compound of claim 31, wherein $R^{5a}$ and $R^{5b}$ are taken together to form a cyclopropyl ring system substituted by $C_{1-6}$ alkyl or $C_{2-6}$ alkenyl.

33. The compound of claim 32, wherein $R^{5a}$ and $R^{5b}$ are taken together to form a cyclopropyl ring system substituted by $C_{2-6}$ alkenyl.

34. The compound of claim 1, wherein:

W is OR$^{3a}$, O(CO)R$^{3a}$, O(CO)NR$^{3a}$R$^{3b}$, SR$^{3a}$, NHR$^{3a}$, NH(CO)R$^{3a}$, CHR$^{3a}$R$^{3b}$, NH(CS)R$^{3a}$, optionally substituted heterocycle, optionally substituted phenyl,

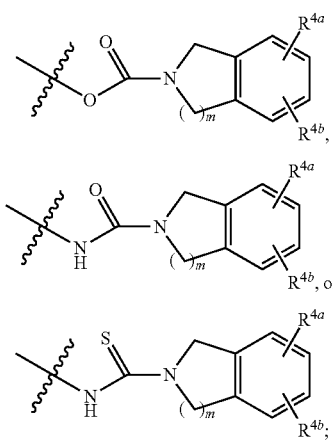

R$^{10}$ is an aryl or heteroaryl optionally substituted by 1-3 substituents selected from the group consisting of halogen, hydroxy, nitro, amino, cyano, $C_{1-8}$ alkyl optionally substituted with up to 5 fluoro, $C_{1-8}$ alkoxy optionally substituted with up to 5 fluoro, $C_{1-8}$ alkylthio group optionally substituted with up to 5 fluoro, $C_{1-8}$ alkylamino optionally substituted with up to 5 fluoro, C(O)R$^{8a}$, C(O)OR$^{8a}$, C(O)NR$^{8a}$R$^{8b}$, C(S)NR$^{8a}$R$^{8b}$, and S(O)$_2$R$^{8a}$; and R$^{8a}$ and R$^{8b}$ are independently hydrogen, optionally substituted alkyl, optionally substituted aryl, or optionally substituted heteroaryl.

35. The compound of claim 1 having a formula selected from the group consisting of:

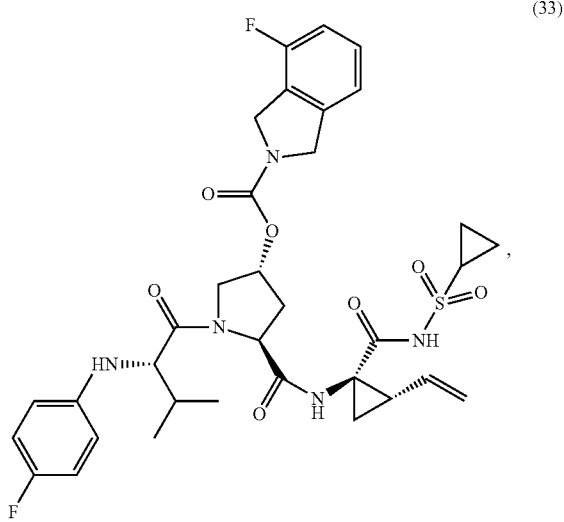

(33)

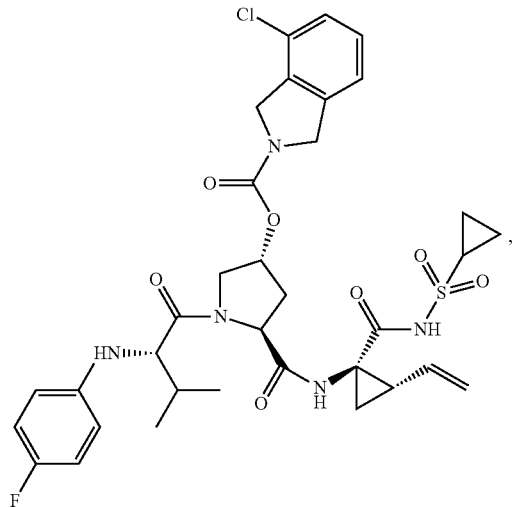
(34)
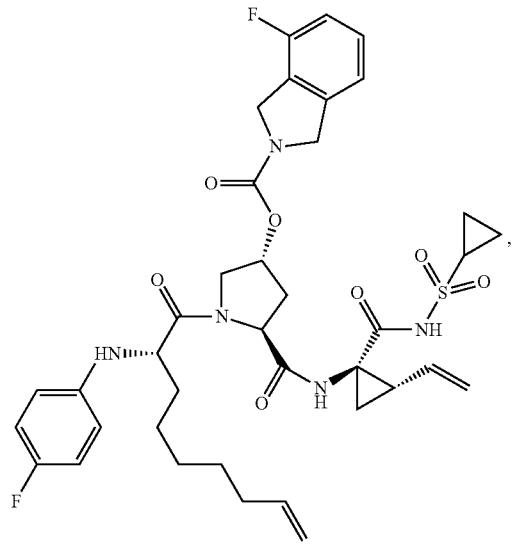
(35)
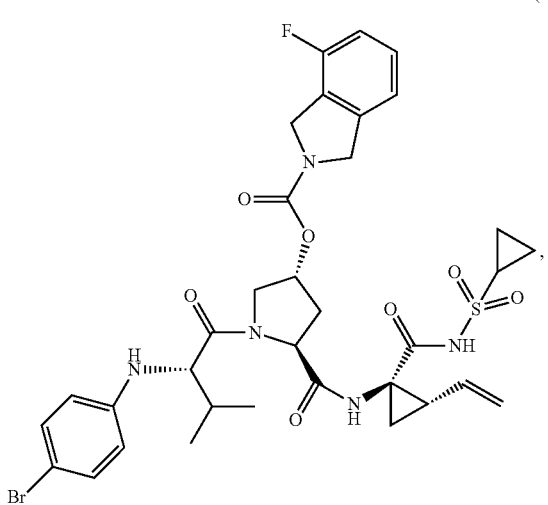
(36)
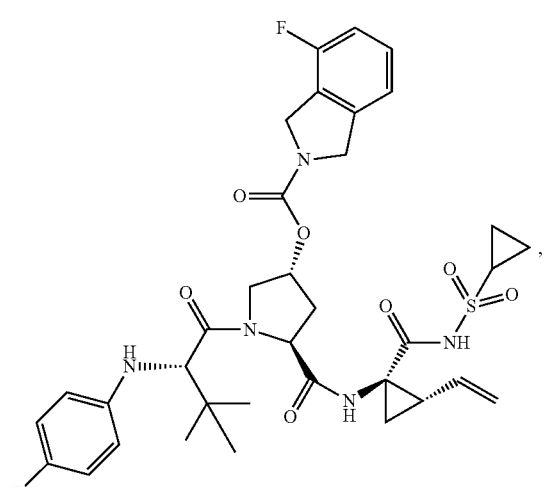
(37)
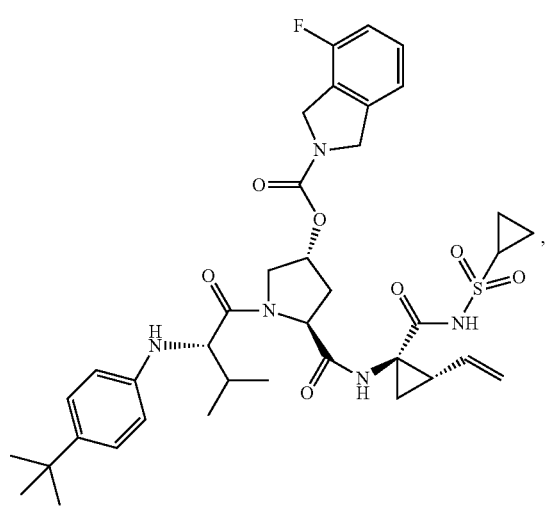
(38)
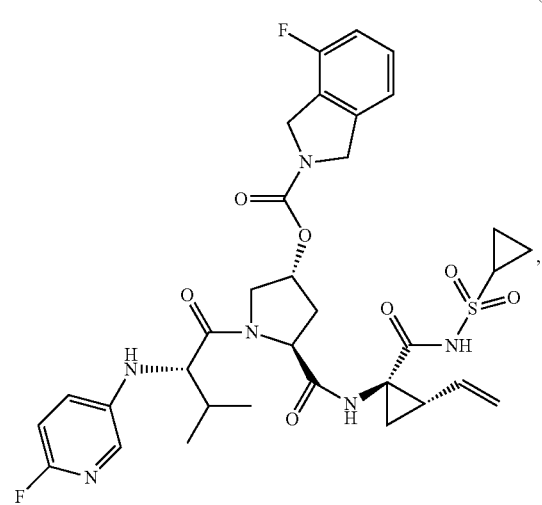
(39)

-continued
(40)
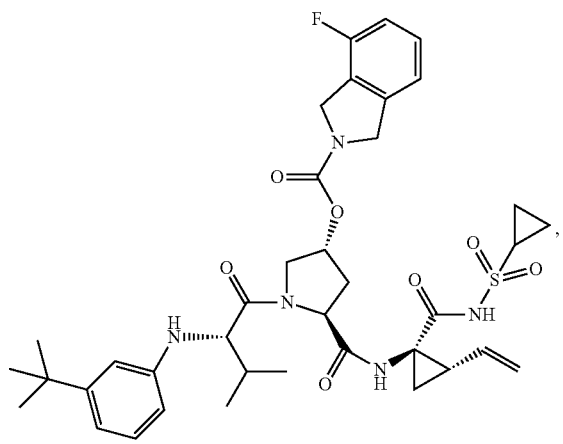
(41)
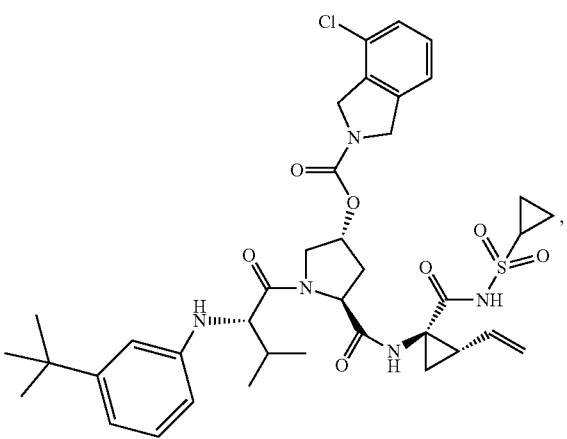
(42)
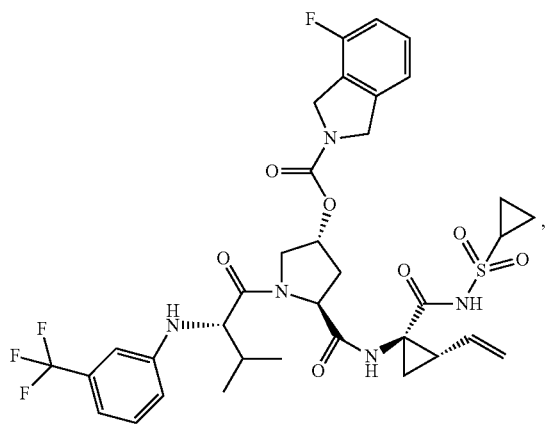
-continued
(43)
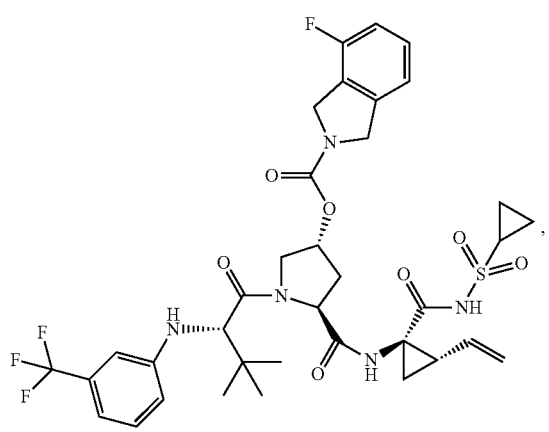
(44)
(45)
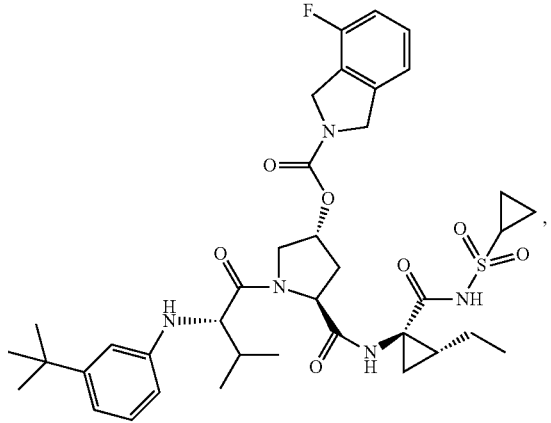

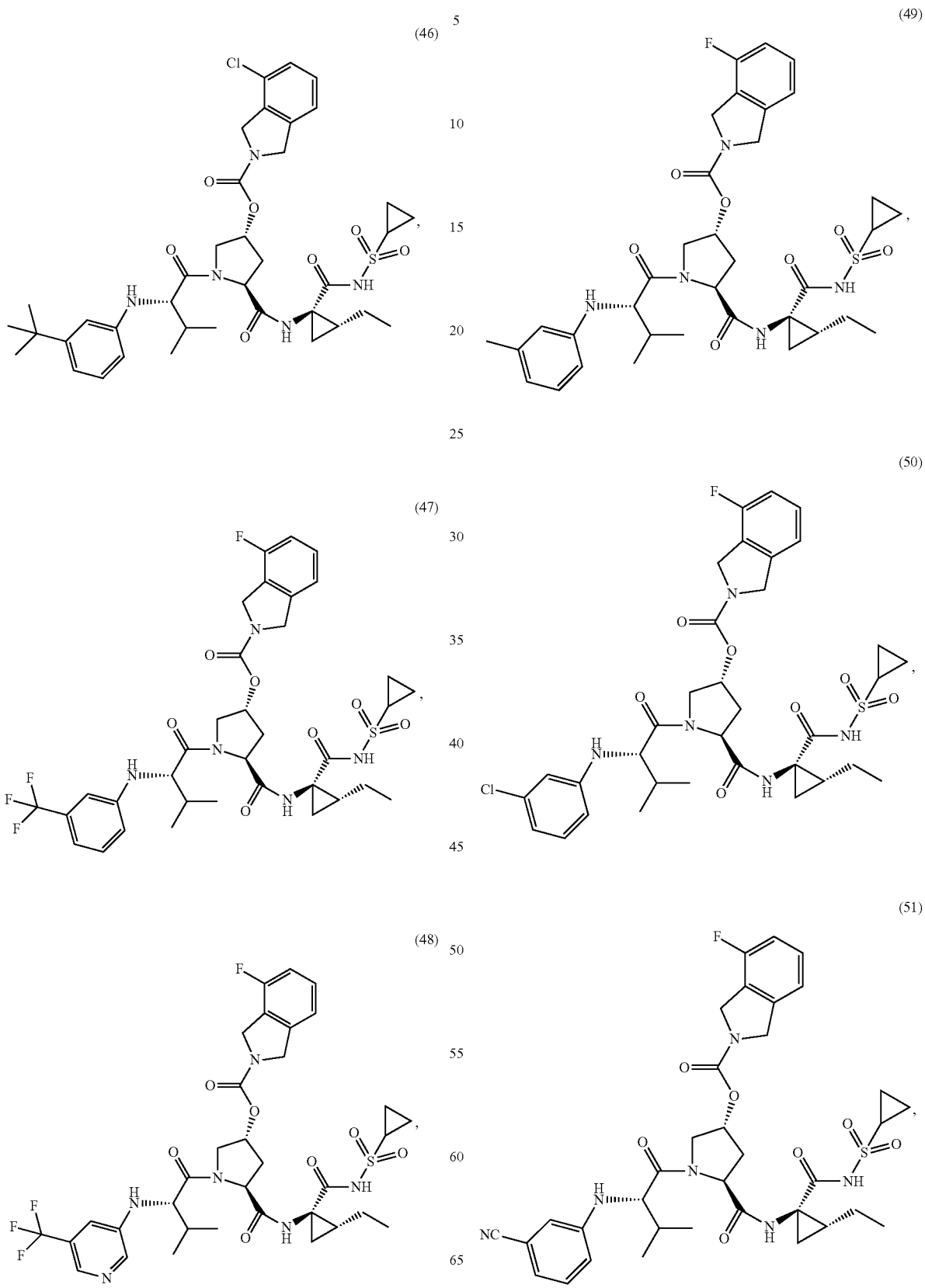

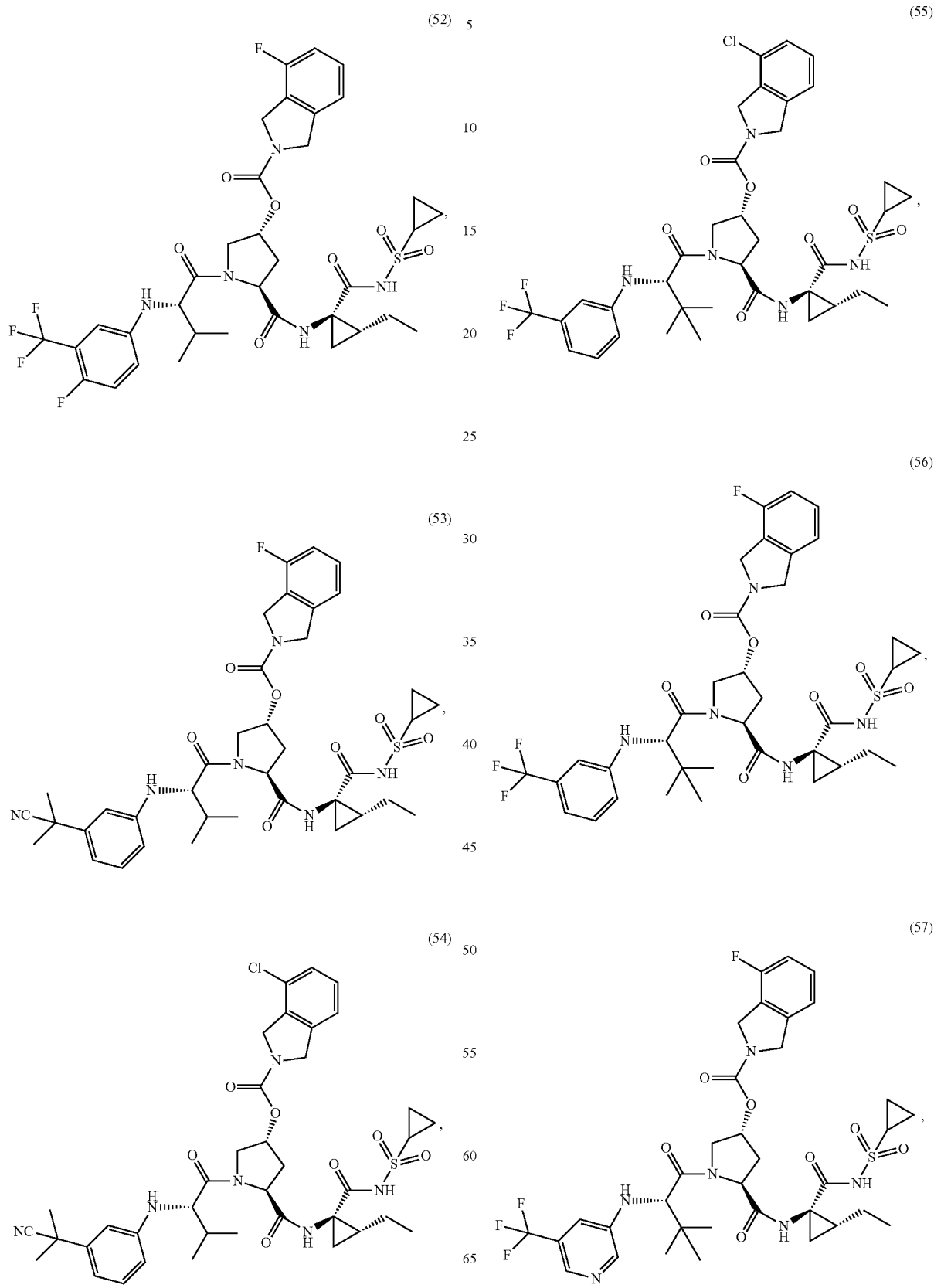

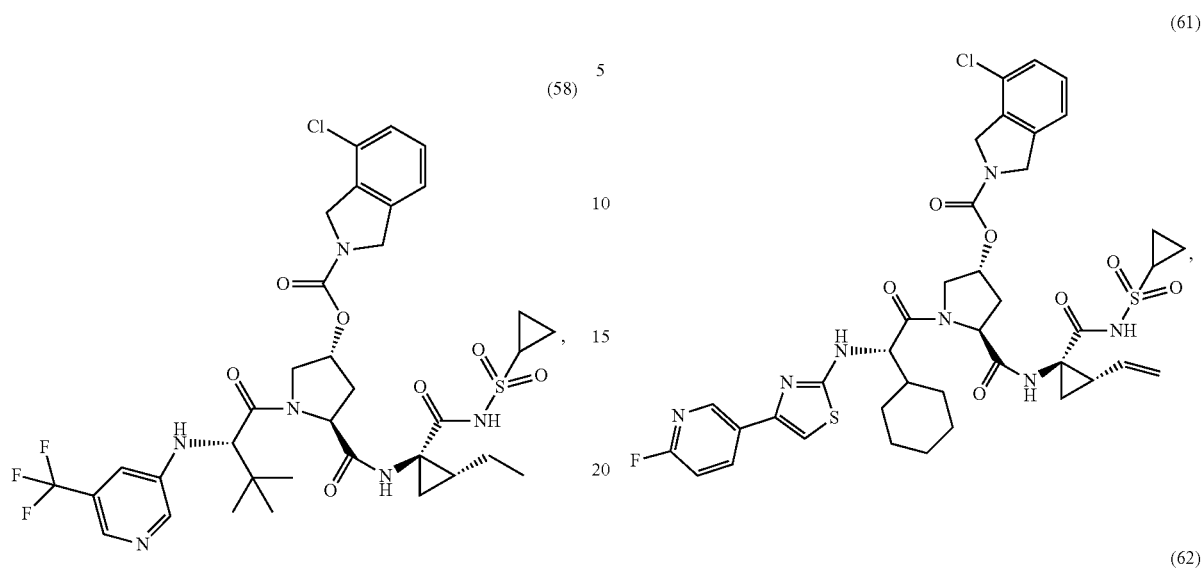
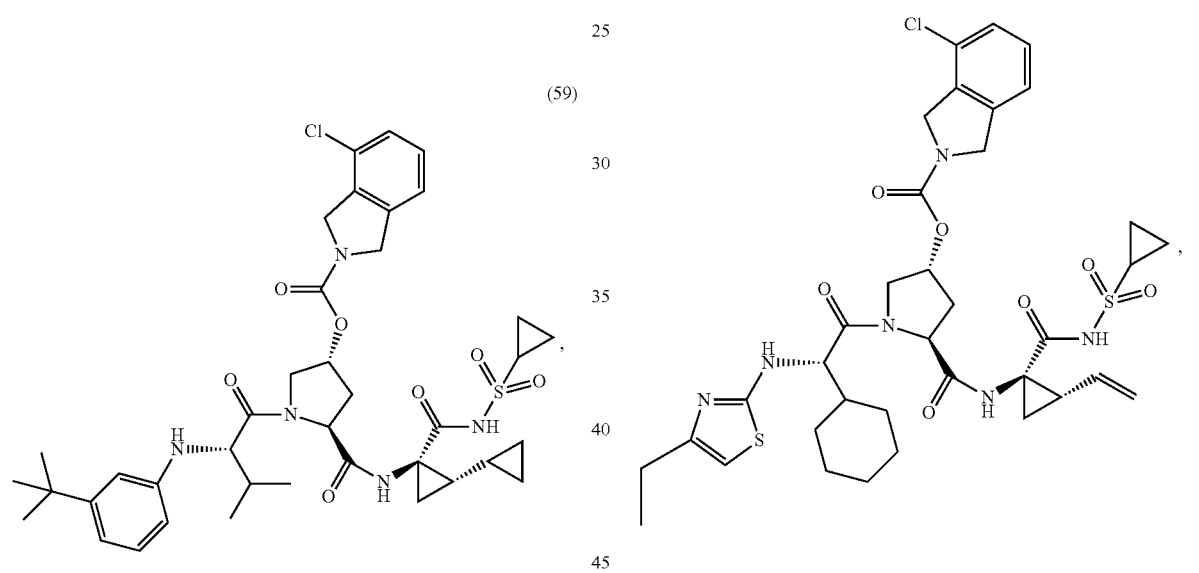
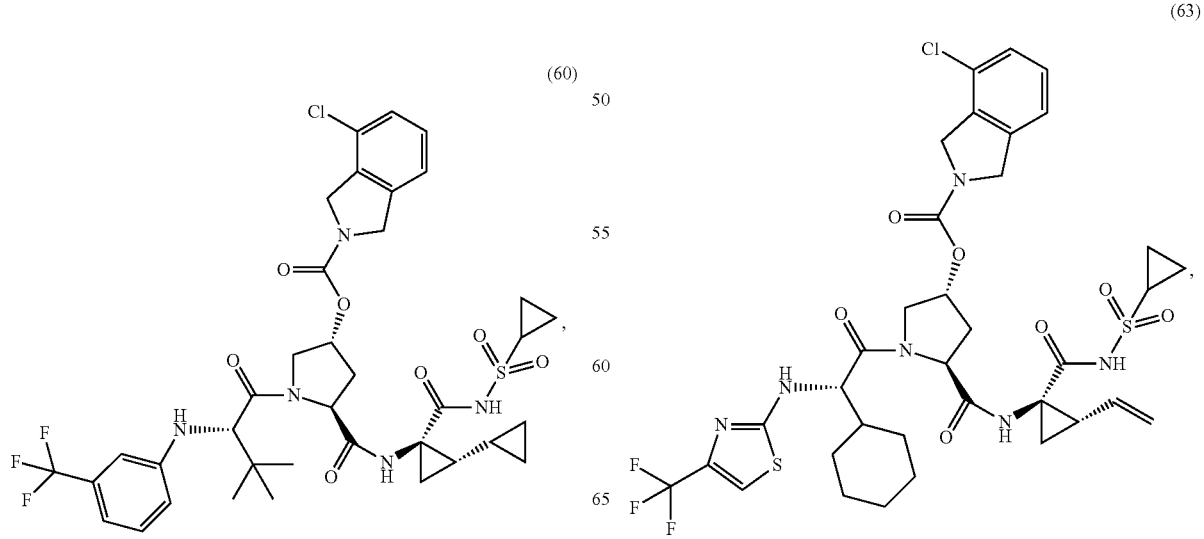

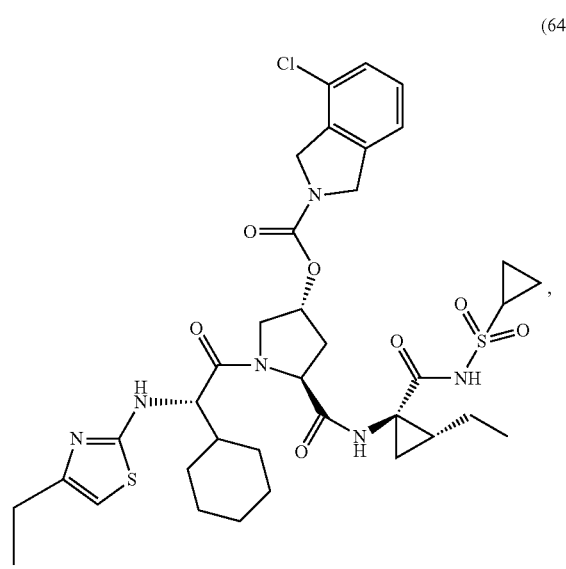
(64)
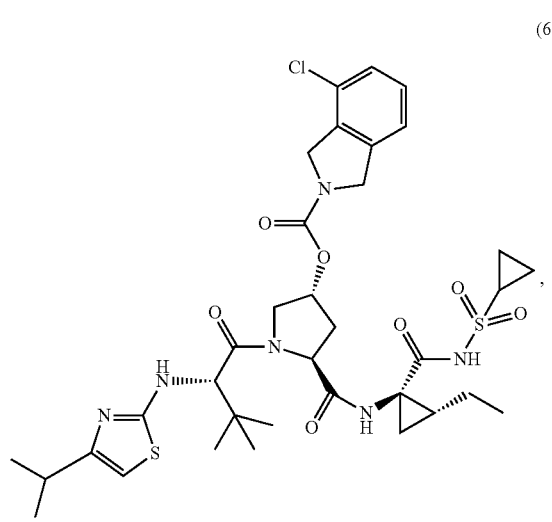
(65)
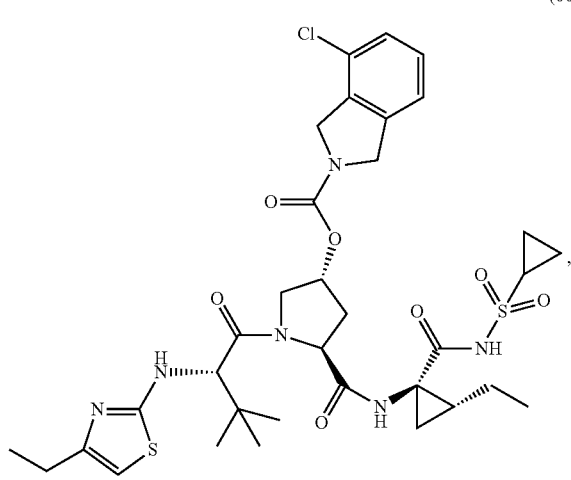
(66)
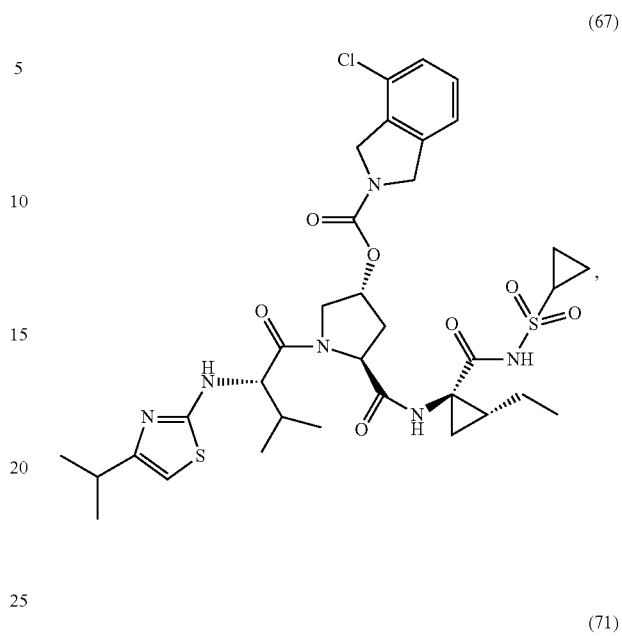
(67)
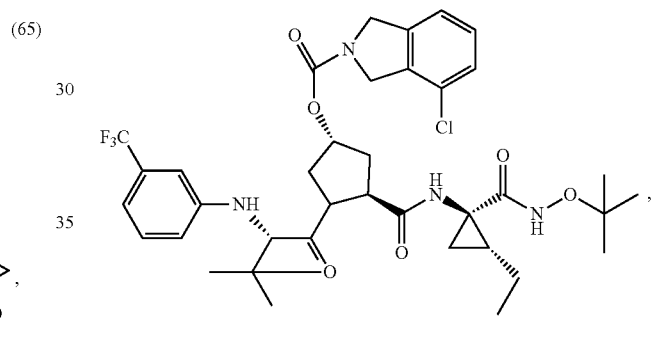
(71)
(72)
(73)
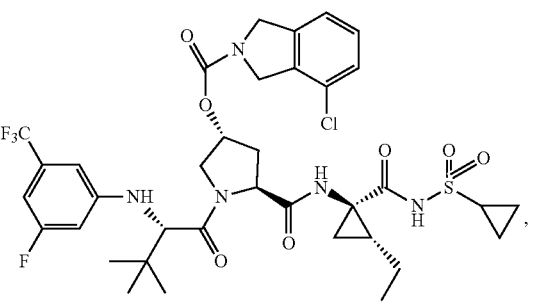

(74)
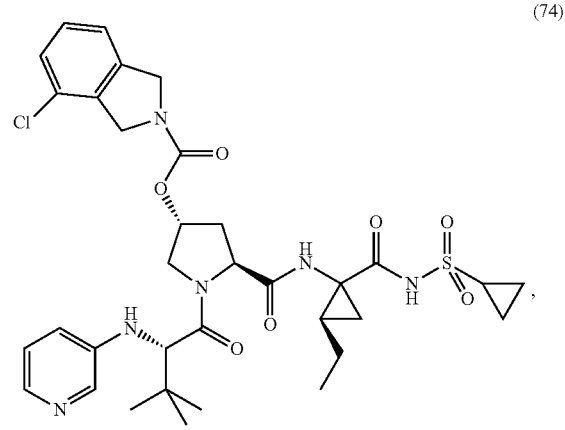
(75)
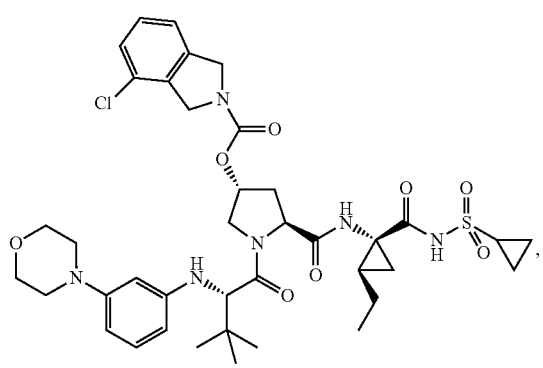
(76)
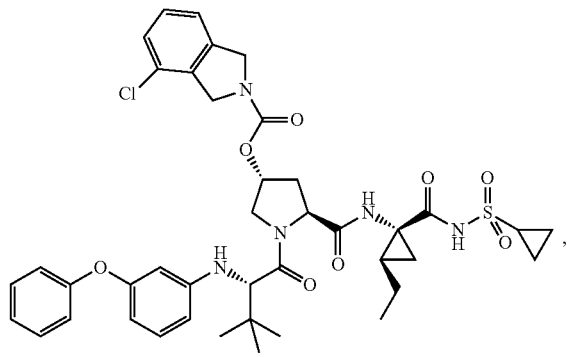
(77)
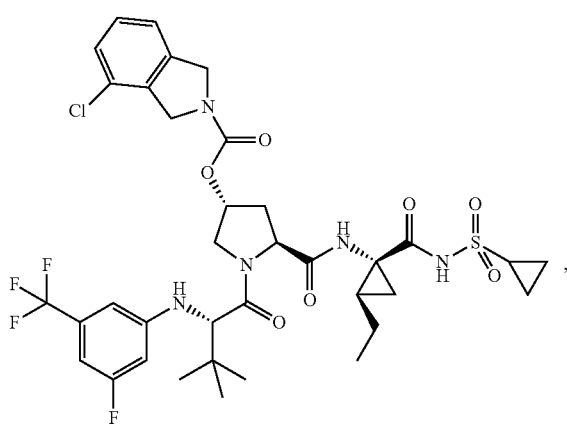
(78)
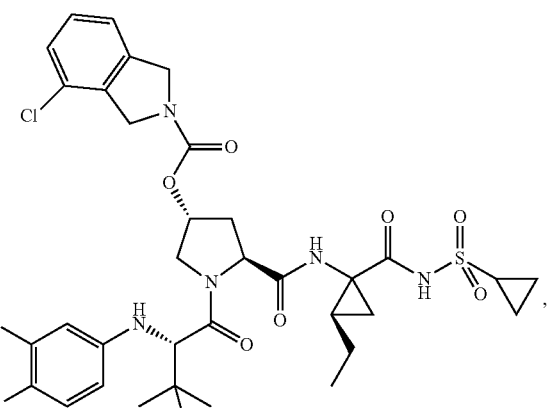
(79)
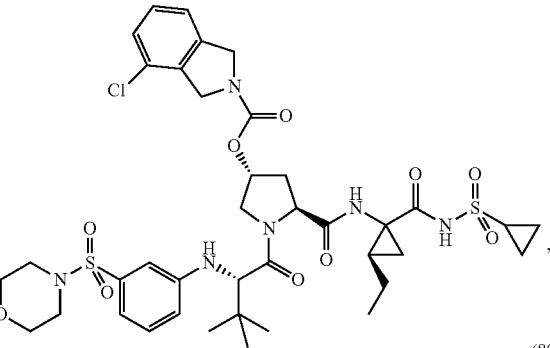
(80)
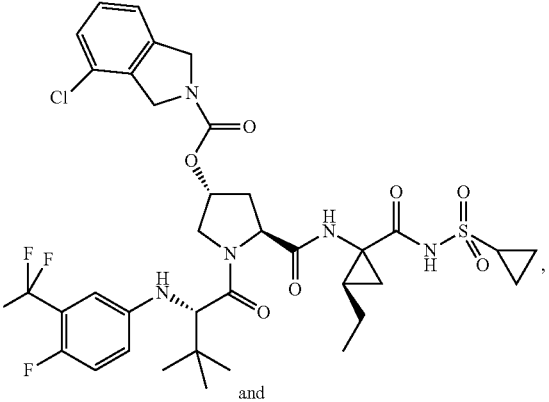
and
(81)
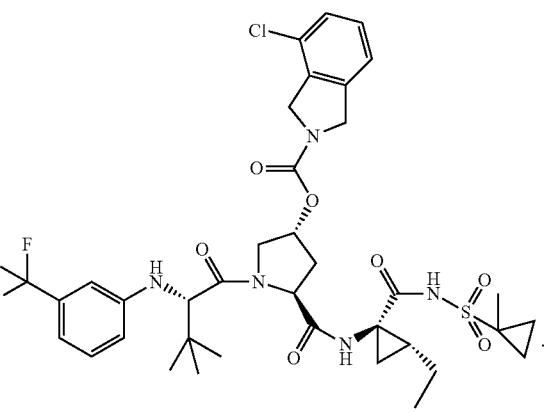

(81)

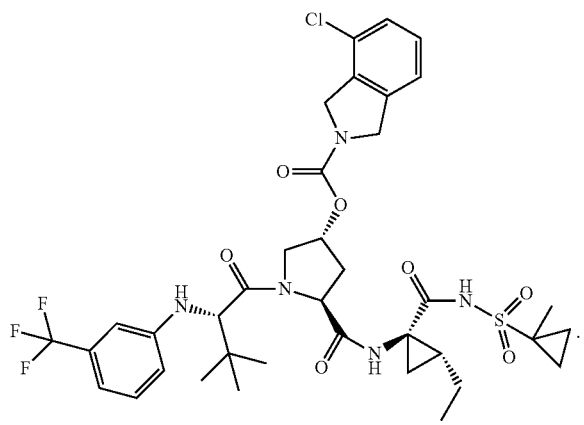

36. A pharmaceutical composition comprising a pharmaceutically acceptable excipient and a compound of claim 1.

37. A method of inhibiting NS3/NS4 protease activity comprising contacting a NS3/NS4 protease with the compound of claim 1 or with the composition of claim 36.

38. The method of claim 37, in which the contacting is conducted in vivo.

39. The method of claim 38, further comprising identifying a subject suffering from a hepatitis C infection and administering the compound to the subject in an amount effective to treat the infection.

40. The method of claim 39, wherein the method further comprises administering to the individual an effective amount of a nucleoside analog.

41. The method of claim 40, wherein the nucleoside analog is selected from ribavirin, levovirin, viramidine, an L-nucleoside, and isatoribine.

42. The method of claim 39, wherein the method further comprises administering to the individual an effective amount of a human immunodeficiency virus 1 protease inhibitor.

43. The method of claim 42, wherein the protease inhibitor is ritonavir.

44. The method of claim 39, wherein the method further comprises administering to the individual an effective amount of an NS5B RNA-dependent RNA polymerase inhibitor.

45. The method of claim 39, wherein the method further comprises administering to the individual an effective amount of interferon-gamma (IFN-γ).

46. The method of claim 45, wherein the IFN-γ is administered subcutaneously in an amount of from about 10μg to about 300μg.

47. The method of claim 38, wherein the method further comprises administering to the individual an effective amount of interferon-alpha (IFN-α).

48. The method of claim 47, wherein the IFN-α is monoPEG-ylated consensus IFN-α administered at a dosing interval of every 8 days to every 14 days.

49. The method of claim 47, wherein the IFN-α is monoPEG-ylated consensus IFN-α administered at a dosing interval of once every 7 days.

50. The method of claim 47, wherein the IFN-α is INFERGEN consensus IFN-α.

51. The method of claim 39, further comprising administering an effective amount of an agent selected from 3'-azidothymidine, 2',3'-dideoxyinosine, 2',3'-dideoxycytidine, 2-,3-didehydro-2',3' -dideoxythymidine, combivir, abacavir, adefovir dipoxil, cidofovir, and an inosine monophosphate dehydrogenase inhibitor.

52. The method of claim 39, wherein a sustained viral response is achieved.

53. The method of claim 37, in which the contacting is conducted ex vivo.

54. A method of treating liver fibrosis in an individual, the method comprising administering to the individual an effective amount of a compound of claim 1.

55. The method of claim 54, wherein the method further comprises administering to the individual an effective amount of a nucleoside analog.

56. The method of claim 55, wherein the nucleoside analog is selected from ribavirin, levovirin, viramidine, an L-nucleoside, and isatoribine.

57. The method of claim 54, wherein the method further comprises administering to the individual an effective amount of a human immunodeficiency virus 1 protease inhibitor.

58. The method of claim 57, wherein the protease inhibitor is ritonavir.

59. The method of claim 54, wherein the method further comprises administering to the individual an effective amount of an NS5B RNA-dependent RNA polymerase inhibitor.

60. The method of claim 54, wherein the method further comprises administering to the individual an effective amount of interferon-gamma (IFN-γ).

61. The method of claim 60, wherein the IFN-γ is administered subcutaneously in an amount of from about 10 μg to about 300 μg.

62. The method of claim 54, wherein the method further comprises administering to the individual an effective amount of interferon-alpha (IFN-α).

63. The method of claim 62, wherein the IFN-α is monoPEG-ylated consensus IFN-α administered at a dosing interval of every 8 days to every 14 days.

64. The method of claim 62, wherein the IFN-α is monoPEG-ylated consensus IFN-α administered at a dosing interval of once every 7 days.

65. The method of claim 62, wherein the IFN-α is INFERGEN consensus IFN-α.

66. The method of claim 54, further comprising administering an effective amount of an agent selected from 3'-azidothymidine, 2',3'-dideoxyinosine, 2',3'-dideoxycytidine, 2-,3-didehydro-2',3' -dideoxythymidine, combivir, abacavir, adefovir dipoxil, cidofovir, and an inosine monophosphate dehydrogenase inhibitor.

67. A method of increasing liver function in an individual having a hepatitis C virus infection, the method comprising administering to the individual an effective amount of a compound of claim 1.

68. The method of claim 67, wherein the method further comprises administering to the individual an effective amount of a nucleoside analog.

69. The method of claim 68, wherein the nucleoside analog is selected from ribavirin, levovirin, viramidine, an L-nucleoside, and isatoribine.

70. The method of claim 67, wherein the method further comprises administering to the individual an effective amount of a human immunodeficiency virus 1 protease inhibitor.

71. The method of claim 70, wherein the protease inhibitor is ritonavir.

72. The method of claim 67, wherein the method further comprises administering to the individual an effective amount of an NS5B RNA-dependent RNA polymerase inhibitor.

73. The method of claim 67, wherein the method further comprises administering to the individual an effective amount of interferon-gamma (IFN-γ).

74. The method of claim 73, wherein the IFN-γ is administered subcutaneously in an amount of from about 10 μg to about 300 μg.

75. The method of claim 67, wherein the method further comprises administering to the individual an effective amount of interferon-alpha (IFN-α).

76. The method of claim 75, wherein the IFN-α is monoPEG-ylated consensus IFN-α administered at a dosing interval of every 8 days to every 14 days.

77. The method of claim 75, wherein the IFN-α is monoPEG-ylated consensus IFN-α administered at a dosing interval of once every 7 days.

78. The method of claim 75, wherein the IFN-α is INFERGEN consensus IFN-α.

79. The method of claim 67, further comprising administering an effective amount of an agent selected from 3'-azidothymidine, 2',3'-dideoxyinosine, 2',3'-dideoxycytidine, 2-,3-didehydro-2',3' -dideoxythymidine, combivir, abacavir, adefovir dipoxil, cidofovir, and an inosine monophosphate dehydrogenase inhibitor.

\* \* \* \* \*